(12) United States Patent
Battista et al.

(10) Patent No.: US 7,579,356 B2
(45) Date of Patent: Aug. 25, 2009

(54) THIA-TETRAAZAACENAPHTHYLENE KINASE INHIBITORS

(75) Inventors: Kathleen A. Battista, Williamstown, NJ (US); Gilles C. Bignan, Bridgewater, NJ (US); Peter J. Connolly, New Providence, NJ (US); Stuart Hayden, Point Pleasant, NJ (US); Sigmond G. Johnson, Flemington, NJ (US); Ronghui Lin, East Brunswick, NJ (US); Niranjan B. Pandey, White Marsh, MD (US); Mark T. Powell, Newtown, PA (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 11/401,339

(22) Filed: Apr. 10, 2006

(65) Prior Publication Data

US 2007/0265264 A1    Nov. 15, 2007

Related U.S. Application Data

(60) Provisional application No. 60/677,542, filed on May 4, 2005.

(51) Int. Cl.
*A01N 43/54* (2006.01)
*A61K 31/515* (2006.01)
*C07D 239/00* (2006.01)
*C07D 471/00* (2006.01)
*C07D 487/00* (2006.01)
*C07D 491/00* (2006.01)

(52) U.S. Cl. ..................... 514/267; 544/251
(58) Field of Classification Search ................. 514/267; 544/251

See application file for complete search history.

(56) References Cited

U.S. PATENT DOCUMENTS 3,635,985 A    1/1972    Santilli et al.

FOREIGN PATENT DOCUMENTS

| WO | WO 98/02434 A1 | 1/1998 |
|---|---|---|
| WO | WO 03/040108 A1 * | 5/2003 |
| WO | WO 2004/046101 A2 | 6/2006 |

OTHER PUBLICATIONS

Wolff, Manfred E., Burger's Medicinal Chemistry and Drug Discovery, Fifth Ed., vol. 1: Principles and Practice, John Wiley & Sons, 1995, 975.*
Banker, Gilbert S. et al., Modern Pharmaceutics, Marcel Dekker, New York, 1996.*
International Search Report, PCT/US06/13257, Aug. 25, 2006.
Olayioye, et al., "The ErbB signaling Network: Receptor Heterodimerization in Development and Cancer," EMBO Journal, vol. 19, No. 13, pp. 3159-3167, 2000.
Yarden, et al., "Untangling The ErbB Signalling Network," Molecular Cell Biology, vol. 2, Feb. 2001, pp. 127-137.
Klijn, et al., "The Clinical Significance of Epidermal Growth Factor Receptor (EGF-R) in Human Breast Cancer: A Review on 5232 Patients," Endocrine Reviews, vol. 13, No. 1, pp. 3-17, 1992.
Salomon, et al., "The ErbB Family of Receptors and Their Ligands: Multiple Targets for Therapy," 2001 Adis Int'l Ltd., vol. 2, Issue 3, pp. 4-11.
Ekstrand, et al., "Amplified and Rearranged Epidermal Growth Factor Receptor Genes in Human Glioblastomas Reveal Deletions of Sequences Encoding Portions of The N- and/or C- Terminal Tails," Proc. Natl Acad. Sci. USA, vol. 89, pp. 4309-4313, May 1992 Medical Sciences.
Wilkstrand, et al., "Monoclonal Antibodies Against EGFRvIII Are Tumor Specific and React with Breast and Lung Carcinomas and Malignant Gliomas," Cancer Research 55, Jul. 15, 1995, pp. 3140-3148.
Koprivica, et al., "EGFR Activation Mediates Inhibition of Axon Regeneration by Myelin and Chondroitin Sulfate Proteoglycans," Science, Oct. 7, 2005, vol. 310, pp. 106-110.
Bertino, Rowinsky, "Targeting Signal Transduction," Horizons, Oct. 30, 2001, vol. 2, 1532-3048.
Slamon, et al., "Human Breast Cancer: Correlation of Relapse and Survival with Amplification of the HER-2/neu Oncogene," Articles, Jan. 9, 1987, pp. 177-182.
Slamon, et al., "Studies of The HER-2/neu Proto-oncogene in Human Breast and Ovarian Cancer," Science, May 12, 1989, pp. 707-712.
Hetzel, et al., "HER-2/neu Expression: A Major Prognostic Factor in Endometrial Cancer," Gynecologic Oncology 47, 1992, pp. 179-185.
Kirsch, et al., "Targeting HER2 in Brain Metastases from Breast Cancer," Clinical Cancer Res., vol. 9, Nov. 15, 2003, pp. 5435-5436.
Grossi, et al., "Efficacy of Intracerebral Microinfusion of Trastuzumab in An Athymic Rat Model of Intracerebral Metastatic Breast Cancer," Clinical Cancer Res., vol. 9, Nov. 15, 2003, pp. 5514-5520.

(Continued)

*Primary Examiner*—James O. Wilson
*Assistant Examiner*—Erich A Lesser
(74) *Attorney, Agent, or Firm*—Laura Donnelly

(57) ABSTRACT

The present invention is directed to novel thia-tetraazaacenaphthylene compounds of Formula (I):

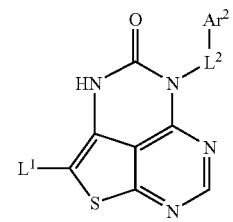

and pharmaceutically acceptable forms thereof and their synthesis and use as inhibitors of ATP-protein kinase interactions.

27 Claims, No Drawings

OTHER PUBLICATIONS

Wang, et al., "Epidermal Growth Factor Receptor is A Cellular Receptor for Human Cytomegalovirus," Nature, vol. 424, Jul. 2003, pp. 456-461.

Yeatman, "A Renaissance for SRC," Nature, vol. 4, Jun. 2004, pp. 470-480.

Goldenberg-Furmanov, et al., "Lyn Is A Target Gene for Prostate Cancer: Sequence-Based Inhibition Induces Regression of Human Tumor Xenografts," Cancer Res. 64, Feb. 1, 2004, pp. 1058-1066.

Shah, et al., "Overriding Imatinib Resistance with A Novel ABL Kinase Inhibitor," Science, vol. 305, Jul. 16, 2004, pp. 399-401.

Donato, et al., "BCR-ABL Independence and LYN Kinase Overexpression in Chronic Myelogenous Leukemia Cells Selected for Resistance to ST1571," Blood, vol. 101, Jan. 15, 2003, No. 2, pp. 690-698.

Klotzer, et al., "Reaktionen Des 4,6-Dichlor-5-Formylpyrimidins," Chem, 96, 1965, pp. 1567-1578.

Shiraishi, et al., "Discovery of Novel, Potent, and Selective Small-Molecule CCR5 Antagonists as Anti-HIV-1 Agents: Synthesis and Biological Evaluation of Anilide Derivatives with A Quaternary Ammonium Moiety," J.Med.Chem 2000, 43, pp. 2049-2063.

Clark, et al., "Heterocyclic Studies, Part 43, Thieno {2,3-d:4,5-d}Dipyrimidines," J.Chem.Soc Perkin Trans 1984, pp. 2005-2008.

Ple, et al., "discovery of A New Class of Anilinoquinazoline Inhibitors with High Affinity and Specificity for The Tyrosine Kinase Domain of c-Src," Amer. Chem. Society, Jan. 14, 2004, 47, pp. 871-887.

Regan, et al., "Pyrazole Urea-Based Inhibitors of p38 MAP Kinase: From Lead Compound to Clinical Candidate," J.Med.Chem 2002, 45, pp. 2994-3008.

* cited by examiner

THIA-TETRAAZAACENAPHTHYLENE KINASE INHIBITORS

CROSS REFERENCE TO RELATED APPLICATIONS

This present application claims benefit of U.S. Provisional Patent Application Ser. No. 60/677,542, filed May 4, 2005, which is incorporated herein by reference in its entirety and for all purposes.

FIELD OF THE INVENTION

The present invention is in the area of novel thia-tetraazaacenaphthylene compounds and pharmaceutically acceptable forms thereof, their syntheses, and their use as kinase inhibitors.

BACKGROUND OF THE INVENTION

In general, protein kinases are the largest set of structurally related phosphoryl transferases, have highly conserved structures and catalytic functions and may be categorized into families by the substrates they phosphorylate (e.g., protein-tyrosine, protein-serine/threonine, histidine and the like) and are responsible for the control of a wide variety of cellular signal transduction processes.

Examples of protein-tyrosine kinases include, but are not limited to, Irk, IGFR-1, Zap-70, Bmx, Btk, CHK (Csk homologous kinase), CSK (C-terminal Src Kinase), Itk-1, Src (c-Src, Lyn, Fyn, Lck, Syk, Hck, Yes, Blk, Fgr and Frk), Tec, Txk/Rlk, Abl, EGFR (EGFR-1/ErbB-1, ErbB-2/NEU/HER-2, ErbB-3 and ErbB4), FAK, FGF1R (also FGFR1 or FGR-1), FGF2R (also FGR-2), MET (also Met-1 or c-MET), PDGFR ($\alpha$ and $\beta$), Tie-1, Tie-2 (also Tek-1 or Tek), VEGFRI (also FLT-1), VEGFR2 (also KDR), FLT-3, FLT-4, c-KIT, JAK1, JAK2, JAK3, TYK2, LOK, RET, TRKA, PYK2, ALK (Anaplastic Lymphoma Kinase), EPHA (1-8), EPHB (1-6), RON, Fes, Fer or EPHB4 (also EPHB4-1).

Examples of protein-serine/threonine kinases include, but are not limited to, Ark, ATM (1-3), CamK (I-IV), CamKK, Chk1 and 2 (Checkpoint kinases), CKI, CK2, Erk, IKK-I (also IKK-ALPHA or CHUK), IKK-2 (also IKK-BETA), Ilk, Jnk (1-3), LimK (1 and 2), MLK3Raf (A, B, and C), CDK (1-10), PKC (including all PKC subtypes), Plk (1-3), NIK, Pak (1-3), PDK1, PKR, RhoK, RIP, RIP-2, GSK3 ($\alpha$ and $\beta$), PKA, P38, Erk (1-3), PKB (including all PKB subtypes) (also AKT-1, AKT-2, AKT-3 or AKT3-1), IRAK1, FRK, SGK, TAK1 or Tpl-2 (also COT).

Protein kinases play very important roles in the normal regulation of cell growth. However, as a result of dysregulation of the tyrosine kinases (receptor or non-receptor) or the ligands of the receptor tyrosine kinases, signaling can become deregulated, resulting in uncontrolled cell proliferation leading to cancer or a related disease, disorder or syndrome.

Protein kinases catalyze and regulate the process of phosphorylation, whereby the kinases covalently attach phosphate groups to proteins or lipid targets in response to a variety of extracellular signals: hormones, neurotransmitters, growth and differentiation factors, cell cycle events, environmental stresses, nutritional stresses and the like.

Phosphorylation modulates or regulates a variety of cellular processes such as proliferation, growth, differentiation, metabolism, apoptosis, motility, transcription, translation and other signaling processes. Uncontrolled signaling for cell growth due to defective control of protein phosphorylation has also been implicated in a number of diseases and disease conditions, such as osteoarthritis, rheumatoid arthritis, synovial pannus invasion in arthritis, multiple sclerosis, myasthenia gravis, diabetes mellitus, diabetic angiopathies or retinopathy, inflammatory bowel disease, Crohn's disease, ulcerative colitis, transplant or bone marrow transplant rejection, lupus, chronic pancreatitis, cachexia, septic shock, skin diseases or disorders (such as papilloma formation, psoriasis, dermatitis, eczema, seborrhea and the like), central nervous system diseases (such as Alzheimer's disease, Parkinson's disease, depression and the like), cancers (such as glioma cancers, epidermoid cancers, head and neck cancers, lung cancers, breast cancers, colorectal cancers, prostate cancers, gastric cancers, esophageal cancers or papillocarcinomas and the like and assoClated pathologies such as unregulated cell proliferation, tumor growth or vascularization or metastatic cancer cell invasion and migration and the like or leukemias or lymphomas), occular diseases (such as macular degeneration, diseases of the cornea, glaucoma and the like), viral infections (such as cytomegalovirus CMV), heart disease (such as atherosclerosis, neointima formation or transplantation-induced vasculopathies (such as restenosis and the like), lung or pulmonary diseases (such as allergic-asthma, lung fibrosis or complications resulting from chronic obstructive pulmonary disorder and the like) or kidney or renal diseases (such as acute, subacute or chronic forms of glomerulonephritis or membranoproliferative glomerulonephritis, glomerulosclerosis, congenital multicystic renal dysplasia, kidney fibrosis and the like). Therefore, kinase inhibitors have potential use as therapeutic agents.

The term "myasthenia gravis" means a disease having the characteristic feature of easy fatigue of certain voluntary muscle groups on repeated use. Muscles of the face or upper trunk are especially likely to be affected. In most and perhaps all cases, the disease is due to the development of autoantibodies against the acetylcholine receptor in neuromuscular junctions. Immunization of animals with this receptor protein leads to a disease with the features of myasthenia gravis (Retrieved from the Internet: <http://cancerweb.ncl.ac.uk/cgi-bin/omd?query=myasthenia+gravis&action=Search+OMD>).

In reference to "synovial pannus invasion in arthritis," the term "pannus" means a disease whereby vascularised granulation tissue rich in fibroblasts, lymphocytes and macrophages, derived from synovial tissue, overgrows the bearing surface of the joint in rheumatoid arthritis and is associated with the breakdown of the articular surface ((Retrieved from the Internet: <http://cancerweb.ncl.ac.uk/cgi-bin/omd?query=pannus>).

The tyrosine kinases can further be categorized by whether they are receptor tyrosine kinases or non-receptor tyrosine kinases. The receptor tyrosine kinases span the cell membrane with a ligand interacting domain protruding from the cell, with a hydrophobic trans-membrane domain, and a cytoplasmic domain that contains the catalytic kinase domain and other regulatory sequences. Non-receptor tyrosine kinases are often myristylated or modified by the addition of other hydrophobic moieties that allow them to be anchored to the cell membrane.

The epidermal growth factor receptor (EGFR) tyrosine-kinase family includes the receptors EGFR (also referred to as EGFR-1 or Erb-B1), HER-2 (or neu), EGFR3 (also referred to as HER-3 or Erb-B4) and EGFR4 (also referred to as HER-4 or Erb-B4) (Olayioye M. A. et al. Eur. Mol. Biol. Org. J. 19 (2000) 3159-3167). Epidermal Growth Factor (EGF) and Transforming Growth Factor -$\alpha$ (TGF-$\alpha$) bind to EGFR and the heregulins, including NRG and NRG2, bind to HER-3 and HER-4 (Yarden Y. et al. Nat. Rev. Mol. Cell. Biol. 2 (2001) 127-137).

EGFR overexpression or mutation of one or more EGFR kinase family members has been commonly involved in cancer and other diseases characterized by uncontrolled or abnormal cell growth. Deregulation of EGFR has also been associated with epidermoid tumors, head and neck tumors, breast tumors and tumors involving other major organs, such as the lungs and gastrointestinal tract. The clinically prevalent cancers related to EGFR include lung, gastric and head and neck cancer (Klijn J G, Berns P M, Schmitz P I and Foekens J A; The clinical significance of epidermal growth factor receptor (EGF-R) in human breast cancer: a review on 5232 patients, *Endocr. Rev.,* 1992, 13, 3-17; Salomon D and Gullick W; The erbB family of receptors and their ligands: Multiple targets for therapy, *Signal,* 2001, 2, 4-11). Other diseases associated with increased EGFR expression include proliferative glomerulonephritis, diabetes-induced renal disease and chronic pancreatitis.

In treating cancers of the head such as brain cancers and the like, the ability of small molecule EGFR inhibitors to penetrate the blood brain barrier could have therapeutic advantages since EGFR is often overexpressed in primary brain tumors and also in breast and non-small cell lung carcinomas that frequently metastasize to the brain (Eckstrand A J, Sugawa N, James C D and Collins V P; Amplified and rearranged epidermal growth factor receptor genes in human glioblastomas reveal deletions of sequences encoding portions of the N- and/or C-terminal tails, *Proc. Acad. Natl. SCl. USA,* 1992, 89, 4309-4313; and, Wickstrand C J, Hale L P, Batra S K, Hill M L, Humphrey P A, Kurpad S N, McLendon R E, Moscatello D, Pegram C N, Reist C J, Traweek S T, Wong A J, Zalutsky M R and Bigner, D D; Monoclonal antibodies against EGFRvIII are tumor specific and react with breast and lung carcinomas and malignant gliomas, *Cancer Res.,* 1995, 55, 3140-3148).

EGFR inhibitors tested in neurite outgrowth assays have activity in promoting neurite outgrowth in both cerebellar granule cells and dorsal root ganglion neurons, likely by acting directly on neurons to block neuronal inhibitory responses to myelin inhibitors, and thus an EGFR inhibitor may have potential use for promoting axon regeneration after brain and spinal cord injury (V. Koprivica, et al, EGFR activation mediates inhibition of axon regeneration by myelin and chondroitin sulfate proteoglycans, *Science,* 2005, 310, 106).

HER1 and HER2 overexpression has been implicated in a variety of cancers, such as bladder, breast, colorectal, endometrial, esophageal, gastric (stomach), glioma head and neck, lung (non-small cell lung cancer), ovarian, pancreatic, renal and prostate cancer.

Comparing the overexpression of HER1 and HER2 in tumors, according to order of prevalence, HER1 overexpression is found in breast, renal cell, lung, colorectal, head and neck, ovarian, pancreatic, glioma, bladder, esophageal, gastric, endometrial and cervical cancer tumors; in contrast, HER2 overexpression is found in esophageal, head and neck, lung, gastric, renal cell, breast, bladder, ovarian and colorectal, prostate and endometrial cancer tumors (Horizons in Cancer Therapeutics: From Bench to Bedside, Signal Transduction Inhibitors, 2001, 2(2), ISSN 1532-3048).

While the degree of HER2 overexpression in breast and ovarian cancer is not as great as in some other cancers, HER2 has been found to be responsible for these clinically prevalent cancers (Slamon D J, Clark G M, Wong S G, Levin W J, Ullrich A and McGuire W L; Human breast cancer: Correlation of relapse and survival with amplification of HER-2/neu oncogene, *Science,* 1987, 235, 177-82; Slamon D J, Godolphin W, Jones L A, Holt J A, Wong S G, Keith D E, et al; Studies of the HER-2/neu proto-oncogene in human breast and ovarian cancer, *Science,* 1989, 244, 707-712; Hetzel DJ, Wilson TO, Keeney GL, Roche P C, Cha SS and Podrantz KC; HER-2/neu expression: A major prognostic factor in endometrial cancer, *Gynecol. Oncol.,* 1992, 47, 179-85).

Furthermore, patients with HER-2 overexpressing breast cancer frequently experience metastases to the brain (Kirsch D G and Hochberg F H; Targeting HER-2 in brain metastases from breast cancer, *Clin. Can. Res.,* 2003, 9, 5435-5436). These patients have an extremely poor prognosis and intracerebral tumors are often the cause of death. Autopsy revealed that 20-30% of patients who die of breast cancer have brain metastases (Grossi P M, Ochiai H, Archer G E, McLendon R E, Zalutsky M R, Friedman A H, Friedman H S, Bigner D D and Sampson J H; Efficacy of intracerebral microinfusion of trastuzumab in an athymic rat model of intracerebral metastatic breast cancer, *Clin. Can. Res.,* 2003, 9, 5514-5520).

Human cytomegalovirus (CMV) is a widespread opportunistic human herpes virus that causes severe and fatal diseases in those who are immune compromised and in transplant recipients. CMV is also a leading cause of atherosclerosis and virally mediated birth defects. The human CMV uses the EGFR receptor to enter cells during infection, EGFR is autophosphorylated and the downstream signal transduction pathway components are activated; however, the EGFR specific inhibitor tyrphostin AG1478 has been shown to reduce the viral load in cells that were infected in the presence of the tyrphostin (Wang X, et al., Nature, 24 Jul. 2003, Vol 424, 456-461). Accordingly, potent EGFR selective inhibitors may be useful in anti-CMV therapy.

The Src family of tyrosine-kinases includes the sub-family proteins c-Src, Lyn, Fyn, Lck, Syk, Hck, Yes, Blk, Fgr and Frk. While various members of the c-Src family are important for normal cellular proliferation, their overexpression and overactivation can promote development of cancer (Yeatman T J, Nature Reviews Cancer, 2004, Vol. 4(6), 470-480). For example, the Lyn kinase has been shown to be upregulated in hormone resistant prostate cancer. Tumor xenografts of hormone resistant prostate cancer cells showed delayed growth upon treatment with peptides that specifically block Lyn kinase activity (Goldenberg-Furmanov, et al., Cancer Research, 1 Feb. 2004, 64, 1058-1064).

The Lyn and Hck Src sub-family tyrosine-kinases have both been implicated in chronic myeloid leukemia (CML). CML is caused by the BCR-Abl fusion protein that results from the t(9;22) chromosomal translocation that juxtaposes the c-Abl non-receptor tyrosine kinase gene on chromosome 9 with a breakpoint cluster region (bcr) gene on chromosome 22. The BCR-Abl fusion protein is a constitutively activated form of the Abl tyrosine kinase that drives uncontrolled growth leading to CML and many cases of adult acute lymphoblastic leukemia. Gleevec, which is an inhibitor of Abl has been successfully used to treat CML. However, Gleevec does not help patients in blast crisis because they carry mutant forms of BCR-Abl that no longer bind Gleevec. Such Gleevec resistant CML cells are sensitive to a dual src/BCR-Abl inhibitor that binds and inhibits the mutant BCR-Abl and members of the src family (Shah N P, et al., Science, 16 Jul. 2004, Vol 305, 399-401). There are also other ways that CML cells can become resistant to treatment with the tyrosine kinase Abl inhibitor Gleevec. For example, CML K562 cells that become resistant to Gleevec minimize reliance on the BCR-Abl translocation for growth and instead upregulate the Lyn and Hck kinases. This was demonstrated by expressing antisense Lyn in these cells, which reduced their rate of proliferation (Donato N J, et al., Blood, 15 Jan. 2003, 101(2), 690-698). c-Src and other Src family members are also involved in cellular adhesion, invasion and motility of tumor cells. Thus, small molecule inhibitors of the Src kinase family could offer new therapeutic opportunities for both leukemias and solid tumors.

There is a need for potent small-molecule kinase inhibitors of one or more of the EGFR, HER-2, HER-4, c-Src, Lyn or c-Abl kinase proteins and the like possessing anti-tumor cell proliferation activity, and as such are useful in treating or ameliorating a EGFR, HER-2, HER4, c-Src, Lyn or c-Abl kinase receptor mediated, angiogenesis-mediated or hyperproliferative disorder.

SUMMARY OF THE INVENTION

A first aspect of the present invention is directed to novel compounds of Formula (I):

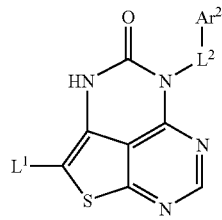

and pharmaceutically acceptable forms thereof.

A second aspect of the present invention is directed to pharmaceutical compositions comprising at least one compound of Formula (I), or a pharmaceutically acceptable form thereof and one or more pharmaceutically acceptable excipients.

A third aspect of the present invention is directed to a method of inhibiting the activity of a protein kinase, comprising contacting the protein kinase domain with one or more compounds of Formula (I).

A fourth aspect of the invention is directed to a method of inhibiting unregulated kinase activity comprising administering to a subject a composition comprising a pharmaceutically effective amount of at least one compound of Formula (I), or a pharmaceutically acceptable form thereof and one or more pharmaceutically-acceptable excipients.

A fifth aspect of the present invention is directed to a method of inhibiting increased or unregulated kinase expression or signaling comprising administering to an animal a pharmaceutically effective amount of at least one compound of Formula (I), or a pharmaceutically acceptable form thereof and one or more pharmaceutically-acceptable excipients.

A sixth aspect of the present invention is directed to a method of treating diseases or conditions caused by increased kinase expression or signaling leading to unregulated cell proliferation comprising administering to an animal a pharmaceutically effective amount of at least one compound of Formula (I), or a pharmaceutically acceptable form thereof and one or more pharmaceutically-acceptable excipients.

A seventh aspect of the present invention is directed to a method of treating cancer comprising administering to an animal a pharmaceutically effective amount of at least one compound of Formula (I), or a pharmaceutically acceptable form thereof and one or more pharmaceutically-acceptable excipients.

An eighth aspect of the present invention is directed to describing thia-tetraazaacenaphthylene compounds as inhibitors of a tyrosine-kinase selected from EGFR, HER-2, HER-4, c-Src, Lyn, or c-Abl and the like.

A ninth aspect of the present invention is to describe thia-tetraazaacenaphthylene compounds that are useful at low dosages as inhibitors of protein kinase-induced mitogenesis. This therefore leads to a further aspect of compounds having extremely low cytotoxicity.

A tenth aspect of the present invention is to describe thia-tetraazaacenaphthylene compounds that are useful in suppressing tumors, especially tumors such as non-small-cell lung cancers, colon cancers, breast cancers and the like where mitogenesis is heavily driven by protein kinases such as EGFR, HER-2, HER-4, c-Src, Lyn or c-Abl and the like.

An eleventh aspect of the present invention is to describe thia-tetraazaacenaphthylene compounds that have utility as chronic therapeutic agents for inhibiting protein kinase-induced responses. This therefore leads to a further aspect of such therapeutic agents being used as a long-term therapy for inducing cancer remission.

A twelfth aspect of the present invention is to describe thia-tetraazaacenaphthylene compounds that have utility as therapeutic agents against chronic or acute diseases characterized by uncontrolled cell proliferation and which may result in metastatic cancer cell invasion and migration.

A thirteenth aspect of the present invention is to describe thia-tetraazaacenaphthylene compounds that have utility as therapeutic agents against EGFR protein kinase mediated cytomegalovirus (CMV) infection.

A fourteenth aspect of the present invention is to describe thia-tetraazaacenaphthylene compounds that have utility as therapeutic agents against chronic or acute kinase mediated diseases or for use as a contraceptive agent.

A fifteenth aspect of the present invention is directed to methods of synthesizing compounds of Formula (I).

These and other aspects and advantages of the invention, which will become apparent in light of the detailed description below, are achieved through use of the compounds of this invention.

DETAILED DESCRIPTION OF THE INVENTION

The present invention provides a substituted thia-tetraazaacenaphthylene compound of Formula (I)

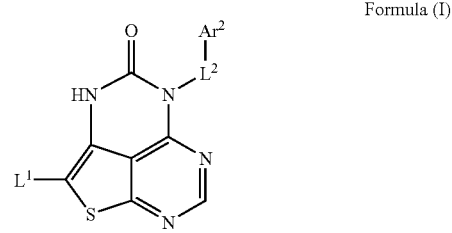

Formula (I)

or a stereoisomer, prodrug or a pharmaceutically acceptable salt thereof, wherein $L^1$ is selected from the group consisting of hydrogen, —N($R_1R_2$), —C(O)N($R_1R_2$), —C(O)O($R_1$), —S($C_{1-4}$alkyl), $NO_2$, —$(CH_2)_p$—$Ar^1$, —C(O)—$(CH_2)_p$—$Ar^1$, —N($R_1$)—$(CH_2)_p$—$Ar^1$, —N($R_1$)C(O)—$(CH_2)_p$—$Ar^1$, —N($R_1$)C(O)N($R_2$)—$(CH_2)_p$—$Ar^1$ and —C(O)N($R_1$)—$(CH_2)_p$—$Ar^1$;

$R_1$ is selected from the group consisting of hydrogen, $C_{1-8}$alkyl, $C_{1-8}$alkoxy-$C_{1-8}$alkyl, amino-$C_{1-8}$alkoxy-$C_{1-8}$alkyl and $C_{1-8}$alkyl-amino-$C_{1-8}$alkoxy-$C_{1-8}$alkyl;

$R_2$ is selected from the group consisting of hydrogen, $C_{1-8}$alkyl, $C_{1-8}$alkoxy-$C_{1-8}$alkyl, hydroxy-$C_{1-8}$alkyl, amino-$C_{1-8}$alkyl, $C_{1-8}$alkyl-amino-$C_{1-8}$alkyl and $C_{1-8}$alkoxy-carbonyl-amino-$C_{1-8}$alkyl;

p is 0, 1, 2, 3 or 4, $L^2$ is selected from the group consisting of —($C_{1-8}$alkyl)-, —N($R_1$)— and a bond, $Ar^1$ is selected from the group consisting of aryl, heteroaryl, benzofused heteroaryl, heterocyclyl and benzofused heterocyclyl, each optionally substituted with one, two, three, four or five substituents independently selected from the group consisting of
(1) $C_{1-8}$alkyl,
(2) $C_{2-8}$alkenyl,
(3) $C_{2-8}$alkynyl,
(4) $C_{1-8}$alkoxy,
  wherein each (1), (2), (3) and (4) is optionally substituted with one, two or three substituents independently selected from the group consisting of
  (i) $C_{3-8}$cycloalkyl,
  (ii) aryl,
  (iii) heteroaryl,
  (iv) heterocyclyl,
    wherein each (i), (ii), (iii) and (iv) is optionally substituted with one, two, three, four or five substituents independently selected from the group consisting of
    (a) $C_{1-8}$alkyl,
    (b) $C_{1-8}$alkoxy,
    (c) $C_{1-8}$alkoxy-$C_{1-8}$alkyl,
    (d) halo-$C_{1-8}$alkyl,
    (e) hydroxy-$C_{1-8}$alkyl,
    (f) $C_{1-8}$alkoxy-carbonyl,
    (g) amino optionally mono or disubstituted with $C_{1-8}$alkyl or $C_{1-8}$alkoxy-carbonyl,
    (h) cyano,
    (i) halogen,
    hydroxy,
    (k) amino-$C_{1-8}$alkyl optionally mono or disubstituted on amino with $C_{1-8}$alkyl,
    (l) $C_{3-8}$cycloalkyl,
    (m) $C_{3-8}$cycloalkyl-$C_{1-8}$alkyl,
    (n) heterocyclyl optionally substituted with one or two $C_{1-8}$alkyl substituents, and
    (o) heterocyclyl-$C_{1-8}$alkyl optionally substituted on heterocyclyl with one or two $C_{1-8}$alkyl substituents,
  (v) amino optionally mono or disubstituted with a substituent independently selected from the group consisting of
    (a) $C_{1-8}$alkyl,
    (b) $C_{1-8}$alkoxy-$C_{1-8}$alkyl,
    (c) hydroxy-$C_{1-8}$alkyl,
    (d) $C_{3-8}$cycloalkyl,
    (e) heterocyclyl optionally substituted with one or two $C_{1-8}$alkyl substituents, and
    (f) heterocyclyl-$C_{1-8}$alkyl optionally substituted on heterocyclyl with one or two $C_{1-8}$alkyl substituents,
  (vi) hydroxy,
  (vii) halogen, and
  (viii) $C_{1-8}$alkoxy-carbonyl,
(5) amino optionally mono or disubstituted with a substituent independently selected from the group consisting of
  (i) $C_{1-8}$alkyl,
  (ii) $C_{1-8}$alkoxy-$C_{1-8}$alkyl,
  (iii) amino-$C_{1-8}$alkyl optionally mono or disubstituted on amino with $C_{1-8}$alkyl,
  (iv) hydroxy-$C_{1-8}$alkyl,
  (v) $C_{3-8}$cycloalkyl,
  (vi) heterocyclyl optionally substituted with one or two $C_{1-8}$alkyl substituents, and
  (vii) heterocyclyl-$C_{1-8}$alkyl optionally substituted on heterocyclyl with one or two $C_{1-8}$alkyl substituents,
(6) cyano,
(7) halogen,
(8) hydroxy,
(9) $C_{3-8}$cycloalkyl,
(10) aryl,
(11) heteroaryl,
(12) heterocyclyl,
(13) —O— substituted with a substituent selected from the group consisting of
  (i) $CF_3$,
  (ii) $C_{3-8}$cycloalkyl,
  (iii) aryl,
  (iv) heteroaryl, and
  (v) heterocyclyl,
(14) heterocyclyl-$SO_2$ optionally substituted on heterocyclyl with one or two $C_{1-8}$alkyl substituents,
(15) C(O) substituted with a substituent selected from the group consisting of
  (i) hydrogen,
  (ii) hydroxy,
  (iii) $C_{1-8}$alkyl,
  (iv) $C_{1-8}$alkoxy, and
  (v) amino optionally mono or disubstituted with a substituent independently selected from the group consisting of
    (a) $C_{1-8}$alkyl,
    (b) $C_{1-8}$alkoxy-$C_{1-8}$alkyl,
    (c) amino-$C_{1-8}$alkyl optionally mono or disubstituted on amino with $C_{1-8}$alkyl,
    (d) hydroxy-$C_{1-8}$alkyl,
    (e) heterocyclyl-$C_{1-8}$alkyl optionally substituted on heterocyclyl with one or two $C_{1-8}$alkyl substituents,
    (f) $C_{3-8}$cycloalkyl, and
    (g) aryl; and
(16) amino-$SO_2$ optionally mono or disubstituted on amino with a substituent independently selected from the group consisting of
  (i) $C_{1-8}$alkyl,
  (ii) $C_{1-8}$alkoxy-$C_{1-8}$alkyl,
  (iii) amino-$C_{1-8}$alkyl optionally mono or disubstituted on amino with $C_{1-8}$alkyl,
  (iv) hydroxy-$C_{1-8}$alkyl,
  (v) heterocyclyl-$C_{1-8}$alkyl optionally substituted on heterocyclyl with one or two $C_{1-8}$alkyl substituents,
  (vi) $C_{3-8}$cycloalkyl, and
  (vii) aryl; and $Ar^2$ is selected from the group consisting of aryl, heteroaryl, benzofused heteroaryl, heterocyclyl and benzofused heterocyclyl, each optionally substituted with one, two, three, four or five substituents independently selected from the group consisting of
(1) $C_{1-8}$alkyl,
(2) $C_{2-8}$alkenyl,
(3) $C_{2-8}$alkynyl,
(4) $C_{1-8}$alkoxy,
  wherein each (1), (2), (3) and (4) is optionally substituted with one, two or three substituents independently selected from the group consisting of
  (i) $C_{1-8}$alkoxy,
  (ii) cyano,
  (iii) halogen,
  (iv) hydroxy, (v) $C_{3-8}$cycloalkyl,
(vi) aryl,
(vii) heteroaryl,
(viii) heterocyclyl,
wherein each (v), (vi), (vii) and (viii) is optionally substituted with one, two, three, four or five substituents independently selected from the group consisting of
(a) $C_{1-8}$alkyl,
(b) $C_{1-8}$alkoxy,
(c) $C_{1-8}$alkoxy-$C_{1-8}$alkyl,
(d) amino optionally mono or disubstituted with $C_{1-8}$alkyl,
(e) cyano,
(f) halogen,
(g) halo-$C_{1-8}$alkyl,
(h) hydroxy,
(i) hydroxy-$C_{1-8}$alkyl,
(j) $C_{3-8}$cycloalkyl, and
(k) heterocyclyl optionally substituted with one or two $C_{1-8}$alkyl substituents,
(ix) amino optionally mono or disubstituted with a substituent independently selected from the group consisting of
(a) $C_{1-8}$alkyl,
(b) $C_{1-8}$alkoxy-$C_{1-8}$alkyl,
(c) hydroxy-$C_{1-8}$alkyl,
(d) $C_{3-8}$cycloalkyl,
(e) heterocyclyl optionally substituted with one or two $C_{1-8}$alkyl substituents, and
(f) heterocyclyl-$C_{1-8}$alkyl optionally substituted on heterocyclyl with one or two $C_{1-8}$alkyl substituents, and
(x) C(O)amino optionally mono or disubstituted with a substituent independently selected from the group consisting of
(a) $C_{1-8}$alkyl,
(b) $C_{1-8}$alkoxy-$C_{1-8}$alkyl,
(c) hydroxy-$C_{1-8}$alkyl,
(d) $C_{3-8}$cycloalkyl,
(e) aryl optionally substituted with one to three halogen substituents,
(f) heterocyclyl optionally substituted with one or two $C_{1-8}$alkyl substituents, and
(g) heterocyclyl-$C_{1-8}$alkyl optionally substituted on heterocyclyl with one or two $C_{1-8}$alkyl substituents,
(5) NH, NHC(O), N, S, S(O), $SO_2$ or O substituted with one or two substituents independently selected from the group consisting of
(i) hydrogen,
(ii) $C_{1-8}$alkyl,
(iii) $C_{1-8}$alkoxy-$C_{1-8}$alkyl,
(iv) amino-$C_{1-8}$alkyl optionally mono or disubstituted on amino with $C_{1-8}$alkyl,
(v) hydroxy-$C_{1-8}$alkyl,
(vi) aryl,
(vii) heteroaryl,
(viii) benzofused heteroaryl,
(ix) $C_{3-8}$cycloalkyl,
(x) heterocyclyl,
(xi) benzofused heterocyclyl,
(xii) aryl-$C_{1-8}$alkyl,
(xiii) heteroaryl-$C_{1-8}$alkyl,
(xiv) benzofused heteroaryl-$C_{1-8}$alkyl,
(xv) $C_{3-8}$cycloalkyl-$C_{1-8}$alkyl,
(xvi) heterocyclyl-$C_{1-8}$alkyl, and
(xvii) benzofused heterocyclyl-$C_{1-8}$alkyl,
wherein each aryl, $C_{3-8}$cycloalkyl, heteroaryl, benzofused heteroaryl, heterocyclyl and benzofused heterocyclyl in one or more of from (vi) to (xvii) is optionally substituted with one, two, three, four or five substituents independently selected from the group consisting of
(a) $C_{1-8}$alkyl,
(b) $C_{1-8}$alkoxy,
(c) $C_{1-8}$alkoxy-$C_{1-8}$alkyl,
(d) amino optionally mono or disubstituted with $C_{1-8}$alkyl, and
(e) halogen,
(6) C(O) substituted with a substituent independently selected from the group consisting of
(i) hydrogen,
(ii) $C_{1-8}$alkyl optionally substituted with one, two or three substituents independently selected from the group consisting of
(a) cyano,
(b) halogen, and
(c) hydroxy,
(iii) $C_{1-8}$alkoxy,
(iv) hydroxy, and
(v) $C_{1-8}$alkoxy-$C_{1-8}$alkoxy,
(7) cyano,
(8) halogen,
(9) hydroxy,
(10) nitro,
(11) $C_{3-8}$cycloalkyl,
(12) aryl,
(13) heteroaryl,
(14) benzofused heteroaryl,
(15) heterocyclyl, and
(16) benzofused heterocyclyl;
wherein each (11), (12), (13), (14), (15) and (16) is optionally substituted with one, two, three, four or five substituents independently selected from the group consisting of
(i) $C_{1-8}$alkyl,
(ii) cyano,
(iii) halogen,
(iv) hydroxy,
(v) nitro,
(vi) $C_{3-8}$cycloalkyl,
(vii) $C_{3-8}$cycloalkyl-$C_{1-8}$alkyl,
(viii) aryl,
(ix) aryl-$C_{1-8}$alkyl,
(x) heteroaryl,
(xi) heteroaryl-$C_{1-8}$alkyl,
(xii) heterocyclyl, and
(xiii) heterocyclyl-$C_{1-8}$alkyl.

An example of a compound of Formula (I) includes a compound and pharmaceutically acceptable forms thereof, wherein $L^1$ is selected from the group consisting of hydrogen, —$N(R_1R_2)$, —$C(O)N(R_1R_2)$, —$C(O)O(R_1)$, $NO_2$, —$(CH_2)_p$—$Ar^1$, —$C(O)$—$(CH_2)_p$—$Ar^1$, —$N(R_1)C(O)$—$(CH_2)_p$—$Ar^1$, —$C(O)N(R_1)$—$(CH_2)_p$—$Ar^1$ and —$N(R_1)C(O)N(R_2)$—$(CH_2)_p$—$Ar^1$.

An example of a compound of Formula (I) includes a compound and pharmaceutically acceptable forms thereof, wherein $L^1$ is selected from the group consisting of hydrogen, —$N(R_1R_2)$, —$C(O)N(R_1R_2)$, —$C(O)O(R_1)$, $NO_2$, —$(CH_2)_p$—$Ar^1$, —$C(O)$—$(CH_2)_p$—$Ar^1$, —$N(R_1)C(O)$—$(CH_2)_p$—$Ar^1$ and —$C(O)N(R_1)$—$(CH_2)_p$—$Ar^1$.

An example of a compound of Formula (I) includes a compound and pharmaceutically acceptable forms thereof, wherein $R_1$ is selected from the group consisting of hydrogen, $C_{1-8}$alkyl and $C_{1-8}$alkoxy-$C_{1-8}$alkyl.

An example of a compound of Formula (I) includes a compound and pharmaceutically acceptable forms thereof, wherein $R_2$ is selected from the group consisting of hydrogen, $C_{1-8}$alkyl, hydroxy-$C_{1-8}$alkyl, amino-$C_{1-8}$alkyl, $C_{1-8}$alkyl-amino-$C_{1-8}$alkyl and $C_{1-8}$alkoxy-carbonyl-amino-$C_{1-8}$alkyl.

An example of a compound of Formula (I) includes a compound and pharmaceutically acceptable forms thereof, wherein p is 0, 1, 2 or 3.

An example of a compound of Formula (I) includes a compound and pharmaceutically acceptable forms thereof, wherein $L^2$ is selected from the group consisting of —($C_{1-8}$alkyl)- and a bond.

An example of a compound of Formula (I) includes a compound and pharmaceutically acceptable forms thereof, wherein $L^2$ is a bond.

An example of a compound of Formula (I) includes a compound and pharmaceutically acceptable forms thereof, wherein $Ar^1$ is selected from the group consisting of aryl, heteroaryl and heterocyclyl, each optionally substituted with one, two, three, four or five substituents independently selected from the group consisting of (1) $C_{1-8}$alkyl, $C_{2-8}$alkenyl and $C_{1-8}$alkoxy, each optionally substituted with one, two or three substituents independently selected from the group consisting of
  (i) heterocyclyl optionally substituted with one, two or three $C_{1-8}$alkyl, $C_{1-8}$alkoxy, hydroxy-$C_{1-8}$alkyl, amino, $C_{1-8}$alkyl-amino, $C_{1-8}$alkoxy-carbonyl-amino, halogen or hydroxy substituents
  (ii) amino optionally mono or disubstituted with a substituent independently selected from the group consisting of
    (a) $C_{1-8}$alkyl,
    (b) heterocyclyl optionally substituted with one or two $C_{1-8}$alkyl substituents, and
    (c) heterocyclyl-$C_{1-8}$alkyl optionally substituted on heterocyclyl with one or two $C_{1-8}$alkyl substituents, and
  (iii) hydroxy,
  (iv) halogen, and
  (v) $C_{1-8}$alkoxy-carbonyl,
(2) amino optionally mono or disubstituted with a substituent independently selected from the group consisting of
  (i) $C_{1-8}$alkyl,
  (ii) heterocyclyl optionally substituted with one or two $C_{1-8}$alkyl substituents, and
  (iii) heterocyclyl-$C_{1-8}$alkyl optionally substituted on heterocyclyl with one or two $C_{1-8}$alkyl substituents,
(3) cyano,
(4) halogen,
(5) hydroxy,
(6) heteroaryl,
(7) heterocyclyl, and
(8) $C_{1-8}$alkoxy-carbonyl.

An example of a compound of Formula (I) includes a compound and pharmaceutically acceptable forms thereof, wherein $Ar^2$ is selected from the group consisting of aryl, heteroaryl, benzofused heteroaryl, heterocyclyl and benzofused heterocyclyl, each optionally substituted with one, two, three, four or five substituents independently selected from the group consisting of
(1) $C_{1-8}$alkyl,
(2) $C_{2-8}$alkynyl,
(3) $C_{1-8}$alkoxy,
  wherein each (1) and (3) is optionally substituted with one, two or three substituents independently selected from the group consisting of aryl, heteroaryl and heterocyclyl, wherein aryl is optionally substituted with one, two, three, four or five substituents independently selected from the group consisting of
    (i) $C_{1-8}$alkyl,
    (ii) $C_{1-8}$alkoxy,
    (iii) amino optionally mono or disubstituted with $C_{1-8}$alkyl,
    (iv) cyano,
    (v) halogen, and
    (vi) hydroxy,
  (4) NH, NHC(O), S, S(O), $SO_2$ or O substituted with a substituent selected from the group consisting of aryl, heteroaryl and aryl-$C_{1-8}$alkyl, each optionally substituted on aryl, and heteroaryl with one, two, three, four or five substituents independently selected from the group consisting of
    (i) $C_{1-8}$alkyl,
    (ii) $C_{1-8}$alkoxy,
    (iii) amino optionally mono or disubstituted with $C_{1-8}$alkyl, and
    (iv) halogen,
  (5) C(O) substituted with a substituent independently selected from the group consisting of
    (i) hydrogen,
    (ii) $C_{1-8}$alkyl,
    (iii) $C_{1-8}$alkoxy, and
    (iv) hydroxy,
  (6) cyano,
  (7) halogen,
  (8) hydroxy,
  (9) nitro,
  (10) $C_{3-8}$cycloalkyl,
  (11) aryl optionally substituted with one, two, three, four or five substituents independently selected from the group consisting of
    (i) $C_{1-8}$alkyl,
    (ii) cyano,
    (iii) halogen,
    (iv) hydroxy, and
    (v) nitro,
  (12) heteroaryl,
  (13) benzofused heteroaryl,
  (14) heterocyclyl, and
  (15) benzofused heterocyclyl.

An example of a compound of Formula (I) includes a compound and pharmaceutically acceptable forms thereof, wherein $Ar^2$ is selected from the group consisting of aryl, heteroaryl, benzofused heteroaryl and benzofused heterocyclyl, each optionally substituted with one, two, three or four substituents independently selected from the group consisting of
(1) $C_{1-8}$alkyl,
(2) $C_{2-8}$alkynyl,
(3) $C_{1-8}$alkoxy,
  wherein each (1) and (3) is optionally substituted with one substituent selected from the group consisting of aryl, heteroaryl and heterocyclyl, wherein aryl is optionally substituted with halogen,
  (4) NHC(O), S, S(O) or O substituted with a substituent selected from the group consisting of aryl, heteroaryl and aryl-$C_{1-8}$alkyl, each optionally substituted on aryl and heteroaryl
(5) halogen,
(6) aryl optionally substituted with $C_{1-8}$alkyl or halogen, and
(7) heterocyclyl.

An example of a compound of Formula (I) includes a compound and pharmaceutically acceptable forms thereof, wherein
$L^1$ is selected from the group consisting of hydrogen, —N($R_1R_2$), —C(O)N($R_1R_2$), —C(O)O($R_1$), $NO_2$, —($CH_2$)$_p$—$Ar^1$, —C(O)—($CH_2$)$_p$—$Ar^1$, —N($R_1$)C(O)—($CH_2$)$_p$—$Ar^1$ and —C(O)N($R_1$)—($CH_2$)$_p$—$Ar^1$;

R₁ is selected from the group consisting of hydrogen, $C_{1-8}$alkyl and $C_{1-8}$alkoxy-$C_{1-8}$alkyl;

R₂ is selected from the group consisting of hydrogen, $C_{1-8}$alkyl, hydroxy-$C_{1-8}$alkyl, amino-$C_{1-8}$alkyl, $C_{1-8}$alkyl-amino-$C_{1-8}$alkyl and $C_{1-8}$alkoxy-carbonyl-amino-$C_{1-8}$alkyl;

p is 0, 1, 2 or 3;

L² is selected from the group consisting of —($C_{1-8}$alkyl)- and a bond;

Ar¹ is selected from the group consisting of aryl, heteroaryl and heterocyclyl, each optionally substituted with one, two, three, four or five substituents independently selected from the group consisting of (1) $C_{1-8}$alkyl, $C_{2-8}$alkenyl and $C_{1-8}$alkoxy, each optionally substituted with one, two or three substituents independently selected from the group consisting of
 (i) heterocyclyl optionally substituted with one, two or three $C_{1-8}$alkyl, $C_{1-8}$alkoxy, hydroxy-$C_{1-8}$alkyl, amino, $C_{1-8}$alkyl-amino, $C_{1-8}$alkoxy-carbonyl-amino, halogen or hydroxy substituents
 (ii) amino optionally mono or disubstituted with a substituent independently selected from the group consisting of
  (a) $C_{1-8}$alkyl,
  (b) heterocyclyl optionally substituted with one or two $C_{1-8}$alkyl substituents, and
  (c) heterocyclyl-$C_{1-8}$alkyl optionally substituted on heterocyclyl with one or two $C_{1-8}$alkyl substituents, and
 (iii) hydroxy,
 (iv) halogen, and
 (v) $C_{1-8}$alkoxy-carbonyl,
(2) amino optionally mono or disubstituted with a substituent independently selected from the group consisting of
 (i) $C_{1-8}$alkyl,
 (ii) heterocyclyl optionally substituted with one or two $C_{1-8}$alkyl substituents, and
 (iii) heterocyclyl-$C_{1-8}$alkyl optionally substituted on heterocyclyl with one or two $C_{1-8}$alkyl substituents,
(3) cyano,
(4) halogen,
(5) hydroxy,
(6) heteroaryl,
(7) heterocyclyl, and
(8) $C_{1-8}$alkoxy-carbonyl; and Ar² is selected from the group consisting of aryl, heteroaryl, benzofused heteroaryl and benzofused heterocyclyl, each optionally substituted with one, two, three or four substituents independently selected from the group consisting of (1) $C_{1-8}$alkyl,
(2) $C_{2-8}$alkynyl,
(3) $C_{1-8}$alkoxy,
 wherein each (1) and (3) is optionally substituted with one substituent selected from the group consisting of aryl, heteroaryl and heterocyclyl, wherein aryl is optionally substituted with halogen,
(4) NHC(O), S, S(O) or O substituted with a substituent selected from the group consisting of aryl, heteroaryl and aryl-$C_{1-8}$alkyl, each optionally substituted on aryl and heteroaryl with $C_{1-8}$alkyl or halogen,
(5) halogen,
(6) aryl optionally substituted with $C_{1-8}$alkyl or halogen, and
(7) heterocyclyl.

An example of a compound of Formula (I) includes a compound of Formula (Ia)

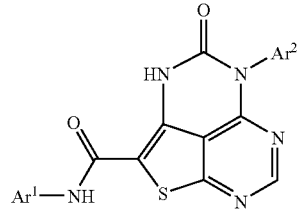

Formula (Ia)

and pharmaceutically acceptable forms thereof, wherein Ar¹ and Ar² are dependently selected from:

| Cpd | Ar¹ | Ar² |
|---|---|---|
| 2 | 3,4-(OCH₃)₂-phenyl | 3-Cl-4-F-phenyl |
| 3 | 4-(CH₂-piperidin-1-yl)phenyl | 3-Cl-4-F-phenyl |
| 4 | thiazol-2-yl | 3-Cl-4-F-phenyl |
| 5 | pyridin-3-yl | 3-Cl-4-F-phenyl |
| 6 | 6-[NH(CH₂)₃-morpholin-4-yl]pyridin-3-yl | 3-Cl-4-F-phenyl |
| 7 | 4-(CH₂-pyrrolidin-1-yl)phenyl | 3-Cl-4-F-phenyl |
| 11 | 4-OCH₃-3-OH-phenyl | 3-Cl-4-F-phenyl |
| 12 | 4-CH₂N(CH₃)₂-phenyl | 3-Cl-4-F-phenyl |
| 13 | 4-(CH₂-morpholin-4-yl)phenyl | 3-Cl-4-F-phenyl |
| 14 | 4-[CH₂-(4-CH₃-piperazin-1-yl)]phenyl | 3-Cl-4-F-phenyl |
| 15 | 4-(CH₂-pyrrolidin-1-yl)phenyl | 3-(C≡CH)-phenyl |
| 16 | 4-(CH₂-morpholin-4-yl)phenyl | 2-Cl-4-F-phenyl |
| 17 | 4-(CH₂NHCH₂-(2R)-tetrahydro-furan-2-yl)phenyl | 3-Cl-4-F-phenyl |
| 18 | 6-CN-pyridin-3-yl | 3-Cl-4-F-phenyl |
| 19 | 4-OH-3-OCH₃-phenyl | 3-Cl-4-F-phenyl |
| 20 | 3-OCH₃-4-[O(CH₂)₂-morpholin-4-yl]phenyl | 3-Cl-4-F-phenyl |
| 21 | 3-OCH₃-4-[O(CH₂)₃-piperidin-1-yl]phenyl | 3-Cl-4-F-phenyl |
| 22 | 3-OCH₃-4-[O(CH₂)₂-piperidin-1-yl]phenyl | 3-Cl-4-F-phenyl |
| 23 | 6-CH₂NH₂-pyridin-3-yl | 3-Cl-4-F-phenyl |
| 24 | 4-(CH₂NH-piperidin-4-yl)phenyl | 3-(C≡CH)-phenyl |
| 25 | 4-(CH₂-piperidin-1-yl)phenyl | 2,4-Cl₂-phenyl |
| 26 | 4-(CH₂-piperidin-1-yl)phenyl | 2-Cl-3,4,5-(OCH₃)₃-phenyl |
| 27 | 3-OCH₃-4-[O(CH₂)₂-morpholin-4-yl]phenyl | 3,4,5-(OCH₃)₃-phenyl |
| 28 | 4-(CH₂-piperidin-1-yl)phenyl | 3,4,5-(OCH₃)₃-phenyl |
| 29 | 4-(CH₂-morpholin-4-yl)phenyl | 2,4-Cl₂-phenyl |

-continued

| Cpd | Ar¹ | Ar² |
|---|---|---|
| 30 | 3-OCH₃-4-(OCH₂-tetrahydro-pyran-2-yl)phenyl | 2-Cl-3,4,5-(OCH₃)₃-phenyl |
| 31 | 3-OCH₃-4-(OCH₂-tetrahydro-pyran-2-yl)phenyl | 3,4,5-(OCH₃)₃-phenyl |
| 32 | 4-[OCH₂-(1-CH₃-piperidin-3-yl)]phenyl | 2,4-Cl₂-phenyl |
| 33 | 4-(CH₂-piperidin-1-yl)phenyl | 2,4-Cl₂-5-OCH₃-phenyl |
| 34 | 3-OCH₃-4-[O(CH₂)₂-morpholin-4-yl]phenyl | 2,4-Cl₂-5-OCH₃-phenyl |
| 35 | 3,4-(OCH₃)₂-phenyl | 2,4-Cl₂-5-OCH₃-phenyl |
| 36 | 4-(CH₂-morpholin-4-yl)phenyl | 3-Br-phenyl |
| 37 | 3,4-(OCH₃)₂-phenyl | 2-F-4-Br-phenyl |
| 39 | 3-OCH₃-4-[O(CH₂)₂-morpholin-4-yl]phenyl | 2-F-4-Br-phenyl |
| 43 | 4-(CH₂-pyrrolidin-1-yl)phenyl | 2,4-Cl₂-5-OCH₃-phenyl |
| 44 | 4-(CH₂-morpholin-4-yl)phenyl | 2,4-Cl₂-5-OCH₃-phenyl |
| 45 | 3-OCH₃-4-(OCH₂-tetrahydro-pyran-2-yl)phenyl | 2,4-Cl₂-5-OCH₃-phenyl |
| 48 | 3,4-(OCH₃)₂-phenyl | 3-Cl-4-(OCH₂-pyridin-2-yl)phenyl |
| 49 | 3,4-(OCH₃)₂-phenyl | 2-Cl-5-OCH₃-phenyl |
| 50 | 3-OCH₃-4-[O(CH₂)₂-morpholin-4-yl]phenyl | 2-Cl-5-OCH₃-phenyl |
| 51 | 4-(CH₂-morpholin-4-yl)phenyl | 2-Cl-5-OCH₃-phenyl |
| 52 | 4-(CH₂-morpholin-4-yl)phenyl | 3-Cl-4-(OCH₂-pyridin-2-yl)phenyl |
| 53 | 4-(CH₂-morpholin-4-yl)phenyl | 2-F-4-Br-phenyl |
| 55 | 4-(CH₂-pyrrolidin-1-yl)phenyl | 2,4-Cl₂-5-(3-F-benzyloxy)phenyl |
| 56 | 3-OCH₃-4-[O(CH₂)₂-piperidin-1-yl]phenyl | 2,4-Cl₂-5-(3-F-benzyloxy)phenyl |
| 57 | 4-(CH₂-piperidin-1-yl)phenyl | 2,4-Cl₂-5-(3-F-benzyloxy)phenyl |
| 59 | 4-[CH₂N(CH₃)CH₂-(2R)-tetrahydro-furan-2-yl]phenyl | 2,4-Cl₂-5-(3-F-benzyloxy)phenyl |
| 60 | 4-[CH₂-(4-CH₃-piperazin-1-yl)]phenyl | 2,4-Cl₂-5-OCH₃-phenyl |
| 61 | 4-[CH₂-(4-CH₃-piperazin-1-yl)]phenyl | 2,4-Cl₂-5-(3-F-benzyloxy)phenyl |
| 62 | 4-(CH₂-morpholin-4-yl)phenyl | 5-Cl-benzo[1,3]dioxol-4-yl |
| 63 | 3-OCH₃-4-[O(CH₂)₂-piperidin-1-yl]phenyl | 3-Br-phenyl |
| 64 | 6-[NH(CH₂)₃-morpholin-4-yl]pyridin-3-yl | 3-Br-phenyl |
| 65 | 4-(CH₂-morpholin-4-yl)phenyl | 2-F-4-OCH₃-phenyl |
| 66 | 4-(CH₂-piperidin-1-yl)phenyl | 2-F-4-OCH₃-phenyl |
| 67 | 3-OCH₃-4-[O(CH₂)₂-morpholin-4-yl]phenyl | 2-F-4-OCH₃-phenyl |
| 68 | 3-OCH₃-4-(OCH₂-tetrahydro-pyran-2-yl)phenyl | 2-F-4-OCH₃-phenyl |
| 69 | 3,4-(OCH₃)₂-phenyl | 2-F-4-OCH₃-phenyl |
| 70 | 4-[CH₂-(4-CH₃-piperazin-1-yl)]phenyl | 2-F-4-Br-phenyl |
| 71 | 6-[NH(CH₂)₃-morpholin-4-yl]pyridin-3-yl | 2-F-4-Br-phenyl |
| 72 | 4-(CH₂-piperidin-1-yl)phenyl | 2-OCH₃-5-Cl-phenyl |
| 73 | 3,4-(OCH₃)₂-phenyl | 2-OCH₃-5-Cl-phenyl |
| 74 | 3-OCH₃-4-[O(CH₂)₂-piperidin-1-yl]phenyl | 2-OCH₃-5-Cl-phenyl |
| 75 | 4-[CH₂N(CH₃)CH₂-(2R)-tetrahydro-furan-2-yl]phenyl | 2-OCH₃-5-Cl-phenyl |
| 76 | 4-(CH₂-morpholin-4-yl)phenyl | 2-(4-CH₃-phenyl)-5-C(CH₃)₃-2H-pyrazol-3-yl |
| 80 | 4-(CH₂-piperidin-1-yl)phenyl | 1-(3-F-benzyl)indazol-5-yl |
| 81 | 4-(CH₂-piperidin-1-yl)phenyl | 3-OCH₃-4-Br-phenyl |
| 82 | 3,4-(OCH₃)₂-phenyl | 3-OCH₃-4-Br-phenyl |
| 84 | 4-(CH₂-morpholin-4-yl)phenyl | 3-OCH₃-4-Br-phenyl |
| 85 | 4-[CH₂-(4-CH₃-piperazin-1-yl)]phenyl | 3-OCH₃-4-Br-phenyl |
| 86 | 3-OCH₃-4-[O(CH₂)₂-morpholin-4-yl]phenyl | 3-Cl-4-(OCH₂-pyridin-2-yl)phenyl |
| 87 | 4-(CH₂-piperidin-1-yl)phenyl | 1-(3-F-benzyl)indol-5-yl |
| 88 | 3-OCH₃-4-[O(CH₂)₂-piperidin-1-yl]phenyl | 2-Cl-5-OCH₃-phenyl |
| 89 | 4-(CH₂-piperidin-1-yl)phenyl | 3-Cl-4-(OCH₂-pyridin-2-yl)phenyl |
| 90 | 4-[CH₂-(4-CH₃-piperazin-1-yl)]phenyl | 3-Cl-4-(OCH₂-pyridin-2-yl)phenyl |
| 91 | 1-CO₂C(CH₃)₃-piperidin-4-yl | 1-(3-F-benzyl)indol-5-yl |
| 92 | 1-CH₃-piperidin-4-yl | 1-(3-F-benzyl)indol-5-yl |
| 94 | 4-(morpholin-4-yl)phenyl | 1-(3-F-benzyl)indol-5-yl |
| 96 | 4-(CH₂-piperidin-1-yl)phenyl | 4-phenoxy-phenyl |
| 97 | 4-(CH₂-morpholin-4-yl)phenyl | 4-phenoxy-phenyl |
| 98 | 4-[CH₂-(4-CH₃-piperazin-1-yl)]phenyl | 4-phenoxy-phenyl |
| 99 | 3,4-(OCH₃)₂-phenyl | 4-phenoxy-phenyl |
| 100 | 3-OCH₃-4-[O(CH₂)₂-piperidin-1-yl]phenyl | 4-phenoxy-phenyl |

-continued

| Cpd | Ar¹ | Ar² |
|---|---|---|
| 104 | 4-(CH₂-morpholin-4-yl)phenyl | 2,6-Cl₂-phenyl |
| 108 | 4-(CH₂-morpholin-4-yl)phenyl | 3-Br-4-CH₃-phenyl |
| 109 | 4-(CH₂-morpholin-4-yl)phenyl | 2-CH₃-5-Br-phenyl |
| 110 | 4-(CH₂-morpholin-4-yl)phenyl | 4-(4-F-phenoxy)phenyl |
| 111 | 4-(CH₂-piperidin-1-yl)phenyl | 3-Br-4-CH₃-phenyl |
| 113 | 4-(CH₂-morpholin-4-yl)phenyl | 3-F-4-phenoxy-phenyl |
| 114 | 4-[(CH₂)₂-piperidin-1-yl]phenyl | 3-F-4-phenoxy-phenyl |
| 115 | 4-[CH₂-(4-CH₃-piperazin-1-yl)]phenyl | 3-F-4-phenoxy-phenyl |
| 116 | 1-CH₃-piperidin-4-yl | 3-Br-4-CH₃-phenyl |
| 117 | 1-CH₃-piperidin-4-yl | 2-CH₃-5-Br-phenyl |
| 118 | 1-CH₃-piperidin-4-yl | 4-(4-F-phenoxy)phenyl |
| 119 | 4-(CH₂-morpholin-4-yl)phenyl | 3-CH₃-4-(6-CH₃-pyridin-3-yloxy)phenyl |
| 120 | 4-[(CH₂)₂-piperidin-1-yl]phenyl | 3-Cl-4-OCH₃-phenyl |
| 121 | 4-(CH₂-piperidin-1-yl)phenyl | 3-Cl-4-OCH₃-phenyl |
| 122 | 4-(CH₂-morpholin-4-yl)phenyl | 3-Cl-4-OCH₃-phenyl |
| 123 | 4-(CH₂-morpholin-4-yl)phenyl | 4-morpholin-4-yl-phenyl |
| 124 | 4-(CH₂-piperidin-1-yl)phenyl | 4-morpholin-4-yl-phenyl |
| 125 | 4-(morpholin-4-yl)phenyl | 4-morpholin-4-yl-phenyl |
| 126 | 1-CO₂C(CH₃)₃-piperidin-4-yl | 4-morpholin-4-yl-phenyl |
| 129 | 4-(CH₂-morpholin-4-yl)phenyl | 3-Cl-4-(6-CH₃-pyridin-3-yloxy)phenyl |
| 130 | phenyl | 3-Br-phenyl |
| 131 | 4-(CH₂-piperidin-1-yl)phenyl | 4-(3-F-phenoxy)phenyl |
| 132 | 4-[(CH₂)₂-piperidin-1-yl]phenyl | 4-(3-F-phenoxy)phenyl |
| 134 | 4-(CH₂-morpholin-4-yl)phenyl | 4-(3-F-phenoxy)phenyl |
| 135 | 4-(CH₂-piperidin-1-yl)phenyl | 3-Cl-4-phenoxy-phenyl |
| 136 | 4-[(CH₂)₂-piperidin-1-yl]phenyl | 3-Cl-4-phenoxy-phenyl |
| 138 | 4-(CH₂-morpholin-4-yl)phenyl | 3-Cl-4-phenoxy-phenyl |
| 139 | 4-(CH₂-piperidin-1-yl)phenyl | 4-(4-Cl-phenyl)phenyl |
| 140 | 4-(CH₂-morpholin-4-yl)phenyl | 4-(4-Cl-phenyl)phenyl |
| 143 | 4-(CH₂-morpholin-4-yl)phenyl | 1-(3-F-benzyl)indol-5-yl |
| 144 | 3-OCH₃-4-[O(CH₂)₂-piperidin-1-yl]phenyl | 2-Cl-4-F-phenyl |
| 145 | 4-(CH₂-piperidin-1-yl)phenyl | 2-Cl-4-F-phenyl |
| 146 | 4-(CH₂-morpholin-4-yl)phenyl | 2-Cl-6-CH₃-phenyl |
| 147 | 4-(CH₂-piperidin-1-yl)phenyl | 2-Cl-6-CH₃-phenyl |
| 148 | 4-[CH(OH)CH₂-morpholin-4-yl]phenyl | 2-Cl-6-CH₃-phenyl |
| 149 | 4-(CH₂-morpholin-4-yl)phenyl | 2-Cl-phenyl |
| 150 | 4-(CH₂-piperidin-1-yl)phenyl | 2-Cl-phenyl |
| 151 | 4-[CH₂-(4-CH₃-piperazin-1-yl)]phenyl | 2-Cl-phenyl |
| 153 | 4-(CH₂-morpholin-4-yl)phenyl | 3-Br-4-F-phenyl |
| 155 | 4-(CH₂-piperidin-1-yl)phenyl | 3-Br-4-F-phenyl |
| 160 | 4-(CH₂-piperidin-1-yl)phenyl | 3-Cl-4-(3-F-phenoxy)phenyl |
| 161 | 3-OCH₃-4-[O(CH₂)₂-piperidin-1-yl]phenyl | 3-Cl-4-(3-F-phenoxy)phenyl |
| 162 | 4-(CH₂-morpholin-4-yl)phenyl | 3-Cl-4-(3-F-phenoxy)phenyl |
| 163 | 3-OCH₃-4-[O(CH₂)₂-piperidin-1-yl]phenyl | 4-(benzyl)phenyl |
| 164 | 4-(CH₂-piperidin-1-yl)phenyl | 4-(benzyl)phenyl |
| 165 | 4-(CH₂-morpholin-4-yl)phenyl | 4-(benzyl)phenyl |
| 166 | 4-[(CH₂)₂-piperidin-1-yl]phenyl | 4-phenoxy-phenyl |
| 167 | 3-OCH₃-4-[O(CH₂)₂-morpholin-4-yl]phenyl | 4-phenoxy-phenyl |
| 169 | 4-(CH₂-piperidin-1-yl)phenyl | 4-(S-phenyl)phenyl |
| 174 | 4-[CH(OH)CH₂-morpholin-4-yl]phenyl | 4-phenoxy-phenyl |
| 175 | 4-(CH₂-morpholin-4-yl)phenyl | 1-(3-F-benzyl)indazol-5-yl |
| 176 | 3-OCH₃-4-(CH₂-morpholin-4-yl)phenyl | 4-phenoxy-phenyl |
| 177 | 1-CH₃-piperidin-4-yl | 1-(3-F-benzyl)indazol-5-yl |
| 178 | 4-(CH₂-morpholin-4-yl)phenyl | 4-(S-phenyl)phenyl |
| 180 | 4-(CH₂-morpholin-4-yl)phenyl | 3-Br-4-(OCH₂-pyridin-2-yl)phenyl |
| 181 | 4-(CH₂-morpholin-4-yl)phenyl | 3-Br-4-OCH₃-phenyl |
| 182 | 4-(CH₂-piperidin-1-yl)phenyl | 3-Br-4-OCH₃-phenyl |
| 183 | 3-OCH₃-4-(CH₂-morpholin-4-yl)phenyl | 3-Br-4-OCH₃-phenyl |
| 184 | 3-OCH₃-4-(CH₂-morpholin-4-yl)phenyl | 3-Br-phenyl |
| 187 | 4-(CH₂-morpholin-4-yl)phenyl | 3-Br-4-phenoxy-phenyl |
| 188 | 4-(CH₂-piperidin-1-yl)phenyl | 3-Br-4-phenoxy-phenyl |
| 189 | 3-OCH₃-4-(CH₂-morpholin-4-yl)phenyl | 3-Br-4-phenoxy-phenyl |
| 191 | 1-CH₃-piperidin-4-yl | 4-(S-phenyl)phenyl |
| 192 | 4-(CH₂-piperidin-1-yl)phenyl | 2-(3-F-benzyl)-3H-benzoimidazol-5-yl |
| 193 | 4-(CH₂-morpholin-4-yl)phenyl | 2-(3-F-benzyl)-3H-benzoimidazol-5-yl |
| 194 | 1-CH₃-piperidin-4-yl | 2-(3-F-benzyl)-3H-benzoimidazol-5-yl |
| 195 | 4-(CH₂-piperidin-1-yl)phenyl | 4-Br-phenyl |
| 196 | 4-(CH₂-morpholin-4-yl)phenyl | 4-Br-phenyl |
| 197 | 4-(CH₂-piperidin-1-yl)phenyl | 3-phenoxy-phenyl |
| 199 | 4-[CH₂-(1-CH₃-piperazin-4-yl)]phenyl | 3-phenoxy-phenyl |

-continued

| Cpd | Ar¹ | Ar² |
|---|---|---|
| 200 | 3-OCH₃-4-(CH₂-morpholin-4-yl)phenyl | 3-phenoxy-phenyl |
| 201 | 3-OCH₃-4-(CH₂-morpholin-4-yl)phenyl | 4-Br-phenyl |
| 203 | 3-F-4-(CH₂-morpholin-4-yl)phenyl | 4-phenoxy-phenyl |
| 204 | 4-(tetrazol-2-yl)phenyl | 4-phenoxy-phenyl |
| 205 | 4-(CH₂-piperidin-1-yl)phenyl | 4-[S(O)-phenyl]phenyl |
| 206 | 4-[CH=CHC(O)OCH₂CH₃]phenyl | 2-(3-F-benzyl)-3H-benzoimidazol-5-yl |
| 207 | 3-OCH₂CH₃-4-(CH₂-morpholin-4-yl)phenyl | 4-phenoxy-phenyl |
| 208 | 4-(CH₂-morpholin-4-yl)phenyl | 3-Cl-4-(pyridin-3-yloxy)phenyl |
| 209 | 4-(CH₂-piperidin-1-yl)phenyl | 3-Cl-4-(pyridin-3-yloxy)phenyl |
| 211 | 1-CH₃-piperidin-4-yl | 4-phenoxy-phenyl |
| 215 | 4-CH₃-piperazin-1-yl | 4-phenoxy-phenyl |
| 218 | 4-[CH₂-(1-CH₃-piperazin-4-yl)]phenyl | 4-(S-phenyl)phenyl |
| 219 | 3-OCH₃-4-(CH₂-morpholin-4-yl)phenyl | 4-(S-phenyl)phenyl |
| 220 | 3-(CH₂-morpholin-4-yl)phenyl | 4-phenoxy-phenyl |
| 221 | 3-Cl-4-(CH₂-morpholin-4-yl)phenyl | 4-phenoxy-phenyl |
| 224 | 3-OCH₃-4-(CH₂-piperidin-1-yl)phenyl | 4-(S-phenyl)phenyl |
| 226 | 4-(CH₂-morpholin-4-yl)phenyl | 3-Cl-4-(OCH₂-thien-2-yl)phenyl |
| 227 | 4-(CH₂-piperidin-1-yl)phenyl | 3-Cl-4-(OCH₂-thien-2-yl)phenyl |
| 228 | 3-OCH₃-4-(CH₂-piperidin-1-yl)phenyl | 3-Cl-4-(OCH₂-thien-2-yl)phenyl |
| 229 | 3-OCH₃-4-(CH₂-morpholin-4-yl)phenyl | 3-Cl-4-(OCH₂-thien-2-yl)phenyl |
| 230 | 1-CH₃-piperidin-4-yl | 3-Cl-4-(OCH₂-thien-2-yl)phenyl |
| 231 | 3-CF₃-4-(CH₂-morpholin-4-yl)phenyl | 4-phenoxy-phenyl |
| 232 | 3-CH₃-4-(CH₂-morpholin-4-yl)phenyl | 4-phenoxy-phenyl |
| 233 | 4-[CH₂-(4-OH-piperidin-1-yl)]phenyl | 4-phenoxy-phenyl |
| 234 | 4-[CH₂-(3-F-piperidin-1-yl)]phenyl | 4-phenoxy-phenyl |
| 236 | 3-OCH₃-4-(CH₂-morpholin-4-yl)phenyl | 4-(pyridin-3-yloxy)phenyl |
| 237 | 4-(CH₂-morpholin-4-yl)phenyl | 4-(pyridin-3-yloxy)phenyl |
| 238 | 4-(CH₂-piperidin-1-yl)phenyl | 4-(pyridin-3-yloxy)phenyl |
| 239 | 3-OCF₃-4-(CH₂-morpholin-1-yl)phenyl | 4-phenoxy-phenyl |
| 240 | 4-{CH₂-[2,6-cis-(CH₃)₂-morpholin-4-yl]}phenyl | 4-phenoxy-phenyl |
| 242 | 3-OCH₃-4-(CH₂-piperidin-1-yl)phenyl | 4-phenoxy-phenyl |
| 243 | 3-OCH₃-4-(CH₂-piperidin-1-yl)phenyl | 3-Cl-4-(OCH₂-furan-2-yl)phenyl |
| 244 | 4-(CH₂-piperidin-1-yl)phenyl | 3-Cl-4-(OCH₂-furan-2-yl)phenyl |
| 245 | 4-(CH₂-morpholin-4-yl)phenyl | 3-Cl-4-(OCH₂-furan-2-yl)phenyl |
| 246 | 3-OCH₃-4-(CH₂-morpholin-1-yl)phenyl | 3-Cl-4-(OCH₂-furan-2-yl)phenyl |
| 247 | 1-CH₃-piperidin-4-yl | 3-Cl-4-(OCH₂-furan-2-yl)phenyl |
| 248 | 4-(CH₂-morpholin-4-yl)phenyl | 4-[NHC(O)-phenyl]phenyl |
| 249 | 4-(CH₂-piperidin-1-yl)phenyl | 4-[NHC(O)-phenyl]phenyl |
| 250 | 4-[CH₂-(4-F-piperidin-1-yl)]phenyl | 4-phenoxy-phenyl |
| 251 | 4-[(CH₂)₂-piperidin-1-yl]phenyl | benzofuran-7-yl |
| 252 | 4-[CH₂-(1-CH₃-piperazin-4-yl)]phenyl | 3-Cl-4-(3-F-benzyloxy)phenyl |
| 253 | 4-{CH₂-[3,5-(CH₃)₂-morpholin-4-yl]}phenyl | 4-phenoxy-phenyl |
| 254 | 4-[CH₂-(4-CH₂OH-piperidin-1-yl)]phenyl | 4-phenoxy-phenyl |
| 255 | 4-[CH₂-(4-CH₃-piperidin-1-yl)]phenyl | 4-phenoxy-phenyl |
| 256 | 4-[CH₂-(3-CH₂OH-piperidin-1-yl)]phenyl | 4-phenoxy-phenyl |
| 257 | 3-N(CH₃)₂-4-(CH₂-morpholin-4-yl)phenyl | 4-phenoxy-phenyl |
| 258 | 4-{CH₂-[4-NHC(O)OC(CH₃)₃-piperidin-1-yl]}phenyl | 4-phenoxy-phenyl |
| 259 | 4-[CH₂-(4-NH₂-piperidin-1-yl)]phenyl | 4-phenoxy-phenyl |
| 260 | 4-{CH₂-[4-N(CH₃)₂-piperidin-1-yl]}phenyl | 4-phenoxy-phenyl |
| 261 | 4-[CH₂-(4-OCH₃-piperidin-1-yl)]phenyl | 4-phenoxy-phenyl |
| 262 | 3-OH-4-(CH₂-morpholin-4-yl)phenyl | 4-phenoxy-phenyl |
| 263 | 4-{CH₂-[4,4-(CH₃)₂-piperidin-1-yl]}phenyl | 4-phenoxy-phenyl |

An example of a compound of Formula (Ia) includes a compound and pharmaceutically acceptable forms thereof, wherein Ar¹ is selected from 3,4-(OCH₃)₂-phenyl, 4-(CH₂-piperidin-1-yl)phenyl, thiazol-2-yl, pyridin-3-yl, 6-[NH(CH₂)₃-morpholin-4-yl]pyridin-3-yl, 4-(CH₂-pyrrolidin-1-yl)phenyl, 4-OCH₃-3-OH-phenyl, 4-CH₂N(CH₃)₂-phenyl, 4-(CH₂-morpholin-4-yl)phenyl, 4-[CH₂-(4-CH₃-piperazin-1-yl)]phenyl, 4-(CH₂NHCH₂-(2R)-tetrahydro-furan-2-yl)phenyl, 6-CN-pyridin-3-yl, 4-OH-3-OCH₃-phenyl, 3-OCH₃-4-[O(CH₂)₂-morpholin-4-yl]phenyl, 3-OCH₃-4-[O(CH₂)₃-piperidin-1-yl]phenyl, 3-OCH₃-4-[O(CH₂)₂-piperidin-1-yl]phenyl, 6-CH₂NH₂-pyridin-3-yl, 4-(CH₂NH-piperidin-4-yl)phenyl, 3-OCH₃-4-(OCH₂-tetrahydro-pyran-2-yl)phenyl, 4-[OCH₂-(1-CH₃-piperidin-3-yl)]phenyl, 4-[CH₂N(CH₃)CH₂-(2R)-tetrahydro-furan-2-yl]phenyl, 1-CO₂C(CH₃)₃-piperidin-4-yl, 1-CH₃-piperidin-4-yl, 4-(morpholin-4-yl)phenyl, 4-[(CH₂)₂-piperidin-1-yl]phenyl, phenyl, 4-[CH(OH)CH₂-morpholin-4-yl]phenyl, 3-OCH₃-4-(CH₂-morpholin-4-yl)phenyl, 4-[CH₂-(1-CH₃-piperazin-4-yl)]phenyl, 3-F-4-(CH₂-morpholin-4-yl)phenyl, 4-(tetrazol-2-yl)phenyl, 4-[CH=CHC(O)OCH₂CH₃]phenyl, 3-OCH₂CH₃-4-(CH₂-morpholin-4-yl)phenyl, 4-CH₃-piperazin-1-yl, 3-(CH₂-morpholin-4-yl)phenyl, 3-Cl-4-(CH₂-morpholin-4-yl)phenyl, 3-OCH₃-4-(CH₂-piperidin-1-yl)phenyl, 3-CF₃-4-(CH₂-morpholin-4-yl)phenyl, 3-CH₃-4-(CH₂-morpholin-4-yl)phenyl, 4-[CH₂-(4-OH-piperidin-1-yl)]phenyl, 4-[CH₂-(3-F-piperidin-1-yl)]phenyl, 3-OCF₃-4-(CH₂-morpholin-1-yl)phenyl, 4-{CH₂-[2,6-Cls-(CH₃)₂-morpholin-4-yl]}phenyl, 3-OCH₃-4-(CH₂-morpholin-1-yl)phenyl, 4-[CH₂-(4-F-piperidin-1-yl)]phenyl, 4-{CH₂-[3,5-(CH₃)₂-morpholin-4-yl]}phenyl, 4-[CH₂-(4-CH₂OH-piperidin-1-yl)]phenyl, 4-[CH₂-(4-CH₃-piperidin-1-yl)]phenyl, 4-[CH₂-(3-CH₂OH-piperidin-1-yl)]phenyl, 3-N(CH₃)₂-4-(CH₂-morpholin-4-yl)phenyl, 4-{CH₂-[4-NHC(O)OC(CH₃)₃-piperidin-1-yl]}phenyl, 4-[CH₂-(4-NH₂-piperidin-1-yl)]phenyl, 4-{CH₂-[4-N(CH₃)₂-piperidin-1-yl]}phenyl, 4-[CH₂-(4-OCH₃-piperidin-1-yl)]phenyl, 3-OH-4-(CH₂-morpholin-4-yl)phenyl or 4-{CH₂-[4,4-(CH₃)₂-piperidin-1-yl]}phenyl; and Ar² is selected from 3-Cl-4-F-phenyl, 3-(C≡CH)-phenyl, 2-Cl-4-F-phenyl, 2,4-Cl₂-phenyl, 2-Cl-3,4,5-(OCH₃)₃-phenyl, 3,4,5-(OCH₃)₃-phenyl, 2,4-Cl₂-5-OCH₃-phenyl, 3-Br-phenyl, 2-F-4-Br-phenyl, 3-Cl-4-(OCH₂-pyridin-2-yl)phenyl, 2-Cl-5-OCH₃-phenyl, 2,4-Cl₂-5-(3-F-benzyloxy)phenyl, 5-Cl-benzo[1,3]dioxol-4-yl, 2-F-4-OCH₃-phenyl, 2-OCH₃-5-Cl-phenyl, 2-(4-CH₃-phenyl)-5-C(CH₃)₃-2H-pyrazol-3-yl, 1-(3-F-benzyl)indazol-5-yl, 3-OCH₃-4-Br-phenyl, 1-(3-F-benzyl)indol-5-yl, 4-phenoxy-phenyl, 2,6-Cl₂-phenyl, 3-Br-4-CH₃-phenyl, 2-CH₃-5-Br-phenyl, 4-(4-F-phenoxy)phenyl, 3-F-4-phenoxy-phenyl, 3-CH₃-4-(6-CH₃-pyridin-3-yloxy)phenyl, 3-Cl-4-OCH₃-phenyl, 4-morpholin-4-yl-phenyl, 3-Cl-4-(6-CH₃-pyridin-3-yloxy)phenyl, 4-(3-F-phenoxy)phenyl, 3-Cl-4-phenoxy-phenyl, 4-(4-Cl-phenyl)phenyl, 2-Cl-4-F-phenyl, 2-Cl-6-CH₃-phenyl, 2-Cl-phenyl, 3-Br-4-F-phenyl, 3-Cl-4-(3-F-phenoxy)phenyl, 4-(benzyl)phenyl, 4-(S-phenyl)phenyl, 3-Br-4-(OCH₂-pyridin-2-yl)phenyl, 3-Br-4-OCH₃-phenyl, 3-Br-4-phenoxy-phenyl, 2-(3-F-benzyl)-3H-benzoimidazol-5-yl, 4-Br-phenyl, 3-phenoxy-phenyl, 4-[S(O)-phenyl]phenyl, 3-Cl-4-(pyridin-3-yloxy)phenyl, 3-Cl-4-(OCH₂-thien-2-yl)phenyl, 4-(pyridin-3-yloxy)phenyl, 3-Cl-4-(OCH₂-furan-2-yl)phenyl, 4-[NHC(O)-phenyl]phenyl, benzofuran-7-yl or 3-Cl-4-(3-F-benzyloxy)phenyl.

An example of a compound of Formula (I) includes a compound of Formula (Ib)

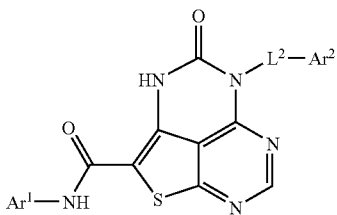

Formula (Ib)

and pharmaceutically acceptable forms thereof, wherein Ar¹, L² and Ar² are dependently selected from:

| Cpd | Ar¹ | L² | Ar² |
|---|---|---|---|
| 171 | 4-(CH₂-piperidin-1-yl)phenyl | CH(R—CH₃) | phenyl |
| 172 | 4-(CH₂-morpholin-4-yl)phenyl | CH(R—CH₃) | phenyl |
| 173 | 1-CH₃-piperidin-4-yl | CH(R—CH₃) | phenyl |

An example of a compound of Formula (Ib) includes a compound and pharmaceutically acceptable forms thereof, wherein Ar¹ is selected from 4-(CH₂-piperidin-1-yl)phenyl, 4-(CH₂-morpholin-4-yl)phenyl or 1-CH₃-piperidin-4-yl;

L² is CH(R—CH₃); and

Ar² is phenyl.

An example of a compound of Formula (I) includes a compound of Formula (Ic)

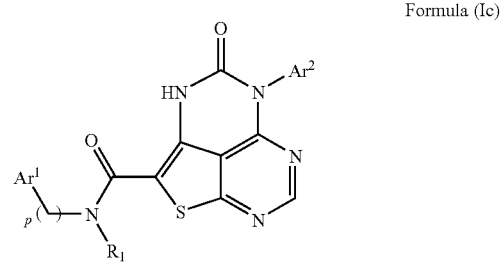

Formula (Ic)

and pharmaceutically acceptable forms thereof, wherein R₁, p, Ar¹ and Ar² are dependently selected from:

| Cpd | R₁ | p | Ar¹ | Ar² |
|---|---|---|---|---|
| 10 | (CH₂)₂OCH(CH₃)₂ | 1 | 4-NH₂-phenyl | 3-Cl-4-F-phenyl |
| 93 | H | 2 | morpholin-4-yl | 1-(3-F-benzyl)indol-5-yl |
| 95 | H | 3 | morpholin-4-yl | 1-(3-F-benzyl)indol-5-yl |
| 105 | H | 2 | morpholin-4-yl | 4-phenoxy-phenyl |
| 127 | H | 1 | furan-2-yl | 4-(morpholin-4-yl)phenyl |
| 128 | H | 1 | 2-F-phenyl | 4-(morpholin-4-yl)phenyl |
| 198 | CH₃ | 0 | 4-(CH₂-morpholin-4-yl)phenyl | 4-phenoxy-phenyl |
| 217 | H | 2 | pyridin-2-yl | 4-phenoxy-phenyl |

An example of a compound of Formula (Ic) includes a compound and pharmaceutically acceptable forms thereof, wherein R₁ is selected from hydrogen, CH₃ or (CH₂)₂OCH(CH₃)₂;

p is 0, 1, 2 or 3;

Ar¹ is selected from 4-NH₂-phenyl, morpholin-4-yl, furan-2-yl, 2-F-phenyl, 4-(CH₂-morpholin-4-yl)phenyl or pyridin-2-yl; and Ar² is selected from 3-Cl-4-F-phenyl, 1-(3-F-benzyl)indol-5-yl, 4-phenoxy-phenyl or 4-(morpholin-4-yl)phenyl.

An example of a compound of Formula (I) includes a compound of Formula (Id)

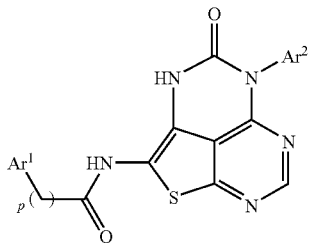

Formula (Id)

and pharmaceutically acceptable forms thereof, wherein $Ar^1$, p and $Ar^2$ are dependently selected from:

| Cpd | $Ar^1$ | p | $Ar^2$ |
|---|---|---|---|
| 158 | 3,4-$(OCH_3)_2$-phenyl | 1 | 3-Cl-4-F-phenyl |
| 159 | 3,4-$(OCH_3)_2$-phenyl | 0 | 3-Cl-4-F-phenyl |

An example of a compound of Formula (Id) includes a compound and pharmaceutically acceptable forms thereof, wherein $Ar^1$ is 3,4-$(OCH_3)_2$-phenyl; p is 0 or 1; and $Ar^2$ is 3-Cl-4-F-phenyl.

An example of a compound of Formula (I) includes a compound of Formula (Ie)

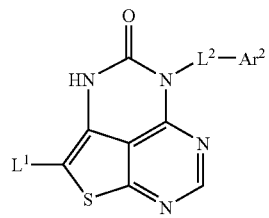

Formula (Ie)

and pharmaceutically acceptable forms thereof, wherein $L^1$, $L^2$ and $Ar^2$ are dependently selected from:

| Cpd | $L^1$ | $L^2$ | $Ar^2$ |
|---|---|---|---|
| 1 | $CO_2H$ | bond | 3-Cl-4-F-phenyl |
| 8 | phenyl | bond | 3-Cl-4-F-phenyl |
| 9 | 3,4-$(OCH_3)_2$-phenyl | bond | 3-Cl-4-F-phenyl |
| 38 | $CO_2H$ | bond | 3-Cl-4-$(OCH_2$-pyridin-2-yl)phenyl |
| 40 | $CO_2H$ | bond | 2-F-4-Br-phenyl |
| 41 | $CO_2H$ | bond | 2,4-$Cl_2$-5-$OCH_3$-phenyl |
| 42 | $CO_2H$ | bond | 3,4,5-$(OCH_3)_3$-phenyl |
| 46 | C(O)-pyrrolidin-1-yl | bond | 2,4-$Cl_2$-5-$OCH_3$-phenyl |
| 47 | $CO_2H$ | bond | 2-Cl-5-$OCH_3$-phenyl |
| 54 | $CO_2CH_3$ | bond | 5-Cl-benzo[1,3]dioxol-4-yl |
| 58 | $CO_2H$ | bond | 2,4-$Cl_2$-5-(3-F-benzyloxy)phenyl |
| 77 | $CO_2H$ | bond | 1-(3-F-benzyl)indol-5-yl |
| 78 | $CO_2CH_2CH_3$ | bond | 1-(3-F-benzyl)indazol-5-yl |
| 79 | $CO_2H$ | bond | 1-(3-F-benzyl)indazol-5-yl |
| 83 | $C(O)N(CH_3)_2$ | bond | 3-$OCH_3$-4-Br-phenyl |
| 101 | $CO_2CH_2CH_3$ | bond | 4-(4-F-phenoxy)phenyl |
| 102 | $CO_2CH_2CH_3$ | bond | 3-Br-4-$CH_3$-phenyl |
| 103 | $CO_2CH_2CH_3$ | bond | 2-$CH_3$-5-Br-phenyl |
| 106 | $C(O)NH(CH_2)_3OH$ | bond | 4-phenoxy-phenyl |
| 107 | $CO_2H$ | bond | 4-(morpholin-4-yl)phenyl |
| 112 | $CO_2H$ | bond | 3-F-4-phenoxy-phenyl |
| 133 | $C(O)NH(CH_2)_3OH$ | bond | 4-(3-F-phenoxy)phenyl |
| 137 | $C(O)NH(CH_2)_3OH$ | bond | 3-Cl-4-phenoxy-phenyl |
| 141 | $C(O)NH(CH_2)_3NH$—$CO_2C(CH_3)_2$ | bond | 1-(3-F-benzyl)indol-5-yl |
| 142 | $C(O)NH(CH_2)_3NH_2$ | bond | 1-(3-F-benzyl)indol-5-yl |
| 152 | H | bond | 1-(3-F-benzyl)indol-5-yl |
| 154 | $C(O)NH(CH_2)_3OH$ | bond | 3-Br-4-F-phenyl |
| 156 | $NO_2$ | bond | 3-Cl-4-F-phenyl |
| 157 | $NH_2$ | bond | 3-Cl-4-F-phenyl |
| 168 | $CO_2H$ | bond | 4-phenoxy-phenyl |
| 170 | $CO_2H$ | —CH(R—$CH_3$)— | phenyl |
| 179 | $CO_2CH_2CH_3$ | —CH(R—$CH_3$)— | 4-Br-phenyl |
| 185 | $CO_2CH_2CH_3$ | —$CH_2$— | 3-F-phenyl |
| 186 | $CO_2H$ | bond | 4-(S-phenyl)phenyl |
| 190 | $CO_2H$ | bond | 2-(3-F-benzyl)-3H-benzoimidazol-5-yl |
| 202 | C(O)-[3,4-$(OCH_3)_2$-phenyl] | bond | 4-phenoxy-phenyl |
| 210 | $CO_2CH_2CH_3$ | bond | 4-(S-phenyl)phenyl |
| 212 | $C(O)NH(CH_2)_3N(CH_3)_2$ | bond | 4-(S-phenyl)phenyl |
| 213 | C(O)-{4-[$(CH_2)_2$-morpholin-4-yl]-piperazin-1-yl} | bond | 4-phenoxy-phenyl |
| 214 | C(O)-(4-$CH_3$-[1,4]diazepan-1-yl) | bond | 4-phenoxy-phenyl |
| 216 | C(O)-(4-$CH_3$-piperazin-1-yl) | bond | 4-phenoxy-phenyl |

| Cpd | L¹ | L² | Ar² |
|---|---|---|---|
| 222 | CO₂CH₂CH₃ | bond | 3-Cl-4-(OCH₂-furan-2-yl)phenyl |
| 223 | CO₂CH₂CH₃ | bond | 3-Cl-4-(OCH₂-thien-2-yl)phenyl |
| 225 | CO₂H | bond | 3-Cl-4-(OCH₂-thien-2-yl)phenyl |
| 235 | CO₂H | bond | 3-Cl-4-(OCH₂-furan-2-yl)phenyl |
| 241 | CO₂CH₂CH₃ | bond | 4-[NHC(O)-phenyl]phenyl |
| 264 | CO₂H | bond | 2-Cl-4-F-phenyl |

An example of a compound of Formula (Ic) includes a compound and pharmaceutically acceptable forms thereof, wherein $L^1$ is selected from hydrogen, CO₂H, phenyl, 3,4-(OCH₃)₂-phenyl, C(O)-pyrrolidin-1-yl, CO₂CH₃, CO₂CH₂CH₃, C(O)N(CH₃)₂, C(O)NH(CH₂)₃OH, C(O)NH(CH₂)₃NH—CO₂C(CH₃)₃, NO₂, NH₂, C(O)-[3,4-(OCH₃)₂-phenyl], C(O)NH(CH₂)₃N(CH₃)₂, C(O)-{4-[(CH₂)₂-morpholin-4-yl]-piperazin-1-yl}, C(O)-(4-CH₃-[1,4]diazepan-1-yl) or C(O)-(4-CH₃-piperazin-1-yl);

$L^2$ is selected from a bond, —CH₂— or —CH(R—CH₃)—; and $Ar^2$ is selected from 3-Cl-4-F-phenyl, 3-Cl-4-(OCH₂-pyridin-2-yl)phenyl, 2-F-4-Br-phenyl, 2,4-Cl₂-5-OCH₃-phenyl, 3,4,5-(OCH₃)₃-phenyl, 2-Cl-5-OCH₃-phenyl, 5-Cl-benzo[1,3]dioxol-4-yl, 2,4-Cl₂-5-(3-F-benzyloxy)phenyl, 1-(3-F-benzyl)indol-5-yl, 1-(3-F-benzyl)indazol-5-yl, 3-OCH₃-4-Br-phenyl, 4-(4-F-phenoxy)phenyl, 3-Br-4-CH₃-phenyl, 2-CH₃-5-Br-phenyl, 4-phenoxy-phenyl, 4-(morpholin-4-yl)phenyl, 3-F-4-phenoxy-phenyl, 4-(3-F-phenoxy)phenyl, 3-C₁₋₄-phenoxy-phenyl, 3-Br-4-F-phenyl, phenyl, 4-Br-phenyl, 3-F-phenyl, 4-(S-phenyl)phenyl, 2-(3-F-benzyl)-3H-benzoimidazol-5-yl, 3-Cl-4-(OCH₂-furan-2-yl)phenyl, 3-Cl-4-(OCH₂-thien-2-yl)phenyl, 4-[NHC(O)-phenyl]phenyl or 2-Cl-4-F-phenyl.

Examples of a compound of Formula (I) include compounds selected from the group consisting of:

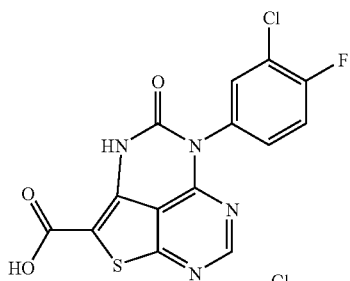

Cpd 1

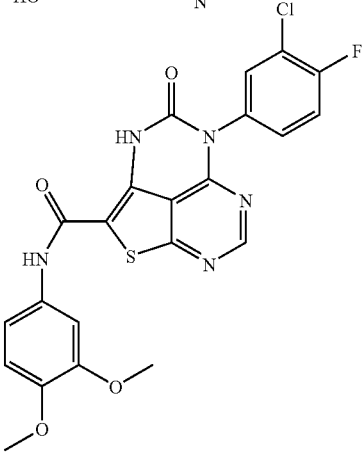

Cpd 2

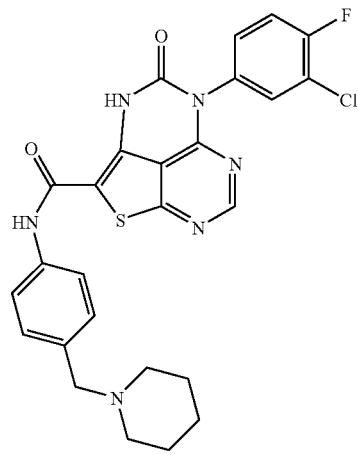

Cpd 3

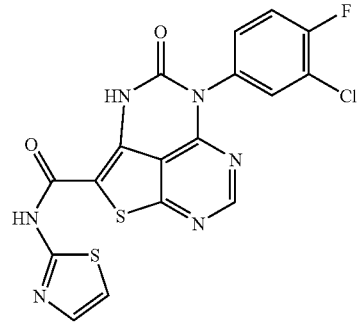

Cpd 4

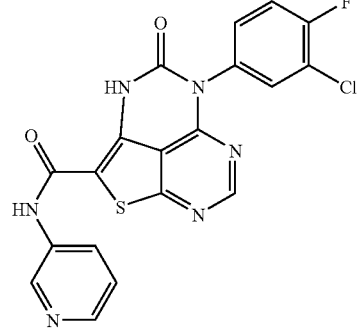

Cpd 5

-continued
Cpd 6
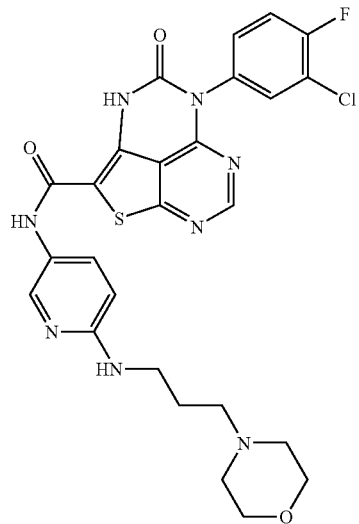
Cpd 7
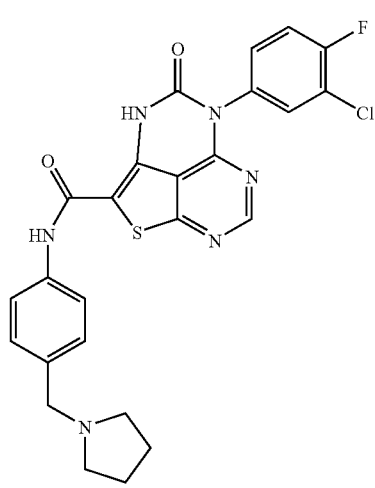
Cpd 8
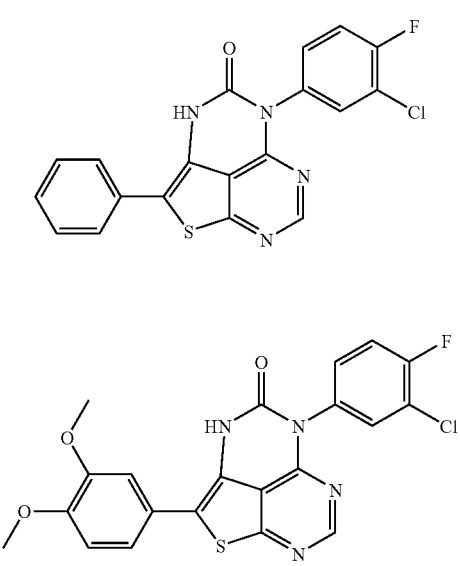
Cpd 9
-continued
Cpd 10
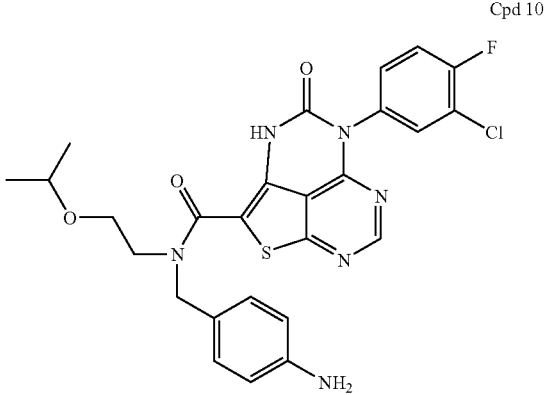
Cpd 11
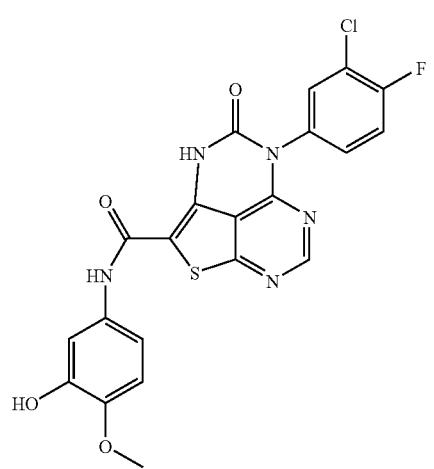
Cpd 12
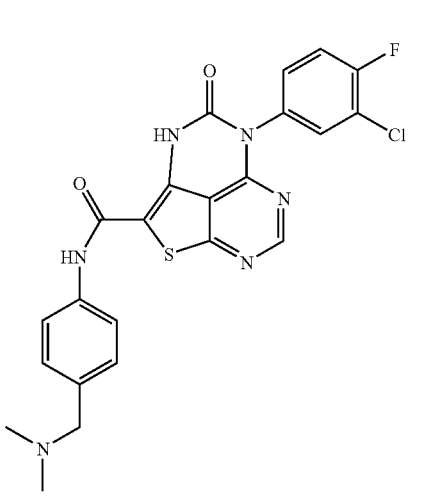

-continued
Cpd 13
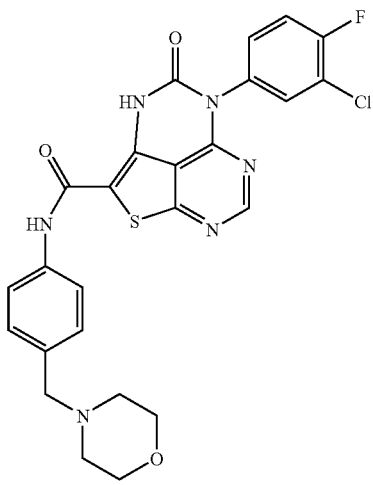
Cpd 14
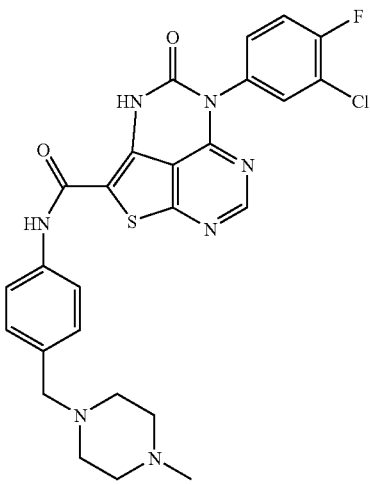
Cpd 15
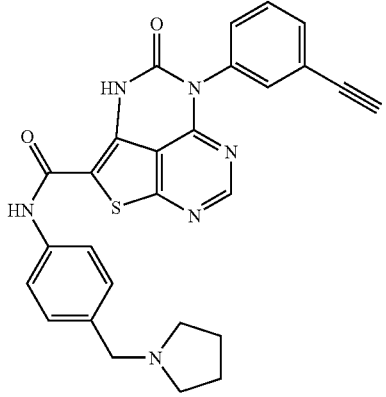
-continued
Cpd 16
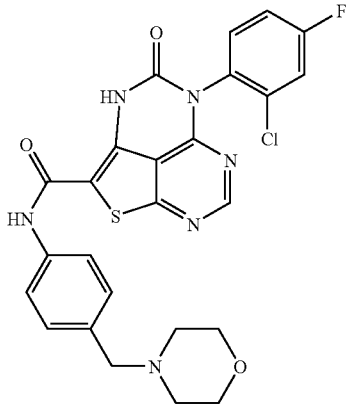
Cpd 17
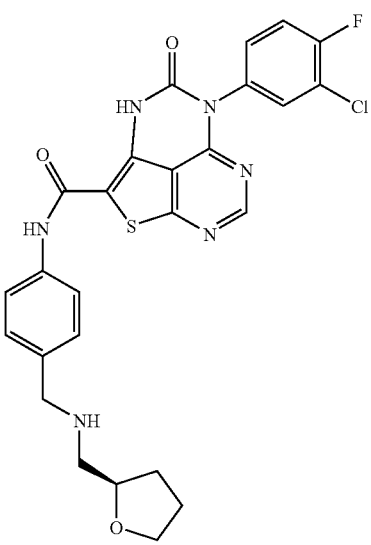
Cpd 18

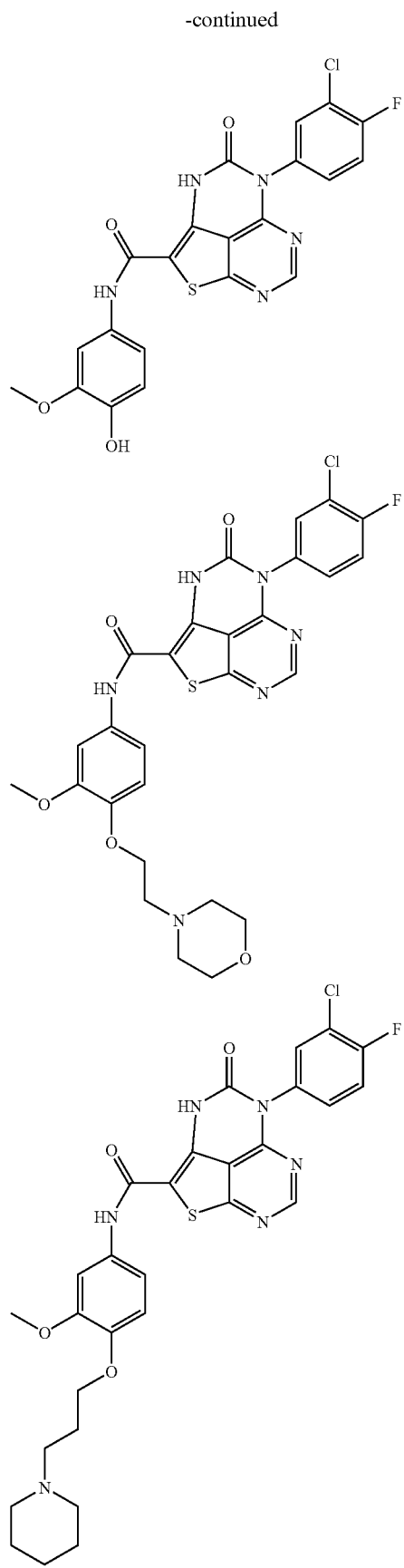

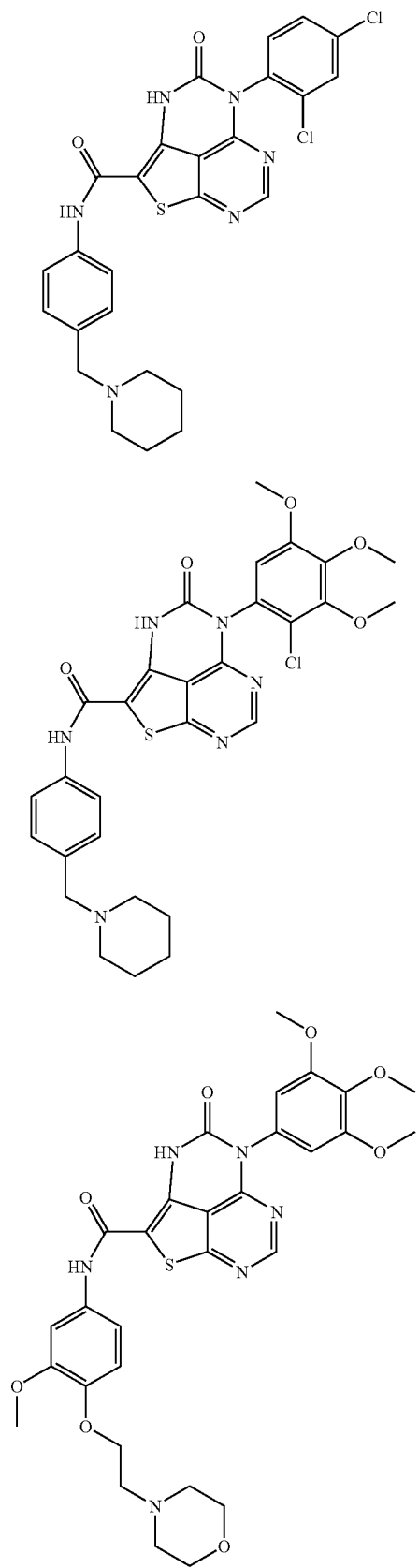

-continued
Cpd 31
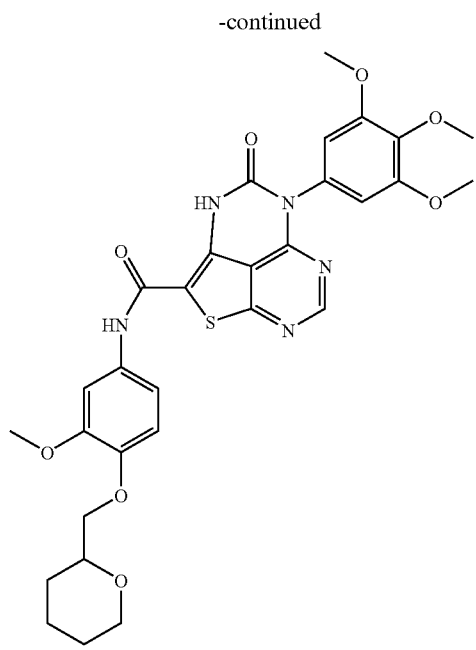
Cpd 32
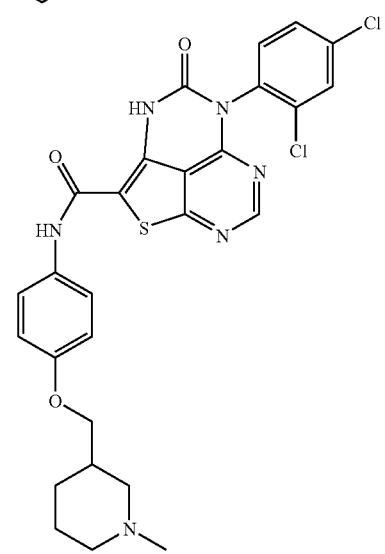
Cpd 33
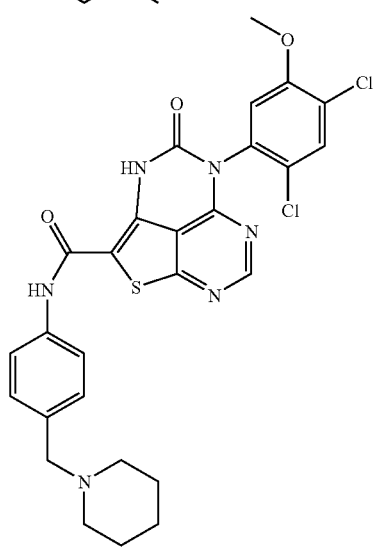
-continued
Cpd 34
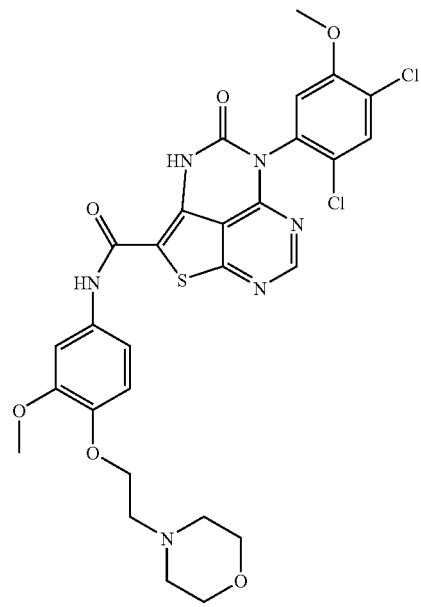
Cpd 35
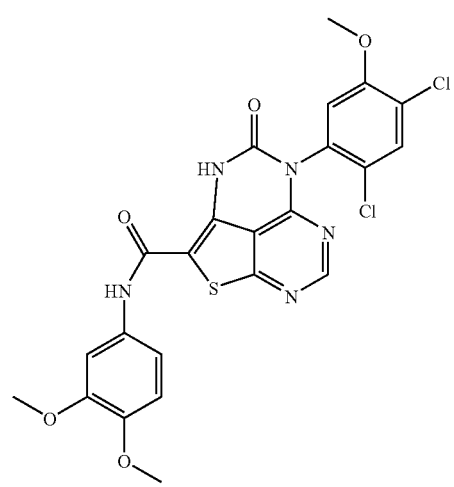
Cpd 36
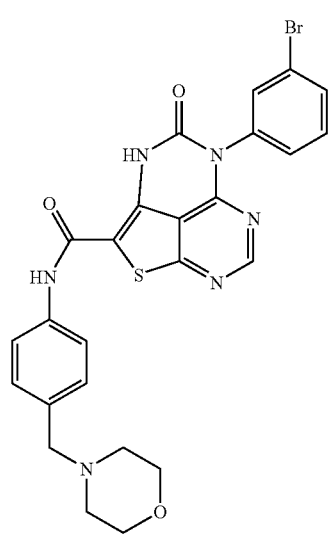

-continued
Cpd 37
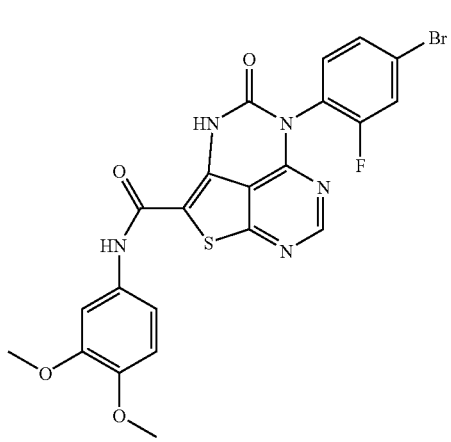
Cpd 38
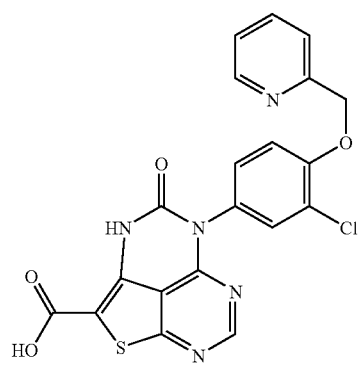
Cpd 39
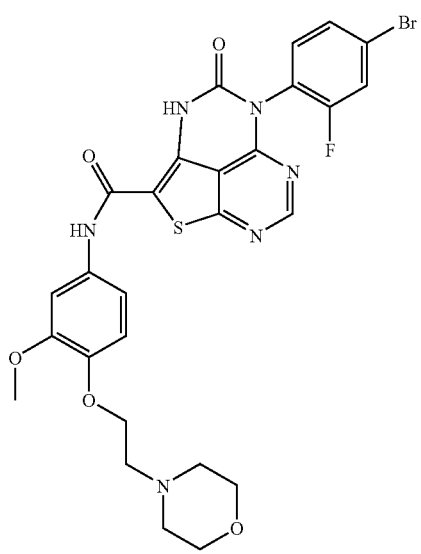
Cpd 40
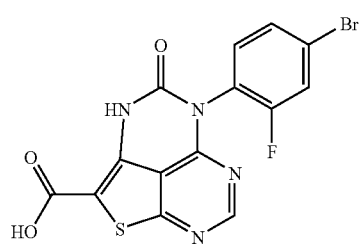
-continued
Cpd 41
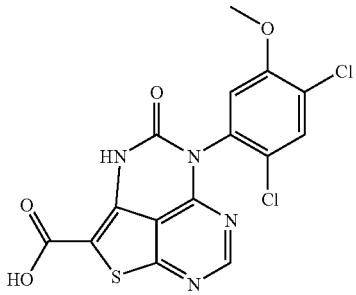
Cpd 42
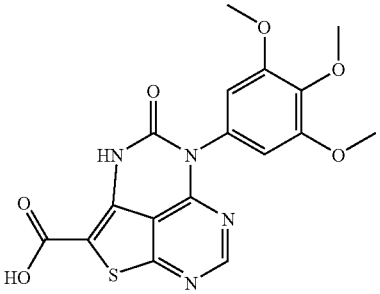
Cpd 43
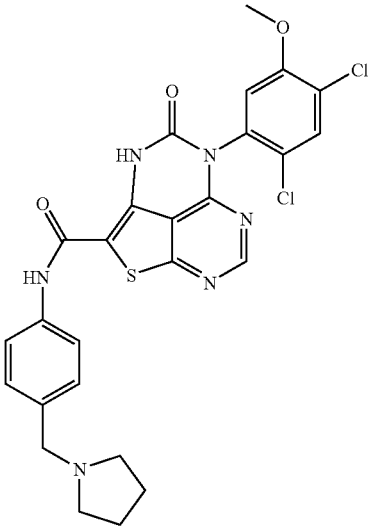
Cpd 44
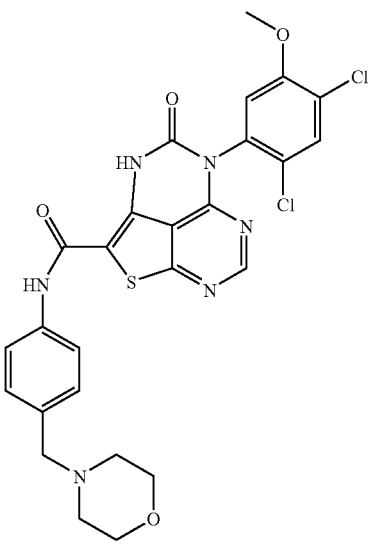

-continued
Cpd 45
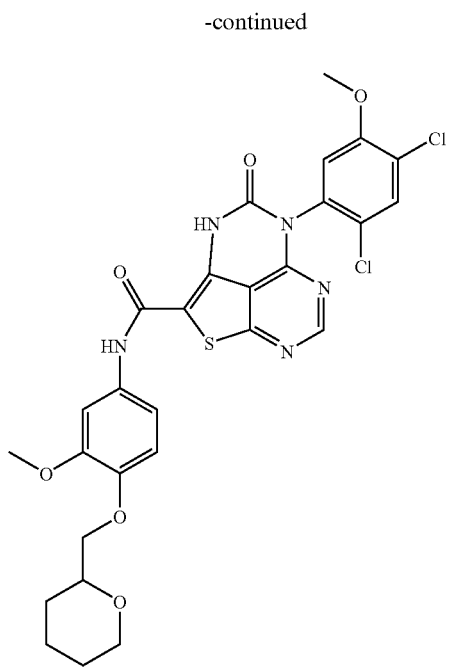
Cpd 46
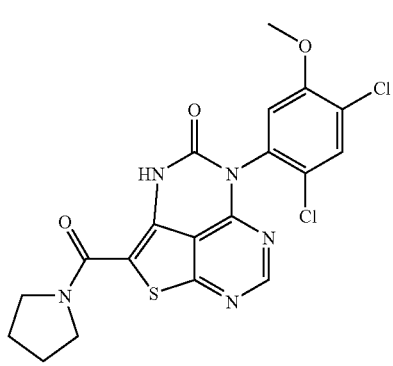
Cpd 47
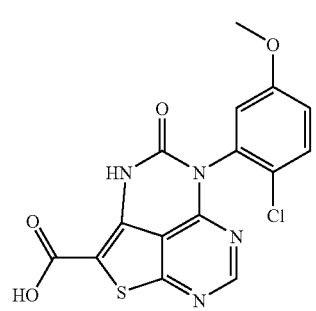
-continued
Cpd 48
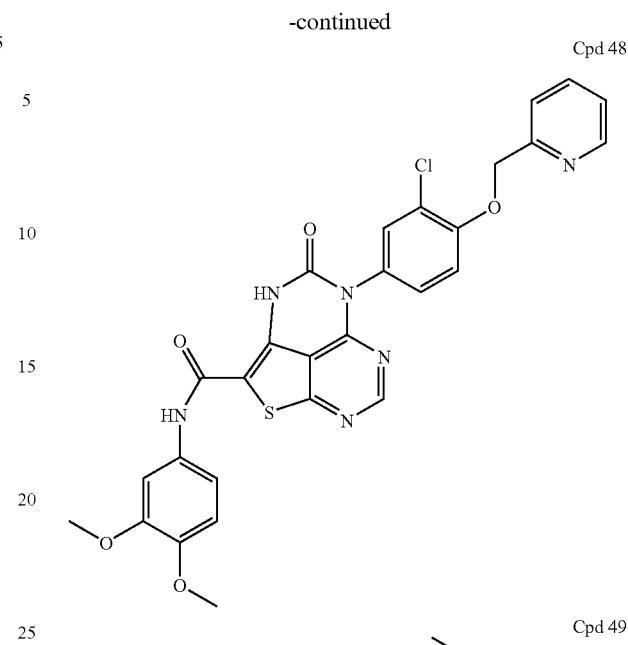
Cpd 49
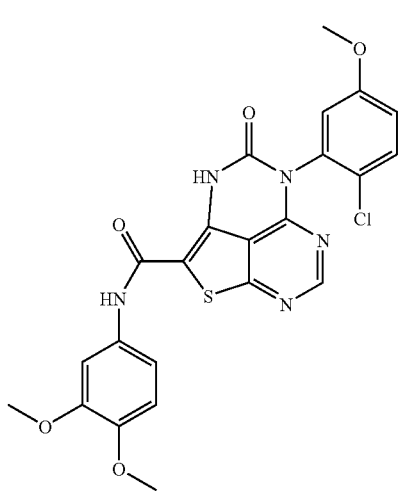
Cpd 50
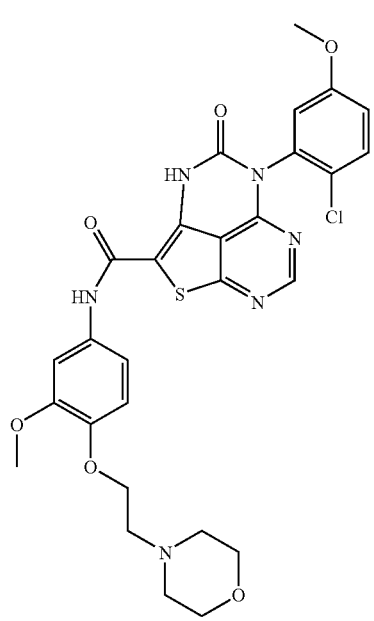

-continued
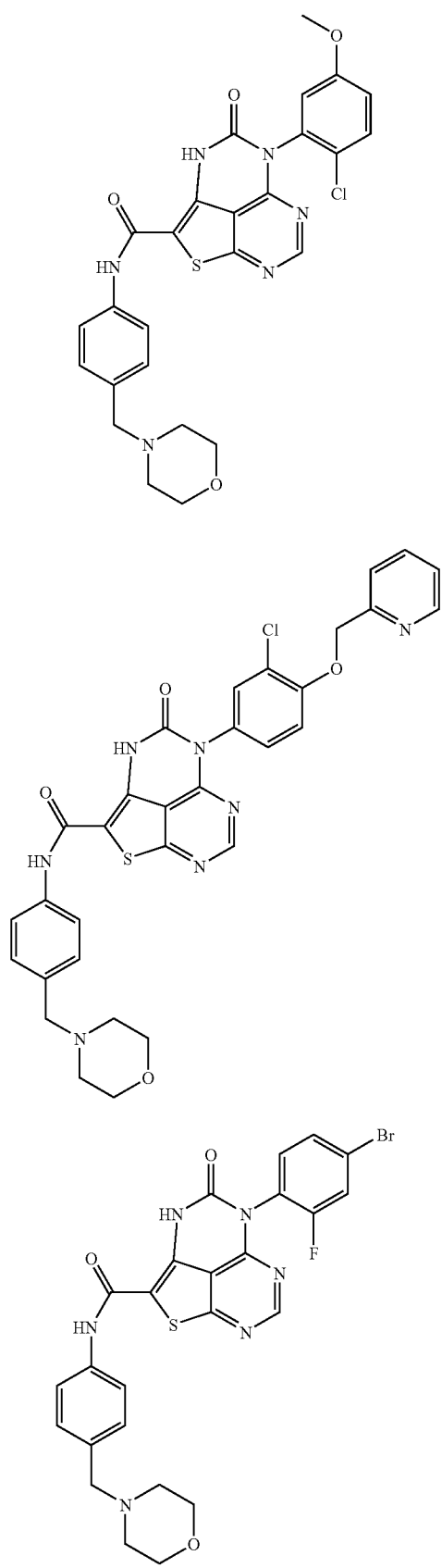
Cpd 51
Cpd 52
Cpd 53
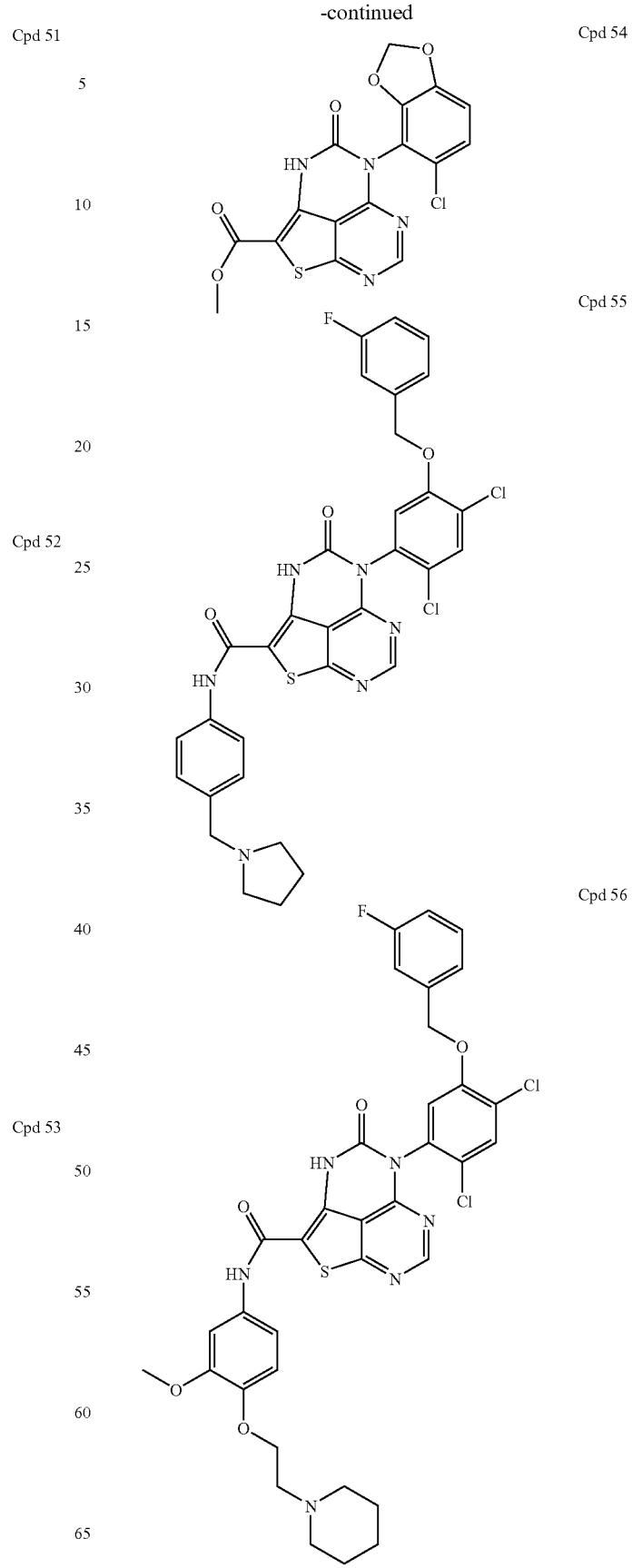
Cpd 54
Cpd 55
Cpd 56

Cpd 57
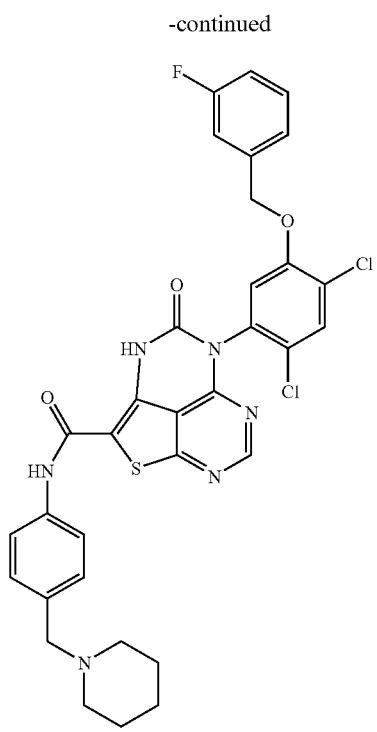
Cpd 59
Cpd 58
Cpd 60
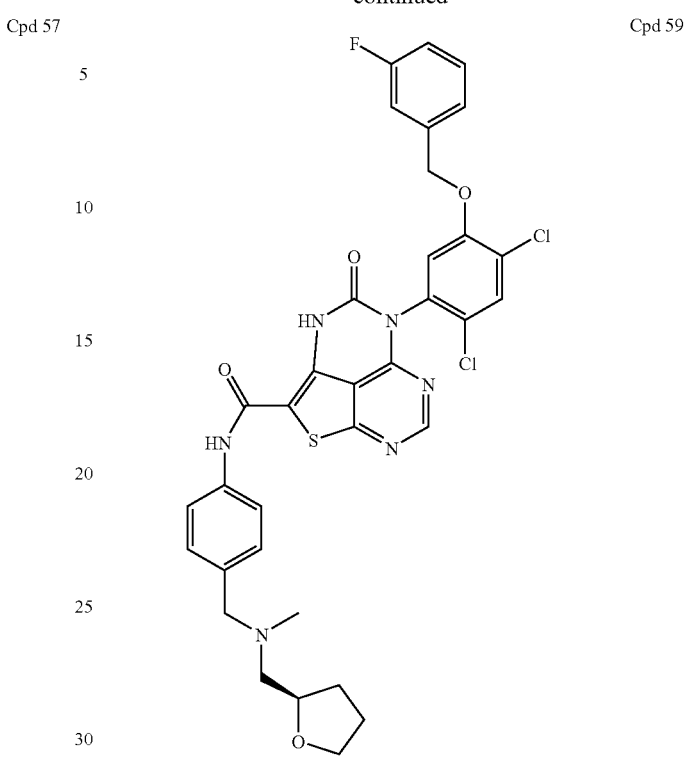
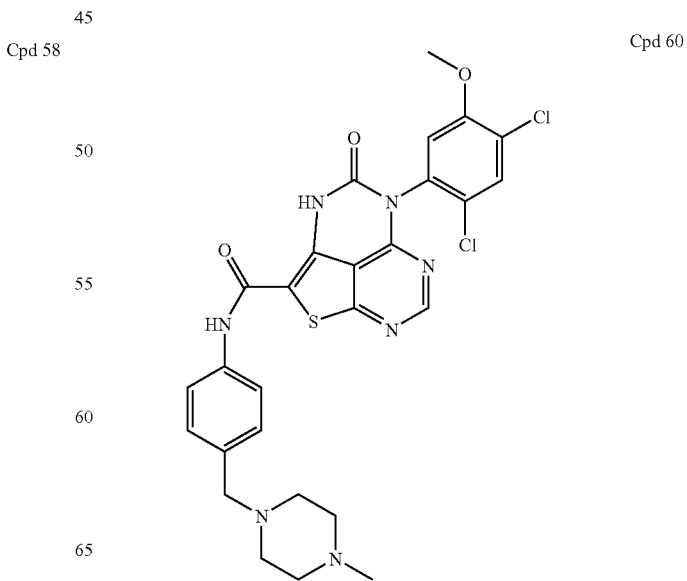

Cpd 61
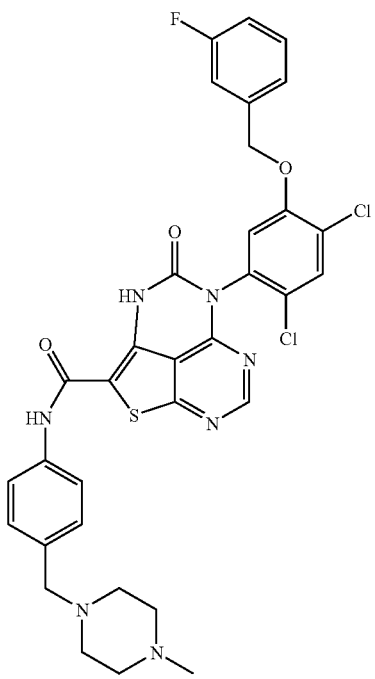
Cpd 62
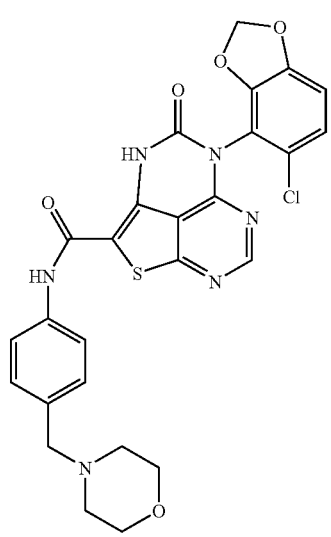
Cpd 63
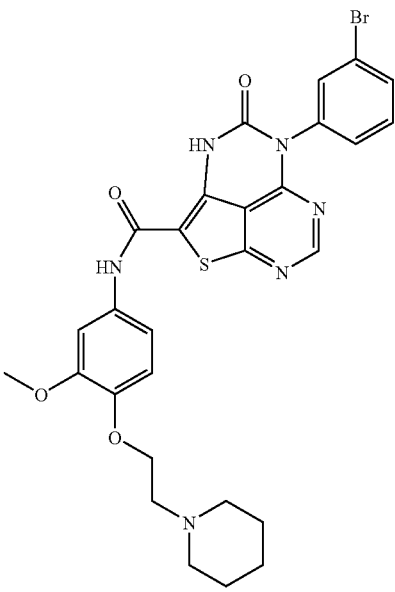
Cpd 64
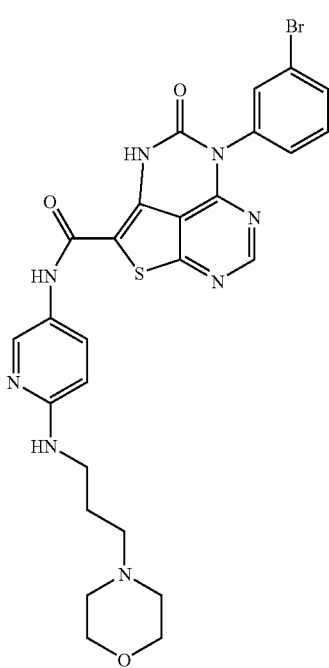

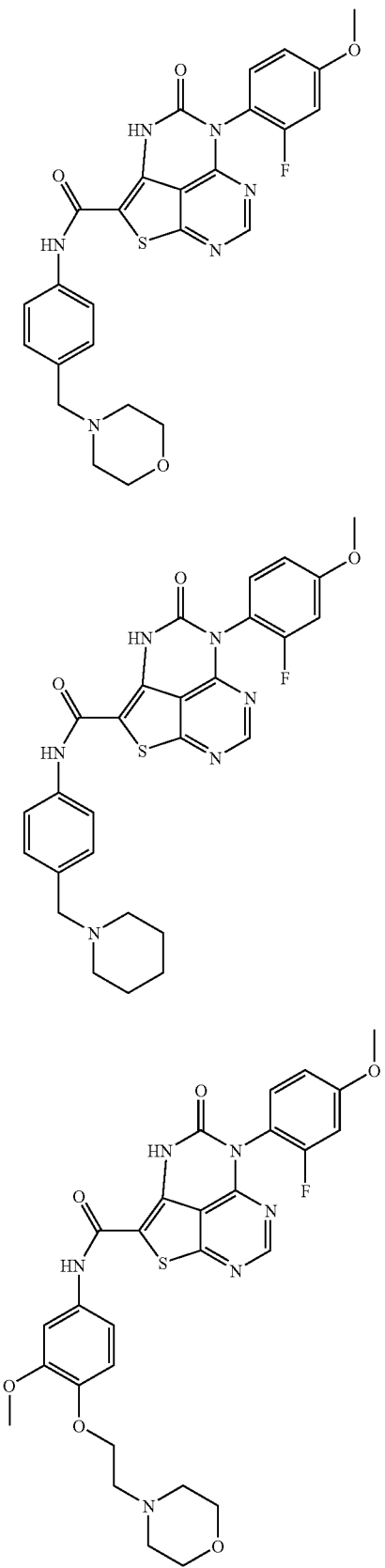
Cpd 65
Cpd 66
Cpd 67
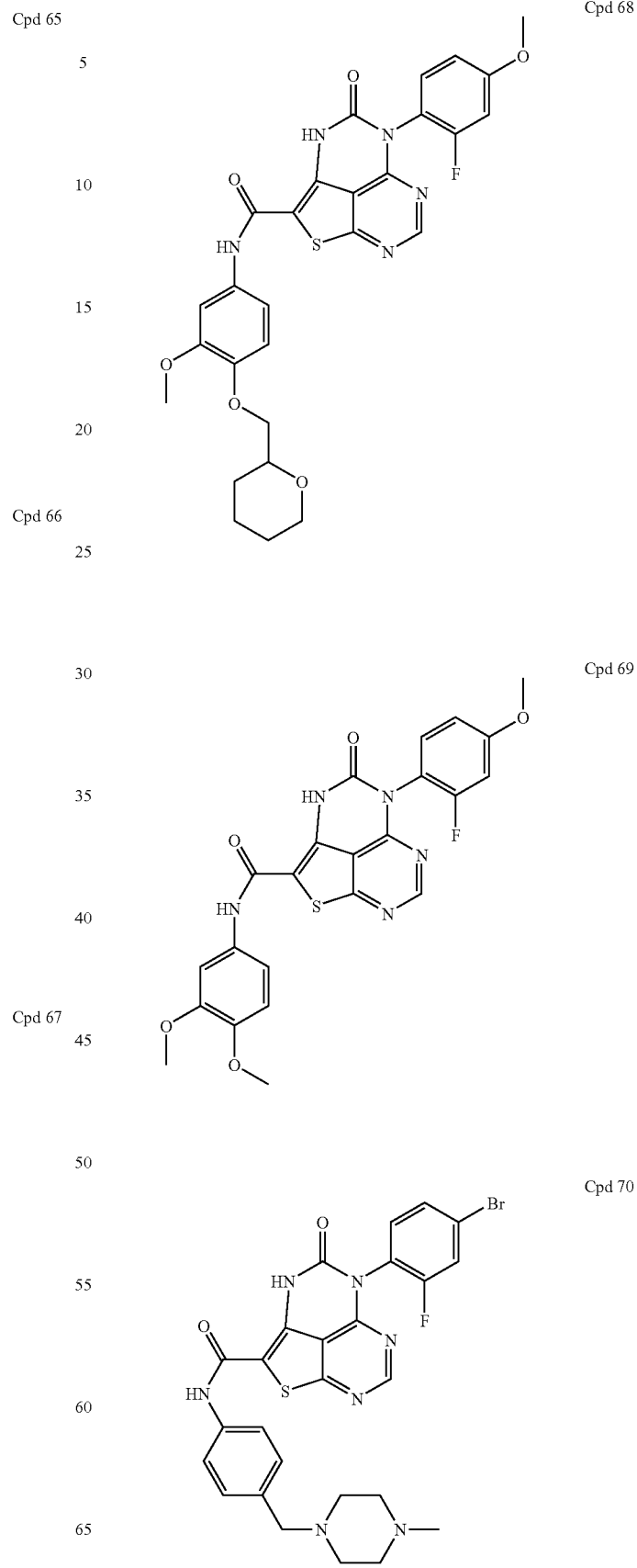
Cpd 68
Cpd 69
Cpd 70

-continued
Cpd 71
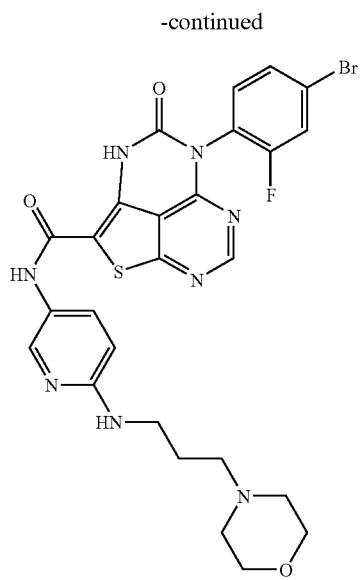
Cpd 72
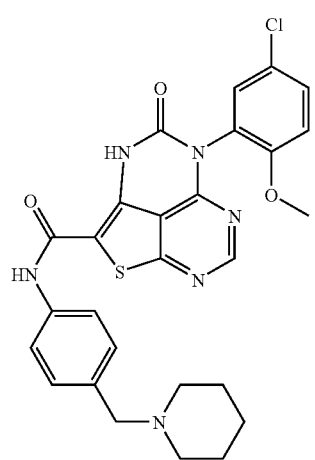
Cpd 73
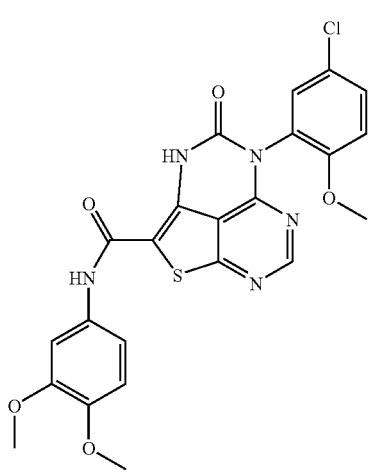
-continued
Cpd 74
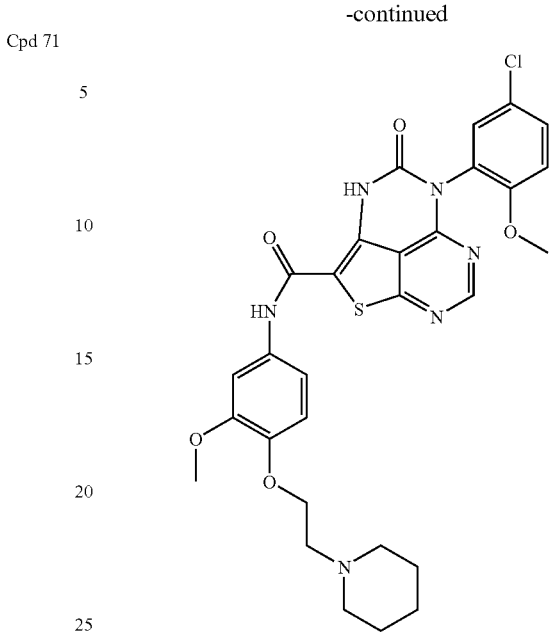
Cpd 75
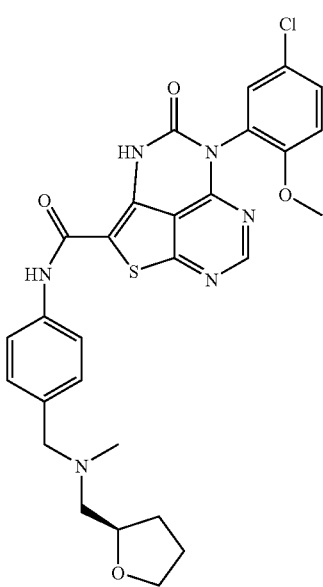

Cpd 76
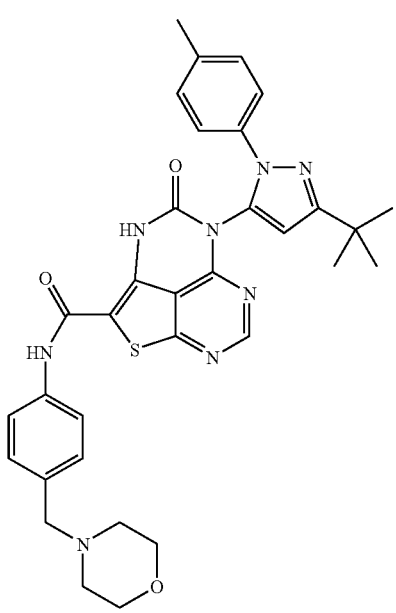
Cpd 77
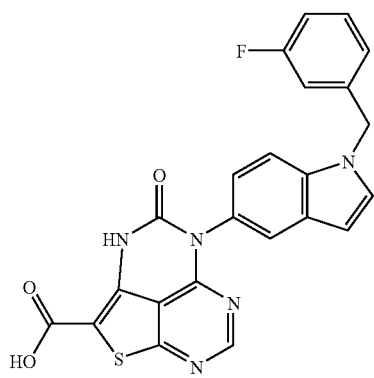
Cpd 78
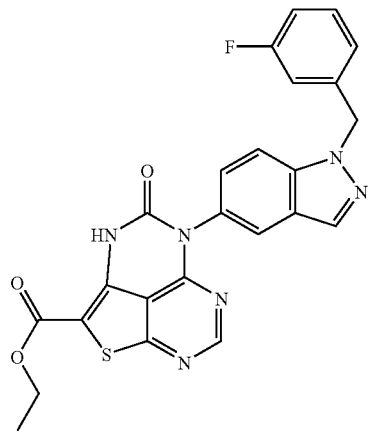
Cpd 79
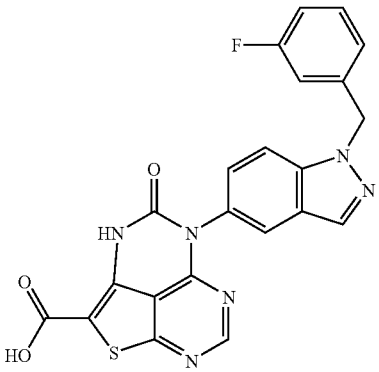
Cpd 80
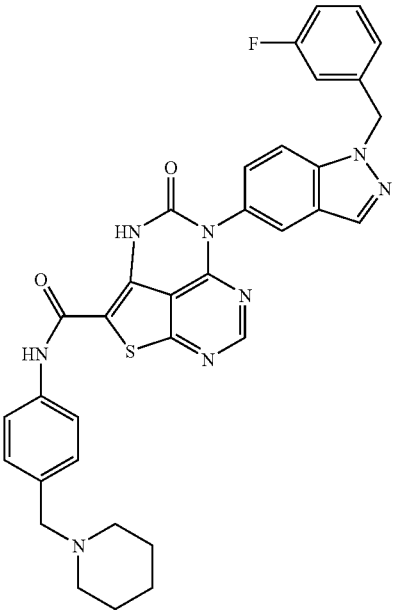
Cpd 81

-continued
Cpd 82
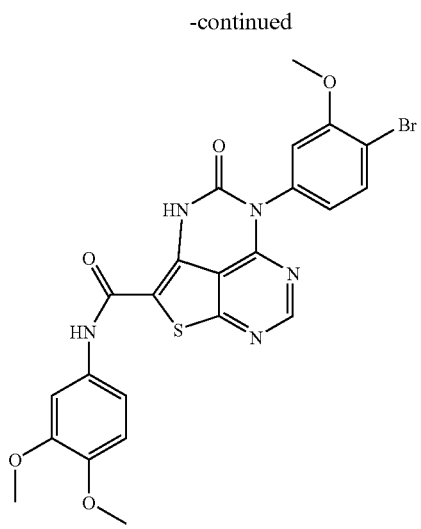
Cpd 85
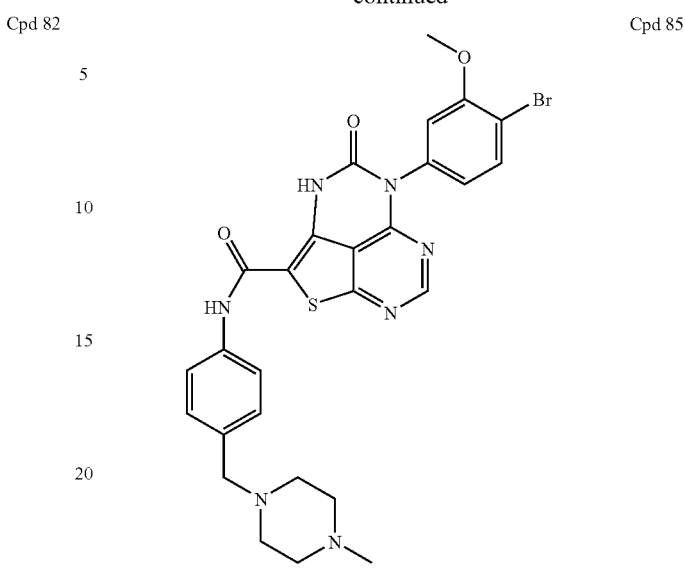
Cpd 83
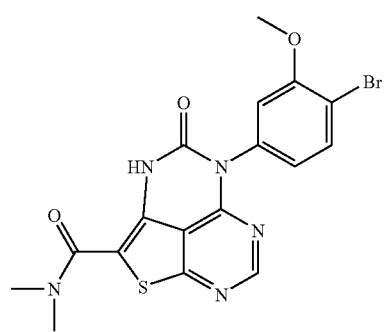
Cpd 84
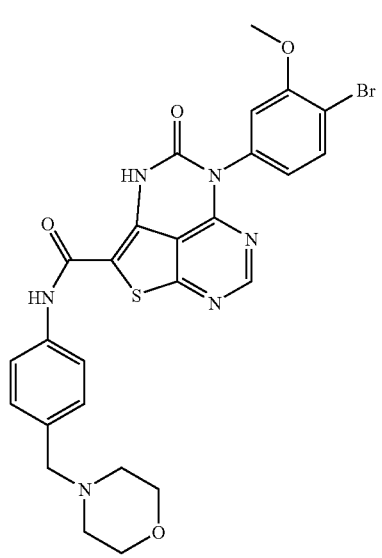
Cpd 86

Cpd 87
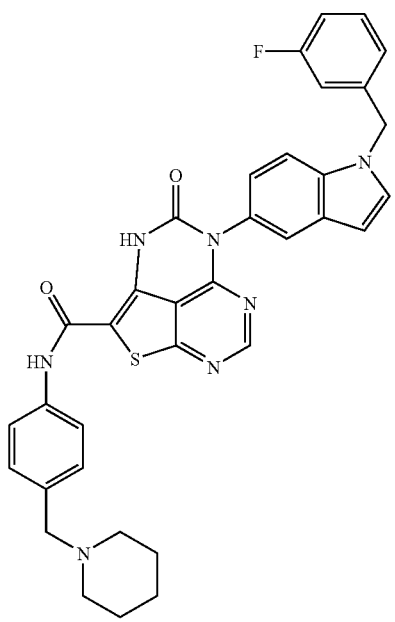
Cpd 89
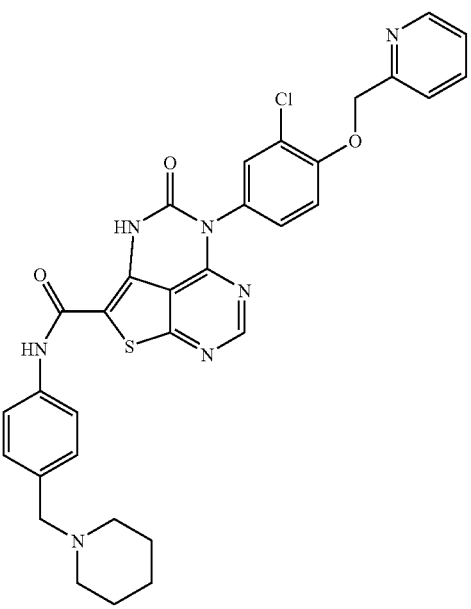
Cpd 88
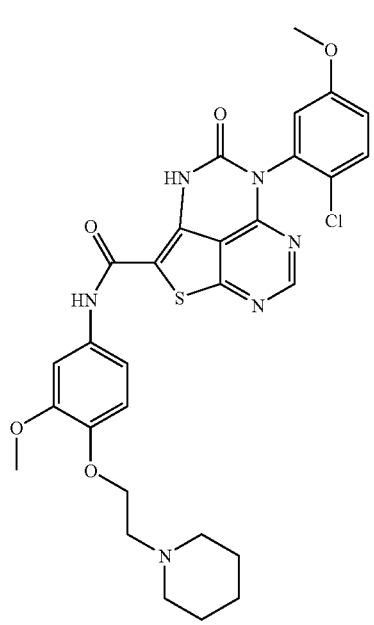
Cpd 90
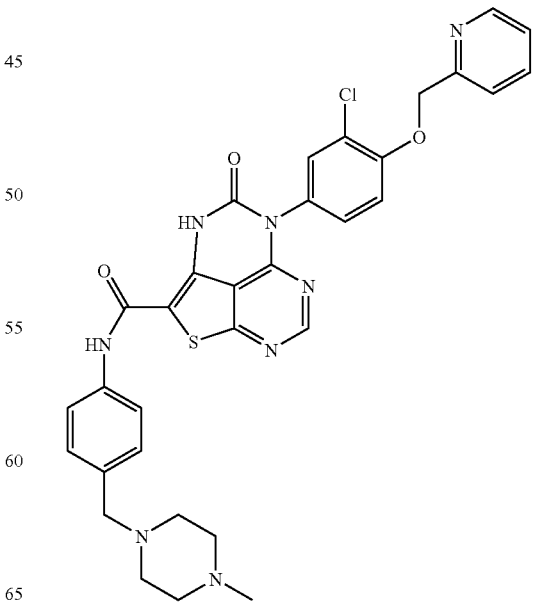

-continued
Cpd 91
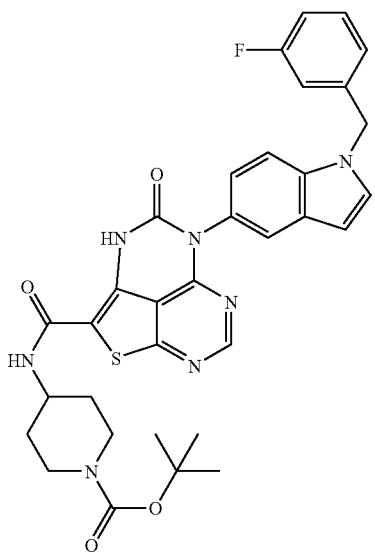
Cpd 92
Cpd 93
-continued
Cpd 94
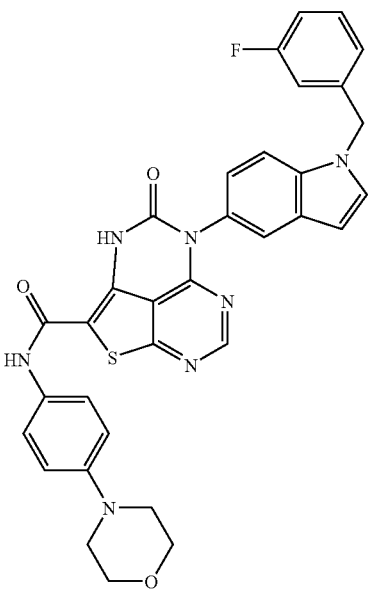
Cpd 95
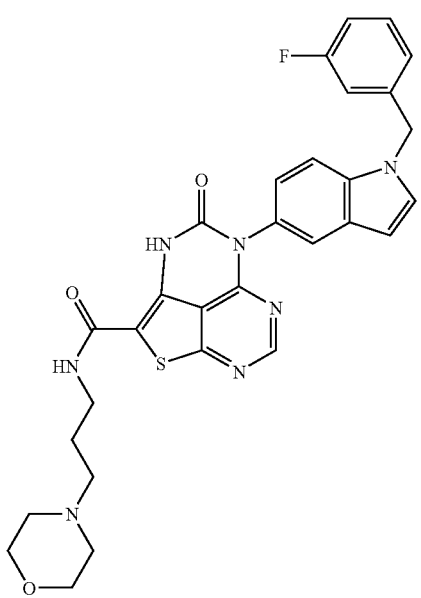

-continued
Cpd 96
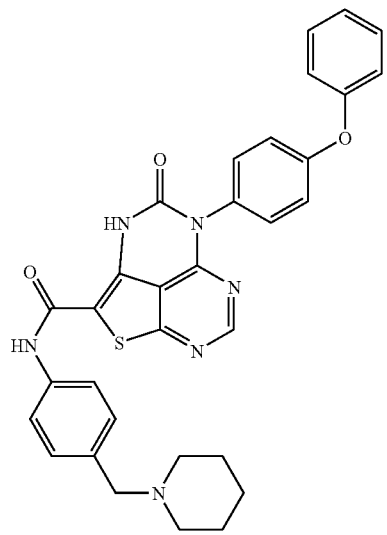
Cpd 97
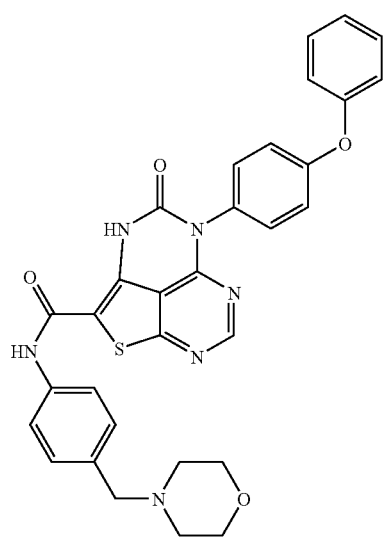
Cpd 98
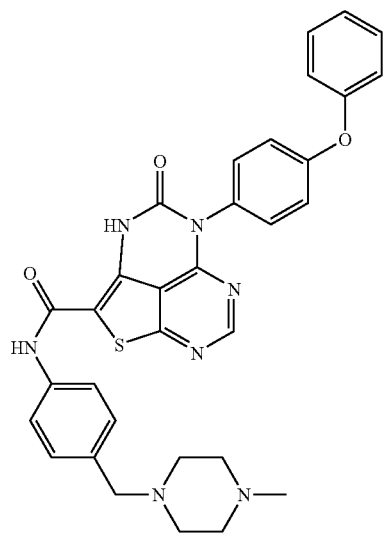
-continued
Cpd 99
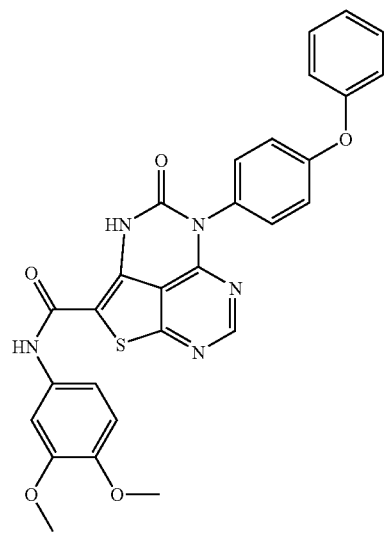
Cpd 100
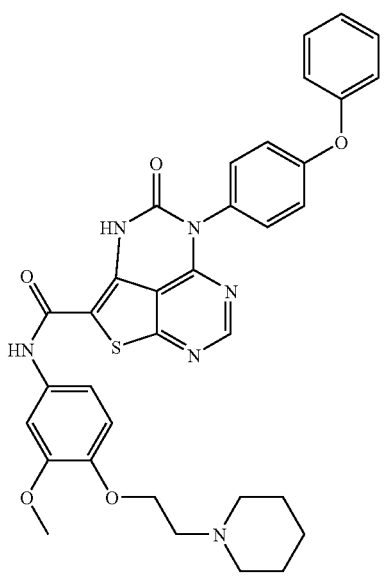
Cpd 101
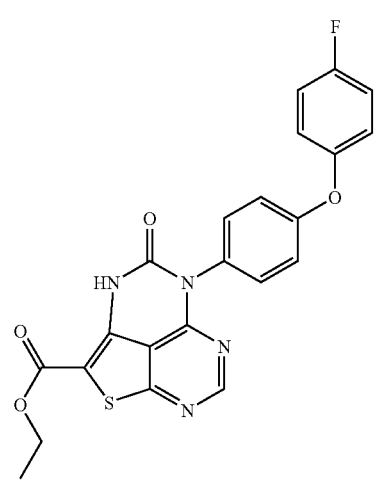

-continued
Cpd 102
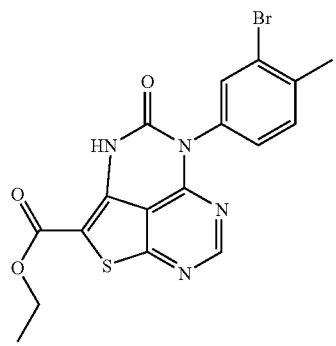
Cpd 103
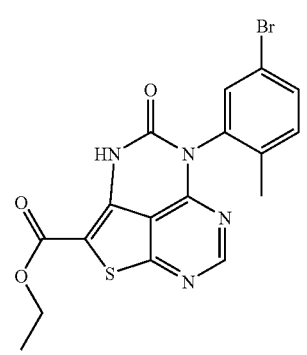
Cpd 104
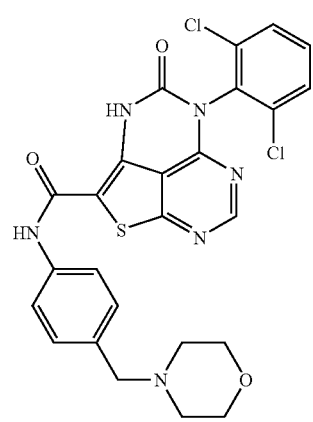
Cpd 105
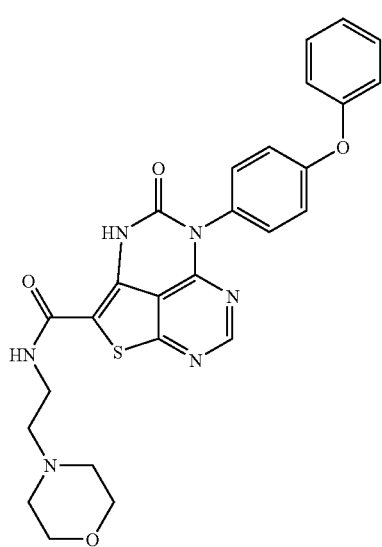
-continued
Cpd 106
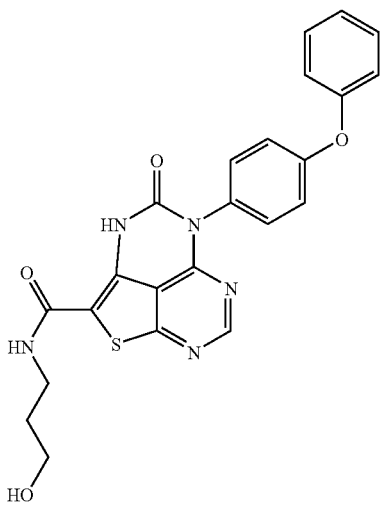
Cpd 107
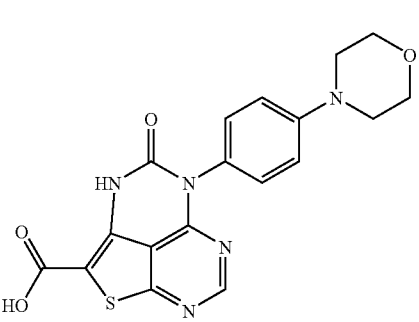
Cpd 108
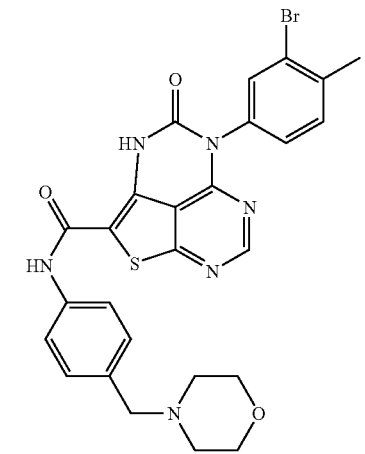

Cpd 109
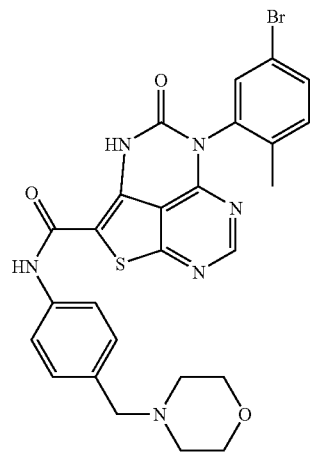
Cpd 110
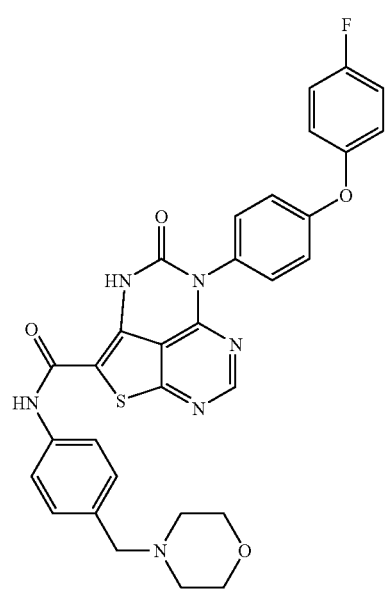
Cpd 111
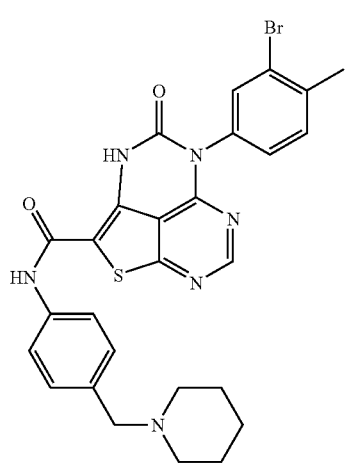
Cpd 112
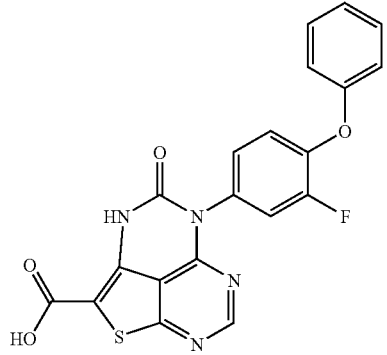
Cpd 113
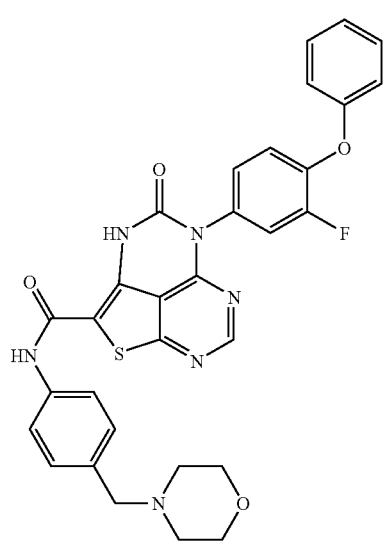
Cpd 114
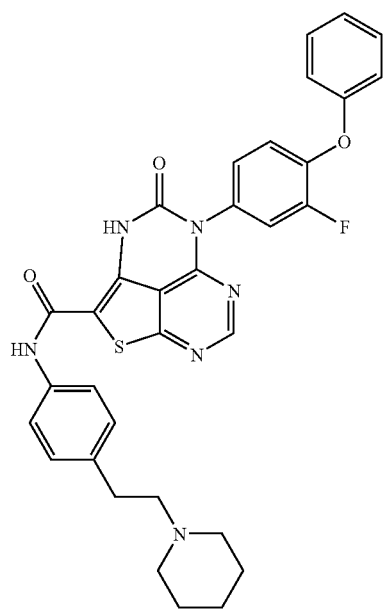

-continued
Cpd 115
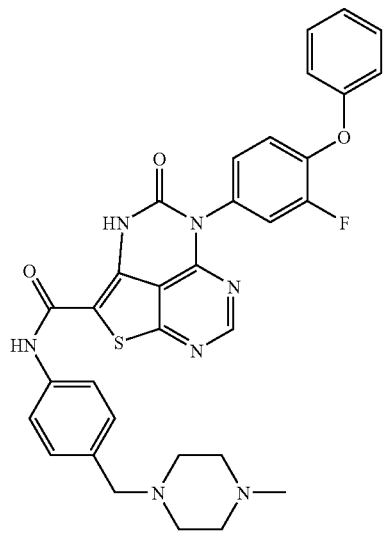
Cpd 116
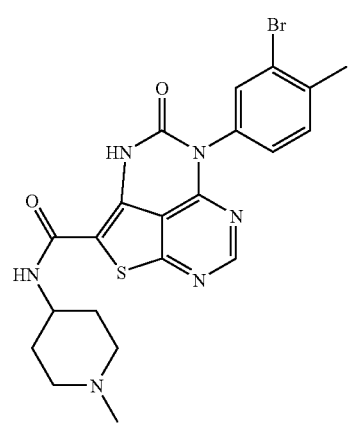
Cpd 117
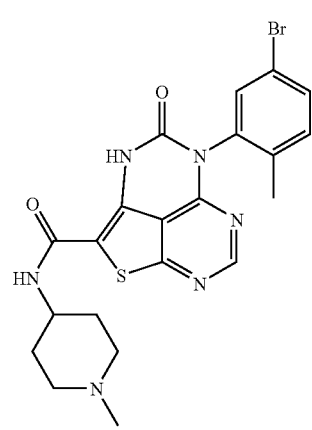
-continued
Cpd 118
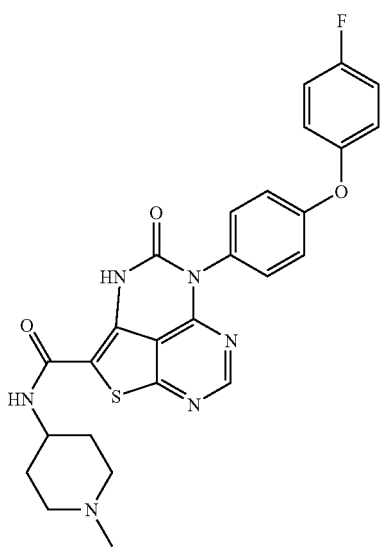
Cpd 119
Cpd 120
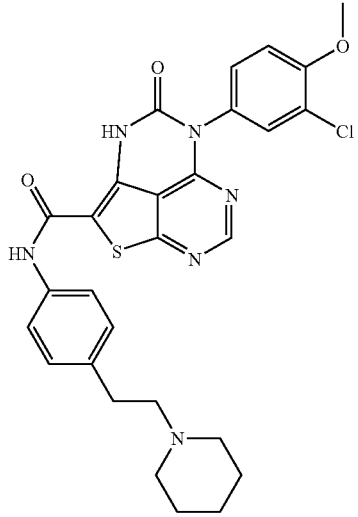

Cpd 121
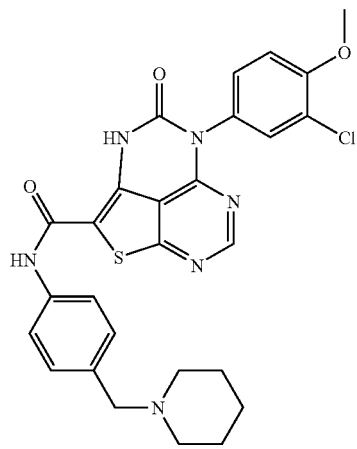
Cpd 122
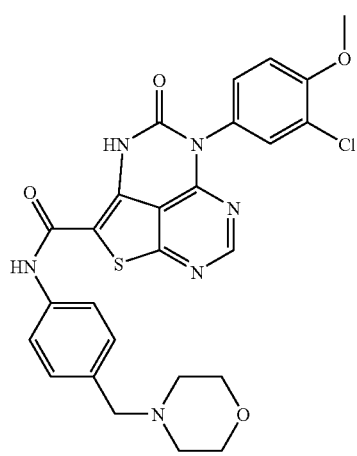
Cpd 123
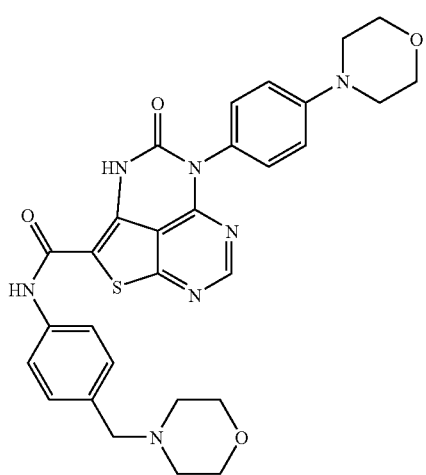
Cpd 124
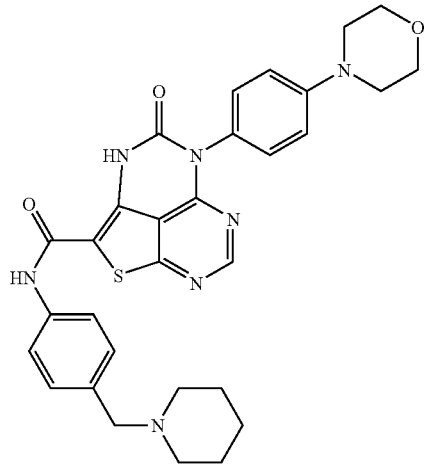
Cpd 125
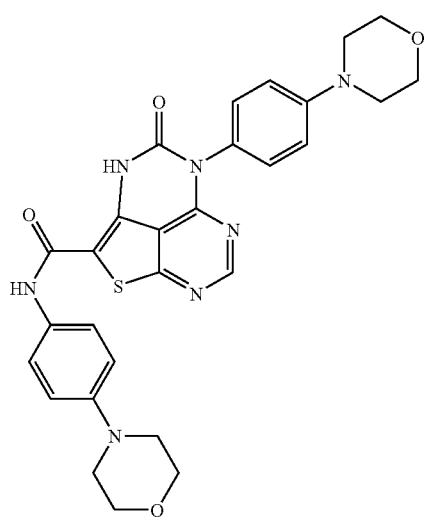
Cpd 126
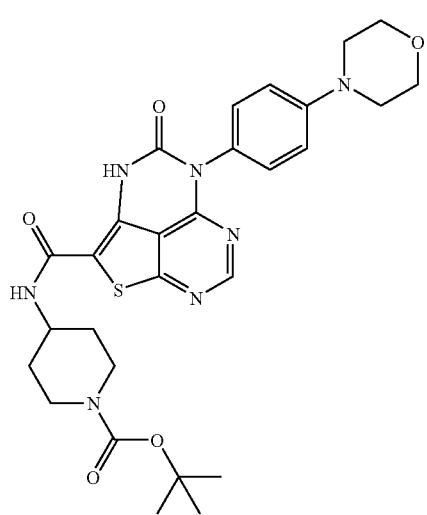

Cpd 127
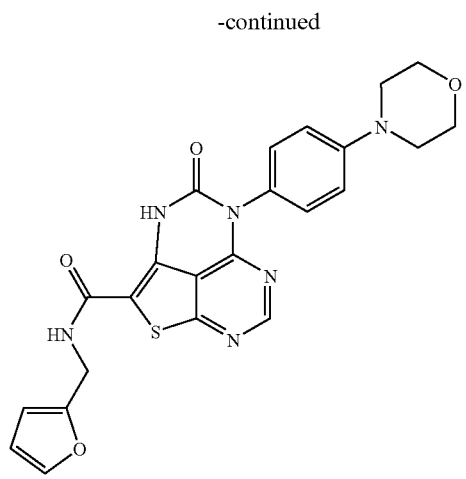
Cpd 128
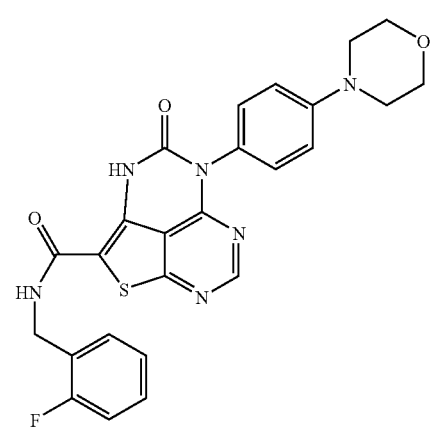
Cpd 129
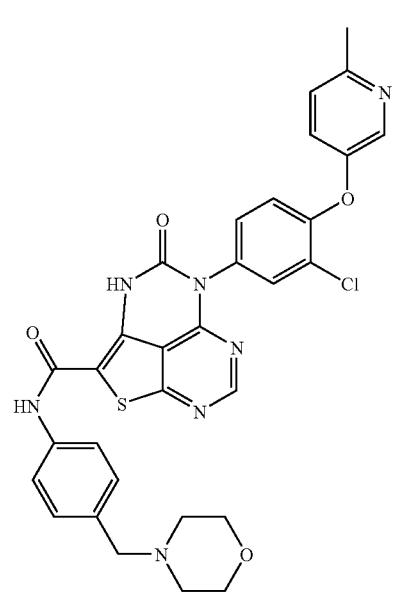
Cpd 130
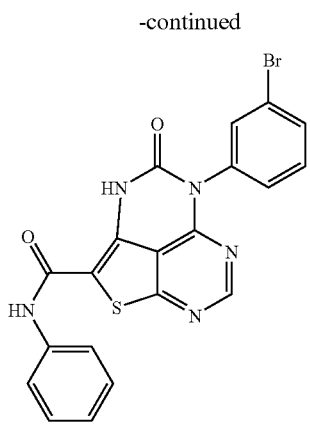
Cpd 131
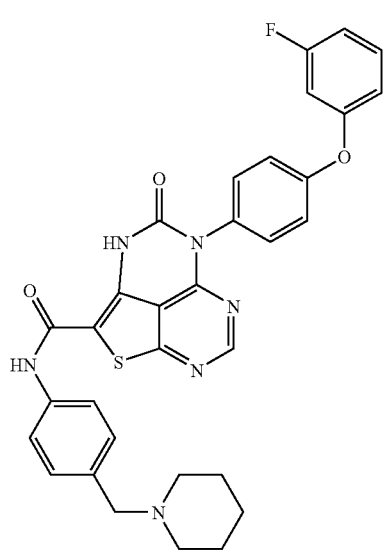
Cpd 132
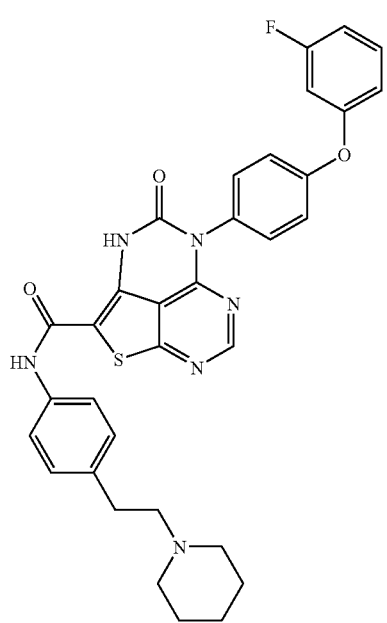

Cpd 133
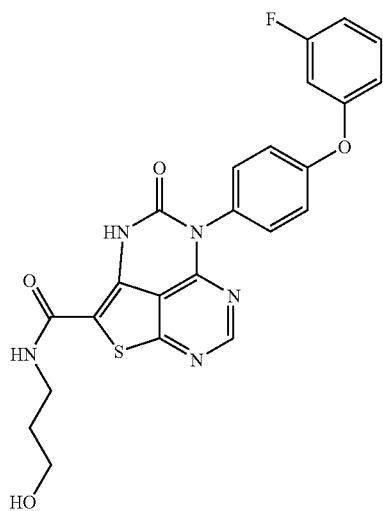
Cpd 134
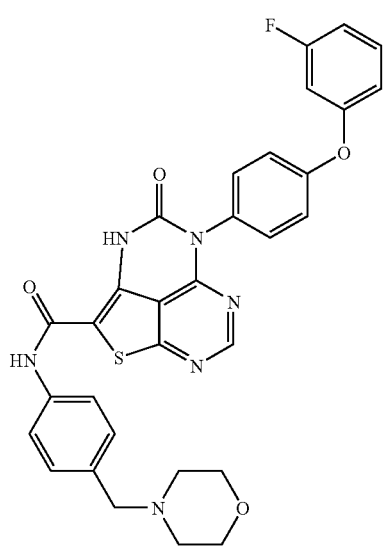
Cpd 135
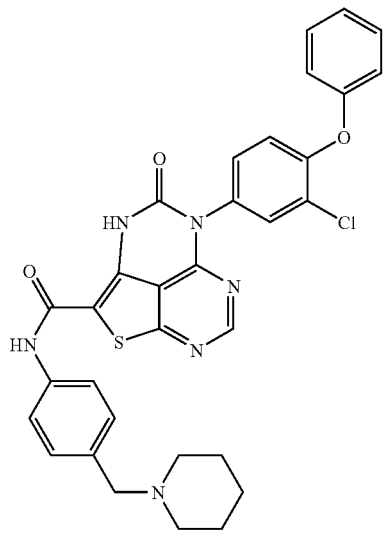
Cpd 136
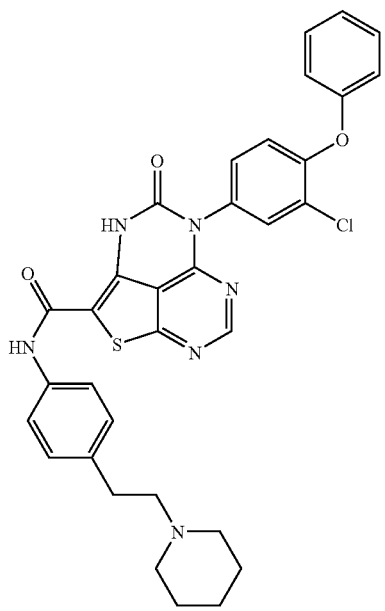
Cpd 137
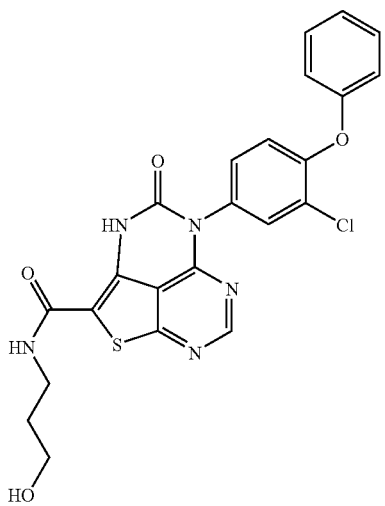
Cpd 138
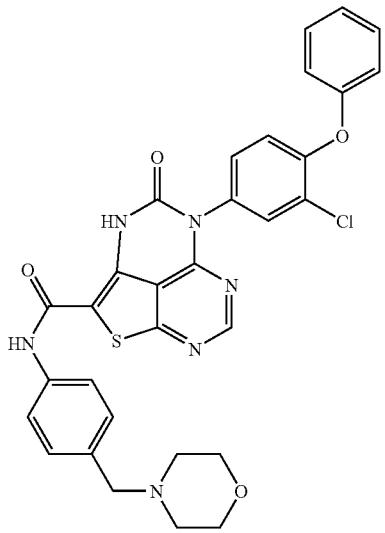

-continued
Cpd 139
Cpd 140
Cpd 141
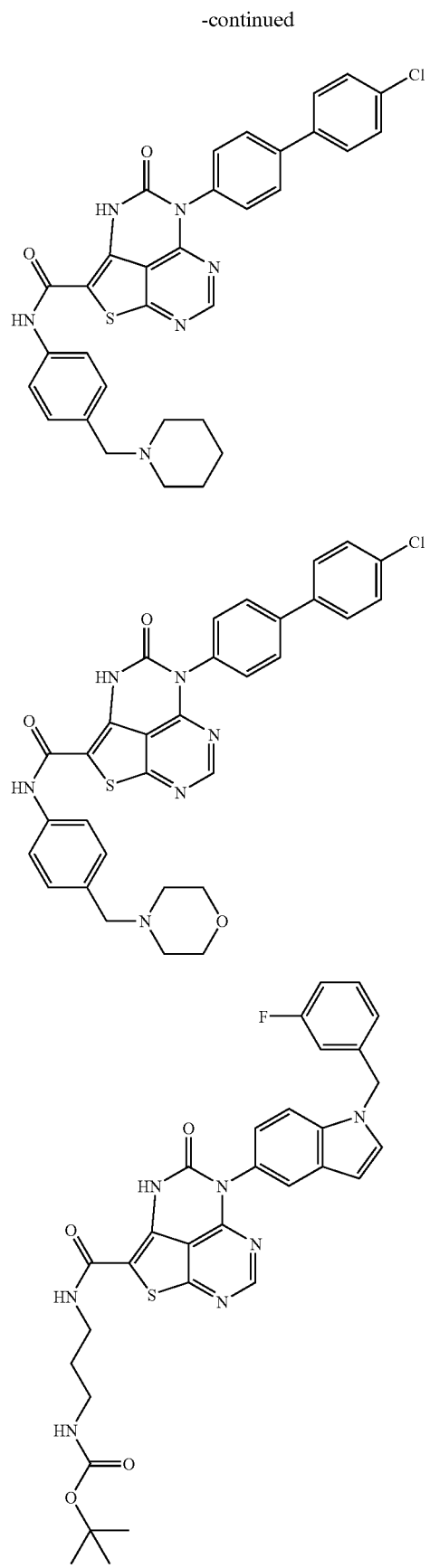
-continued
Cpd 142
Cpd 143
Cpd 144
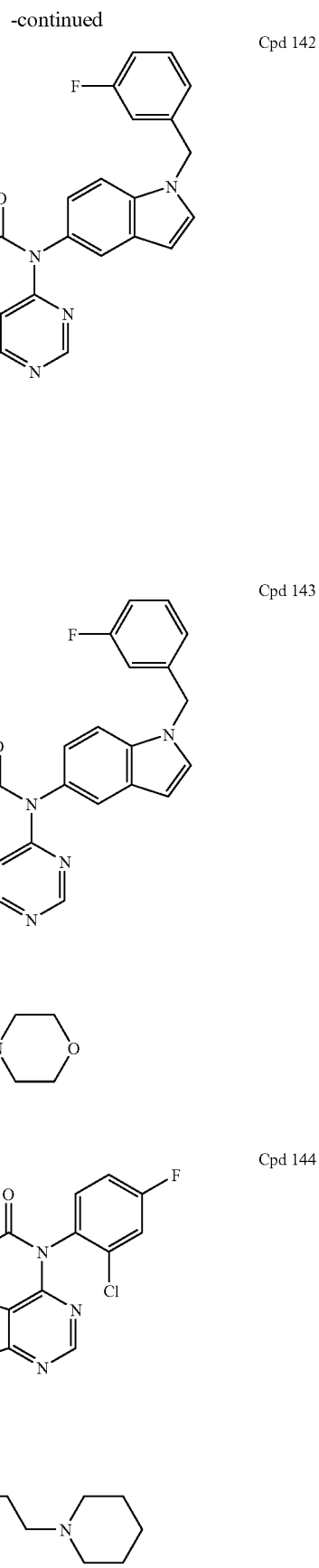

-continued
Cpd 145
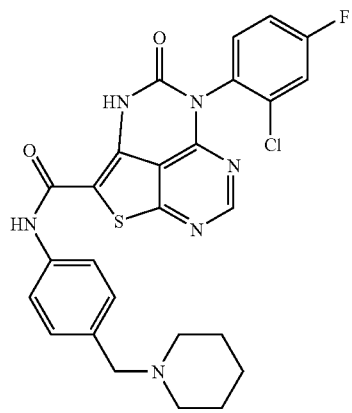
Cpd 146
Cpd 147
-continued
Cpd 148
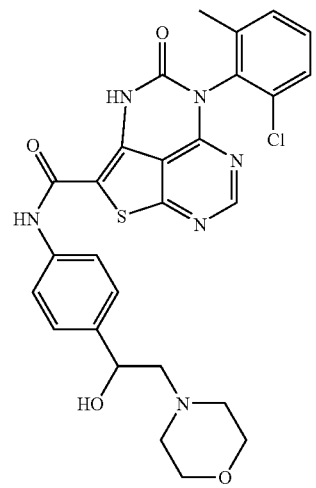
Cpd 149
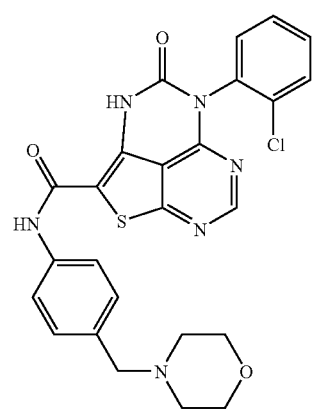
Cpd 150
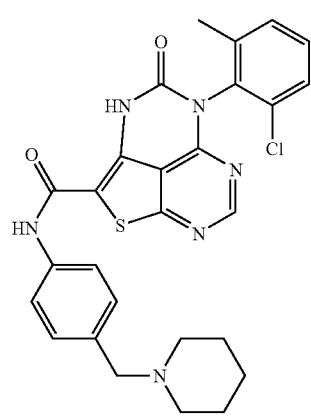

-continued
Cpd 151
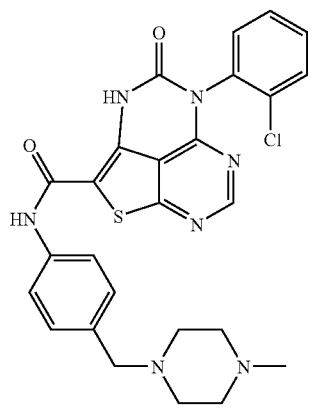
Cpd 152
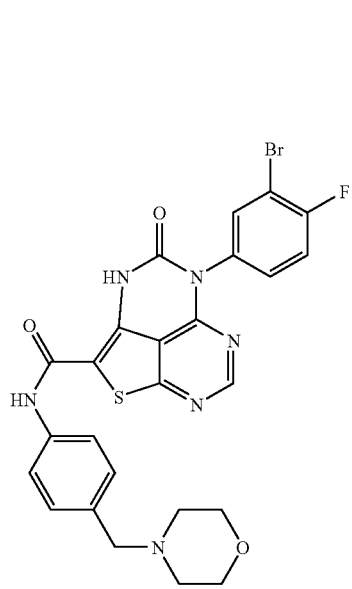
Cpd 153
-continued
Cpd 154
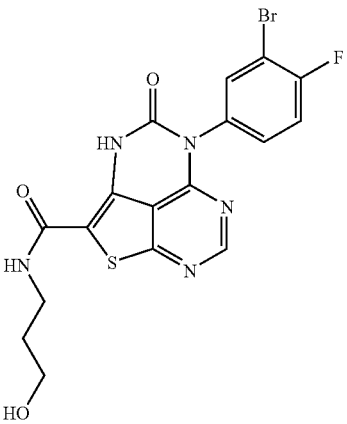
Cpd 155
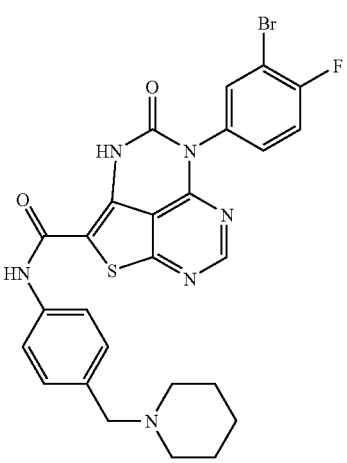
Cpd 156
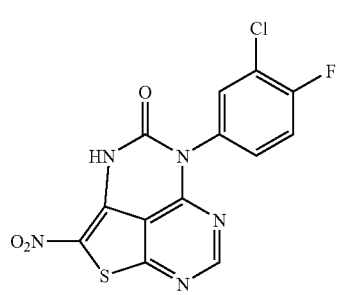
Cpd 157

-continued
Cpd 158
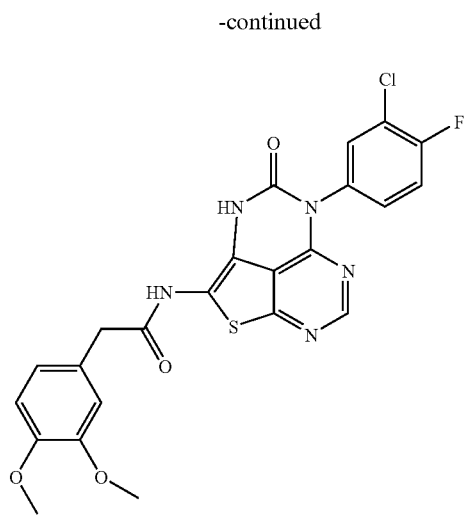
Cpd 159
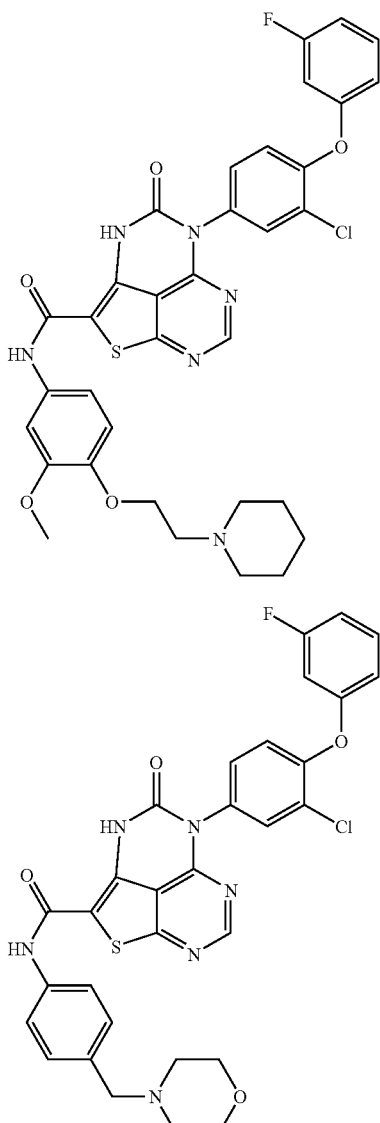
Cpd 160
-continued
Cpd 161
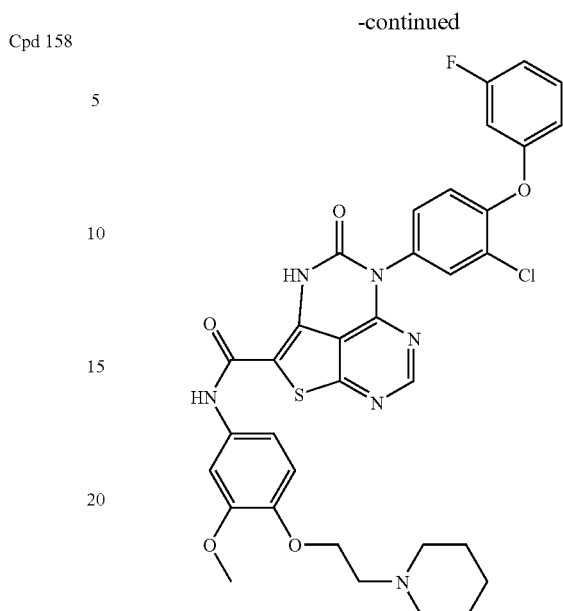
Cpd 162
Cpd 163
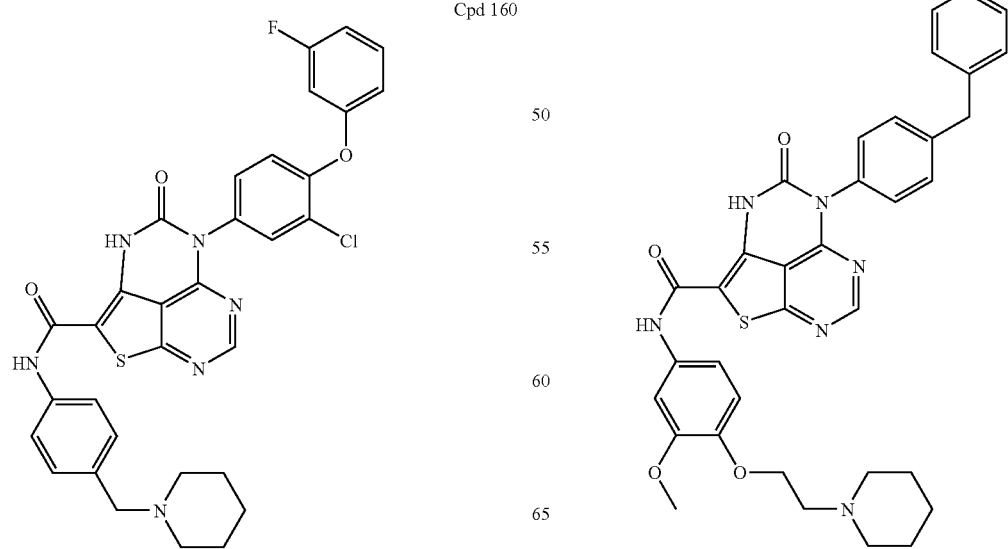

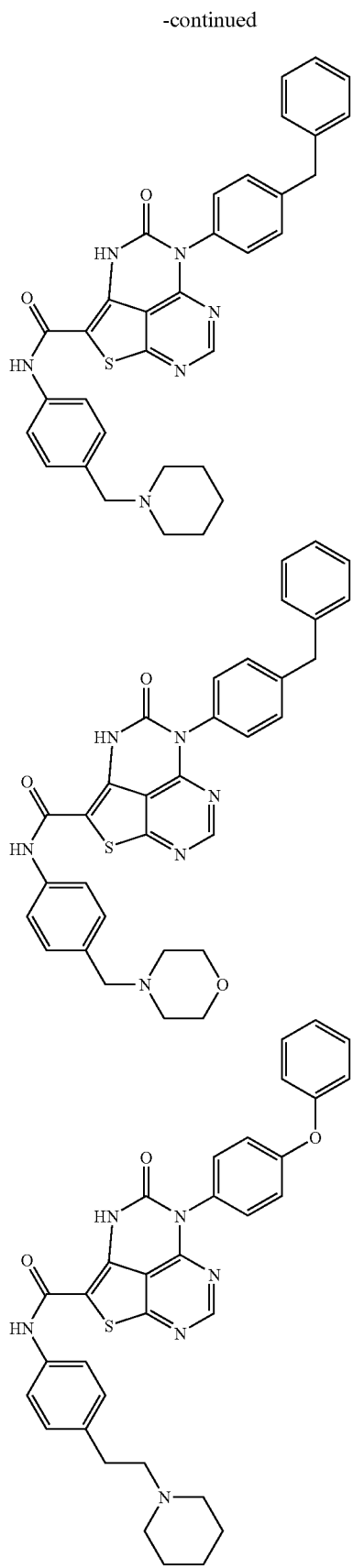
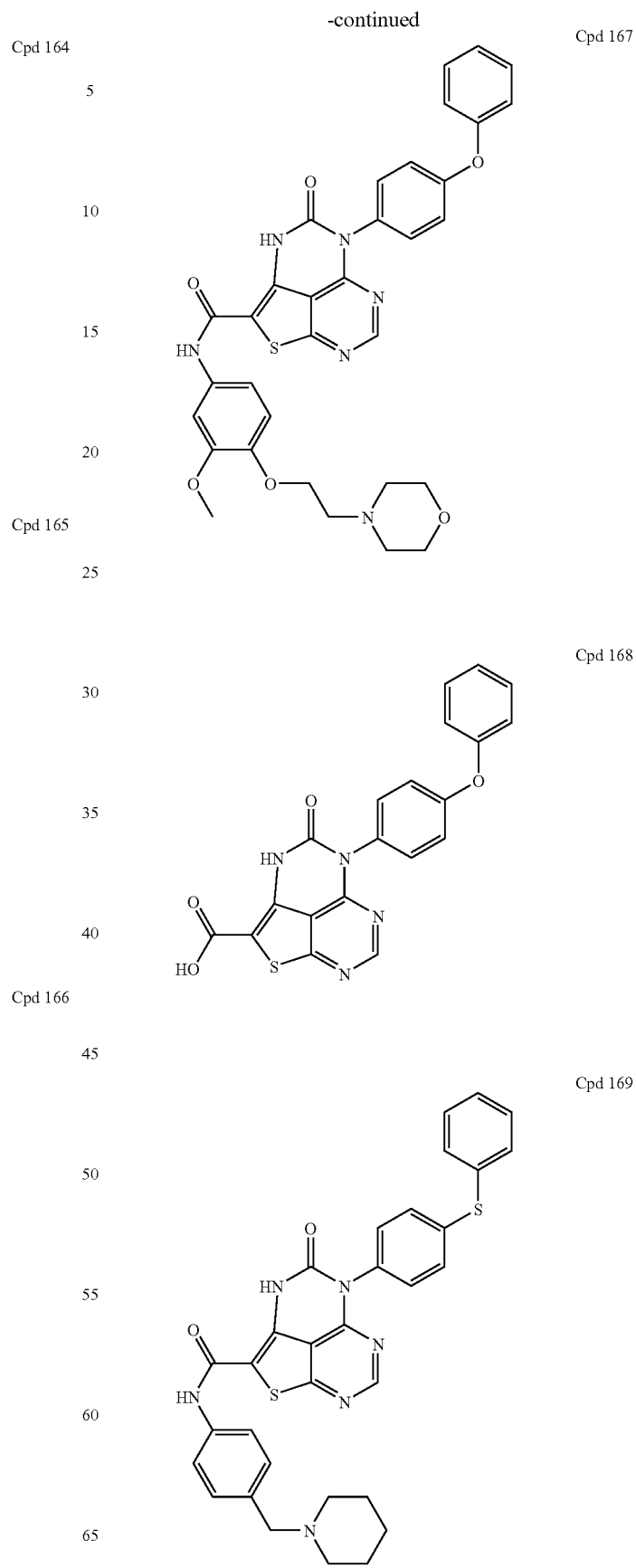

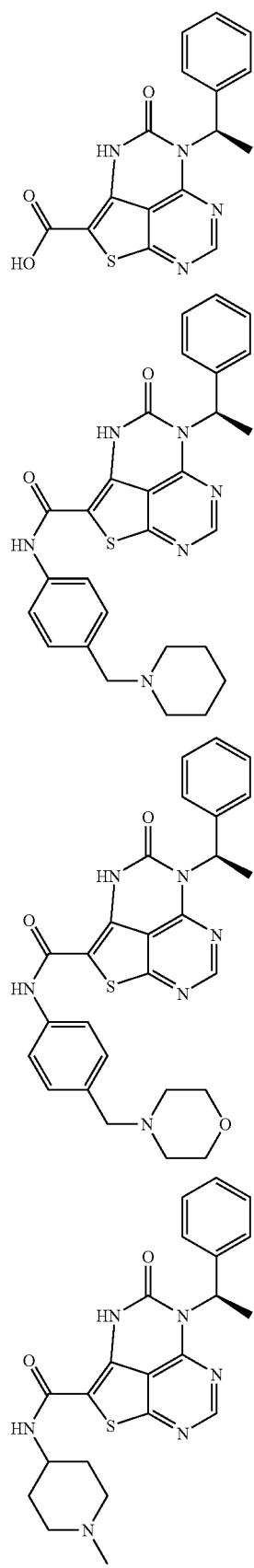
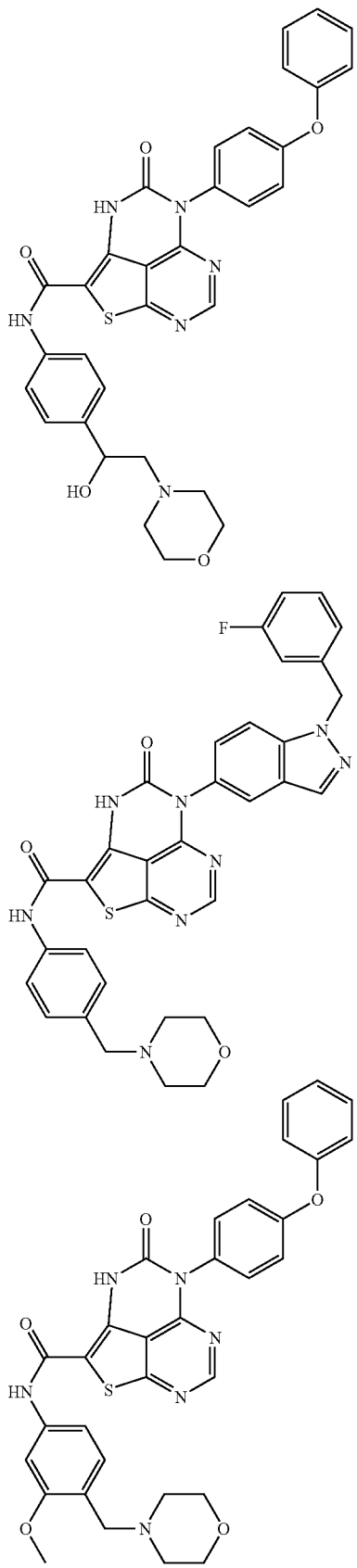

-continued
Cpd 177
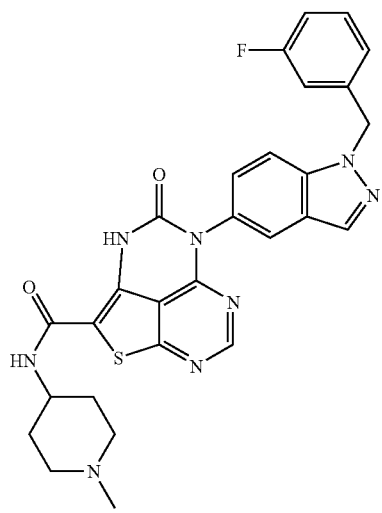
Cpd 178
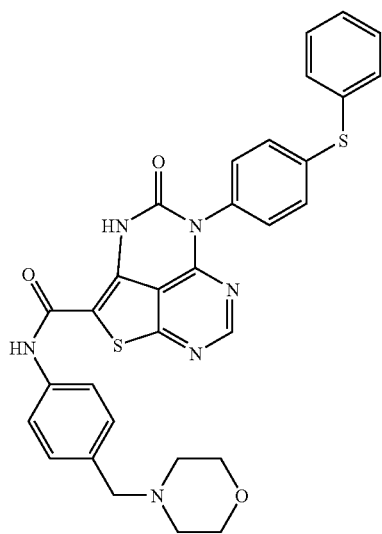
Cpd 179
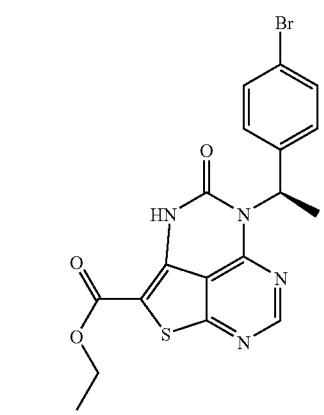
-continued
Cpd 180
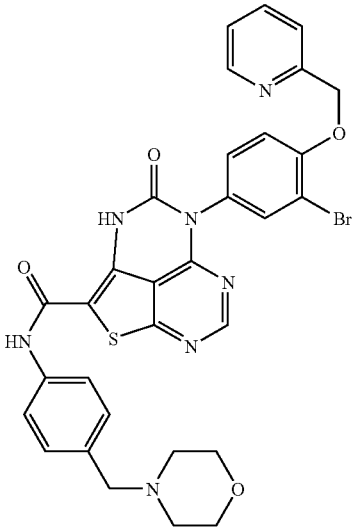
Cpd 181
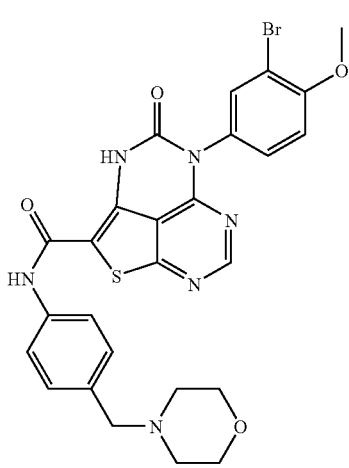
Cpd 182
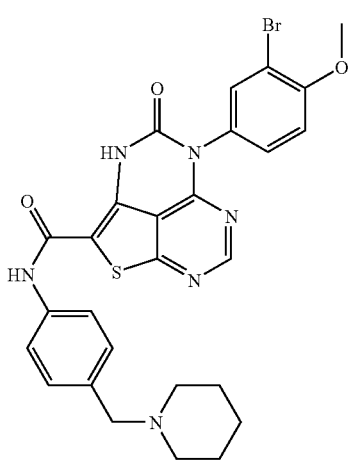

Cpd 183
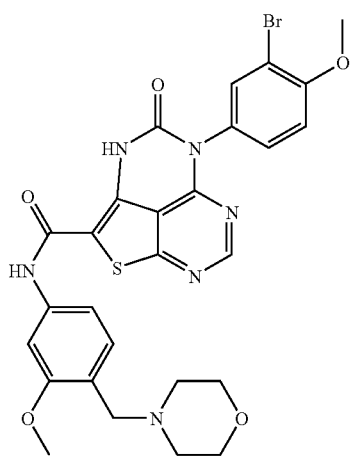
Cpd 184
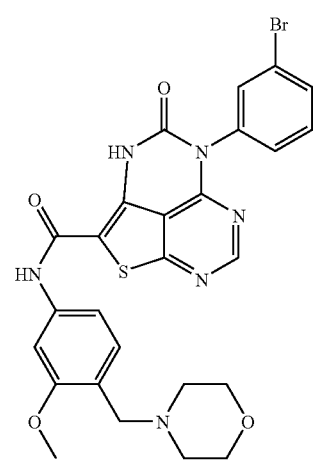
Cpd 185
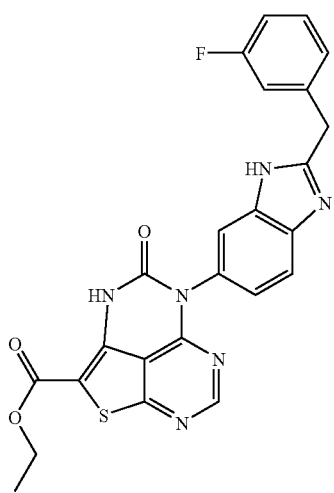
Cpd 186
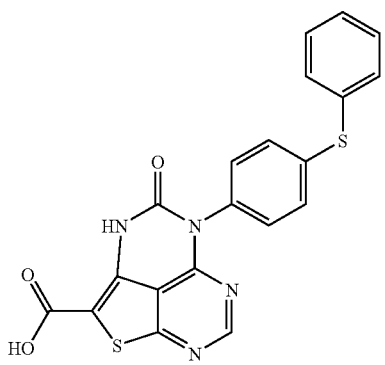
Cpd 187
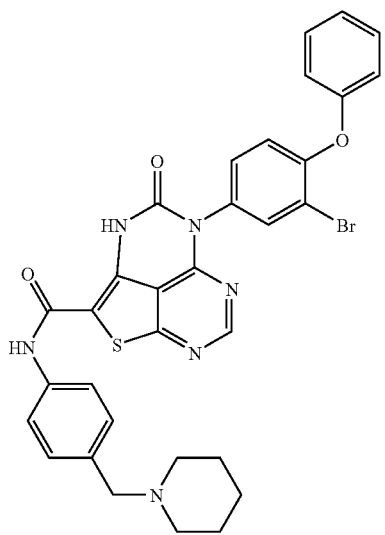
Cpd 188

Cpd 189
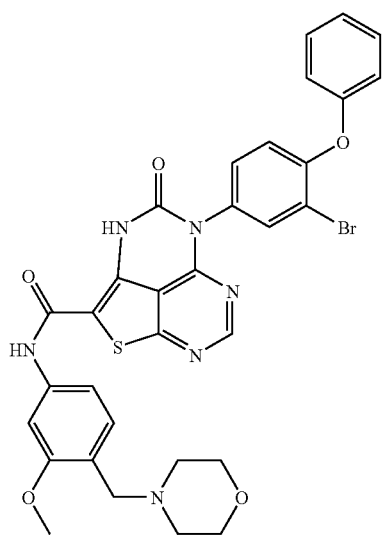
Cpd 190
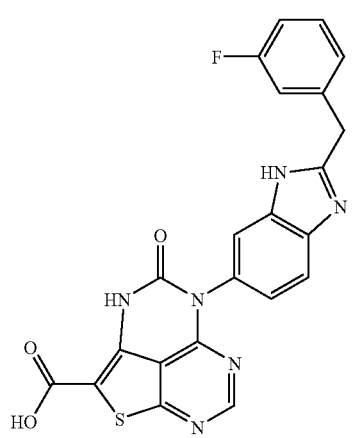
Cpd 191
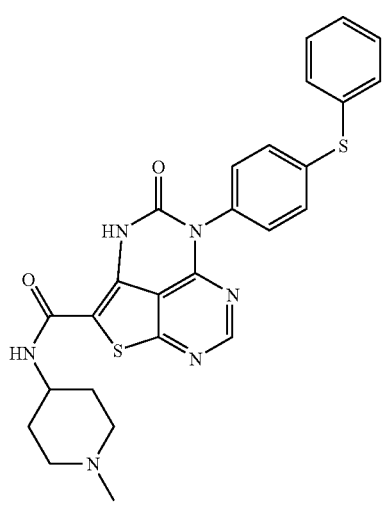
Cpd 192
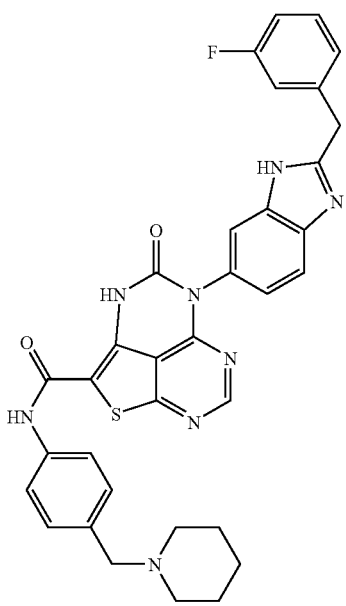
Cpd 193
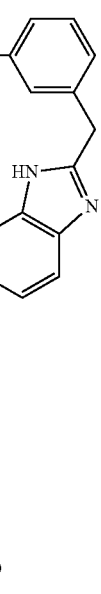

Cpd 194
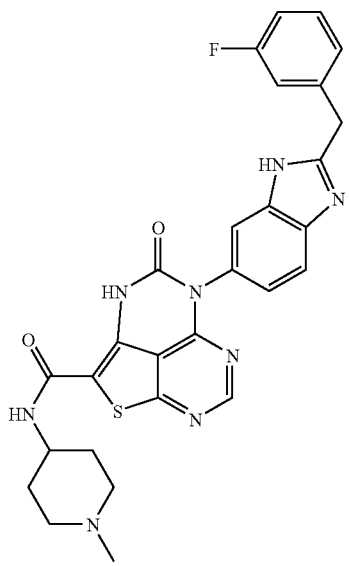
Cpd 195
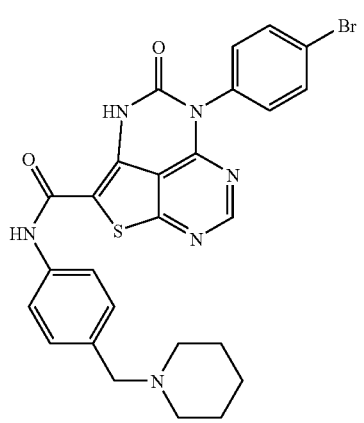
Cpd 196
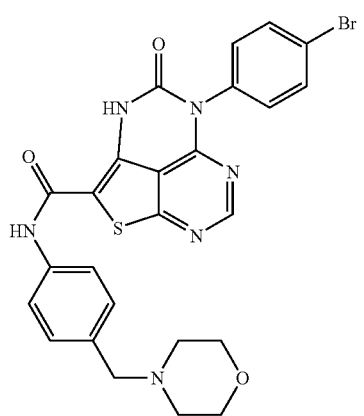
Cpd 197
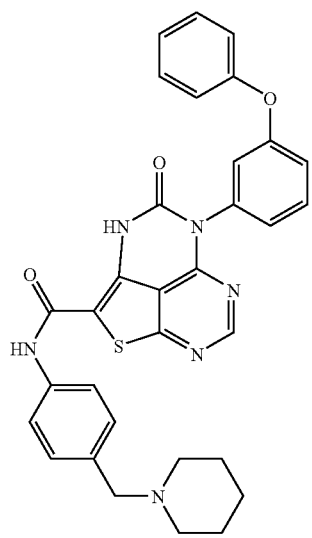
Cpd 198
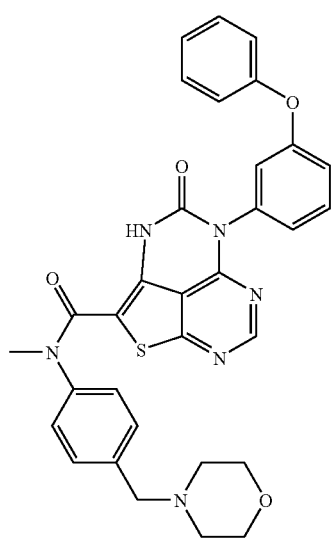
Cpd 199
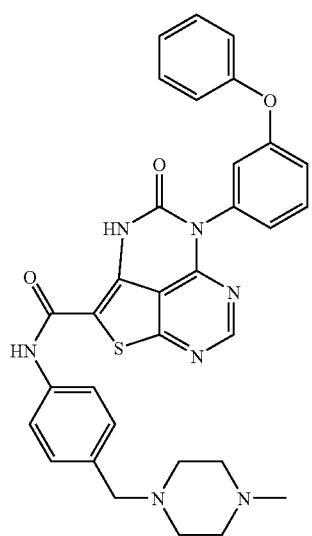

-continued
Cpd 200
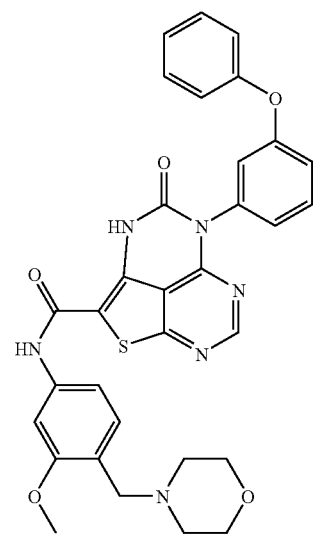
Cpd 201
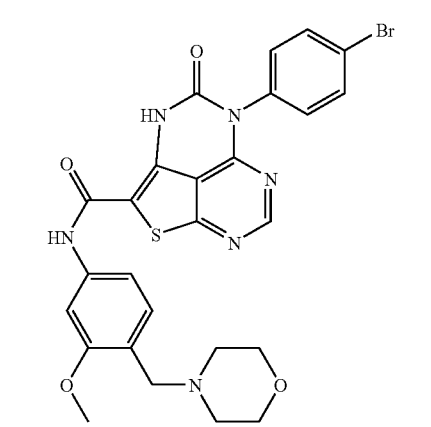
Cpd 202
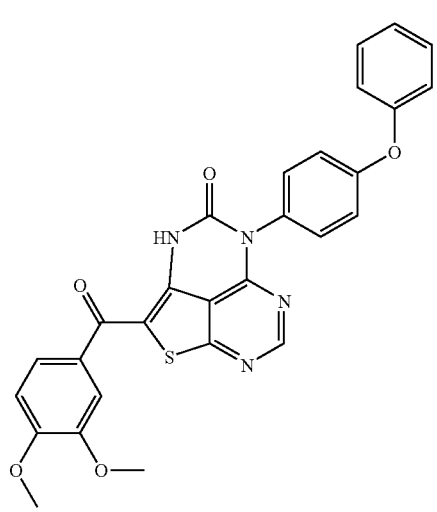
-continued
Cpd 203
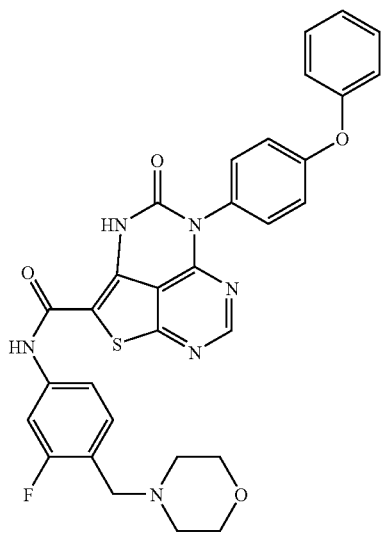
Cpd 204
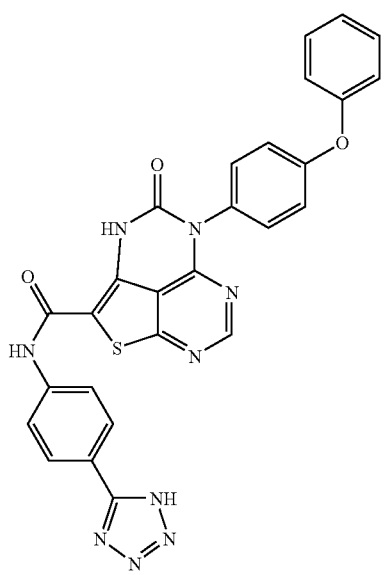
Cpd 205
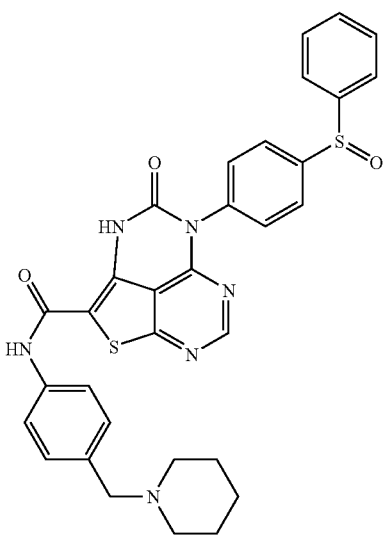

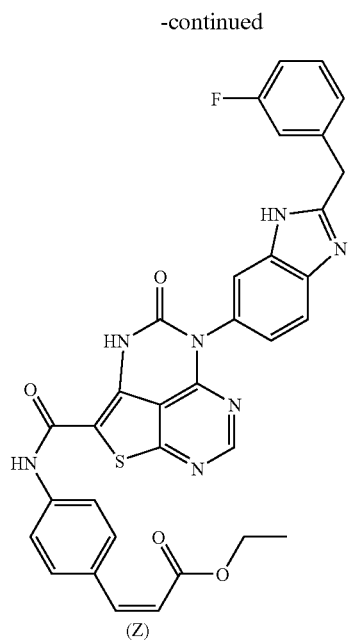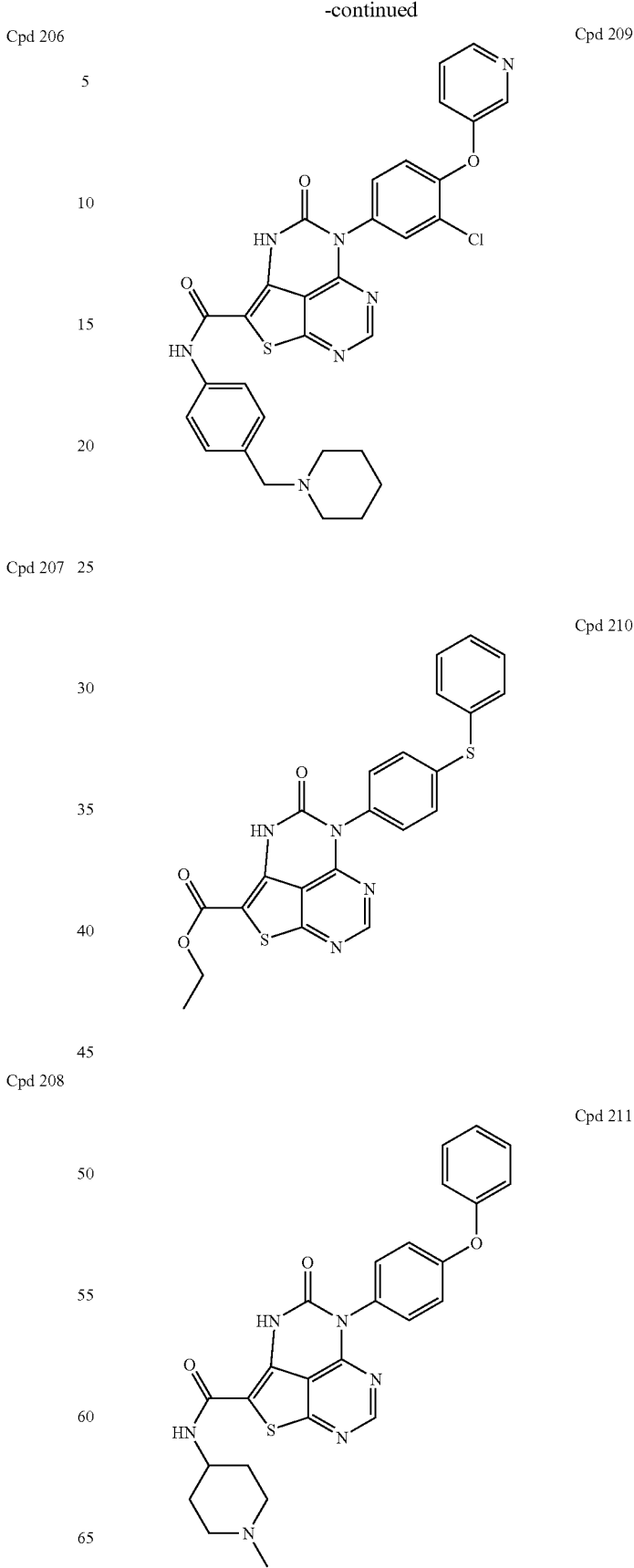

-continued
Cpd 212
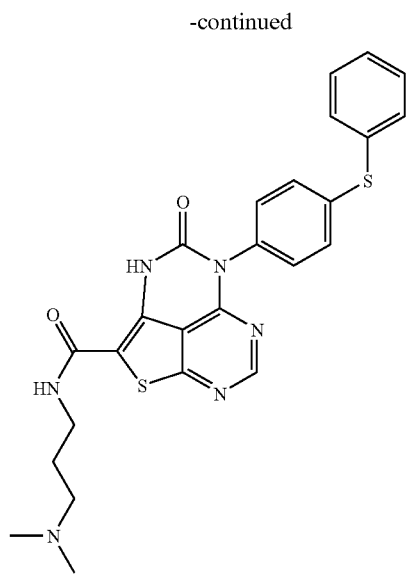
Cpd 213
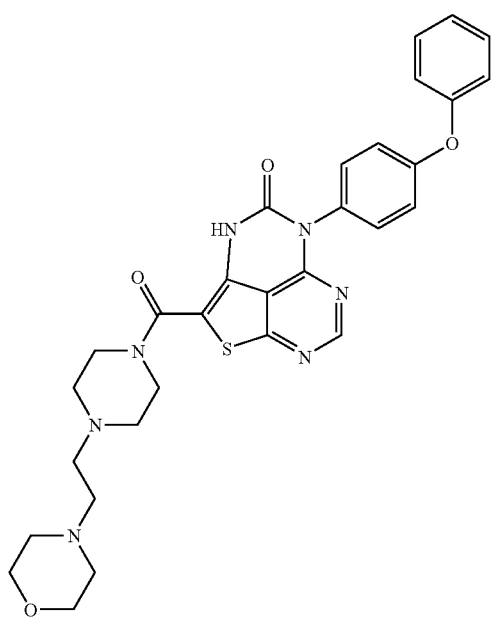
Cpd 214
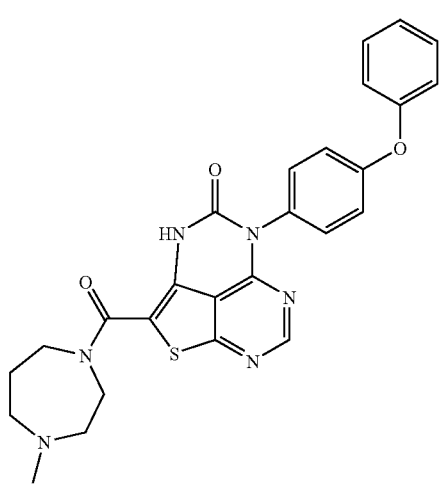
-continued
Cpd 215
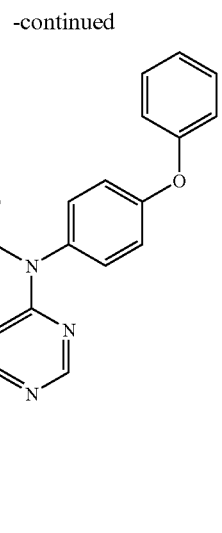
Cpd 216
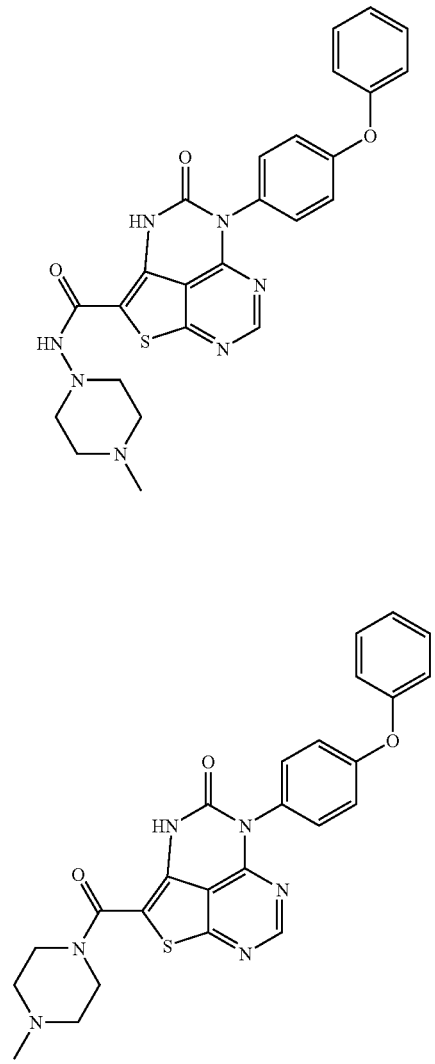
Cpd 217
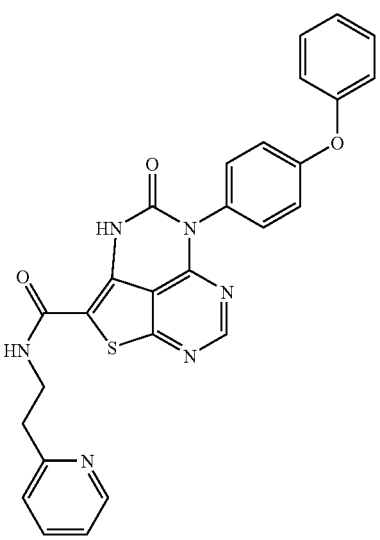

-continued
Cpd 218
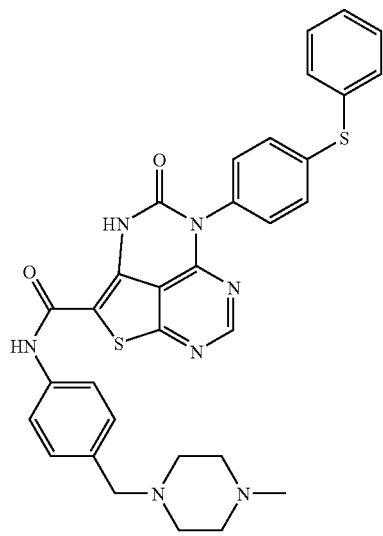
Cpd 219
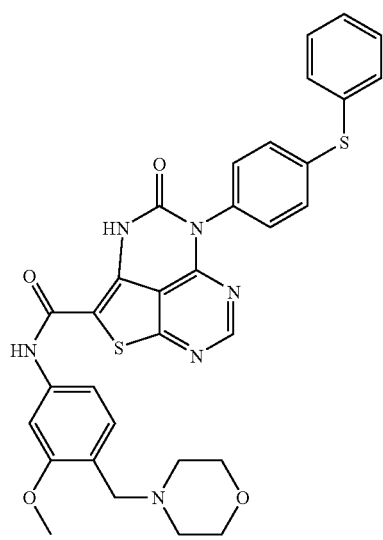
-continued
Cpd 220
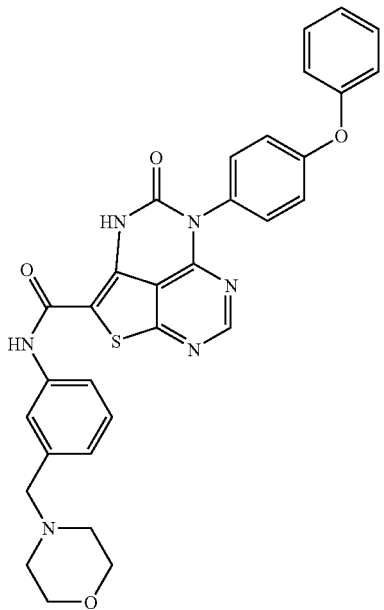
Cpd 221
Cpd 222
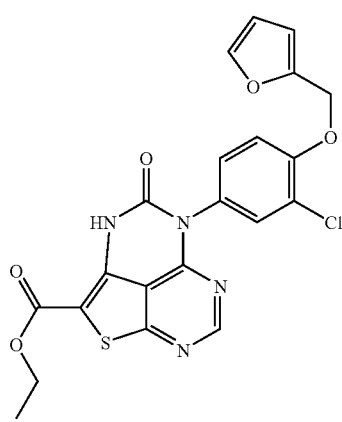

-continued
Cpd 223
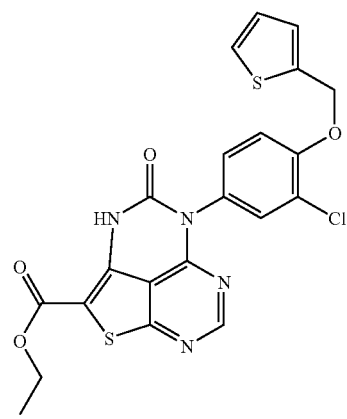
Cpd 224
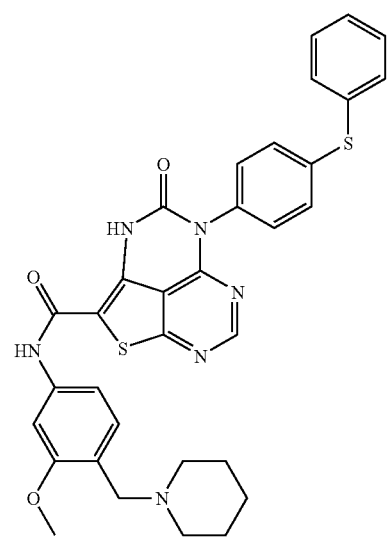
Cpd 225
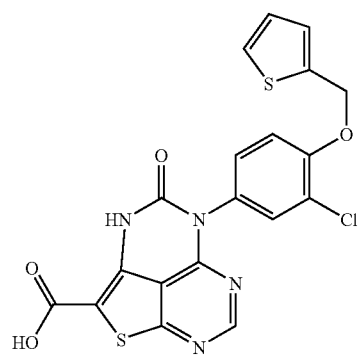
-continued
Cpd 226
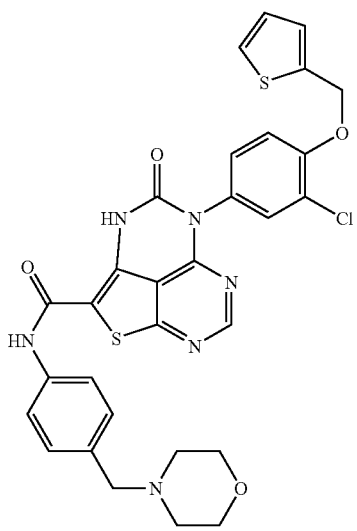
Cpd 227
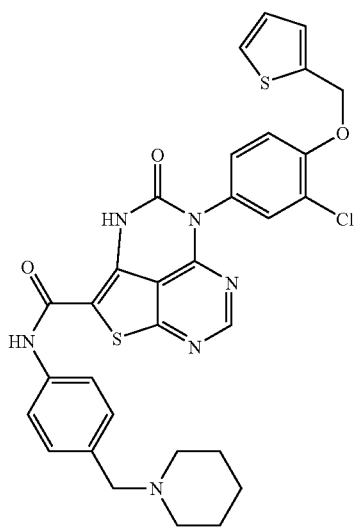
Cpd 228
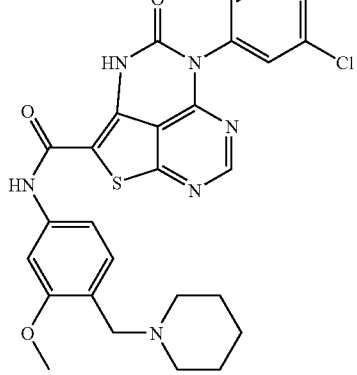

-continued
Cpd 229
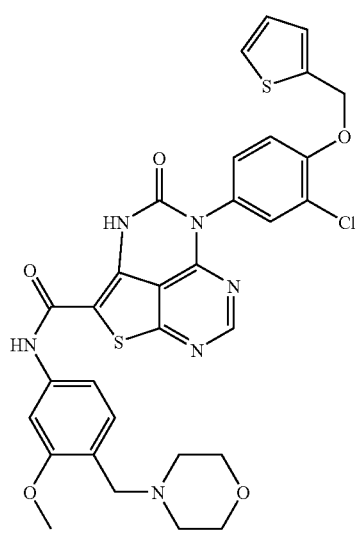
Cpd 230
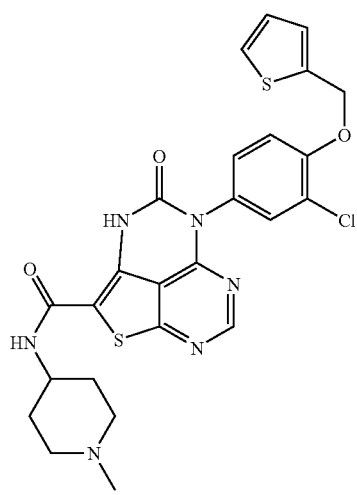
Cpd 231
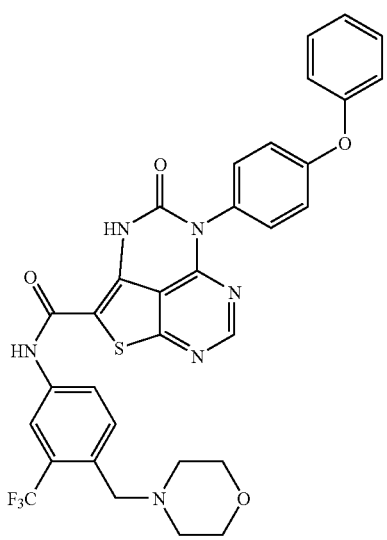
-continued
Cpd 232
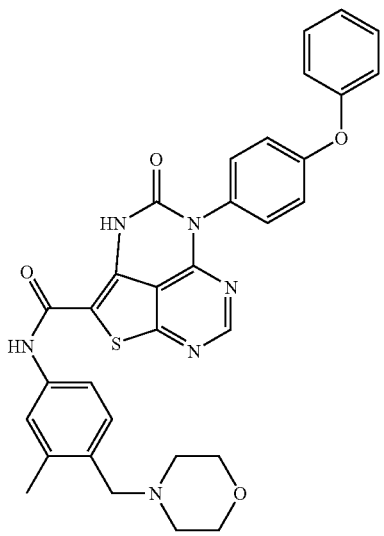
Cpd 233
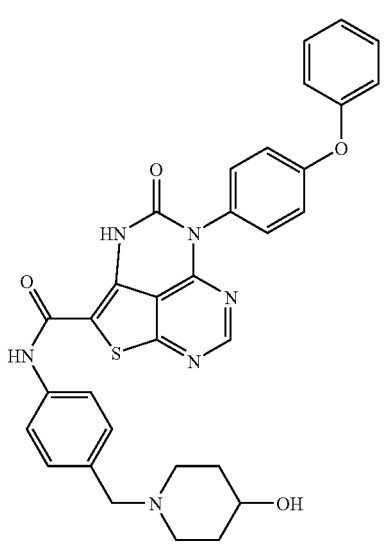
Cpd 234
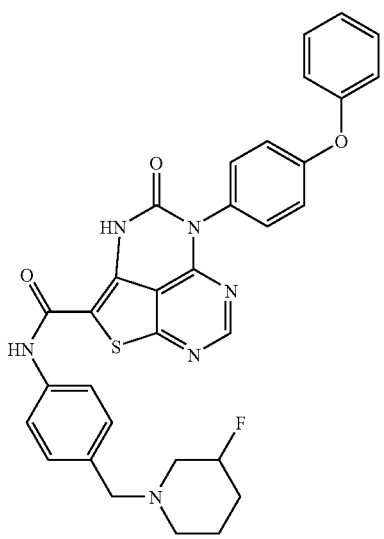

-continued
Cpd 235
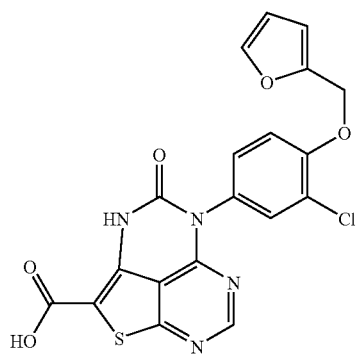
Cpd 236
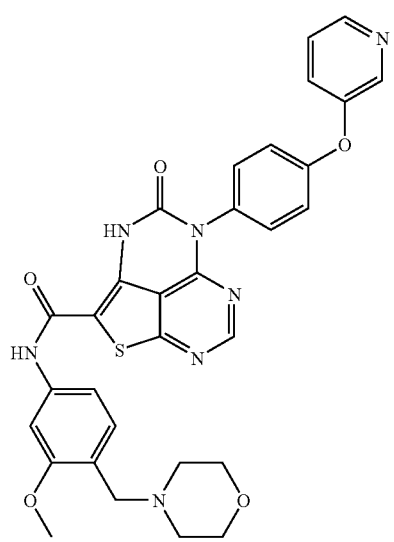
Cpd 237
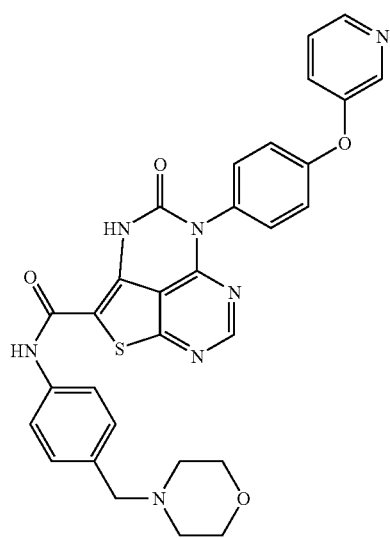
-continued
Cpd 238
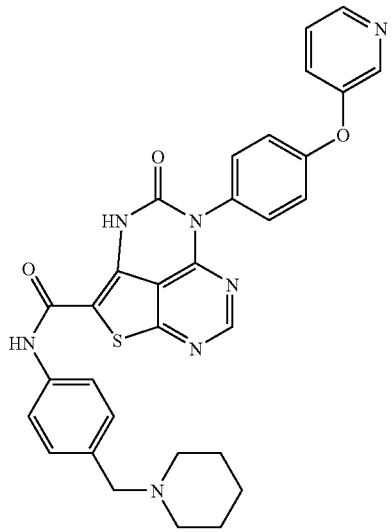
Cpd 239
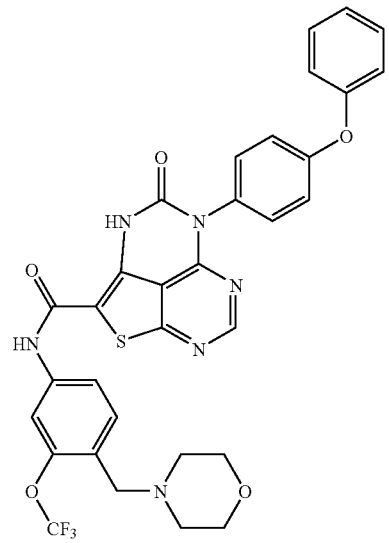
Cpd 240
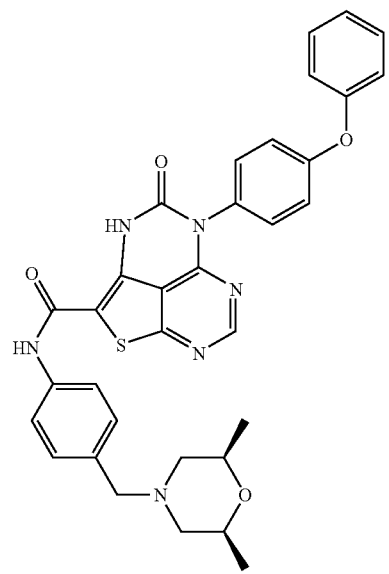

-continued
Cpd 241
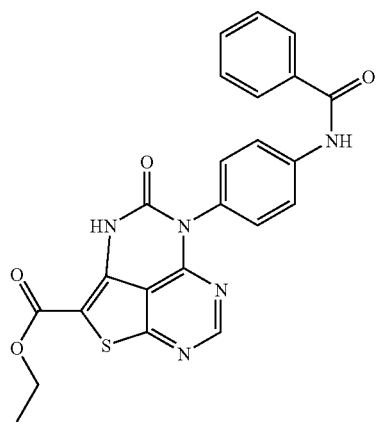
Cpd 242
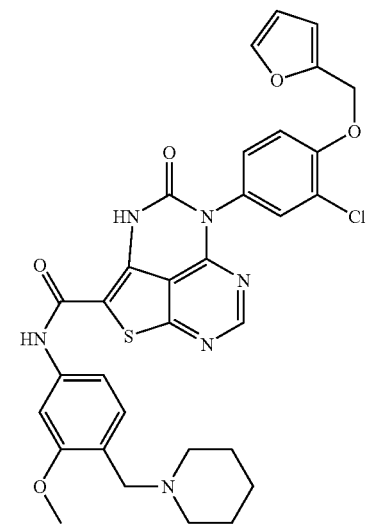
Cpd 243
-continued
Cpd 244
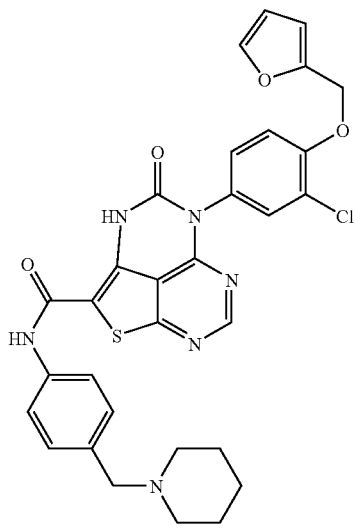
Cpd 245
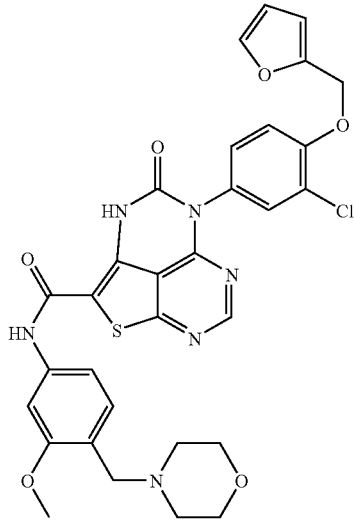
Cpd 246

-continued
Cpd 247
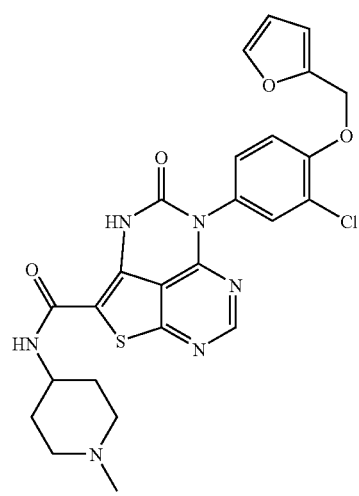
Cpd 248
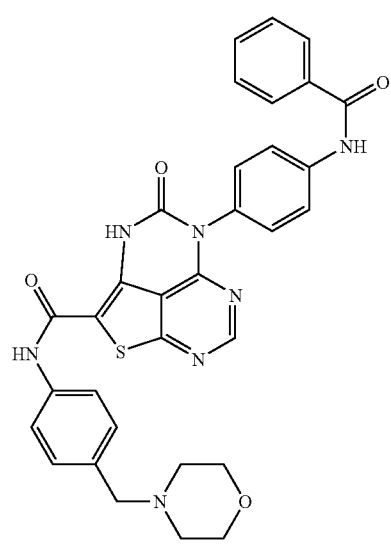
Cpd 249
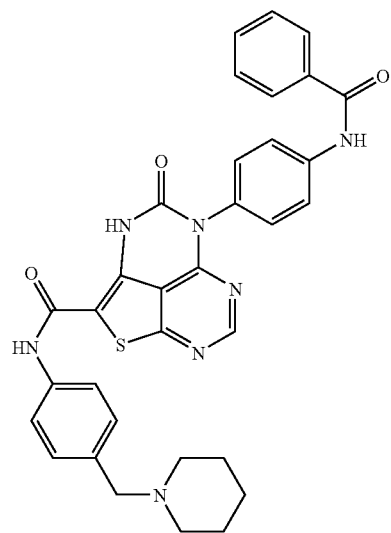
-continued
Cpd 250
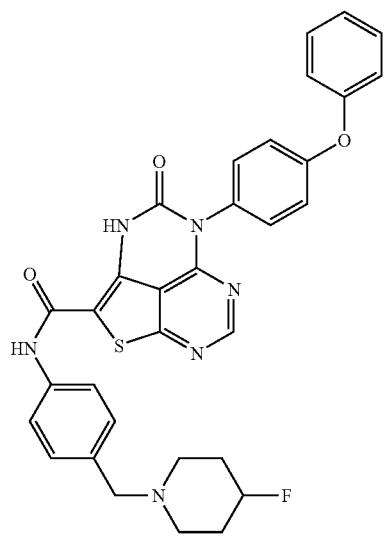
Cpd 251
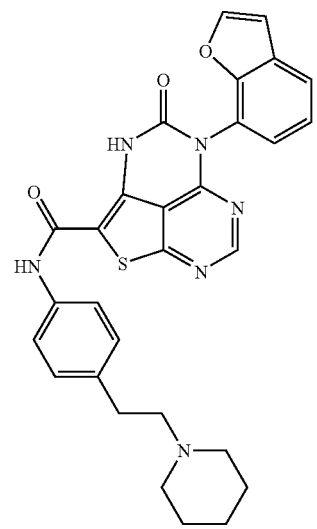
Cpd 252
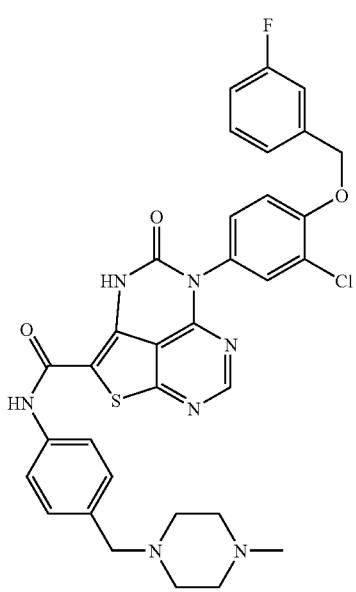

Cpd 253
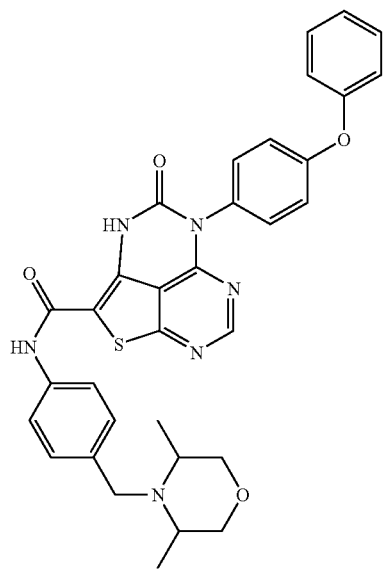
Cpd 256
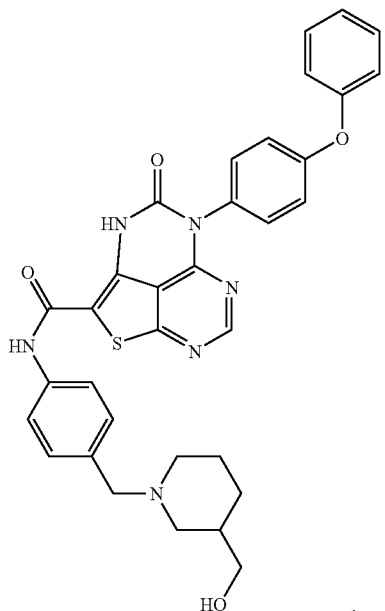
Cpd 254
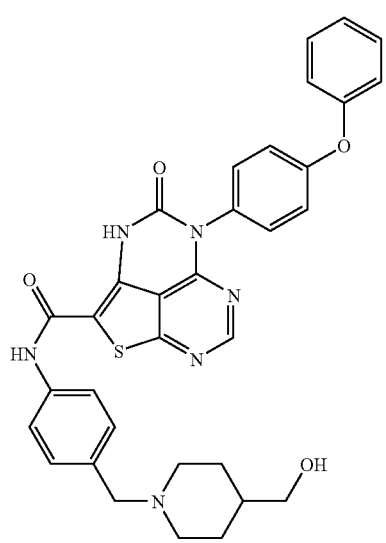
Cpd 257
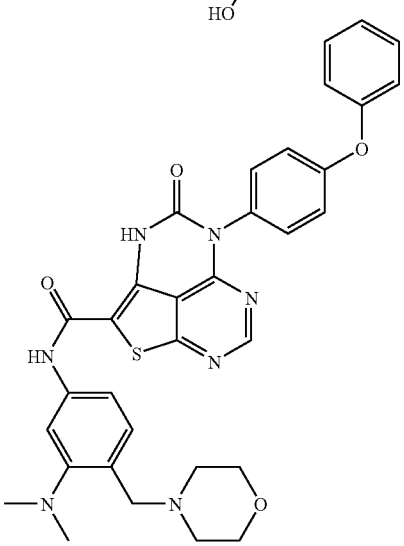
Cpd 255
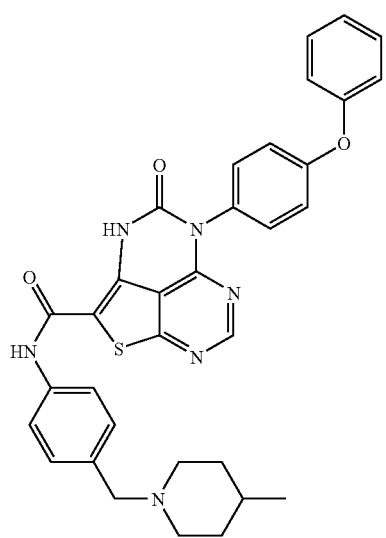
Cpd 258
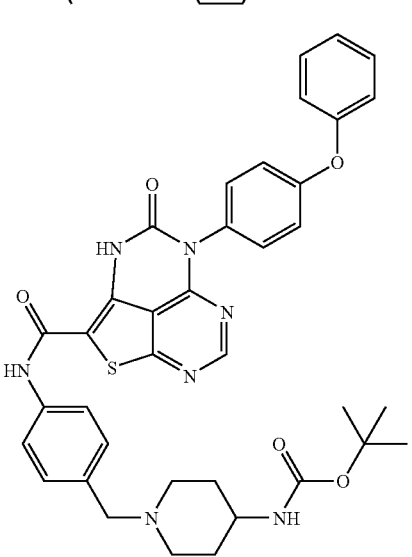

Cpd 259

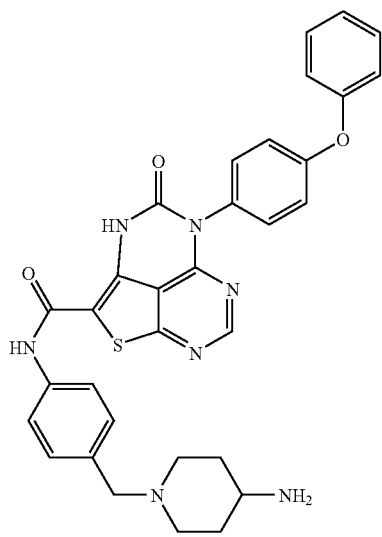

Cpd 260

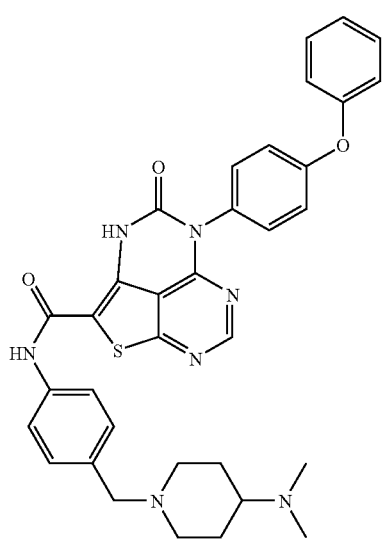

Cpd 261

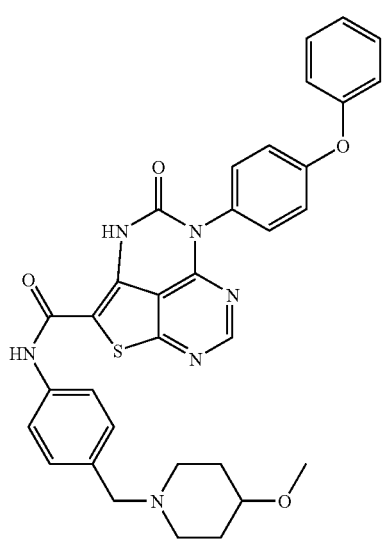

Cpd 262

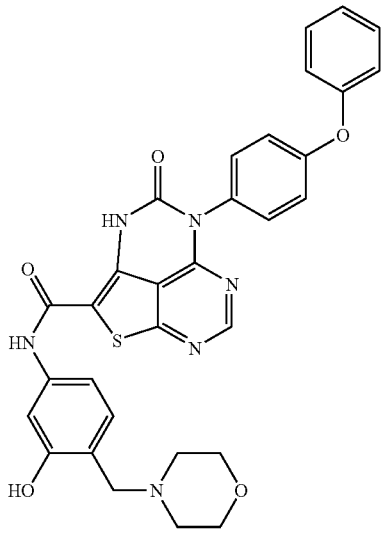

Cpd 263

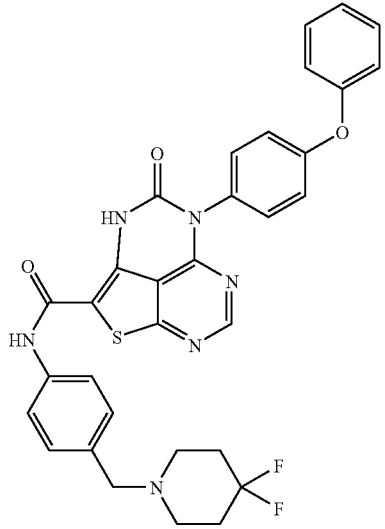

Cpd 264

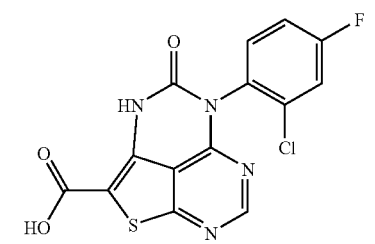

and pharmaceutically acceptable forms thereof.

Chemical Definitions & Nomenclature

Bond lines drawn into a ring system from a substituent variable indicate that the substituent may be attached to any of the substitutable ring atoms.

As used herein, the following terms are intended to have the following definitions. The definitions herein may specify that a chemical term has an indicated formula. The particular formula provided is not intended to limit the scope of the invention, but is provided as an illustration of the term. The scope of the per se definition of the term is intended to include the plurality of variations expected to be included by one of ordinary skill in the art.

The term "$C_{1-8}$alkyl" means a saturated aliphatic branched or straight-chain hydrocarbon radical or linking group having from 1-8 carbon atoms in a linear or branched arrangement, wherein the radical is derived by the removal of one hydrogen atom from a carbon atom and the linking group is derived by the removal of one hydrogen atom from each of two carbon atoms in the chain. The term "$C_{1-8}$alkyl" also includes a "$C_{1-6}$alkyl" and "$C_{1-4}$alkyl" radical or linking group having from 1 up to 6 carbon atoms and 1 up to 4 carbon atoms respectively, such as methyl, ethyl, 1-propyl, 2-propyl, 1-butyl, 2-butyl, tert-butyl, 1-pentyl, 2-pentyl, 3-pentyl, 1-hexyl, 2-hexyl, 3-hexyl, 1-heptyl, 2-heptyl, 3-heptyl, 1-octyl, 2-octyl, 3-octyl butyl, pentyl, hexyl and the like. Alkyl radicals or linking groups may be attached to a core molecule via a terminal carbon atom or via a carbon atom within the chain. Similarly, substituent variables may be attached to an alkyl linking group when allowed by available valences.

The term "$C_{2-8}$alkenyl" means an alkyl radical or linking group having from 2-8 carbon atoms in a linear or branched arrangement having at least one carbon-carbon double bond, wherein the double bond is derived by the removal of one hydrogen atom from each of two adjacent carbon atoms in the chain. "$C_{2-8}$alkenyl" includes ethenyl, propenyl and the like.

The term "$C_{2-8}$alkynyl" means an alkyl radical or linking group having from 2-8 carbon atoms in a linear or branched arrangement having at least one carbon-carbon triple bond, wherein the triple bond is derived by the removal of two hydrogen atoms from each of two adjacent carbon atoms in the chain. "$C_{2-8}$alkynyl" includes ethynyl, propynyl and the like.

The term "$C_{1-8}$alkoxy" means an alkyl radical or linking group having from 1-8 carbon atoms in a linear or branched arrangement, wherein the radical or linking group is attached through an oxygen linking atom, as in the formula: —O—$C_{1-8}$alkyl. The term "$C_{1-8}$alkoxy" also includes includes a "$C_{1-6}$alkoxy" and "$C_{1-4}$alkoxy" radical or linking group having from 1 up to 6 carbon atoms and from 1 up to 4 carbon atoms respectively, such as methoxy, ethoxy, propoxy, butoxy and the like. An alkoxy radical or linking group may be attached to a core molecule and further substituted as a linking group where indicated.

The term "$C_{3-12}$cycloalkyl" means a saturated or partially unsaturated monocyclic or polycyclic hydrocarbon ring system radical. The term "$C_{3-12}$cycloalkyl" also includes a $C_{3-8}$cycloalkyl, $C_{3-10}$cycloalkyl, $C_{5-6}$cycloalkyl, $C_{5-8}$cycloalkyl, $C_{5-12}$cycloalkyl, $C_{9-13}$cycloalkyl or benzofused-$C_{3-12}$cycloalkyl ring system radical and the like, such as cyclopropyl, cyclobutyl, cyclopentyl, cyclohexyl, cycloheptyl, cyclooctyl, 1H-indenyl, indanyl, 9H-fluorenyl, 1,2,3,4-tetrahydro-naphthalenyl, acenaphthenyl, adamantanyl and the like. $C_{3-12}$cycloalkyl radicals may be attached to a core molecule and further substituted on any atom when allowed by available valences.

"Aryl" means an aromatic, unsaturated monocyclic or polycyclic cycloalkyl radical. Aryl ring systems include phenyl, naphthalenyl, azulenyl, anthracenyl and the like. Aryl radicals may be attached to a core molecule and further substituted on any atom when allowed by available valences.

"Hetero," when used as a prefix for a ring system, refers to the replacement of at least one carbon atom member in the ring system with a heteroatom selected from N, O, S, S(O), or $SO_2$. A hetero ring may have 1, 2, 3, or 4 carbon atom members replaced by a nitrogen atom. Alternatively, a ring may have 0, 1, 2, or 3 nitrogen atom members and 1 oxygen or sulfur atom member. Alternatively, up to two adjacent ring members may be heteroatoms, wherein one heteroatom is nitrogen and the other heteroatom is selected from N, S, or O.

"Heterocyclyl" means a saturated or partially unsaturated monocyclic or polycyclic "hetero" ring system radical having a cycloalkyl ring as the core molecule. Heterocyclyl ring systems include 2H-pyrrole, 2-pyrrolinyl, 3-pyrrolinyl, pyrrolidinyl, 1,3-dioxolanyl, 2-imidazolinyl (also referred to as 4,5-dihydro-1H-imidazolyl), imidazolidinyl, 2-pyrazolinyl, pyrazolidinyl, tetrazolyl, tetrazolidinyl, piperidinyl, 1,4-dioxanyl, morpholinyl, 1,4-dithianyl, thiomorpholinyl, piperazinyl, azetidinyl, azepanyl, hexahydro-1,4-diazepinyl, hexahydro-1,4-oxazepinyl, tetrahydro-furanyl, tetrahydro-thienyl, tetrahydro-pyranyl, tetrahydro-pyridazinyl and the like. The term "heterocyclyl" also includes a benzofused-heterocyclyl ring system radical and the like, such as indolinyl (also referred to as 2,3-dihydro-indolyl), benzo[1,3]dioxolyl (also referred to as 1,3-benzodioxolyl), 2,3-dihydro-1,4-benzodioxinyl, 2,3-dihydro-benzofuranyl, 1,2-dihydro-phthalazinyl and the like. Heterocyclyl radicals may be attached to a core molecule and further substituted on any atom when allowed by available valences.

"Heteroaryl" means an aromatic monocyclic or polycyclic unsaturated heterocyclyl radical. Heteroaryl ring systems include furyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl, pyrazinyl and the like. Heteroaryl radicals may be attached to a core molecule and further substituted on any atom when allowed by available valences.

The term "heteroaryl" also includes a benzofused-heteroaryl ring system radical and the like, such as indolizinyl, indolyl, azaindolyl, isoindolyl, benzo[b]furyl, benzo[b]thienyl, indazolyl, azaindazolyl, benzoimidazolyl, benzothiazolyl, benzooxazolyl, benzoisoxazolyl, benzothiadiazolyl, benzotriazolyl, purinyl, 4H-quinolizinyl, quinolinyl, isoquinolinyl, Clnnolinyl, phthalzinyl, quinazolinyl, quinoxalinyl, 1,8-naphthyridinyl, pteridinyl and the like. Benzofused-heteroaryl radicals may be attached to a core molecule and further substituted on any atom when allowed by available valences.

The term "benzofused," when used as a prefix for a ring system, refers to a radical formed by any monocyclic radical fused with a benzene ring; the benzofused radical may be attached to a core molecule via either ring of the bicyclic system.

The term "$C_{1-8}$alkoxy-$C_{1-8}$alkyl" means a radical of the formula: —$C_{1-8}$alkyl-O—$C_{1-8}$alkyl.

The term "$C_{1-8}$alkoxy-$C_{1-8}$alkoxy" means a radical of the formula: —O—$C_{1-8}$alkyl-O—$C_{1-8}$alkyl.

The term "amino-$C_{1-8}$alkyl" means a radical of the formula: —$C_{1-8}$alkyl-$NH_2$.

The term "$C_{1-8}$alkyl-amino-$C_{1-8}$alkyl" means a radical of the formula: —$C_{1-8}$alkyl-NH—$C_{1-8}$alkyl or —$C_{1-8}$alkyl-N($C_{1-8}$alkyl)$_2$, optionally substituted on one or more of the alkyl portions of the radical.

The term "amino" means a radical of the formula: —$NH_2$.

The term "amino-$C_{1-8}$alkoxy-$C_{1-8}$alkyl" means a radical of the formula: —$C_{1-8}$alkyl-O—$C_{1-8}$alkyl-$NH_2$.

The term "$C_{1-8}$alkyl-amino-$C_{1-8}$alkoxy-$C_{1-8}$alkyl" means a radical of the formula: —$C_{1-8}$alkyl-O—$C_{1-8}$alkyl-NH—$C_{1-8}$alkyl or —$C_{1-8}$alkyl-O—$C_{1-8}$alkyl-N($C_{1-8}$alkyl)$_2$, optionally substituted on one or more of the alkyl portions of the radical.

The term "$C_{1-8}$alkoxy-carbonyl-amino-$C_{1-8}$alkyl" means a radical of the formula: —$C_{1-8}$alkyl-NH—C(O)—O—$C_{1-8}$alkyl or —$C_{1-8}$alkyl-N[C(O)—O—$C_{1-8}$alkyl]$_2$.

The term "$C_{1-8}$alkoxy-carbonyl" means a radical of the formula: —C(O)—O—$C_{1-8}$alkyl.

The term "$C_{1-8}$alkoxy-carbonyl-amino" means a radical of the formula: —NH—C(O)—O—$C_{1-8}$alkyl or —N[C(O)—O—$C_{1-8}$alkyl]$_2$.

The term "$C_{1-8}$alkyl-amino" means a radical of the formula: —NH—$C_{1-8}$alkyl or —N($C_{1-8}$alkyl)$_2$.

The term "$C_{3-8}$cycloalkyl-$C_{1-8}$alkyl" means a radical of the formula: —$C_{1-8}$alkyl-$C_{3-8}$cycloalkyl.

The term "heterocyclyl-$C_{1-8}$alkyl" means a radical of the formula: —$C_{1-8}$alkyl-heterocyclyl.

The term "aryl-$C_{1-8}$alkyl" means a radical of the formula: —$C_{1-8}$alkyl-aryl.

The term "heteroaryl-$C_{1-8}$alkyl" means a radical of the formula: —$C_{1-8}$alkyl-heteroaryl.

The term "heterocyclyl-$SO_2$" means a radical of the formula: —$SO_2$-heterocyclyl.

The term "amino-$SO_2$" means a radical of the formula: —$SO_2$—$NH_2$.

The term "halogen" or "halo" means the group chloro, bromo, fluoro or iodo.

The term "halo-$C_{1-8}$alkyl" means a radical of the formula: —$C_{1-8}$alkyl-(halo)$_n$, wherein one or more halogen atoms may be substituted on $C_{1-8}$alkyl when allowed by available valences (wherein n represents that amount of available valences based on the number of carbon atoms in the chain), and includes monofluoromethyl, difluoromethyl, trifluoromethyl, trifluoroethyl and the like.

The term "hydroxy-$C_{1-8}$alkyl" means a radical of the formula: —$C_{1-8}$alkyl-hydroxy, wherein $C_{1-8}$alkyl is substituted on one or more available carbon chain atoms with one or more hydroxy radicals when allowed by available valences.

The term "substituted," refers to a core molecule on which one or more hydrogen atoms have been replaced with one or more functional radical moieties. The number that is allowed by available valences limits the amount of substituents. Substitution is not limited to the core molecule, but may also occur on a substituent radical, whereby the substituent radical becomes a linking group.

"Independently selected" means one or more substituents are selected from a group of substituents in a structure variable group, wherein the selected substituents may be the same or different.

"Dependently selected" means that one or more substituents are specified in an indicated combination of structure variables.

In general, IUPAC nomenclature rules are used herein.

Compound Forms

The term "form" means, in reference to compounds of the present invention, such may exist as, without limitation, a salt, stereoisomer, tautomer, crystalline, polymorph, amorphous, solvate, hydrate, ester, prodrug or metabolite form. The present invention encompasses all such compound forms and mixtures thereof.

The term "isolated form" means, in reference to compounds of the present invention, such may exist in an essentially pure state such as, without limitation, an enantiomer, a racemic mixture, a geometric isomer (such as a cis or trans stereoisomer), a mixture of geometric isomers, and the like. The present invention encompasses all such compound forms and mixtures thereof.

Certain compounds of Formula (I) may exist in various stereoisomeric or tautomeric forms and mixtures thereof. The invention encompasses all such compounds, including active compounds in the form of essentially pure enantiomers, racemic mixtures and tautomers.

The compounds of the invention may be present in the form of pharmaceutically acceptable salts. For use in medicines, the "pharmaceutically acceptable salts" of the compounds of this invention refer to non-toxic acidic/anionic or basic/cationic salt forms.

Pharmaceutically acceptable acidic/anionic salts include the acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate and triethiodide salts.

The compounds of the invention include pharmaceutically acceptable anionic salt forms, wherein the anionic salts include the acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate and triethiodide salts.

The anionic salt form of a compound of the invention includes an anionic salt selected from the acetate, bromide, camsylate, chloride, edisylate, fumarate, hydrobromide, hydrochloride, iodide, isethionate, lactate, mesylate, napsylate, salicylate, sulfate and tosylate salts.

During any of the processes for preparation of the compounds of the invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, 3$^{rd}$ Edition, John Wiley & Sons, 1999. The protecting groups may be removed at a convenient subsequent stage using methods known in the art.

The invention includes compounds of various isomers and mixtures thereof. The term "isomer" refers to compounds that have the same composition and molecular weight but differ in physical and/or chemical properties. Such substances have the same number and kind of atoms but differ in structure. The structural difference may be in constitution (geometric isomers) or in an ability to rotate the plane of polarized light (stereoisomers).

The term "optical isomer" means isomers of identical constitution that differ only in the spatial arrangement of their groups. Optical isomers rotate the plane of polarized light in different directions. The term "optical activity" means the degree to which an optical isomer rotates the plane of polarized light.

The term "racemate" or "racemic mixture" means an equimolar mixture of two enantiomeric species, wherein each of the isolated species rotates the plane of polarized light in the opposite direction such that the mixture is devoid of optical activity.

The term "enantiomer" means an isomer having a nonsuperimposable mirror image. The term "diastereomer" means stereoisomers that are not enantiomers.

The term "chiral" means a molecule which, in a given configuration, cannot be superimposed on its mirror image. This is in contrast to achiral molecules which can be superimposed on their mirror images.

The two distinct mirror image versions of the chiral molecule are also known as levo (left-handed), abbreviated L, or dextro (right-handed), abbreviated D, depending on which way they rotate polarized light. The symbols "R" and "S" represent the configuration of groups around a stereogenic carbon atom(s).

An isolated form of a chiral mixture means those forms that are substantially free of one mirror image molecule. Such substantially pure forms include those wherein one mirror image is present in a range of less than 25% in the mixture, of less than 10%, of less than 5%, of less than 2% or less than 1%.

An example of an enantiomerically enriched form isolated from a racemic mixture includes a dextrorotatory enantiomer, wherein the mixture is substantially free of the levorotatory isomer. In this context, substantially free means the levorotatory isomer may, in a range, comprise less than 25% of the mixture, less than 10%, less than 5%, less than 2% or less than 1% of the mixture according to the formula:

$$\% \text{ levorotatory} = \frac{(\text{mass levorotatory})}{(\text{mass dextrorotatory}) + (\text{mass levorotatory})} \times 100$$

Similarly, an example of an enantiomerically enriched form isolated from a racemic mixture includes a levorotatory enantiomer, wherein the mixture is substantially free of the dextrorotatory isomer. In this context, substantially free means the dextrorotatory isomer may, in a range, comprise less than 25% of the mixture, less than 10%, less than 5%, less than 2% or less than 1% of the mixture according to the formula:

$$\% \text{ dextrorotatory} = \frac{(\text{mass dextrorotatory})}{(\text{mass dextrorotatory}) + (\text{mass levorotatory})} \times 100$$

"Geometric isomer" means isomers that differ in the orientation of substituent atoms in relationship to a carbon-carbon double bond, to a cycloalkyl ring, or to a bridged bicyclic system. Substituent atoms (other than hydrogen) on each side of a carbon-carbon double bond may be in an E or Z configuration. In the "E" configuration, the substituents are on opposite sides in relationship to the carbon-carbon double bond. In the "Z" configuration, the substituents are oriented on the same side in relationship to the carbon-carbon double bond.

Substituent atoms (other than hydrogen) attached to a ring system may be in a cis or trans configuration. In the "cis" configuration, the substituents are on the same side in relationship to the plane of the ring; in the "trans" configuration, the substituents are on opposite sides in relationship to the plane of the ring. Compounds having a mixture of "cis" and "trans" speCies are designated "cis/trans".

The isomeric descriptors ("R," "S," "E," and "Z") indicate atom configurations relative to a core molecule and are intended to be used as defined in the literature.

The compounds of the invention may be prepared as individual isomers by either isomer-specific synthesis or resolved from an isomeric mixture. Conventional resolution techniques include combining the free base (or free acid) of each isomer of an isomeric pair using an optically active acid (or base) to form an optically active salt (followed by fractional crystallization and regeneration of the free base), forming an ester or amide of each of the isomers of an isomeric pair by reaction with an appropriate chiral auxiliary (followed by fractional crystallization or chromatographic separation and removal of the chiral auxiliary), or separating an isomeric mixture of either an intermediate or a final product using various well known chromatographic methods.

Furthermore, compounds of the invention may have at least one crystalline, polymorph or amorphous form. The plurality of such forms are included in the scope of the invention. In addition, some of the compounds may form solvates with water (i.e., hydrates) or common organic solvents (e.g., organic esters such as ethanolate and the like). The plurality of such solvates are also intended to be encompassed within the scope of this invention.

Methods of Use

The compounds of Formula (I) are inhibitors of a protein kinase such as EGFR, HER-2, HER-4, c-Src, Lyn or c-Abl, having an $IC_{50}$ (50% inhibition concentration) or an $EC_{50}$ (50% effective concentration) in a range of about 50 µM or less, of about 25 µM or less, of about 15 µM or less, of about 10 µM or less, of about 5 µM or less, of about 1 µM or less, of about 0.5 µM or less, of about 0.25 µM or less or of about 0.1 µM or less.

The present invention includes a compound of Formula (I) and forms thereof as a protein kinase inhibitor, wherein the protein kinase is selected from EGFR, HER-2, HER-4, c-Src, Lyn or c-Abl.

The present invention includes a prodrug of a compound of Formula (I) and forms thereof as a protein kinase inhibitor.

The present invention includes a metabolite of a compound of Formula (I) and forms thereof as a protein kinase inhibitor.

The present invention includes an isolated form of a compound of Formula (I) and forms thereof as a protein kinase inhibitor.

The present invention includes use of a compound of Formula (I) and forms thereof as an inhibitor of a protein kinase such as EGFR, HER-2, HER-4, c-Src, Lyn or c-Abl comprising contacting the protein kinase domain or receptor with one or more compounds of Formula (I).

The use of a compound of Formula (I) and forms thereof also includes inhibiting increased or unregulated protein kinase expression or signaling leading to unregulated cell proliferation comprising contacting a protein kinase receptor with one or more compounds of Formula (I).

The use of a compound of Formula (I) and forms thereof further comprises inhibiting the unregulated expression of a protein kinase such as EGFR, HER-2, HER-4, c-Src, Lyn, or c-Abl and the like.

The use of a compound of Formula (I) and forms thereof further includes use as a therapeutic agent for treating or preventing a chronic or acute kinase mediated disease in a subject in need thereof comprising administering to the subject an effective amount of a compound of Formula (I) and forms thereof.

The use as a therapeutic agent includes administering to the subject an effective amount of a compound of Formula (I) and forms thereof as a pharmaceutical composition, medicine or medicament. Consequently, the invention encompasses the use of the compound of Formula (I) as a medicine or medicament.

The use as a therapeutic agent includes for treating or preventing a chronic or acute disease mediated by a tyrosine-kinase selected from EGFR, HER-2, HER-4, c-Src, Lyn or c-Abl.

The use as a therapeutic agent includes inhibiting the effects of unregulated kinase activity, expression or signaling in a subject in need thereof comprising administering to the subject an effective amount of a compound of Formula (I) and forms thereof.

The use as a therapeutic agent includes inhibiting the effects of unregulated activity, expression or signaling of a tyrosine-kinase selected from EGFR, HER-2, HER-4, c-Src, Lyn or c-Abl.

The use as a therapeutic agent includes treating or preventing a chronic or acute kinase mediated cancer in a subject in need thereof comprising administering to the subject an effective amount of a compound of Formula (I) and forms thereof.

The use as a therapeutic agent includes suppressing a chronic or acute tumor associated with non-small-cell lung cancers, colon cancers, breast cancers and the like wherein the cancer is mediated by a tyrosine-kinase selected from EGFR, HER-2, HER-4, c-Src, Lyn or c-Abl.

The use as a therapeutic agent also includes treating or preventing chronic unregulated cell proliferation whereby cancer remission is induced in the subject.

The use as a therapeutic agent includes treating or preventing chronic or acute kinase mediated diseases characterized by unregulated cell proliferation or metastatic cancer cell invasion and migration.

The present invention includes use of a compound of Formula (I) and forms thereof as a marker, wherein the compound is labeled with a ligand for use as a marker, and wherein the ligand is a radioligand (selected from deuterium, tritium and the like).

The present invention includes the use of a compound of Formula (I) and forms thereof for the manufacture of a medicament for treating any of the above mentioned conditions.

Any of the foregoing uses of a compound of Formula (I) and forms thereof further includes the use of a prodrug or metabolite of a compound of Formula (I) and forms thereof.

The present invention is also directed to a method for treating, preventing or ameliorating a chronic or acute protein kinase mediated disease, disorder or condition in a subject in need thereof comprising administering to the subject an effective amount of a compound of Formula (I) and forms thereof.

The method of the present invention further comprises treating, preventing or ameliorating a chronic or acute EGFR, HER-2, HER-4, c-Src, Lyn or c-Abl mediated disease, disorder or condition in the subject.

The method also comprises treating, preventing or ameliorating viral infection by an EGFR kinase mediated cytomegalovirus in the subject.

The chronic or acute kinase mediated disease, disorder or condition also includes an EGFR kinase mediated head or brain cancer in the subject, wherein the compound of Formula (I) and forms thereof penetrates the blood brain barrier.

The method further comprises treating or ameliorating nerve damage and promoting axon regeneration subsequent to a brain or spinal cord injury in the subject, wherein the compound of Formula (I) and forms thereof is an EGFR inhibitor.

The method also includes administering the compound of Formula (I) and forms thereof as an adjunct to chemotherapy and radiation therapy.

The term "chronic or acute kinase mediated disorder" as used herein, includes, and is not limited to disorders and diseases associated with unregulated kinase activity and conditions that accompany such activity.

The term "unregulated kinase activity" refers to 1) increased or unregulated kinase expression or signaling, 2) increased kinase expression leading to unregulated cell proliferation, 3) increased kinase signalling leading to unregulated cell proliferation, or 4) mutations leading to constitutive kinase activation. The existence of unregulated kinase activity may be determined by procedures well known in the art.

The term "unregulated cell proliferation" refers to cell proliferation of one or more subset of cells in a multicellular organism resulting in harm (such as discomfort or decreased life expectancy) to the multicellular organism.

Tumor cells which result from unregulated cell proliferation use many mechanisms to enhance their survival and spread and often have high rates of proliferation because growth control signals that keep normal cells in check are defective. Many tumor cells secrete autocrine growth factors that increase proliferation rates or they induce other cells to secrete growth factors that they utilize.

Tumor cells grow and spread by dislodging from a primary tumor site, using proteases to digest the extracellular matrix, spreading in response to migration cues, allowing them to migrate to certain tissues preferentially where overexpressed adhesion molecules allow attachment and growth at the new site. The totality of these and other biological processes are responsible for the lethal effects of a tumor. A kinase inhibitor may affect one or more aspects of tumor survival mechanisms and thus be therapeutically useful. Alternatively, a kinase inhibitor may not affect one particular tumor survival mechanism but may still be therapeutically useful by affecting tumor survival by an unknown or as yet unelucidated mechanism of action.

The foregoing methods contemplate that the compounds of the present invention are therapeutically useful for treating, preventing or ameliorating diseases disorders or conditions such as, without limitation, osteoarthritis, rheumatoid arthritis, synovial pannus invasion in arthritis, multiple sclerosis, myasthenia gravis, diabetes mellitus, diabetic angiopathy or retinopathy, retinal vessel proliferation, inflammatory bowel disease, Crohn's disease, ulcerative colitis, bone diseases, transplant or bone marrow transplant rejection, lupus, chronic pancreatitis, cachexia, septic shock, fibroproliferative and differentiative skin diseases or disorders (such as papilloma formation, psoriasis, dermatitis, eczema, seborrhea and the like), central nervous system diseases (such as Alzheimer's disease, Parkinson's disease, depression and the like), neurodegenerative diseases, disorders or conditions related to nerve damage and axon degeneration subsequent to a brain or spinal cord injury, acute or chronic cancers (such as glioma cancers, epidermoid cancers, head and neck cancers, lung cancers, breast cancers, colorectal cancers, prostate cancers, gastric cancers, esophageal cancers or papillocarcinomas and the like and associated pathologies such as unregulated cell proliferation, tumor growth or vascularization or metastatic cancer cell invasion and migration and the like or leukemias or lymphomas), occular diseases (such as macular degeneration, diseases of the cornea, glaucoma and the like), viral infections (such as cytomegalovirus), heart disease (such as atherosclerosis, neointima formation or transplantation-induced vasculopathies (such as restenosis and the like), lung or pulmonary diseases (such as allergic-asthma, lung fibrosis or complications resulting from chronic obstructive pulmonary disorder and the like) or kidney or renal diseases (such as acute, subacute or chronic forms of glomerulonephritis or membranoproliferative glomerulonephritis, glomerulosclerosis, congenital multicystic renal dysplasia, kidney fibrosis and the like).

Certain diseases, disorders or conditions further include, without limitation, acute or chronic cancer selected from bladder cancer, brain, head or neck cancer, breast cancer, colorectal cancer, endometrial cancer, epidermoid cancer, esophageal cancer, gastric cancer, glioma cancer, lung cancer, ovarian cancer, pancreatic cancer, prostate cancer, renal cell cancer, Kaposi's sarcoma, leukemia, lymphoma or papillocarcinoma; and, cancer-associated pathologies selected from abnormal cell proliferation, unregulated cell proliferation, tumor growth, tumor angiopathy, tumor angiogenesis, tumor vascularization or metastatic cancer cell invasion and migration.

Certain diseases, disorders or conditions further include, without limitation, fibroproliferative and differentiative skin diseases or disorders selected from papilloma formation, psoriasis, dermatitis, eczema, seborrhea or chemotherapy-induced alopecia; central nervous system diseases selected from Alzheimer's disease, Parkinson's disease or depression; occular diseases selected from macular degeneration, diseases of the cornea or glaucoma; viral infections selected from mycotic infection, autoimmune disease or cytomegalovirus; heart disease selected from atherosclerosis, neointima formation or transplantation-induced vasculopathies such as arterial restenosis; lung or pulmonary diseases selected from allergic-asthma, lung fibrosis, pulmonary fibrosis or chronic obstructive pulmonary disorder; and, kidney or renal diseases selected from acute, subacute or chronic forms of glomerulonephritis or membranoproliferative glomerulonephritis, glomerulosclerosis, congenital multicystic renal dysplasia or kidney fibrosis.

Certain HER1 kinase mediated cancer includes, without limitation, bladder cancer, brain, head or neck cancer, breast cancer, cervical cancer, colorectal cancer, gastric cancer, glioma cancer, endometrial cancer, esophageal cancer, lung cancer, ovarian cancer, pancreatic cancer or renal cell cancer.

Certain HER2 kinase mediated cancer includes, without limitation, bladder cancer, brain, head or neck cancer, breast cancer, colorectal cancer, gastric cancer, endometrial cancer, esophageal cancer, lung cancer, ovarian cancer, prostate cancer or renal cell cancer.

The term "administering," with respect to the methods of the present invention, refers to a means for treating, ameliorating or preventing a disease, disorder or syndrome as described herein with a compound specifically disclosed or a compound or prodrug thereof, which would obviously be included within the scope of the invention albeit not specifically disclosed for certain of the instant compounds.

Such methods include therapeutically administering an effective amount of one or more compounds of Formula (I) or a composition or medicament thereof at different times during the course of a therapy or concurrently in a combination form. Such methods further include therapeutically administering an effective amount of one or more compounds of Formula (I) with one or more therapeutic agents at different times during the course of a therapy or concurrently in a combination form.

The term "prodrug" refers to a metabolic precursor of a compound of Formula (I) or pharmaceutically acceptable form thereof. In general, a prodrug is a functional derivative of a compound which may be inactive when administered to a subject but is readily convertible in vivo into an active metabolite compound.

The term "active metabolite" refers to a metabolic product of a compound that is pharmaceutically acceptable and effective. Conventional procedures for the selection and preparation of suitable prodrug derivatives are described, for example, in "Design of Prodrugs", ed. H. Bundgaard, Elsevier, 1985.

The term "subject" as used herein, refers to a patient, such as an animal, preferably a mammal, most preferably a human, who has been the object of treatment, observation or experiment and is at risk of (or susceptible to) developing a disease or disorder or having a disease or disorder related to unregulated kinase activity.

The term "effective amount" refers to that amount of active compound or pharmaceutical agent that elicits the biological or medicinal response (such as inhibiting activation of unregulated kinase activity) in a tissue system, animal or human, that is being sought by a researcher, veterinarian, medical doctor, or other clinician, which includes alleviation of the symptoms of the disease or disorder being treated. The effective amount of a compound of Formula (I) exemplified in such a method is from about 0.001 mg/kg/day to about 300 mg/kg/day or has an $IC_{50}$ (50% inhibition concentration) of about 25 µM or less, or about 10 µM or less, preferably of about 1 µM or less, more preferably of about 0.5 µM or less, and most preferably of about 0.1 µM or less.

The term "composition" refers to a product containing a compound of the present invention (such as a product comprising the specified ingredients in the specified amounts, as well as any product which results, directly or indirectly, from such combinations of the specified ingredients in the specified amounts).

The term "medicament" refers to a product for use in treating or ameliorating a kinase mediated disorder or condition.

The term "pharmaceutically acceptable" refers to molecular entities and compositions that are of sufficient purity and quality for use in the formulation of a composition or medicament of the present invention and that, when appropriately administered to an animal or a human, do not produce an adverse, allergic or other untoward reaction. Since both human use (clinical and over-the-counter) and veterinary use are equally included within the scope of the present invention, a pharmaceutically acceptable formulation would include a composition or medicament for either human or veterinary use.

The term "combination form" refers to the use of a combination product comprising a compound of Formula (I) or a form, pharmaceutical composition, medicine or medicament thereof in combination with at least one therapeutic agent for treating, preventing or ameliorating a chronic or acute protein kinase mediated disease, disorder or condition.

Advantageously, the effective amount of a combination product for treating, preventing or ameliorating a chronic or acute protein kinase mediated disease, disorder or condition may facilitate the use of a reduced amount of the compound of Formula (I) or the therapeutic agent compared to the effective amount of the compound or therapeutic agent than would otherwise be recommended for treating, preventing or ameliorating a chronic or acute protein kinase mediated disease, disorder or condition. Therefore, it is contemplated that the compounds of this invention can be administered to the subject before, during or after treatment with a particular therapeutic agent.

The term "therapeutic agent" refers to chemotherapeutic agents used to treat a kinase mediated cancer or antiviral agents used to treat cytomegalovirus. Chemotherapeutic agents include and are not limited to anti-angiogenic agents, anti-tumor agents, cytotoxic agents, inhibitors of cell proliferation, radiation therapy and the like or mixtures thereof.

The terms "treating" or "preventing" refer, without limitation, to facilitating the eradication of, inhibiting the progression of or promoting stasis of a malignancy.

The term "radiation therapy" refers to a therapy that comprises exposing the subject in need thereof to radiation. The present invention includes a method for administering one or more compounds of Formula (I) or composition or medicament thereof in combination with radiation therapy. Procedures for administering such therapy are known to those skilled in the art. The appropriate scheme of radiation therapy will be similar to those already employed in clinical therapies wherein the radiation therapy is used alone or in combination with other chemotherapeutic agents.

An example of the present invention includes a pharmaceutical composition comprising an admixture of one or more compounds of Formula (I) and/or one or more pharmaceutically acceptable forms thereof and one or more pharmaceutically acceptable excipients.

The pharmaceutically acceptable forms for a compound of Formula (I) include a pharmaceutically acceptable salt, ester, prodrug or active metabolite of a compound of Formula (I).

The present invention further includes the use of a process for making the composition or medicament comprising mixing one or more of the instant compounds and an optional pharmaceutically acceptable carrier; and, includes those compositions or medicaments resulting from such a process. Contemplated processes include both conventional and unconventional pharmaceutical techniques.

The composition or medicament may take a wide variety of forms to effectuate mode of administration, including, but not limited to, intravenous (both bolus and infusion), oral, nasal, transdermal, topical with or without occlusion, and injection intraperitoneally, subcutaneously, intramuscularly, intratumorally or parenterally. The composition or medicament may be in a dosage unit such as a tablet, pill, capsule, powder, granule, sterile parenteral solution or suspension, metered aerosol or liquid spray, drop, ampoule, auto-injector device or suppository; for administration orally, parenterally, intranasally, sublingually or rectally or by inhalation or insufflation. Compositions or medicaments suitable for oral administration include solid forms such as pills, tablets, caplets, capsules (each including immediate release, timed release and sustained release formulations), granules and powders; and, liquid forms such as solutions, syrups, elixirs, emulsions and suspensions. Forms useful for parenteral administration include sterile solutions, emulsions and suspensions. Alternatively, the composition or medicament may be presented in a form suitable for once-weekly or once-monthly administration; for example, an insoluble salt of the active compound, such as the decanoate salt, may be adapted to provide a depot preparation for intramuscular injection.

The dosage form (tablet, capsule, powder, injection, suppository, teaspoonful and the like) containing the composition or medicament contains an effective amount of the active ingredient necessary to be therapeutically or prophylactically effective as described above. The composition or medicament may contain from about 0.001 mg to about 5000 mg (preferably, from about 0.001 to about 500 mg) of the active compound or prodrug thereof and may be constituted into any form suitable for the mode of administration selected for a subject in need. A contemplated effective amount may range from about 0.001 mg to about 300 mg/kg of body weight per day. Preferably, the range is from about 0.003 to about 100 mg/kg of body weight per day. Most preferably, the range is from about 0.005 to about 15 mg/kg of body weight per day.

The composition or medicament may be administered according to a dosage regimen of from about 1 to about 5 times per day.

For oral administration, the composition or medicament is preferably in the form of a tablet containing, e.g., 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the patient to be treated. Optimal dosages will vary depending on factors associated with the particular patient being treated (e.g., age, weight, diet and time of administration), the severity of the condition being treated, the compound being employed, the mode of administration and the strength of the preparation. The use of either daily administration or post-periodic dosing may be employed.

A representative compound of Formula (I) or a form thereof for use in the therapeutic methods and pharmaceutical compositions, medicines or medicaments described herein includes a compound selected from:

5-(3-chloro-4-fluoro-phenyl)-4-oxo-4,5-dihydro-3H-1-thia-3,5,6,8-tetraaza-acenaphthylene-2-carboxylic acid (3,4-dimethoxy-phenyl)-amide, 5-(3-chloro-4-fluoro-phenyl)-4-oxo-4,5-dihydro-3H-1-thia-3,5,6,8-tetraaza-acenaphthylene-2-carboxylic acid (4-piperidin-1-ylmethyl-phenyl)-amide, 5-(3-chloro-4-fluoro-phenyl)-4-oxo-4,5-dihydro-3H-1-thia-3,5,6,8-tetraaza-acenaphthylene-2-carboxylic acid thiazol-2-ylamide, 5-(3-chloro-4-fluoro-phenyl)-4-oxo-4,5-dihydro-3H-1-thia-3,5,6,8-tetraaza-acenaphthylene-2-carboxylic acid pyridin-3-ylamide, 5-(3-chloro-4-fluoro-phenyl)-4-oxo-4,5-dihydro-3H-1-thia-3,5,6,8-tetraaza-acenaphthylene-2-carboxylic acid [6-(3-morpholin-4-yl-propylamino)-pyridin-3-yl]-amide, 5-(3-chloro-4-fluoro-phenyl)-4-oxo-4,5-dihydro-3H-1-thia-3,5,6,8-tetraaza-acenaphthylene-2-carboxylic acid (4-pyrrolidin-1-ylmethyl-phenyl)-amide, 5-(3-chloro-4-fluoro-phenyl)-4-oxo-4,5-dihydro-3H-1-thia-3,5,6,8-tetraaza-acenaphthylene-2-carboxylic acid (4-morpholin-1-ylmethyl-phenyl)-amide, 5-(3-chloro-4-fluoro-phenyl)-4-oxo-4,5-dihydro-3H-1-thia-3,5,6,8-tetraaza-acenaphthylene-2-carboxylic acid [4-(4-methyl-piperazin-1-ylmethyl)-phenyl]-amide, 5-(3-ethynyl-phenyl)-4-oxo-4,5-dihydro-3H-1-thia-3,5,6,8-tetraaza-acenaphthylene-2-carboxylic acid (4-pyrrolidin-1-ylmethyl-phenyl)-amide, 5-(2-chloro-4-fluoro-phenyl)-4-oxo-4,5-dihydro-3H-1-thia-3,5,6,8-tetraaza-acenaphthylene-2-carboxylic acid (4-morpholin-4-ylmethyl-phenyl)-amide, 5-(3-chloro-4-fluoro-phenyl)-4-oxo-4,5-dihydro-3H-1-thia-3,5,6,8-tetraaza-acenaphthylene-2-carboxylic acid [4-({[(2R)-tetrahydro-furan-2-ylmethyl]-amino}-methyl)-phenyl]-amide, 5-(3-chloro-4-fluoro-phenyl)-4-oxo-4,5-dihydro-3H-1-thia-3,5,6,8-tetraaza-acenaphthylene-2-carboxylic acid (4-hydroxy-3-methoxy-phenyl)-amide, 5-(3-chloro-4-fluoro-phenyl)-4-oxo-4,5-dihydro-3H-1-thia-3,5,6,8-tetraaza-acenaphthylene-2-carboxylic acid [3-methoxy-4-(2-morpholin-4-yl-ethoxy)-phenyl]-amide, 5-(3-chloro-4-fluoro-phenyl)-4-oxo-4,5-dihydro-3H-1-thia-3,5,6,8-tetraaza-acenaphthylene-2-carboxylic acid [3-methoxy-4-(3-piperidin-1-yl-propoxy)-phenyl]-amide, 5-(3-chloro-4-fluoro-phenyl)-4-oxo-4,5-dihydro-3H-1-thia-3,5,6,8-tetraaza-acenaphthylene-2-carboxylic acid [3-methoxy-4-(2-piperidin-4-yl-ethoxy)-phenyl]-amide, 5-(3-chloro-4-fluoro-phenyl)-4-oxo-4,5-dihydro-3H-1-thia-3,5,6,8-tetraaza-acenaphthylene-2-carboxylic acidd (6-aminomethyl-pyridin-3-yl)-amide,
5-(2,4-dichloro-phenyl)-4-oxo-4,5-dihydro-3H-1-thia-3,5,6,8-tetraaza-acenaphthylene-2-carboxylic acid (4-piperidin-1-ylmethyl-phenyl)-amide,
5-(2,4-dichloro-phenyl)-4-oxo-4,5-dihydro-3H-1-thia-3,5,6,8-tetraaza-acenaphthylene-2-carboxylic acid (4-morpholin-4-ylmethyl-phenyl)-amide,
5-(3-bromo-phenyl)-4-oxo-4,5-dihydro-3H-1-thia-3,5,6,8-tetraaza-acenaphthylene-2-carboxylic acid (4-morpholin-4-ylmethyl-phenyl)-amide,
5-(2,4-dichloro-5-methoxy-phenyl)-4-oxo-4,5-dihydro-3H-1-thia-3,5,6,8-tetraaza-acenaphthylene-2-carboxylic acid (4-pyrrolidin-1-ylmethyl-phenyl)-amide,
5-[3-chloro-4-(pyridin-2-ylmethoxy)-phenyl]-4-oxo-4,5-dihydro-3H-1-thia-3,5,6,8-tetraaza-acenaphthylene-2-carboxylic acid (3,4-dimethoxy-phenyl)-amide,
5-(2-chloro-5-methoxy-phenyl)-4-oxo-4,5-dihydro-3H-1-thia-3,5,6,8-tetraaza-acenaphthylene-2-carboxylic acid [3-methoxy-4-(2-morpholin-4-yl-ethoxy)-phenyl]-amide,
5-(2-chloro-5-methoxy-phenyl)-4-oxo-4,5-dihydro-3H-1-thia-3,5,6,8-tetraaza-acenaphthylene-2-carboxylic acid (4-morpholin-4-ylmethyl-phenyl)-amide,
5-[3-chloro-4-(pyridin-2-ylmethoxy)-phenyl]-4-oxo-4,5-dihydro-3H-1-thia-3,5,6,8-tetraaza-acenaphthylene-2-carboxylic acid (4-morpholin-4-ylmethyl-phenyl)-amide,
5-(5-chloro-benzo[1,3]dioxol-4-yl)-4-oxo-4,5-dihydro-3H-1-thia-3,5,6,8-tetraaza-acenaphthylene-2-carboxylic acid (4-morpholin-4-ylmethyl-phenyl)-amide,
5-(3-bromo-phenyl)-4-oxo-4,5-dihydro-3H-1-thia-3,5,6,8-tetraaza-acenaphthylene-2-carboxylic acid [3-methoxy-4-(2-piperidin-1-yl-ethoxy)-phenyl]-amide,
5-(3-bromo-phenyl)-4-oxo-4,5-dihydro-3H-1-thia-3,5,6,8-tetraaza-acenaphthylene-2-carboxylic acid [6-(3-morpholin-4-yl-propylamino)-pyridin-3-yl]-amide,
5-(2-fluoro-4-methoxy-phenyl)-4-oxo-4,5-dihydro-3H-1-thia-3,5,6,8-tetraaza-acenaphthylene-2-carboxylic acid (4-morpholin-4-ylmethyl-phenyl)-amide,
5-(2-fluoro-4-methoxy-phenyl)-4-oxo-4,5-dihydro-3H-1-thia-3,5,6,8-tetraaza-acenaphthylene-2-carboxylic acid [3-methoxy-4-(2-morpholin-4-yl-ethoxy)-phenyl]-amide,
5-(5-chloro-2-methoxy-phenyl)-4-oxo-4,5-dihydro-3H-1-thia-3,5,6,8-tetraaza-acenaphthylene-2-carboxylic acid (4-piperidin-1-ylmethyl-phenyl)-amide,
5-(5-chloro-2-methoxy-phenyl)-4-oxo-4,5-dihydro-3H-1-thia-3,5,6,8-tetraaza-acenaphthylene-2-carboxylic acid (3,4-dimethoxy-phenyl)-amide,
5-(5-chloro-2-methoxy-phenyl)-4-oxo-4,5-dihydro-3H-1-thia-3,5,6,8-tetraaza-acenaphthylene-2-carboxylic acid [3-methoxy-4-(2-piperidin-1-yl-ethoxy)-phenyl]-amide,
5-[1-(3-fluoro-benzyl)-1H-indazol-5-yl]-4-oxo-4,5-dihydro-3H-1-thia-3,5,6,8-tetraaza-acenaphthylene-2-carboxylic acid (4-piperidin-1-ylmethyl-phenyl)-amide,
5-(4-bromo-3-methoxy-phenyl)-4-oxo-4,5-dihydro-3H-1-thia-3,5,6,8-tetraaza-acenaphthylene-2-carboxylic acid (4-piperidin-1-ylmethyl-phenyl)-amide,
5-(4-bromo-3-methoxy-phenyl)-4-oxo-4,5-dihydro-3H-1-thia-3,5,6,8-tetraaza-acenaphthylene-2-carboxylic acid (4-morpholin-4-ylmethyl-phenyl)-amide,
5-[3-chloro-4-(pyridin-2-ylmethoxy)-phenyl]-4-oxo-4,5-dihydro-3H-1-thia-3,5,6,8-tetraaza-acenaphthylene-2-carboxylic acid [3-methoxy-4-(2-morpholin-4-yl-ethoxy)-phenyl]-amide,
5-[1-(3-fluoro-benzyl)-1H-indol-5-yl]-4-oxo-4,5-dihydro-3H-1-thia-3,5,6,8-tetraaza-acenaphthylene-2-carboxylic acid (4-piperidin-1-ylmethyl-phenyl)-amide,
5-[3-chloro-4-(pyridin-2-ylmethoxy)-phenyl]-4-oxo-4,5-dihydro-3H-1-thia-3,5,6,8-tetraaza-acenaphthylene-2-carboxylic acid (4-piperidin-1-ylmethyl-phenyl)-amide,
5-[3-chloro-4-(pyridin-2-ylmethoxy)-phenyl]-4-oxo-4,5-dihydro-3H-1-thia-3,5,6,8-tetraaza-acenaphthylene-2-carboxylic acid [4-(4-methyl-piperazin-1-ylmethyl)-phenyl]-amide,
4-({5-[1-(3-fluoro-benzyl)-1H-indol-5-yl]-4-oxo-4,5-dihydro-3H-1-thia-3,5,6,8-tetraaza-acenaphthylene-2-carbonyl}-amino)-piperidine-1-carboxylic acid tert-butyl ester,
5-[1-(3-fluoro-benzyl)-1H-indol-5-yl]-4-oxo-4,5-dihydro-3H-1-thia-3,5,6,8-tetraaza-acenaphthylene-2-carboxylic acid (1-methyl-piperidin-4-yl)-amide,
5-[1-(3-fluoro-benzyl)-1H-indol-5-yl]-4-oxo-4,5-dihydro-3H-1-thia-3,5,6,8-tetraaza-acenaphthylene-2-carboxylic acid (2-morpholin-4-yl-ethyl)-amide,
5-[1-(3-fluoro-benzyl)-1H-indol-5-yl]-4-oxo-4,5-dihydro-3H-1-thia-3,5,6,8-tetraaza-acenaphthylene-2-carboxylic acid (3-morpholin-4-yl-propyl)-amide,
4-oxo-5-(4-phenoxy-phenyl)-4,5-dihydro-3H-1-thia-3,5,6,8-tetraaza-acenaphthylene-2-carboxylic acid (4-piperidin-1-ylmethyl-phenyl)-amide,
4-oxo-5-(4-phenoxy-phenyl)-4,5-dihydro-3H-1-thia-3,5,6,8-tetraaza-acenaphthylene-2-carboxylic acid (4-morpholin-4-ylmethyl-phenyl)-amide,
4-oxo-5-(4-phenoxy-phenyl)-4,5-dihydro-3H-1-thia-3,5,6,8-tetraaza-acenaphthylene-2-carboxylic acid [4-(4-methyl-piperazin-1-ylmethyl)-phenyl]-amide,
4-oxo-5-(4-phenoxy-phenyl)-4,5-dihydro-3H-1-thia-3,5,6,8-tetraaza-acenaphthylene-2-carboxylic acid (3,4-dimethoxy-phenyl)-amide,
4-oxo-5-(4-phenoxy-phenyl)-4,5-dihydro-3H-1-thia-3,5,6,8-tetraaza-acenaphthylene-2-carboxylic acid [3-methoxy-4-(2-piperidin-1-yl-ethoxy)-phenyl]-amide,
5-(2,6-dichloro-phenyl)-4-oxo-4,5-dihydro-3H-1-thia-3,5,6,8-tetraaza-acenaphthylene-2-carboxylic acid (4-morpholin-4-ylmethyl-phenyl)-amide,
4-oxo-5-(4-phenoxy-phenyl)-4,5-dihydro-3H-1-thia-3,5,6,8-tetraaza-acenaphthylene-2-carboxylic acid (3-hydroxy-propyl)-amide,
5-(3-bromo-4-methyl-phenyl)-4-oxo-4,5-dihydro-3H-1-thia-3,5,6,8-tetraaza-acenaphthylene-2-carboxylic acid (4-morpholin-4-ylmethyl-phenyl)-amide,
5-(5-bromo-2-methyl-phenyl)-4-oxo-4,5-dihydro-3H-1-thia-3,5,6,8-tetraaza-acenaphthylene-2-carboxylic acid (4-morpholin-4-ylmethyl-phenyl)-amide,
5-[4-(4-fluoro-phenoxy)-phenyl]-4-oxo-4,5-dihydro-3H-1-thia-3,5,6,8-tetraaza-acenaphthylene-2-carboxylic acid (4-morpholin-4-ylmethyl-phenyl)-amide,
5-(3-bromo-4-methyl-phenyl)-4-oxo-4,5-dihydro-3H-1-thia-3,5,6,8-tetraaza-acenaphthylene-2-carboxylic acid (4-piperidin-1-ylmethyl-phenyl)-amide,
5-(3-fluoro-4-phenoxy-phenyl)-4-oxo-4,5-dihydro-3H-1-thia-3,5,6,8-tetraaza-acenaphthylene-2-carboxylic acid (4-morpholin-4-ylmethyl-phenyl)-amide,
5-(3-fluoro-4-phenoxy-phenyl)-4-oxo-4,5-dihydro-3H-1-thia-3,5,6,8-tetraaza-acenaphthylene-2-carboxylic acid [4-(2-piperidin-1-yl-ethyl)-phenyl]-amide,
5-(3-fluoro-4-phenoxy-phenyl)-4-oxo-4,5-dihydro-3H-1-thia-3,5,6,8-tetraaza-acenaphthylene-2-carboxylic acid [4-(4-methyl-piperazin-1-ylmethyl)-phenyl]-amide,
5-(4-morpholin-4-yl-phenyl)-4-oxo-4,5-dihydro-3H-1-thia-3,5,6,8-tetraaza-acenaphthylene-2-carboxylic acid (4-morpholin-4-ylmethyl-phenyl)-amide,
5-[3-chloro-4-(6-methyl-pyridin-3-yloxy)-phenyl]-4-oxo-4,5-dihydro-3H-1-thia-3,5,6,8-tetraaza-acenaphthylene-2-carboxylic acid (4-morpholin-4-ylmethyl-phenyl)-amide, 5-[4-(3-fluoro-phenoxy)-phenyl]-4-oxo-4,5-dihydro-3H-1-thia-3,5,6,8-tetraaza-acenaphthylene-2-carboxylic acid (4-piperidin-1-ylmethyl-phenyl)-amide, 5-[4-(3-fluoro-phenoxy)-phenyl]-4-oxo-4,5-dihydro-3H-1-thia-3,5,6,8-tetraaza-acenaphthylene-2-carboxylic acid [4-(2-piperidin-1-yl-ethyl)-phenyl]-amide, 5-[4-(3-fluoro-phenoxy)-phenyl]-4-oxo-4,5-dihydro-3H-1-thia-3,5,6,8-tetraaza-acenaphthylene-2-carboxylic acid (3-hydroxy-propyl)-amide, 5-[4-(3-fluoro-phenoxy)-phenyl]-4-oxo-4,5-dihydro-3H-1-thia-3,5,6,8-tetraaza-acenaphthylene-2-carboxylic acid (4-morpholin-4-ylmethyl-phenyl)-amide, 5-(3-chloro-4-phenoxy-phenyl)-4-oxo-4,5-dihydro-3H-1-thia-3,5,6,8-tetraaza-acenaphthylene-2-carboxylic acid (4-piperidin-1-ylmethyl-phenyl)-amide, 5-(3-chloro-4-phenoxy-phenyl)-4-oxo-4,5-dihydro-3H-1-thia-3,5,6,8-tetraaza-acenaphthylene-2-carboxylic acid [4-(2-piperidin-1-yl-ethyl)-phenyl]-amide, 5-(3-chloro-4-phenoxy-phenyl)-4-oxo-4,5-dihydro-3H-1-thia-3,5,6,8-tetraaza-acenaphthylene-2-carboxylic acid (3-hydroxy-propyl)-amide, 5-(3-chloro-4-phenoxy-phenyl)-4-oxo-4,5-dihydro-3H-1-thia-3,5,6,8-tetraaza-acenaphthylene-2-carboxylic acid (4-morpholin-4-ylmethyl-phenyl)-amide, 5-[1-(3-fluoro-benzyl)-1H-indol-5-yl]-4-oxo-4,5-dihydro-3H-1-thia-3,5,6,8-tetraaza-acenaphthylene-2-carboxylic acid (3-amino-propyl)-amide, 5-(2-chloro-4-fluoro-phenyl)-4-oxo-4,5-dihydro-3H-1-thia-3,5,6,8-tetraaza-acenaphthylene-2-carboxylic acid [3-methoxy-4-(2-piperidin-1-yl-ethoxy)-phenyl]-amide, 5-(2-chloro-4-fluoro-phenyl)-4-oxo-4,5-dihydro-3H-1-thia-3,5,6,8-tetraaza-acenaphthylene-2-carboxylic acid (4-piperidin-1-ylmethyl-phenyl)-amide, 5-(2-chloro-6-methyl-phenyl)-4-oxo-4,5-dihydro-3H-1-thia-3,5,6,8-tetraaza-acenaphthylene-2-carboxylic acid (4-morpholin-4-ylmethyl-phenyl)-amide, 5-(2-chloro-6-methyl-phenyl)-4-oxo-4,5-dihydro-3H-1-thia-3,5,6,8-tetraaza-acenaphthylene-2-carboxylic acid (4-piperidin-1-ylmethyl-phenyl)-amide, 5-(2-chloro-6-methyl-phenyl)-4-oxo-4,5-dihydro-3H-1-thia-3,5,6,8-tetraaza-acenaphthylene-2-carboxylic acid [4-(1-hydroxy-2-morpholin-4-yl-ethyl)-phenyl]-amide, 5-(2-chloro-phenyl)-4-oxo-4,5-dihydro-3H-1-thia-3,5,6,8-tetraaza-acenaphthylene-2-carboxylic acid (4-morpholin-4-ylmethyl-phenyl)-amide, 5-(2-chloro-phenyl)-4-oxo-4,5-dihydro-3H-1-thia-3,5,6,8-tetraaza-acenaphthylene-2-carboxylic acid (4-piperidin-1-ylmethyl-phenyl)-amide, 5-(2-chloro-phenyl)-4-oxo-4,5-dihydro-3H-1-thia-3,5,6,8-tetraaza-acenaphthylene-2-carboxylic acid [4-(4-methyl-piperazin-1-ylmethyl)-phenyl]-amide, 5-(3-bromo-4-fluoro-phenyl)-4-oxo-4,5-dihydro-3H-1-thia-3,5,6,8-tetraaza-acenaphthylene-2-carboxylic acid (4-morpholin-4-ylmethyl-phenyl)-amide, 5-(3-bromo-4-fluoro-phenyl)-4-oxo-4,5-dihydro-3H-1-thia-3,5,6,8-tetraaza-acenaphthylene-2-carboxylic acid (4-piperidin-1-ylmethyl-phenyl)-amide, 5-[3-chloro-4-(3-fluoro-phenoxy)-phenyl]-4-oxo-4,5-dihydro-3H-1-thia-3,5,6,8-tetraaza-acenaphthylene-2-carboxylic acid (4-piperidin-1-ylmethyl-phenyl)-amide, 5-[3-chloro-4-(3-fluoro-phenoxy)-phenyl]-4-oxo-4,5-dihydro-3H-1-thia-3,5,6,8-tetraaza-acenaphthylene-2-carboxylic acid [3-methoxy-4-(2-piperidin-1-yl-ethoxy)-phenyl]-amide, 5-[3-chloro-4-(3-fluoro-phenoxy)-phenyl]-4-oxo-4,5-dihydro-3H-1-thia-3,5,6,8-tetraaza-acenaphthylene-2-carboxylic acid (4-morpholin-4-ylmethyl-phenyl)-amide, 5-(4-benzyl-phenyl)-4-oxo-4,5-dihydro-3H-1-thia-3,5,6,8-tetraaza-acenaphthylene-2-carboxylic acid [3-methoxy-4-(2-piperidin-1-yl-ethoxy)-phenyl]-amide, 5-(4-benzyl-phenyl)-4-oxo-4,5-dihydro-3H-1-thia-3,5,6,8-tetraaza-acenaphthylene-2-carboxylic acid (4-piperidin-1-ylmethyl-phenyl)-amide, 5-(4-benzyl-phenyl)-4-oxo-4,5-dihydro-3H-1-thia-3,5,6,8-tetraaza-acenaphthylene-2-carboxylic acid (4-morpholin-4-ylmethyl-phenyl)-amide, 4-oxo-5-(4-phenoxy-phenyl)-4,5-dihydro-3H-1-thia-3,5,6,8-tetraaza-acenaphthylene-2-carboxylic acid [4-(2-piperidin-1-yl-ethyl)-phenyl]-amide, 4-oxo-5-(4-phenoxy-phenyl)-4,5-dihydro-3H-1-thia-3,5,6,8-tetraaza-acenaphthylene-2-carboxylic acid [3-methoxy-4-(2-morpholin-4-yl-ethoxy)-phenyl]-amide, 4-oxo-5-(4-phenylsulfanyl-phenyl)-4,5-dihydro-3H-1-thia-3,5,6,8-tetraaza-acenaphthylene-2-carboxylic acid (4-piperidin-1-ylmethyl-phenyl)-amide, 4-oxo-5-(4-phenoxy-phenyl)-4,5-dihydro-3H-1-thia-3,5,6,8-tetraaza-acenaphthylene-2-carboxylic acid [4-(1-hydroxy-2-morpholin-4-yl-ethyl)-phenyl]-amide, 5-[1-(3-fluoro-benzyl)-1H-indazol-5-yl]-4-oxo-4,5-dihydro-3H-1-thia-3,5,6,8-tetraaza-acenaphthylene-2-carboxylic acid (4-morpholin-4-ylmethyl-phenyl)-amide, 4-oxo-5-(4-phenoxy-phenyl)-4,5-dihydro-3H-1-thia-3,5,6,8-tetraaza-acenaphthylene-2-carboxylic acid (3-methoxy-4-morpholin-4-ylmethyl-phenyl)-amide, 5-[1-(3-fluoro-benzyl)-1H-indazol-5-yl]-4-oxo-4,5-dihydro-3H-1-thia-3,5,6,8-tetraaza-acenaphthylene-2-carboxylic acid (1-methyl-piperidin-4-yl)-amide, 4-oxo-5-(4-phenylsulfanyl-phenyl)-4,5-dihydro-3H-1-thia-3,5,6,8-tetraaza-acenaphthylene-2-carboxylic acid (4-morpholin-4-ylmethyl-phenyl)-amide, 5-[3-bromo-4-(pyridin-2-ylmethoxy)-phenyl]-4-oxo-4,5-dihydro-3H-1-thia-3,5,6,8-tetraaza-acenaphthylene-2-carboxylic acid (4-morpholin-4-ylmethyl-phenyl)-amide, 5-(3-bromo-phenyl)-4-oxo-4,5-dihydro-3H-1-thia-3,5,6,8-tetraaza-acenaphthylene-2-carboxylic acid (3-methoxy-4-morpholin-4-ylmethyl-phenyl)-amide, 5-(3-bromo-4-phenoxy-phenyl)-4-oxo-4,5-dihydro-3H-1-thia-3,5,6,8-tetraaza-acenaphthylene-2-carboxylic acid (4-morpholin-4-ylmethyl-phenyl)-amide, 5-(3-bromo-4-phenoxy-phenyl)-4-oxo-4,5-dihydro-3H-1-thia-3,5,6,8-tetraaza-acenaphthylene-2-carboxylic acid (4-piperidin-1-ylmethyl-phenyl)-amide, 5-(3-bromo-4-phenoxy-phenyl)-4-oxo-4,5-dihydro-3H-1-thia-3,5,6,8-tetraaza-acenaphthylene-2-carboxylic acid (3-methoxy-4-morpholin-4-ylmethyl-phenyl)-amide, 4-oxo-5-(4-phenylsulfanyl-phenyl)-4,5-dihydro-3H-1-thia-3,5,6,8-tetraaza-acenaphthylene-2-carboxylic acid (1-methyl-piperidin-4-yl)-amide, 5-(4-bromo-phenyl)-4-oxo-4,5-dihydro-3H-1-thia-3,5,6,8-tetraaza-acenaphthylene-2-carboxylic acid (4-piperidin-1-ylmethyl-phenyl)-amide, 5-(4-bromo-phenyl)-4-oxo-4,5-dihydro-3H-1-thia-3,5,6,8-tetraaza-acenaphthylene-2-carboxylic acid (4-morpholin-4-ylmethyl-phenyl)-amide, 4-oxo-5-(3-phenoxy-phenyl)-4,5-dihydro-3H-1-thia-3,5,6,8-tetraaza-acenaphthylene-2-carboxylic acid (4-piperidin-1-ylmethyl-phenyl)-amide, 4-oxo-5-(3-phenoxy-phenyl)-4,5-dihydro-3H-1-thia-3,5,6,8-tetraaza-acenaphthylene-2-carboxylic acid [4-(4-methyl-piperazin-1-ylmethyl)-phenyl]-amide, 4-oxo-5-(3-phenoxy-phenyl)-4,5-dihydro-3H-1-thia-3,5,6,8-tetraaza-acenaphthylene-2-carboxylic acid (3-methoxy-4-morpholin-4-ylmethyl-phenyl)-amide, 5-(4-bromo-phenyl)-4-oxo-4,5-dihydro-3H-1-thia-3,5,6,8-teciaaza-acenaphthylene-2-carboxylic acid (3-methoxy-4-morpholin-4-ylmethyl-phenyl)-amide, 4-oxo-5-(4-phenoxy-phenyl)-4,5-dihydro-3H-1-thia-3,5,6,8-tetraaza-acenaphthylene-2-carboxylic acid (3-fluoro-4-morpholin-4-ylmethyl-phenyl)-amide, 4-oxo-5-(4-phenoxy-phenyl)-4,5-dihydro-3H-1-thia-3,5,6,8-tetraaza-acenaphthylene-2-carboxylic acid (3-ethoxy-4-morpholin-4-ylmethyl-phenyl)-amide, 5-[3-chloro-4-(pyridin-3-yloxy)-phenyl]-4-oxo-4,5-dihydro-3H-1-thia-3,5,6,8-tetraaza-acenaphthylene-2-carboxylic acid (4-morpholin-4-ylmethyl-phenyl)-amide, 5-[3-chloro-4-(pyridin-3-yloxy)-phenyl]-4-oxo-4,5-dihydro-3H-1-thia-3,5,6,8-tetraaza-acenaphthylene-2-carboxylic acid (4-piperidin-1-ylmethyl-phenyl)-amide, 4-oxo-5-(4-phenoxy-phenyl)-4,5-dihydro-3H-1-thia-3,5,6,8-tetraaza-acenaphthylene-2-carboxylic acid (1-methyl-piperidin-4-yl)-amide, 4-oxo-5-(4-phenylsulfanyl-phenyl)-4,5-dihydro-3H-1-thia-3,5,6,8-tetraaza-acenaphthylene-2-carboxylic acid (3-dimethylamino-propyl)-amide, 4-oxo-5-(4-phenylsulfanyl-phenyl)-4,5-dihydro-3H-1-thia-3,5,6,8-tetraaza-acenaphthylene-2-carboxylic acid [4-(4-methyl-piperazin-1-ylmethyl)-phenyl]-amide, 4-oxo-5-(4-phenylsulfanyl-phenyl)-4,5-dihydro-3H-1-thia-3,5,6,8-tetraaza-acenaphthylene-2-carboxylic acid (3-methoxy-4-morpholin-4-ylmethyl-phenyl)-amide, 4-oxo-5-(4-phenoxy-phenyl)-4,5-dihydro-3H-1-thia-3,5,6,8-tetraaza-acenaphthylene-2-carboxylic acid (3-morpholin-4-ylmethyl-phenyl)-amide, 4-oxo-5-(4-phenoxy-phenyl)-4,5-dihydro-3H-1-thia-3,5,6,8-tetraaza-acenaphthylene-2-carboxylic acid (3-chloro-4-morpholin-4-ylmethyl-phenyl)-amide, 4-oxo-5-(4-phenylsulfanyl-phenyl)-4,5-dihydro-3H-1-thia-3,5,6,8-tetraaza-acenaphthylene-2-carboxylic acid (3-methoxy-4-piperidin-1-ylmethyl-phenyl)-amide, 5-[3-chloro-4-(thiophen-2-ylmethoxy)-phenyl]-4-oxo-4,5-dihydro-3H-1-thia-3,5,6,8-tetraaza-acenaphthylene-2-carboxylic acid (4-morpholin-4-ylmethyl-phenyl)-amide, 5-[3-chloro-4-(thiophen-2-ylmethoxy)-phenyl]-4-oxo-4,5-dihydro-3H-1-thia-3,5,6,8-tetraaza-acenaphthylene-2-carboxylic acid (4-piperidin-1-ylmethyl-phenyl)-amide, 5-[3-chloro-4-(thiophen-2-ylmethoxy)-phenyl]-4-oxo-4,5-dihydro-3H-1-thia-3,5,6,8-tetraaza-acenaphthylene-2-carboxylic acid (3-methoxy-4-piperidin-1-ylmethyl-phenyl)-amide, 5-[3-chloro-4-(thiophen-2-ylmethoxy)-phenyl]-4-oxo-4,5-dihydro-3H-1-thia-3,5,6,8-tetraaza-acenaphthylene-2-carboxylic acid (3-methoxy-4-morpholin-4-ylmethyl-phenyl)-amide, 5-[3-chloro-4-(thiophen-2-ylmethoxy)-phenyl]-4-oxo-4,5-dihydro-3H-1-thia-3,5,6,8-tetraaza-acenaphthylene-2-carboxylic acid (1-methyl-piperidin-4-yl)-amide, 4-oxo-5-(4-phenoxy-phenyl)-4,5-dihydro-3H-1-thia-3,5,6,8-tetraaza-acenaphthylene-2-carboxylic acid (3-methyl-4-morpholin-4-ylmethyl-phenyl)-amide, 4-oxo-5-(4-phenoxy-phenyl)-4,5-dihydro-3H-1-thia-3,5,6,8-tetraaza-acenaphthylene-2-carboxylic acid [4-(4-hydroxy-piperidin-1-ylmethyl)-phenyl]-amide, 4-oxo-5-(4-phenoxy-phenyl)-4,5-dihydro-3H-1-thia-3,5,6,8-tetraaza-acenaphthylene-2-carboxylic acid [4-(3-fluoro-piperidin-1-ylmethyl)-phenyl]-amide, 4-oxo-5-[4-(pyridin-3-yloxy)-phenyl]-4,5-dihydro-3H-1-thia-3,5,6,8-tetraaza-acenaphthylene-2-carboxylic acid (3-methoxy-4-morpholin-4-ylmethyl-phenyl)-amide, 4-oxo-5-[4-(pyridin-3-yloxy)-phenyl]-4,5-dihydro-3H-1-thia-3,5,6,8-tetraaza-acenaphthylene-2-carboxylic acid (4-morpholin-4-ylmethyl-phenyl)-amide, 4-oxo-5-(4-phenoxy-phenyl)-4,5-dihydro-3H-1-thia-3,5,6,8-tetraaza-acenaphthylene-2-carboxylic acid (4-morpholin-4-ylmethyl-3-trifluoromethoxy-phenyl)-amide, 4-oxo-5-(4-phenoxy-phenyl)-4,5-dihydro-3H-1-thia-3,5,6,8-tetraaza-acenaphthylene-2-carboxylic acid (4-morpholin-4-ylmethyl-3-trifluoromethoxy-phenyl)-amide, 4-oxo-5-(4-phenoxy-phenyl)-4,5-dihydro-3H-1-thia-3,5,6,8-tetraaza-acenaphthylene-2-carboxylic acid (3-methoxy-4-piperidin-1-ylmethyl-phenyl)-amide, 5-[3-chloro-4-(furan-2-ylmethoxy)-phenyl]-4-oxo-4,5-dihydro-3H-1-thia-3,5,6,8-tetraaza-acenaphthylene-2-carboxylic acid (3-methoxy-4-piperidin-1-ylmethyl-phenyl)-amide, 5-[3-chloro-4-(furan-2-ylmethoxy)-phenyl]-4-oxo-4,5-dihydro-3H-1-thia-3,5,6,8-tetraaza-acenaphthylene-2-carboxylic acid (4-piperidin-1-ylmethyl-phenyl)-amide, 5-[3-chloro-4-(furan-2-ylmethoxy)-phenyl]-4-oxo-4,5-dihydro-3H-1-thia-3,5,6,8-tetraaza-acenaphthylene-2-carboxylic acid (4-morpholin-4-ylmethyl-phenyl)-amide, 5-[3-chloro-4-(furan-2-ylmethoxy)-phenyl]-4-oxo-4,5-dihydro-3H-1-thia-3,5,6,8-tetraaza-acenaphthylene-2-carboxylic acid (3-methoxy-4-morpholin-4-ylmethyl-phenyl)-amide, 4-oxo-5-(4-phenoxy-phenyl)-4,5-dihydro-3H-1-thia-3,5,6,8-tetraaza-acenaphthylene-2-carboxylic acid [4-(4-fluoro-piperidin-1-ylmethyl)-phenyl]-amide, 5-benzofuran-7-yl-4-oxo-4,5-dihydro-3H-1-thia-3,5,6,8-tetraaza-acenaphthylene-2-carboxylic acid [4-(2-piperidin-1-yl-ethyl)-phenyl]-amide, 5-[3-chloro-4-(3-fluoro-benzyloxy)-phenyl]-4-oxo-4,5-dihydro-3H-1-thia-3,5,6,8-tetraaza-acenaphthylene-2-carboxylic acid [4-(4-methyl-piperazin-1-ylmethyl)-phenyl]-amide, 4-oxo-5-(4-phenoxy-phenyl)-4,5-dihydro-3H-1-thia-3,5,6,8-tetraaza-acenaphthylene-2-carboxylic acid [4-(3,5-dimethyl-morpholin-4-ylmethyl)-phenyl]-amide, 4-oxo-5-(4-phenoxy-phenyl)-4,5-dihydro-3H-1-thia-3,5,6,8-tetraaza-acenaphthylene-2-carboxylic acid [4-(4-hydroxymethyl-piperidin-1-ylmethyl)-phenyl]-amide, 4-oxo-5-(4-phenoxy-phenyl)-4,5-dihydro-3H-1-thia-3,5,6,8-tetraaza-acenaphthylene-2-carboxylic acid [4-(4-methyl-piperidin-1-ylmethyl)-phenyl]-amide, 4-oxo-5-(4-phenoxy-phenyl)-4,5-dihydro-3H-1-thia-3,5,6,8-tetraaza-acenaphthylene-2-carboxylic acid [4-(3-hydroxymethyl-piperidin-1-ylmethyl)-phenyl]-amide, 4-oxo-5-(4-phenoxy-phenyl)-4,5-dihydro-3H-1-thia-3,5,6,8-tetraaza-acenaphthylene-2-carboxylic acid (3-dimethylamino-4-morpholin-4-ylmethyl-phenyl)-amide,

[1-(4-{[4-oxo-5-(4-phenoxy-phenyl)-4,5-dihydro-3H-1-thia-3,5,6,8-tetraaza-acenaphthylene-2-carbonyl]-amino}-benzyl)-piperidin-4-yl]-carbamic acid tert-butyl ester, 4-oxo-5-(4-phenoxy-phenyl)-4,5-dihydro-3H-1-thia-3,5,6,8-tetraaza-acenaphthylene-2-carboxylic acid [4-(4-amino-piperidin-1-ylmethyl)-phenyl]-amide, 4-oxo-5-(4-phenoxy-phenyl)-4,5-dihydro-3H-1-thia-3,5,6,8-tetraaza-acenaphthylene-2-carboxylic acid [4-(4-dimethylamino-piperidin-1-ylmethyl)-phenyl]-amide, 4-oxo-5-(4-phenoxy-phenyl)-4,5-dihydro-3H-1-thia-3,5,6,8-tetraaza-acenaphthylene-2-carboxylic acid [4-(4-methoxy-piperidin-1-ylmethyl)-phenyl]-amide, 4-oxo-5-(4-phenoxy-phenyl)-4,5-dihydro-3H-1-thia-3,5,6,8-tetraaza-acenaphthylene-2-carboxylic acid (3-hydroxy-4-morpholin-4-ylmethyl-phenyl)-amide, and 4-oxo-5-(4-phenoxy-phenyl)-4,5-dihydro-3H-1-thia-3,5,6, 8-tetraaza-acenaphthylene-2-carboxylic acid [4-(4,4-difluoro-piperidin-1-ylmethyl)-phenyl]-amide.

Synthetic Methods

Representative compounds of the present invention can be synthesized in accordance with the general synthetic schemes described below and are illustrated more particularly in the specific synthetic examples that follow. The general schemes and specific examples are offered by way of illustration; the invention should not be construed as being limited by the chemical reactions and conditions expressed. Except where indicated, starting materials and intermediates used in the schemes and examples are prepared by known methodologies well within the ordinary skill of persons versed in the art. No attempt has been made to optimize the yields obtained in any of the example reactions. One skilled in the art would also know how to increase such yields through routine variations in materials, solvents, reagents, reaction conditions and the like. All commercially available chemicals were obtained from commercial suppliers and used without further purification. Particular equipment components used in the examples such as reaction vessels and the like are also commercially available.

The terms used in describing the invention are commonly used and known to those skilled in the art. When used herein, the following abbreviations have the indicated meanings:

| | |
|---|---|
| AcOH | acetic acid |
| ATP | adenosine triphosphate |
| Boc$_2$O | tert-butoxycarbonyl anhydride |
| CDI | carbonyl diimidazole |
| Cpd | compound |
| DBU | 1,8-diazabicyclo[4.3.0]undec-7-ene |
| DCM | dichloromethane |
| DIPEA | diisopropyl ethyl amine |
| DMF | N,N-dimethylformamide |
| DMSO | dimethyl sulfoxide |
| DTT | dithiothreitol |
| EDTA | ethylenediaminetetraacetic acid |
| EtOAc | ethyl acetate |
| HATU | O-(7-azabenzotriazol-1-yl)-N,N,N',N'-tetramethyluronium hexafluorophosphate |
| Hepes | 4-(2-hydroxyethyl)-1-piperazineethanesulfonic acid |
| HPLC | high pressure liquid chromatography |
| hr(s)/min(s) | hour(s)/min(s) |
| IC$_{50}$ | 50% inhibition constant |
| IPA | isopropyl alcohol |
| LAH | lithium aluminum hydride |
| MCPBA | meta-chloroperoxybenzoic acid or 3-chloroperoxybenzoic acid |
| MeOH | methanol |
| MOPS | 4-morpholinepropanesulfonic acid |
| NBS | N-bromosuccinimide |
| NMP | n-methyl pyrrolidinone or 1-methyl-2-pyrrolidinone |
| PBS | phosphate-buffered saline |
| PCR | polymerase chain reaction |
| PSI | pounds per square inch |
| PyBop | 1-benzotriazolyloxytripyrrolidinylphosphonium hexafluorophosphate |
| RT/rt/r.t. | room temperature |
| sat'd | saturated |
| TEA or Et$_3$N | triethylamine |
| TFA | trifluoroacetic acid |
| THF | tetrahydrofuran |
| Tris | tris(hydroxymethyl)aminomethane |

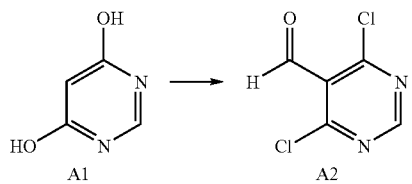

DMF is added to a solution of POCl$_3$ at 0° C. and the reaction mixture is stirred for 1 hour at ambient temperature. 4,6-dihydroxypyrimidine Compound A1 is added to the mixture at RT. After 1 hour, the reaction is heated to reflux for 3 hours. The mixture is concentrated in vacuo to remove the excess POCl$_3$ and the remaining residue is diluted with EtOAc and carefully quenched, with stirring, by the slow addition of ice. The isolated organic solution is sequentially washed with an aqueous saturated NaHCO$_3$ solution and brine. The organic layer is dried over Na$_2$SO$_4$, then filtered and concentrated to give a solid. The product, carboxaldehyde Compound A2, is extracted from the solid residue using a solvent such as hot hexanes.

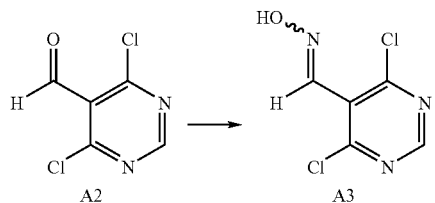

Hydroxylamine hydrochloride in a solvent such as 10% aqueous ethanol is added dropwise to a solution of Compound A2 (in an acidic solvent such as acetic acid). The reaction mixture is stirred for 1 hour at ambient temperature, then diluted with EtOAc and sequentially washed with a saturated NaHCO$_3$ solution and brine. The organic layer is dried (as above), filtered and concentrated to give a solid that upon trituration (using a solvent such as hexanes) gives a carbaldehyde oxime Compound A3.

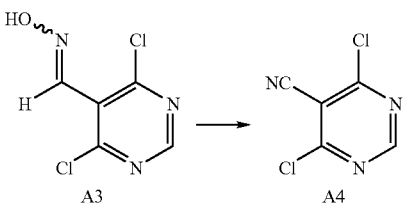

Compound A3 is added portionwise with great care to a stirring solution of SOCl$_2$ at 0° C. After completion of the addition process and no evidence of exothermic reaction, the reaction mixture is gradually brought to reflux and maintained at reflux for 3 hrs; then concentrated to remove the excess SOCl$_2$. The residue is diluted in EtOAc and then concentrated down again. The resulting solid is triturated (using a solvent such as hexanes) to yield carbonitrile Compound A4, as described in Kloetzer W and Herberz M, Reactions of 4,6-dichloro-5-formylpyrimidine, Monatshefte fuer Chemie, 1965, 96(5), 1573-8.

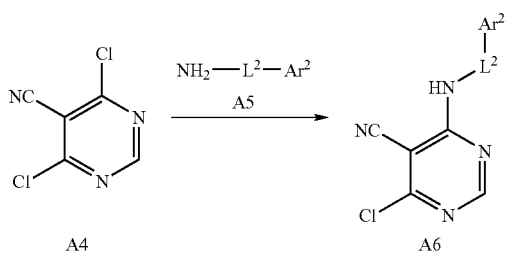

A solution of Compound A5 (in a solvent such as THF, CH₃CN, DMF, dioxane and the like) is added dropwise to a solution containing Compound A4 (in a solvent as above) and a base (such as DIPEA or Et₃N) at 0° C. After the reaction is complete, the mixture is partitioned (using solvents such as EtOAc and 10% NH₄Cl). The EtOAc layer is washed (using agents such as aqueous 10% NH₄Cl, aqueous 1M HCl and water). The organic layer is dried (using an agent such as MgSO₄), filtered and concentrated. Recrystallization (using a mixture such as ether:hexane) gives a pyrimidine carbonitrile Compound A6.

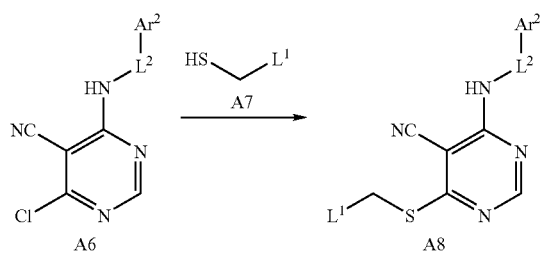

A solution of $L^1$ substituted-methylenethiol Compound A7 (in a solvent such as THF) is added dropwise to a solution of Compound A6 (in an organic base such as pyridine or a solvent such as THF and TEA).

Upon completion of the reaction, the mixture is partitioned (using solvents such as EtOAc and an aqueous solution such as 1M HCl). The organic layer is washed (with an agent such as aqueous 1M HCl, aqueous 10% NH₄Cl, water, brine and the like or mixtures thereof), then dried (using an agent such as MgSO₄ or Na₂SO₄), filtered and concentrated to provide a solid. The solid is suspended in a solvent (such as hexane and the like) and is collected by filtration to provide a substituted pyrimidine carbonitrile Compound A8 which in some cases may be optionally purified via flash chromatography (using an eluent such as 1% MeOH:DCM).

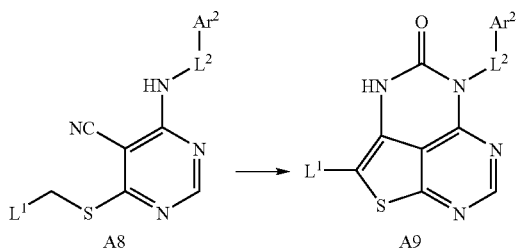

A basic solution (such as 1M potassium t-butoxide or triethylamine in THF) is added dropwise to a solution of Compound A8 (in a solvent such as THF) at 0° C. After 2 hrs, a reagent (such as CDI, triphosgene and the like) is added to the mixture. The reaction mixture is monitored for completion and then the reaction is quenched and precipitated using an agent such as aqueous 0.5M NaH₂PO₄. In some cases the addition of another solvent such as DCM aids the precipitation of product. The product is collected by filtration and rinsed successively (using agents such as DCM and ether) to give a $L^1$ substituted thia-tetraazaacenaphthylene Compound A9, representative of a compound of Formula (I).

Scheme B

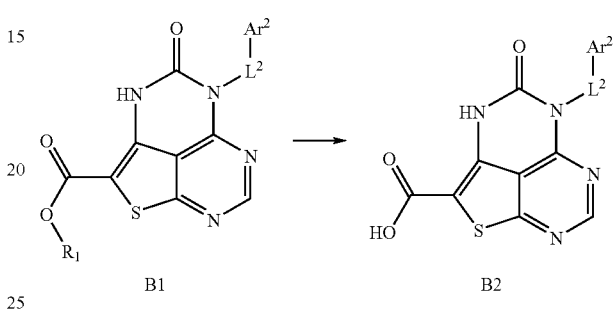

When $L^1$ is an ester Compound B1, representative of a compound of Formula (I), a solution of Compound B1 (in solvent such as THF, MeOH, EtOH and the like containing water) is hydrolyzed with a reagent (such as NaOH or LiOH). Upon completion, the reaction is acidified (using an agent such as aqueous 0.5M NaH₂PO₄ or aqueous 1M HCl) to precipitate Compound B2. When required, the compound is extracted (using a solvent such as EtOAc or DCM) and the combined organic layers are dried (using an agent such as MgSO₄ or Na₂SO₄), then filtered and concentrated to provide the carboxylic acid Compound B2, representative of a compound of Formula (I).

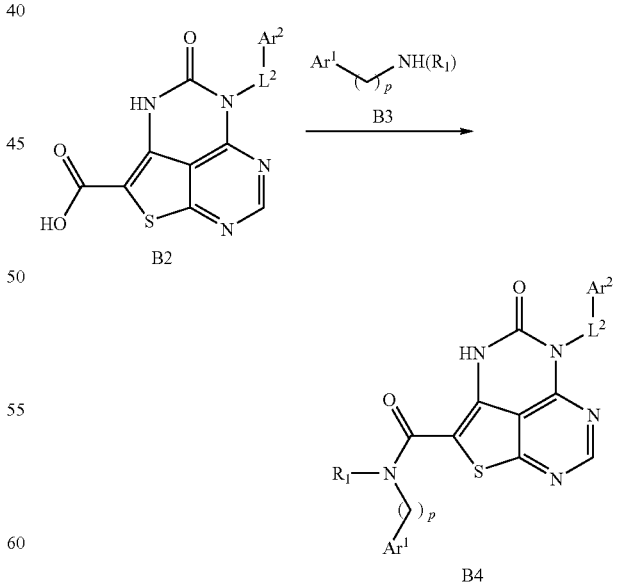

The carboxylic acid functionality in Compound B2 is activated (using reagents such as SOCl₂ or coupling reagents such as HATU, PyBop and the like) for displacement by standard amide bond-forming protocols and combined with a suitably substituted amine Compound B3. Upon completion the reaction mixture is diluted (using a solvent such as DCM or EtOAc) and washed successively (with aqueous 10% NH₄Cl, water and brine). The organic layer is dried (using an agent such as MgSO₄ or Na₂SO₄), filtered and, as required, may be treated with an acidic solution (such as excess 2M HCl in ether) to precipitate Compound B4, representative of a compound of Formula (I), as an HCl salt.

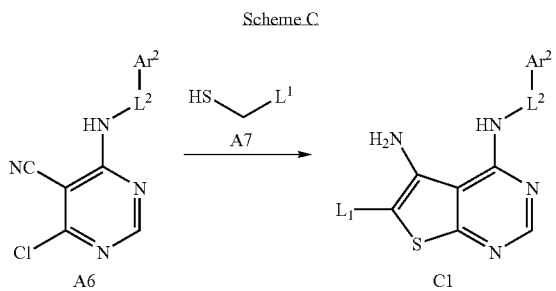

Alternatively, Compound A6 may be directly cyclized to the intermediate Compound C1 by using a strong base (such as 21% sodium ethoxide in a solvent such as ethanol) to install the substituted-methylenethiol Compound A7. The desired material is precipitated by addition of an acidic solution such as 1 M HCl, collected by filtration and washed with an appropriate solvent such as water and MeOH to give the Compound C1.

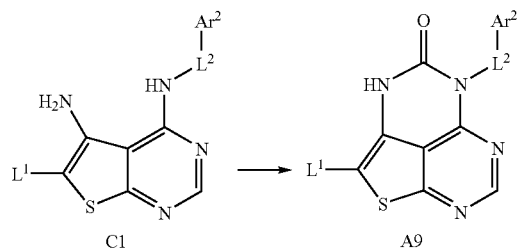

Using the procedure described above for preparing Compound A9, Compound C1 is cyclized with a reagent (such as CDI, triphosgene and the like) to give the thia-tetraazaacenaphthylene carboxylic acid Compound A9, representative of a compound of Formula (I).

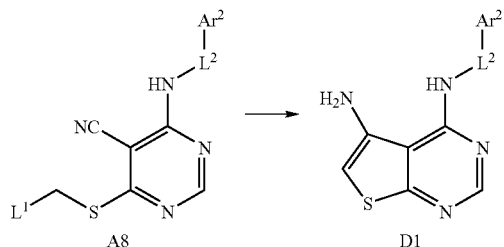

A base (such as DBU) is added to a solution of Compound A8 (in a solvent such as THF) and heated at reflux for a period of about 24 hrs. The reaction mixture is monitored for completion and then the reaction is partitioned between an aqueous solution (such as 0.5M NaH₂PO₄) and an organic solvent (such as EtOAc, DCM and the likes). The organic layer is washed (with an agent such as aqueous 0.5M NaH₂PO₄, aqueous 10% NH₄Cl, water, brine and the like or mixtures thereof), then dried (using an agent such as MgSO₄ or Na₂SO₄), filtered and concentrated to dryness. The product is purified via flash chromatography to give a thienopyrimidine Compound D1.

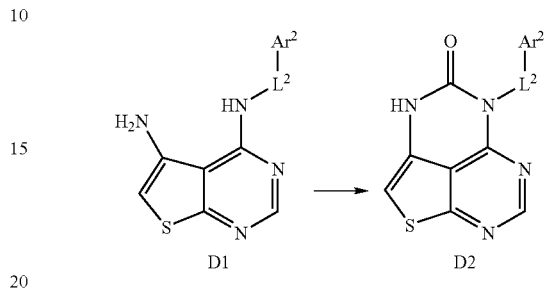

A reagent (such as CDI, triphosgene, and the like) is added to a mixture of Compound D1 (in a solvent such as THF) and a base (such as DIPEA, Et₃N, KOtBu and the like). After a period of time, a product precipitates and is collected by filtration and rinsed successively (using agents such as hexanes, DCM and ether) to give a thia-tetraazaacenaphthylene Compound D2, representative of a compound of Formula (I).

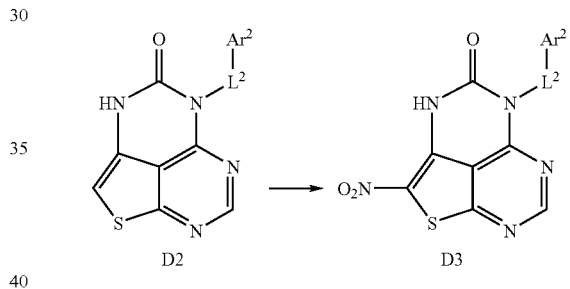

To a solution of Compound D2 (in a solvent such as DCM, THF, AcOH, H₂SO₄ or a mixture thereof) is added an electrophilic or nascent electrophilic reagent (such as KNO₃ and the like). The reaction mixture is monitored for completion and then the reaction is partitioned between water and an organic solvent (such as EtOAc, DCM and the like). The organic layer is washed (with an agent such as water, an aqueous saturated NaHCO₃, brine and the like or mixtures thereof) and dried (using an agent such as MgSO₄ or Na₂SO₄), then filtered and concentrated to dryness. The product is purified via flash chromatography to give a substituted thia-tetraazaacenaphthylene Compound D3, representative of a compound of Formula (I).

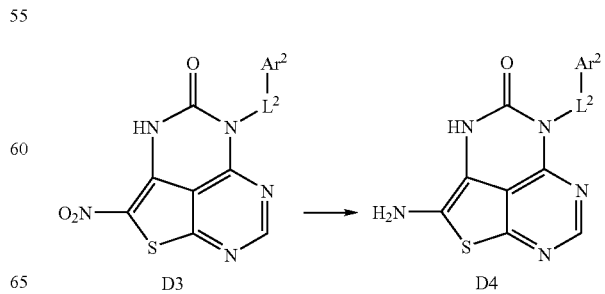

A solution of Compound D3 (in a solvent such as EtOAc, THF, MeOH, EtOH and the like) to subjected to hydrogen (typically at a pressure between 30-50 psi) in the presence of a transition metal (such as Pd/C). The completed reaction is filtered through a Celite 545 plug, rinsed with the reaction solvent of choice and concentrated down to give an amine substituted thia-tetraazaacenaphthylene Compound D4, representative of a compound of Formula (I).

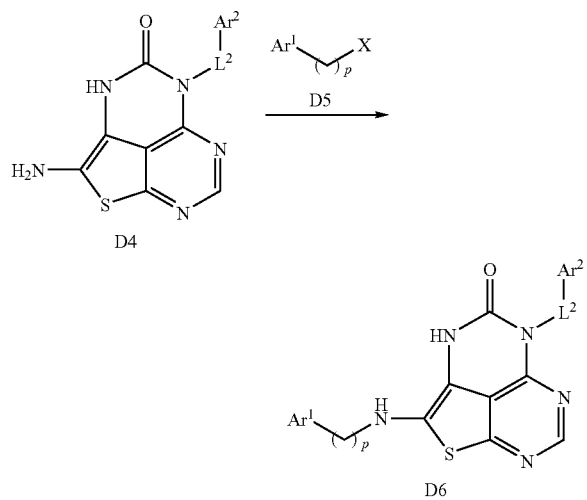

Compound D5 (wherein X is an acid chloride, isocyanate, sulfonyl chloride and the like) is added to a solution of Compound D4 (in a solvent such as THF, DMF, NMP, 1,4-dioxane and the like) and an organic base (such as DIPEA, Et₃N and the like) at a temperature in a range of from about −20° C. to about RT. The reaction mixture is monitored for completion and the mixture is partitioned between water and an organic solvent (such as EtOAc, DCM and the like). The extracted layers are dried, filtered and concentrated to dryness. The product is purified via flash or reverse phase chromatography to give a substituted thia-tetraazaacenaphthylene Compound D6, representative of a compound of Formula (I).

Scheme E

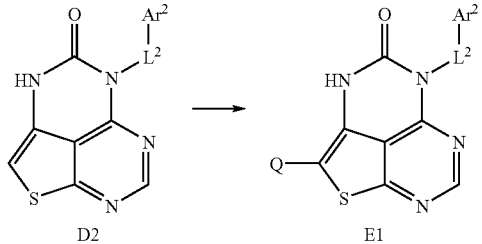

Alternatively, an electrophilic or nascent electrophilic reagent (such as NBS, I₂ and the like) is added to a solution of Compound D2, representative of a compound of Formula (I) (in a solvent such as DCM, THF, AcOH or a mixture thereof). The reaction mixture is monitored for completion and then the reaction is partitioned between water and an organic solvent (such as EtOAc, DCM and the like). The organic layer is washed (with an agent such as water, an aqueous saturated NaHCO₃, brine and the like or mixtures thereof) and dried (using an agent such as MgSO₄ or Na₂SO₄), then filtered and concentrated to dryness. The product is purified via flash chromatography to give a substituted thia-tetraazaacenaphthylene Compound E1, wherein Q is halogen or another suitable leaving group.

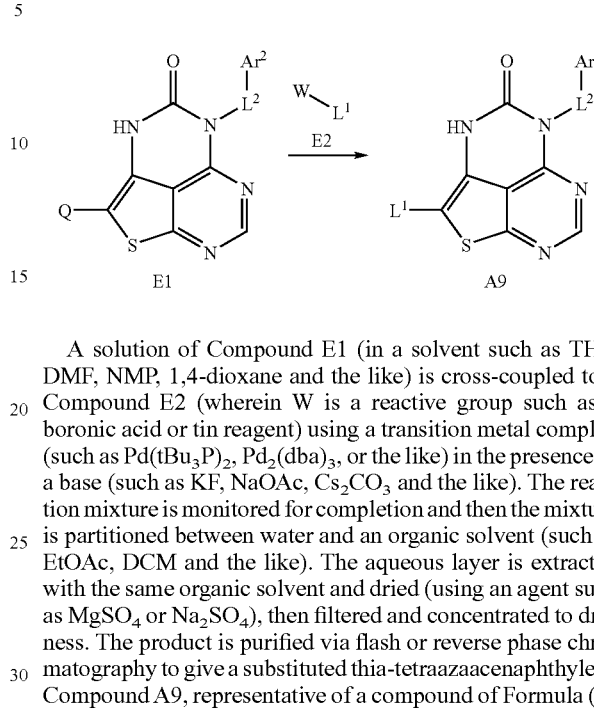

A solution of Compound E1 (in a solvent such as THF, DMF, NMP, 1,4-dioxane and the like) is cross-coupled to a Compound E2 (wherein W is a reactive group such as a boronic acid or tin reagent) using a transition metal complex (such as Pd(tBu₃P)₂, Pd₂(dba)₃, or the like) in the presence of a base (such as KF, NaOAc, Cs₂CO₃ and the like). The reaction mixture is monitored for completion and then the mixture is partitioned between water and an organic solvent (such as EtOAc, DCM and the like). The aqueous layer is extracted with the same organic solvent and dried (using an agent such as MgSO₄ or Na₂SO₄), then filtered and concentrated to dryness. The product is purified via flash or reverse phase chromatography to give a substituted thia-tetraazaacenaphthylene Compound A9, representative of a compound of Formula (I).

EXAMPLE 1

5-(3-chloro-4-fluoro-phenyl)-4-oxo-4,5-dihydro-3H-1-thia-3,5,6,8-tetraaza-acenaphthylene-2-carboxylic acid (Cpd 1)

5-(3-chloro-4-fluoro-phenyl)-4-oxo-4,5-dihydro-3H-1-thia-3,5,6,8-tetraaza-acenaphthylene-2-carboxylic acid (4-piperidin-1-ylmethyl-phenyl)-amide (Cpd 3)

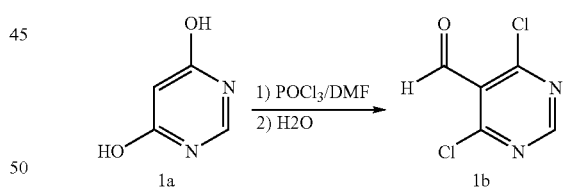

DMF (40 mL) was added to a solution of POCl₃ (400 mL, 4.4 mol) at 0° C. and the mixture was stirred for 1 hour at ambient temperature. 4,6-Dihydroxypyrimidine Compound 1a (50 g, 0.45 mol) was added to the reaction mixture at RT. After 1 hour, the reaction was heated at reflux for 3 hours. The reaction mixture was concentrated in vacuo to remove the excess POCl₃. The remaining residue was diluted with ethyl acetate and carefully quenched, while stirring, by the slow addition of ice. The isolated organic solution was sequentially washed with an aqueous saturated NaHCO₃ solution and brine. The organic layer was dried over Na₂SO₄, then filtered and concentrated to give a solid. The solid was extracted with hot hexanes and the solution evaporated down to yield 4,6-dichloro-pyrimidine-5-carboxaldehyde Compound 1b (60 g). MS 177 (MH⁺).

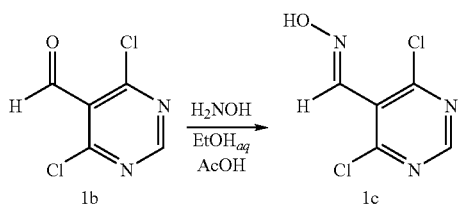

Hydroxylamine hydrochloride (18.0 g, 0.257 mol) in 10% aqueous ethanol (220 mL) was added dropwise to a solution of Compound 1b (39 g, 0.22 mol) in acetic acid (300 mL). The reaction mixture was stirred for 1 hour at ambient temperature before diluting with ethyl acetate and washing with water followed by a saturated NaHCO$_3$ solution and brine. The organic layer was dried over Na$_2$SO$_4$, then filtered and concentrated to give a solid that upon trituration with hexanes gave 4,6-dichloro-pyrimidine-5-carbaldehyde oxime Compound 1c (44 g). MS192 (MH$^+$). Note: DSC (differential scanning calorimetry) results of the oxime show a major exothermic decomposition initiating at 85° C.

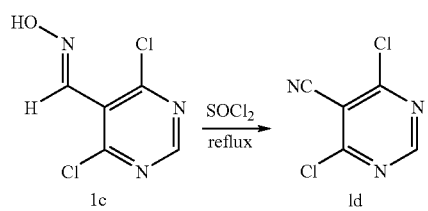

Compound 1c (16.3 g, 84.9 mmol) was added portionwise with great care to stirring SOCl$_2$ (100 mL) at 0° C. After completion of the addition process, and no evidence of exothermic reaction, the reaction mixture was gradually brought to reflux for 3 hours. The reaction mixture was concentrated to remove the excess SOCl$_2$. The residue was diluted in ethyl acetate, and then concentrated a second time. The resulting solid was triturated with hot hexanes to yield 4,6-dichloro-pyrimidine-5-carbonitrile Compound 1d (13.9 g). MS174 (MH$^+$). (see also, Kloetzer, W.; Herberz, M.; Monatsh. Chem.; GE; 96; 1965; 1573-1578)

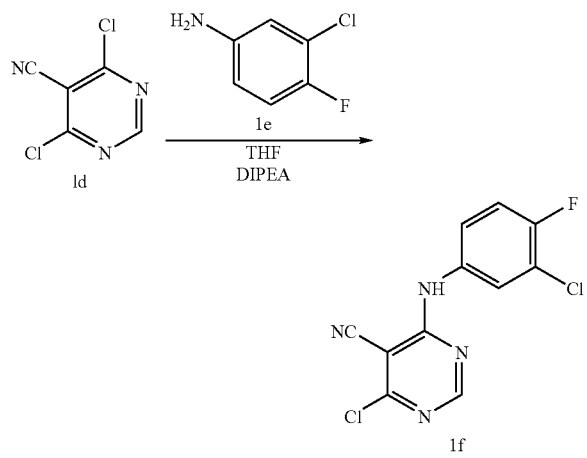

3-chloro-4-fluoro-phenylamine Compound 1e (15.3 g, 105 mmol) in THF (100 mL) was added dropwise to a solution containing Compound 1d (22.0 g, 105 mmol), THF (200 mL) and DIPEA (34 mL, 195 mmol) at 0° C. After 1.5 hours, the reaction mixture was partitioned between ethyl acetate and aqueous 10% NH$_4$Cl. The ethyl acetate layer washed consecutively with aqueous 10% NH$_4$Cl, aqueous 1M HCl and water. The organic layer was dried over MgSO$_4$, then filtered and concentrated to a yellow solid. Recrystallization from ether/hexane gave 4-chloro-6-(3-chloro-4-fluoro-phenylamino)-pyrimidine-5-carbonitrile Compound 1f (28.0 g, 95%). MS 283 (MH$^+$). (see also, Clark, J. et al.; J. Chem. Soc. Perkin Trans. 1; 1976; 1004-1007)

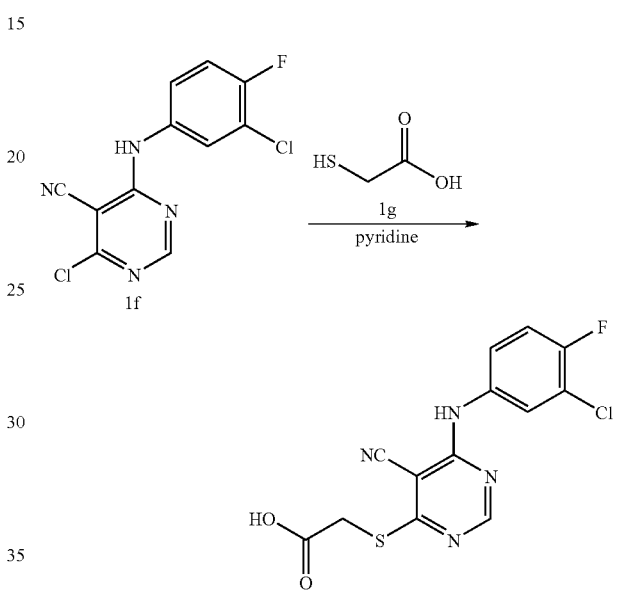

A solution of 97% mercaptoacetic acid Compound 1g (16 mL, 223 mmol) in pyridine (100 mL) was added dropwise to a solution of 4-chloro-6-(3-chloro-4-fluoro-phenylamino)-pyrimidine-5-carbonitrile Compound 1f (60.0 g, 213 mmol) in pyridine (400 mL). After 18 hours, the reaction mixture was partitioned between ethyl acetate and aqueous 1M HCl. The ethyl acetate layer was washed repeatedly with aqueous 1M HCl, then by water and brine. The dried organic layer (MgSO$_4$) was filtered and concentrated to give a brown solid. The solid was suspended in hexane and collected by filtration. The isolated solid [6-(3-chloro-4-fluoro-phenylamino)-5-cyano-pyrimidin-4-ylsulfanyl]-acetic acid Compound 1h required no further purification (53 g, 86%). MS 339 (MH$^+$).

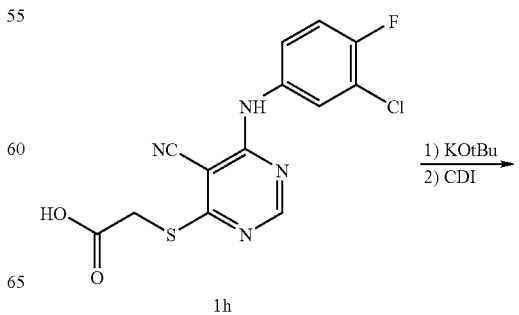

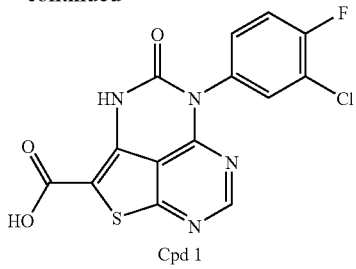

Cpd 1

1M potassium t-butoxide (110 mL, 110 mmol) was added dropwise to a solution of Compound 1h (12.4 g, 36.7 mmol) in THF (200 mL) at 0° C. After 2 hours, carbonyl diimidazole (14.9 g, 91.8 mmol) was added to the reaction mixture. The mixture was stirred for 5 hours, then the reaction was quenched with aqueous 0.5M $NaH_2PO_4$ and diluted with DCM. The resulting brown paste was collected by filtration and rinsed successively with DCM and ether to give 5-(3-chloro-4-fluoro-phenyl)-4-oxo-4,5-dihydro-3H-1-thia-3,5,6,8-tetraaza-acenaphthylene-2-carboxylic acid Compound 1 (11.4 g, 85%). MS 365, 367 ($MH^+$).

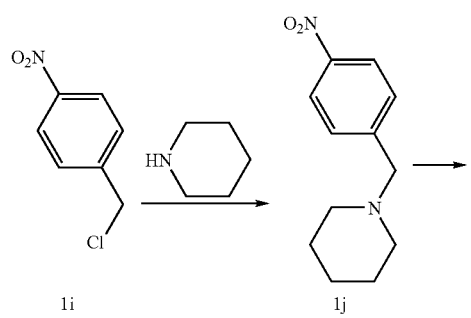

1i  1j

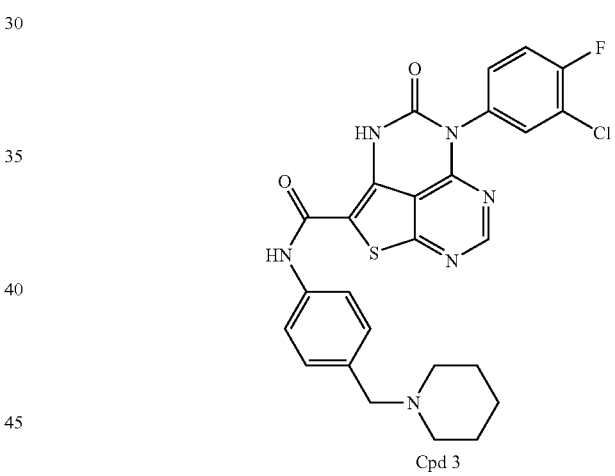

1k 1-chloromethyl-4-nitro-benzene Compound 1i (5.0 g, 29 mmol) and piperidine (5.8 mL, 58 mmol) were combined in THF (30 mL) at ambient temperature. The reaction was refluxed for 4 hours, then diluted with aqueous 10% $NH_4Cl$ and extracted with EtOAc. The combined organic layers were dried over $MgSO_4$, filtered and evaporated in vacuo to provide 1-(4-nitro-benzyl)-piperidine Compound 1j (5.0 g) as a pale yellow oil requiring no further purification (see, Mitsuru Shiraishi, et al., *J. Med. Chem.*, 2000, 43, 2049-2063). $^1$H NMR (DMSO-$d_6$) δ 8.18 (d, 2H); 7.59 (d, 2H); 3.57 (s, 2H); 2.43-2.25 (m, 4H); 1.58-1.32 (m, 6H).

10% Pd/C (300 mg) was added to a solution of Compound 1j (5.0 g, 23 mmol) in EtOAc (50 mL). The mixture was hydrogenated at 50 psi for a period of 2 hrs and filtered through Celite. The filtrate was evaporated and the residue was dissolved in 10% $NH_4Cl$ and washed with ethyl ether. The aqueous layer was then adjusted to pH 10 with NaOH and extracted with EtOAc. The combined organic layers were dried over $MgSO_4$, then filtered, evaporated in vacuo and isolated from hexanes to provide 4-piperidin-1-ylmethyl-phenylamine Compound 1k (3.5 g) as an off-white solid. MS191 ($MH^+$).

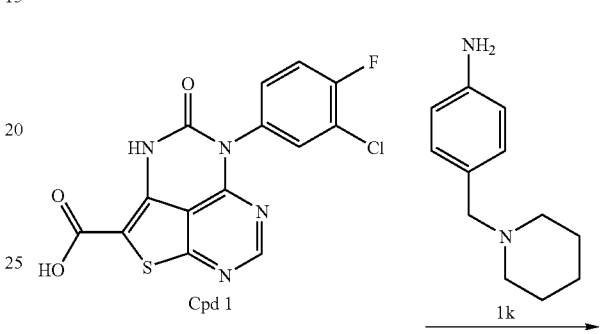

Cpd 1  1k

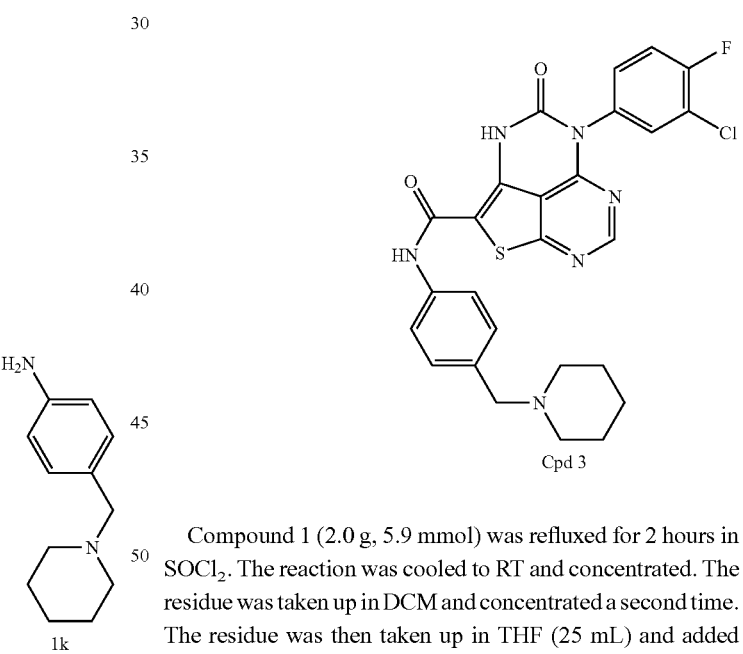

Cpd 3

Compound 1 (2.0 g, 5.9 mmol) was refluxed for 2 hours in $SOCl_2$. The reaction was cooled to RT and concentrated. The residue was taken up in DCM and concentrated a second time. The residue was then taken up in THF (25 mL) and added dropwise to a solution containing Compound 1k (1.1 g, 5.9 mmol), THF (25 mL) and DIPEA (2.5 mL, 14.4 mmol) at 0° C. After 30 mins, the reaction was diluted with DCM and washed successively with 10% $NH_4Cl$, water and brine. The organic layer was dried ($Na_2SO_4$), then filtered and treated with excess 2M HCl in ether to precipitate Compound 3 as an HCl salt (1.45 g). MS 537, 539 ($MH^+$).

Using the procedure of Example 1 and known appropriate reagents and starting materials, the following compounds of the invention were prepared:

| Cpd | Name | MS |
|---|---|---|
| 180 | 5-[3-bromo-4-(pyridin-2-ylmethoxy)-phenyl]-4-oxo-4,5-dihydro-3H-1-thia-3,5,6,8-tetraaza-acenaphthylene-2-carboxylic acid (4-morpholin-4-ylmethyl-phenyl)-amide | 672 |
| 181 | 5-(3-bromo-4-methoxy-phenyl)-4-oxo-4,5-dihydro-3H-1-thia-3,5,6,8-tetraaza-acenaphthylene-2-carboxylic acid (4-morpholin-4-ylmethyl-phenyl)-amide | 595 |
| 182 | 5-(3-bromo-4-methoxy-phenyl)-4-oxo-4,5-dihydro-3H-1-thia-3,5,6,8-tetraaza-acenaphthylene-2-carboxylic acid (4-piperidin-1-ylmethyl-phenyl)-amide | 593 |
| 183 | 5-(3-bromo-4-methoxy-phenyl)-4-oxo-4,5-dihydro-3H-1-thia-3,5,6,8-tetraaza-acenaphthylene-2-carboxylic acid (3-methoxy-4-morpholin-4-ylmethyl-phenyl)-amide | 625 |
| 184 | 5-(3-bromo-phenyl)-4-oxo-4,5-dihydro-3H-1-thia-3,5,6,8-tetraaza-acenaphthylene-2-carboxylic acid (3-methoxy-4-morpholin-4-ylmethyl-phenyl)-amide | 595 |
| 186 | 4-oxo-5-(4-phenylsulfanyl-phenyl)-4,5-dihydro-3H-1-thia-3,5,6,8-tetraaza-acenaphthylene-2-carboxylic acid | 421 |
| 187 | 5-(3-bromo-4-phenoxy-phenyl)-4-oxo-4,5-dihydro-3H-1-thia-3,5,6,8-tetraaza-acenaphthylene-2-carboxylic acid (4-morpholin-4-ylmethyl-phenyl)-amide | 657 |
| 188 | 5-(3-bromo-4-phenoxy-phenyl)-4-oxo-4,5-dihydro-3H-1-thia-3,5,6,8-tetraaza-acenaphthylene-2-carboxylic acid (4-piperidin-1-ylmethyl-phenyl)-amide | 655 |
| 189 | 5-(3-bromo-4-phenoxy-phenyl)-4-oxo-4,5-dihydro-3H-1-thia-3,5,6,8-tetraaza-acenaphthylene-2-carboxylic acid (3-methoxy-4-morpholin-4-ylmethyl-phenyl)-amide | 687 |
| 191 | 4-oxo-5-(4-phenylsulfanyl-phenyl)-4,5-dihydro-3H-1-thia-3,5,6,8-tetraaza-acenaphthylene-2-carboxylic acid (1-methyl-piperidin-4-yl)-amide | 517 |
| 195 | 5-(4-bromo-phenyl)-4-oxo-4,5-dihydro-3H-1-thia-3,5,6,8-tetraaza-acenaphthylene-2-carboxylic acid (4-piperidin-1-ylmethyl-phenyl)-amide | 563 |
| 196 | 5-(4-bromo-phenyl)-4-oxo-4,5-dihydro-3H-1-thia-3,5,6,8-tetraaza-acenaphthylene-2-carboxylic acid (4-morpholin-4-ylmethyl-phenyl)-amide | 565 |
| 197 | 4-oxo-5-(3-phenoxy-phenyl)-4,5-dihydro-3H-1-thia-3,5,6,8-tetraaza-acenaphthylene-2-carboxylic acid (4-piperidin-1-ylmethyl-phenyl)-amide | 577 |
| 199 | 4-oxo-5-(3-phenoxy-phenyl)-4,5-dihydro-3H-1-thia-3,5,6,8-tetraaza-acenaphthylene-2-carboxylic acid [4-(4-methyl-piperazin-1-ylmethyl)-phenyl]-amide | 592 |
| 200 | 4-oxo-5-(3-phenoxy-phenyl)-4,5-dihydro-3H-1-thia-3,5,6,8-tetraaza-acenaphthylene-2-carboxylic acid (3-methoxy-4-morpholin-4-ylmethyl-phenyl)-amide | 609 |
| 201 | 5-(4-bromo-phenyl)-4-oxo-4,5-dihydro-3H-1-thia-3,5,6,8-tetraaza-acenaphthylene-2-carboxylic acid (3-methoxy-4-morpholin-4-ylmethyl-phenyl)-amide | 595 |
| 203 | 4-oxo-5-(4-phenoxy-phenyl)-4,5-dihydro-3H-1-thia-3,5,6,8-tetraaza-acenaphthylene-2-carboxylic acid (3-fluoro-4-morpholin-4-ylmethyl-phenyl)-amide | 597 |
| 204 | 4-oxo-5-(4-phenoxy-phenyl)-4,5-dihydro-3H-1-thia-3,5,6,8-tetraaza-acenaphthylene-2-carboxylic acid [4-(1H-tetrazol-5-yl)-phenyl]-amide | 548 |
| 205 | 5-(4-benzenesulfinyl-phenyl)-4-oxo-4,5-dihydro-3H-1-thia-3,5,6,8-tetraaza-acenaphthylene-2-carboxylic acid (4-piperidin-1-ylmethyl-phenyl)-amide | 609 |
| 207 | 4-oxo-5-(4-phenoxy-phenyl)-4,5-dihydro-3H-1-thia-3,5,6,8-tetraaza-acenaphthylene-2-carboxylic acid (3-ethoxy-4-morpholin-4-ylmethyl-phenyl)-amide | 623 |
| 208 | 5-[3-chloro-4-(pyridin-3-yloxy)-phenyl]-4-oxo-4,5-dihydro-3H-1-thia-3,5,6,8-tetraaza-acenaphthylene-2-carboxylic acid (4-morpholin-4-ylmethyl-phenyl)-amide | 614 |
| 209 | 5-[3-chloro-4-(pyridin-3-yloxy)-phenyl]-4-oxo-4,5-dihydro-3H-1-thia-3,5,6,8-tetraaza-acenaphthylene-2-carboxylic acid (4-piperidin-1-ylmethyl-phenyl)-amide | 612 |
| 211 | 4-oxo-5-(4-phenoxy-phenyl)-4,5-dihydro-3H-1-thia-3,5,6,8-tetraaza-acenaphthylene-2-carboxylic acid (1-methyl-piperidin-4-yl)-amide | 501 |
| 215 | 4-oxo-5-(4-phenoxy-phenyl)-4,5-dihydro-3H-1-thia-3,5,6,8-tetraaza-acenaphthylene-2-carboxylic acid (4-methyl-piperazin-1-yl)-amide | 502 |
| 218 | 4-oxo-5-(4-phenylsulfanyl-phenyl)-4,5-dihydro-3H-1-thia-3,5,6,8-tetraaza-acenaphthylene-2-carboxylic acid [4-(4-methyl-piperazin-1-ylmethyl)-phenyl]-amide | 608 |
| 219 | 4-oxo-5-(4-phenylsulfanyl-phenyl)-4,5-dihydro-3H-1-thia-3,5,6,8-tetraaza-acenaphthylene-2-carboxylic acid (3-methoxy-4-morpholin-4-ylmethyl-phenyl)-amide | 625 |
| 220 | 4-oxo-5-(4-phenoxy-phenyl)-4,5-dihydro-3H-1-thia-3,5,6,8-tetraaza-acenaphthylene-2-carboxylic acid (3-morpholin-4-ylmethyl-phenyl)-amide | 579 |
| 221 | 4-oxo-5-(4-phenoxy-phenyl)-4,5-dihydro-3H-1-thia-3,5,6,8-tetraaza-acenaphthylene-2-carboxylic acid (3-chloro-4-morpholin-4-ylmethyl-phenyl)-amide | 613 |

-continued

| Cpd | Name | MS |
|---|---|---|
| 224 | 4-oxo-5-(4-phenylsulfanyl-phenyl)-4,5-dihydro-3H-1-thia-3,5,6,8-tetraaza-acenaphthylene-2-carboxylic acid (3-methoxy-4-piperidin-1-ylmethyl-phenyl)-amide | 623 |
| 225 | 5-[3-chloro-4-(thiophen-2-ylmethoxy)-phenyl]-4-oxo-4,5-dihydro-3H-1-thia-3,5,6,8-tetraaza-acenaphthylene-2-carboxylic acid | 459 |
| 226 | 5-[3-chloro-4-(thiophen-2-ylmethoxy)-phenyl]-4-oxo-4,5-dihydro-3H-1-thia-3,5,6,8-tetraaza-acenaphthylene-2-carboxylic acid (4-morpholin-4-ylmethyl-phenyl)-amide | 633 |
| 227 | 5-[3-chloro-4-(thiophen-2-ylmethoxy)-phenyl]-4-oxo-4,5-dihydro-3H-1-thia-3,5,6,8-tetraaza-acenaphthylene-2-carboxylic acid (4-piperidin-1-ylmethyl-phenyl)-amide | 631 |
| 228 | 5-[3-chloro-4-(thiophen-2-ylmethoxy)-phenyl]-4-oxo-4,5-dihydro-3H-1-thia-3,5,6,8-tetraaza-acenaphthylene-2-carboxylic acid (3-methoxy-4-piperidin-1-ylmethyl-phenyl)-amide | 661 |
| 229 | 5-[3-chloro-4-(thiophen-2-ylmethoxy)-phenyl]-4-oxo-4,5-dihydro-3H-1-thia-3,5,6,8-tetraaza-acenaphthylene-2-carboxylic acid (3-methoxy-4-morpholin-4-ylmethyl-phenyl)-amide | 663 |
| 230 | 5-[3-chloro-4-(thiophen-2-ylmethoxy)-phenyl]-4-oxo-4,5-dihydro-3H-1-thia-3,5,6,8-tetraaza-acenaphthylene-2-carboxylic acid (1-methyl-piperidin-4-yl)-amide | 555 |
| 231 | 4-oxo-5-(4-phenoxy-phenyl)-4,5-dihydro-3H-1-thia-3,5,6,8-tetraaza-acenaphthylene-2-carboxylic acid (4-morpholin-4-ylmethyl-3-trifluoromethyl-phenyl)-amide | 647 |
| 232 | 4-oxo-5-(4-phenoxy-phenyl)-4,5-dihydro-3H-1-thia-3,5,6,8-tetraaza-acenaphthylene-2-carboxylic acid (3-methyl-4-morpholin-4-ylmethyl-phenyl)-amide | 593 |
| 233 | 4-oxo-5-(4-phenoxy-phenyl)-4,5-dihydro-3H-1-thia-3,5,6,8-tetraaza-acenaphthylene-2-carboxylic acid [4-(4-hydroxy-piperidin-1-ylmethyl)-phenyl]-amide | 593 |
| 234 | 4-oxo-5-(4-phenoxy-phenyl)-4,5-dihydro-3H-1-thia-3,5,6,8-tetraaza-acenaphthylene-2-carboxylic acid [4-(3-fluoro-piperidin-1-ylmethyl)-phenyl]-amide | 595 |
| 235 | 5-[3-chloro-4-(furan-2-ylmethoxy)-phenyl]-4-oxo-4,5-dihydro-3H-1-thia-3,5,6,8-tetraaza-acenaphthylene-2-carboxylic acid | 443 |
| 236 | 4-oxo-5-[4-(pyridin-3-yloxy)-phenyl]-4,5-dihydro-3H-1-thia-3,5,6,8-tetraaza-acenaphthylene-2-carboxylic acid (3-methoxy-4-morpholin-4-ylmethyl-phenyl)-amide | 610 |
| 237 | 4-oxo-5-[4-(pyridin-3-yloxy)-phenyl]-4,5-dihydro-3H-1-thia-3,5,6,8-tetraaza-acenaphthylene-2-carboxylic acid (4-morpholin-4-ylmethyl-phenyl)-amide | 580 |
| 238 | 4-oxo-5-[4-(pyridin-3-yloxy)-phenyl]-4,5-dihydro-3H-1-thia-3,5,6,8-tetraaza-acenaphthylene-2-carboxylic acid (4-piperidin-1-ylmethyl-phenyl)-amide | 578 |
| 239 | 4-oxo-5-(4-phenoxy-phenyl)-4,5-dihydro-3H-1-thia-3,5,6,8-tetraaza-acenaphthylene-2-carboxylic acid (4-morpholin-4-ylmethyl-3-trifluoromethoxy-phenyl)-amide | 663 |
| 240 | 4-oxo-5-(4-phenoxy-phenyl)-4,5-dihydro-3H-1-thia-3,5,6,8-tetraaza-acenaphthylene-2-carboxylic acid (4-morpholin-4-ylmethyl-3-trifluoromethoxy-phenyl)-amide | 607 |
| 242 | 4-oxo-5-(4-phenoxy-phenyl)-4,5-dihydro-3H-1-thia-3,5,6,8-tetraaza-acenaphthylene-2-carboxylic acid (3-methoxy-4-piperidin-1-ylmethyl-phenyl)-amide | 607 |
| 243 | 5-[3-chloro-4-(furan-2-ylmethoxy)-phenyl]-4-oxo-4,5-dihydro-3H-1-thia-3,5,6,8-tetraaza-acenaphthylene-2-carboxylic acid (3-methoxy-4-piperidin-1-ylmethyl-phenyl)-amide | 645 |
| 244 | 5-[3-chloro-4-(furan-2-ylmethoxy)-phenyl]-4-oxo-4,5-dihydro-3H-1-thia-3,5,6,8-tetraaza-acenaphthylene-2-carboxylic acid (4-piperidin-1-ylmethyl-phenyl)-amide | 615 |
| 245 | 5-[3-chloro-4-(furan-2-ylmethoxy)-phenyl]-4-oxo-4,5-dihydro-3H-1-thia-3,5,6,8-tetraaza-acenaphthylene-2-carboxylic acid (4-morpholin-4-ylmethyl-phenyl)-amide | 617 |
| 246 | 5-[3-chloro-4-(furan-2-ylmethoxy)-phenyl]-4-oxo-4,5-dihydro-3H-1-thia-3,5,6,8-tetraaza-acenaphthylene-2-carboxylic acid (3-methoxy-4-morpholin-4-ylmethyl-phenyl)-amide | 647 |
| 247 | 5-[3-chloro-4-(furan-2-ylmethoxy)-phenyl]-4-oxo-4,5-dihydro-3H-1-thia-3,5,6,8-tetraaza-acenaphthylene-2-carboxylic acid (1-methyl-piperidin-4-yl)-amide | 539 |
| 248 | 5-(4-benzoylamino-phenyl)-4-oxo-4,5-dihydro-3H-1-thia-3,5,6,8-tetraaza-acenaphthylene-2-carboxylic acid (4-morpholin-4-ylmethyl-phenyl)-amide | 606 |
| 249 | 5-(4-benzoylamino-phenyl)-4-oxo-4,5-dihydro-3H-1-thia-3,5,6,8-tetraaza-acenaphthylene-2-carboxylic acid (4-piperidin-1-ylmethyl-phenyl)-amide | 604 |
| 250 | 4-oxo-5-(4-phenoxy-phenyl)-4,5-dihydro-3H-1-thia-3,5,6,8-tetraaza-acenaphthylene-2-carboxylic acid [4-(4-fluoro-piperidin-1-ylmethyl)-phenyl]-amide | 595 |
| 252 | 5-[3-chloro-4-(3-fluoro-benzyloxy)-phenyl]-4-oxo-4,5-dihydro-3H-1-thia-3,5,6,8-tetraaza-acenaphthylene-2-carboxylic acid [4-(4-methyl-piperazin-1-ylmethyl)-phenyl]-amide | 658 |

-continued

| Cpd | Name | MS |
|---|---|---|
| 253 | 4-oxo-5-(4-phenoxy-phenyl)-4,5-dihydro-3H-1-thia-3,5,6,8-tetraaza-acenaphthylene-2-carboxylic acid [4-(3,5-dimethyl-morpholin-4-ylmethyl)-phenyl]-amide | 607 |
| 254 | 4-oxo-5-(4-phenoxy-phenyl)-4,5-dihydro-3H-1-thia-3,5,6,8-tetraaza-acenaphthylene-2-carboxylic acid [4-(4-hydroxymethyl-piperidin-1-ylmethyl)-phenyl]-amide | 607 |
| 255 | 4-oxo-5-(4-phenoxy-phenyl)-4,5-dihydro-3H-1-thia-3,5,6,8-tetraaza-acenaphthylene-2-carboxylic acid [4-(4-methyl-piperidin-1-ylmethyl)-phenyl]-amide | 591 |
| 256 | 4-oxo-5-(4-phenoxy-phenyl)-4,5-dihydro-3H-1-thia-3,5,6,8-tetraaza-acenaphthylene-2-carboxylic acid [4-(3-hydroxymethyl-piperidin-1-ylmethyl)-phenyl]-amide | 607 |
| 257 | 4-oxo-5-(4-phenoxy-phenyl)-4,5-dihydro-3H-1-thia-3,5,6,8-tetraaza-acenaphthylene-2-carboxylic acid (3-dimethylamino-4-morpholin-4-ylmethyl-phenyl)-amide | 622 |
| 258 | [1-(4-{[4-oxo-5-(4-phenoxy-phenyl)-4,5-dihydro-3H-1-thia-3,5,6,8-tetraaza-acenaphthylene-2-carbonyl]-amino}-benzyl)-piperidin-4-yl]-carbamic acid tert-butyl ester | 692 |
| 259 | 4-oxo-5-(4-phenoxy-phenyl)-4,5-dihydro-3H-1-thia-3,5,6,8-tetraaza-acenaphthylene-2-carboxylic acid [4-(4-amino-piperidin-1-ylmethyl)-phenyl]-amide | 592 |
| 260 | 4-oxo-5-(4-phenoxy-phenyl)-4,5-dihydro-3H-1-thia-3,5,6,8-tetraaza-acenaphthylene-2-carboxylic acid [4-(4-dimethylamino-piperidin-1-ylmethyl)-phenyl]-amide | 620 |
| 261 | 4-oxo-5-(4-phenoxy-phenyl)-4,5-dihydro-3H-1-thia-3,5,6,8-tetraaza-acenaphthylene-2-carboxylic acid [4-(4-methoxy-piperidin-1-ylmethyl)-phenyl]-amide | 607 |
| 262 | 4-oxo-5-(4-phenoxy-phenyl)-4,5-dihydro-3H-1-thia-3,5,6,8-tetraaza-acenaphthylene-2-carboxylic acid (3-hydroxy-4-morpholin-4-ylmethyl-phenyl)-amide | 595 |
| 263 | 4-oxo-5-(4-phenoxy-phenyl)-4,5-dihydro-3H-1-thia-3,5,6,8-tetraaza-acenaphthylene-2-carboxylic acid [4-(4,4-difluoro-piperidin-1-ylmethyl)-phenyl]-amide | 613 |

EXAMPLE 2

5-(4-bromo-2-fluoro-phenyl)-4-oxo-4,5-dihydro-3H-1-thia-3,5,6,8-tetraaza-acenaphthylene-2-carboxylic acid (Cpd 40)

5-(4-bromo-2-fluoro-phenyl)-4-oxo-4,5-dihydro-3H-1-thia-3,5,6,8-tetraaza-acenaphthylene-2-carboxylic acild (3,4-dimethoxy-phenyl)-amide (Cpd 37)

Using the procedure of Example 1, 4-bromo-2-fluoro-phenylamine Compound 2a was used in place of 3-chloro-4-fluoro-phenylamine Compound 1e to prepare 4-(4-bromo-2-fluoro-phenylamino)-6-chloro-pyrimidine-5-carbonitrile Compound 2b. Using the procedure of Example 1, Compound 2b was used in place of 4-chloro-6-(3-chloro-4-fluoro-phenylamino)-pyrimidine-5-carbonitrile Compound 1f to prepare Compound 40. MS 407, 409 (M−).

Analogously using the procedure of Example 1, HATU (0.22 g, 0.59 mmol), DIPEA (0.26 mL, 1.47 mmol) and 3,4-dimethoxy-phenylamine Compound 2c (0.09 g, 0.59 mmol) were added to a suspension of Compound 40 (0.2 g, 0.49 mmol) in THF (5 mL). The resulting dark solution was stirred for 16 hours, then the reaction was quenched with 10% aq. NH$_4$Cl (25 mL) and extracted with EtOAc. The organic layers were combined and dried (Na$_2$SO$_4$), then filtered and concentrated. The residue was purified by reverse phase HPLC using gradient elution (60% CH$_3$CN/40% H$_2$0 to 100% CH$_3$CN spiked with 0.05% TFA) to yield Compound 37 (110 mg, 42%). MS 544, 546 (MH+).

EXAMPLE 3

5-(2-chloro-4-fluoro-phenyl)-4-oxo-4,5-dihydro-3H-1-thia-3,5,6,8-tetraaza-acenaphthylene-2-carboxylic acid (4-morpholin-4-ylmethyl-phenyl)-amide (Cpd 16)

5-(2-chloro-4-fluoro-phenyl)-4-oxo-4,5-dihydro-3H-1-thia-3,5,6,8-tetraaza-acenaphthylene-2-carboxylic acid (Cpd 264)

Using the procedure of Example 1, 2-chloro-4-fluoro-phenylamine Compound 3a used in place of 3-chloro-4-fluoro-phenylamine Compound 1e to prepare 4-chloro-6-(2-chloro-4-fluoro-phenylamino)-pyrimidine-5-carbonitrile Compound 3b.

A solution of 25% NaOMe (1.2 mL, 5.2 mol) was added to a stirred reaction mixture of Compound 3b (1.2 g, 4.3 mmol), 95% methyl thioglycolate (also referred to as mercapto-acetic acid methyl ester) Compound 3c (0.45 mL, 4.7 mmol) and MeOH (20 mL) at 0° C. After 2 hours, the reaction was quenched with water and precipitated by adding 1M HCl. The solid was collected by filtration and washed successively with water, MeOH and ether to give 5-amino-4-(2-chloro-4-fluoro-phenylamino)-thieno[2,3-d]pyrimidine-6-carboxylic acid methyl ester Compound 3d (1.35 g) as a yellow solid. MS 351, 353 (M−). (see, Clark, J; Hitiris, G. Heterocyclic studies. Part 43. Thieno[2,3-d:4,5-d']dipyrimidines, Journal of the Chemical Society, Perkin Transactions 1: Organic and Bio-Organic Chemistry (1972-1999) (1984), (9), 2005-8)

A solution of Compound 3d (1.05 g, 2.99 mmol) in THF (20 mL) and DIPEA (5.75 mL, 33.0 mmol) was treated with 20% phosgene in toluene (7.42 mL, 14.0 mmol). After 18 hrs, the reaction was diluted with 0.5 M NaH$_2$PO$_4$ and extracted with ethyl acetate. The combined organic layers were dried over Mg$_2$SO$_4$, filtered and evaporated down to provide a 5-(2-chloro-4-fluoro-phenyl)-4-oxo-4,5-dihydro-3H-1-thia-3,5,6,8-tetraaza-acenaphthylene-2-carboxylic acid methyl ester intermediate. MS 377, 379 (M⁻). The intermediate was refluxed in a solution of aqueous 25% KOH (5 mL) in MeOH (20 mL) for 2 hours and allowed to cool. The cooled reaction mixture was diluted with water and 1M HCl was added to precipitate 5-(2-chloro-4-fluoro-phenyl)-4-oxo-4, 5-dihydro-3H-1-thia-3,5,6,8-tetraaza-acenaphthylene-2-carboxylic acid Compound 264 (455 mg). MS 363, 365 (M⁻).

Using the procedure of Example 1, morpholine was used in place of piperidine to prepare 4-(4-nitro-benzyl)-morpholine Compound 3e1. Using the procedure of Example 80, Compound 3e1 was used in place of Compound 80c to prepare 4-morpholin-4-ylmethyl-phenylamine Compound 3e (81%). MS 193 (MH⁺). Using the procedure of Example 1, Compound 264 was used in place of Compound 1 and Compound 3e was used in place of 4-piperidin-1-ylmethyl-phenylamine Compound 1k to provide Compound 16. MS 539, 541 (MH⁺)

EXAMPLE 4

5-[1-(3-fluoro-benzyl)-1H-indazol-5-yl]-4-oxo-4,5-dihydro-3H-1-thia-3,5, 6,8-tetraaza-acenaphthylene-2-carboxylic acid ethyl ester (Cpd 78)

5-[1-(3-fluoro-benzyl)-1H-indazol-5-yl]-4-oxo-4,5-dihydro-3H-1-thia-3,5, 6,8-tetraaza-acenaphthylene-2-carboxylic acid (Cpd 79)

5-[1-(3-fluoro-benzyl)-1H-indazol-5-yl]-4-oxo-4,5-dihydro-3H-1-thia-3,5, 6,8-tetraaza-acenaphthylene-2-carboxylic acid (4-piperidin-1-ylmethyl-phenyl)-amide (Cpd 80)

Sodium hydride (NaH) 95% (0.81 g, 34.1 mmol) was added to a solution of 5-nitro-1H-indazole Compound 4a (5.3 g, 32.5 mmol) in DMF (33 mL) at 0° C. under nitrogen. The mixture was stirred for 1 hour at RT, then 1-bromomethyl-3-fluoro-benzene Compound 4b (6.14 g, 32.5 mmol) was added dropwise at 0° C. After stirring at RT for 12 hours, the reaction mixture was partitioned between ethyl acetate and icy water. The organic layer washed with water, brine, dried ($Na_2SO_4$), filtered and the solvent evaporated in vacuo to yield a crude solid. The crude solid was purified via flash chromatography (100% dichloromethane) to yield 1-(3-fluoro-benzyl)-5-nitro-1H-indazole Compound 4c (4.02 g, 46%) as a solid. ¹H NMR (400 MHz, $CDCl_3$) δ 8.76-8.75 (1H, m), 8.27-8.23 (2H, m), 7.40-7.38 (1H, m), 7.33-2.27 (1H, m), 7.01-6.97 (2H, m), 6.89-6.86 (1H, m), 5.64 (2H, s); MS (ES⁺) m/z 272.1 (MH⁺).

A solution of Compound 4c (2.0 g, 7.37 mmol) in MeOH (60 mL) was added to 5% Pd/C (0.2 g) under nitrogen. The reaction mixture was stirred for 2 hours under hydrogen atmosphere and then filtered through celite. The filtrate was evaporated in vacuo to yield 1-(3-fluoro-benzyl)-1H-indazol-5-ylamine Compound 4d (1.72 g, 97%) as a solid. ¹H NMR (400 MHz, $CDCl_3$) δ 7.84 (1H, d), 7.28-7.21 (1H, m), 7.13 (1H, d, J=8.8 Hz), 9.96-6.90 (3H, m), 6.84-6.81 (2H, m), 5.52 (2H, s), 3.60 (2H, br s); MS (ES⁺) m/z 242.1 (MH⁺).

A solution of Compound 4d (1.38 g, 5.74 mmol) in THF (8 mL) was added dropwise to a solution containing 4,6-dichloro-pyrimidine-5-carbonitrile Compound 1d (1.0 g, 5.74 mmol), THF (10 mL) and DIPEA (1.6 mL, 9.20 mmol) at RT. After 2 hours, the reaction mixture was partitioned between ethyl acetate and water. The ethyl acetate layer washed consecutively with aqueous 10% $NH_4Cl$, water and brine. The organic layer was dried over $Na_2SO_4$, then filtered and concentrated down to a solid. Trituration with hexane gave 4-chloro-6-[1-(3-fluoro-benzyl)-1H-indazol-5-ylamino]-pyrimidine-5-carbonitrile Compound 4e (2.15 g, 99%) as a solid. ¹H NMR (400 MHz, DMSO) δ 10.31 (1H, br s), 8.48 (1H, s), 8.15 (1H, d), 7.82 (1H, d), 7.82 (1H, d, J=8.9 Hz), 7.44 (1H, dd, J=1.9 Hz & 8.9 Hz), 7.37-7.35 (1H, m), 7.10-7.03 (3H, m), 5.70 (2H, s); MS (ES⁺) m/z 379.0 (MH⁺).

Ethyl thioglycolate (also referred to as mercapto-acetic acid ethyl ester) Compound 4f (0.57 g, 4.75 mmol) and triethylamine (0.78 mL, 5.54 mmol) were added to a solution of 4-chloro-6-[1-(3-fluoro-benzyl)-1H-indazol-5-ylamino]-pyrimidine-5-carbonitrile Compound 4e (1.5 g, 3.96 mmol) in THF (20 mL) at RT under nitrogen. The reaction mixture was refluxed for 6 hours, then partitioned between ethyl acetate and water. The organic layer washed with aqueous 10% $NH_4Cl$, water and brine, then dried ($Na_2SO_4$), filtered and the solvent evaporated in vacuo to yield a crude solid. The crude solid was purified via flash chromatography (1% methanol/dichloromethane) to yield {5-cyano-6-[1-(3-fluoro-benzyl)-1H-indazol-5-ylamino]-pyrimidin-4-ylsulfanyl}-acetic acid ethyl ester Compound 4g (0.83 g, 45%) as a solid. ¹H NMR (400 MHz, DMSO) δ 9.99 (1H, br s), 8.42 (1H, s), 8.13 (1H, d), 7.82 (1H, d), 7.82 (1H, d, J=8.9 Hz), 7.43 (1H, dd, J=1.9 Hz & 8.9 Hz), 7.36-7.34 (1H, m), 7.11-7.02 (3H, m), 5.69 (2H, s), 4.15-4.10 (4H, m), 1.18 (3H, t); MS (ES⁺) m/z 463.0 (MH⁺).

A solution of 21% sodium ethoxide in ethanol (0.86 mL, 2.6 mmol) was added to a solution of Compound 4g (0.4 g, 0.86 mmol) in THF (12 mL) at RT under nitrogen. The mixture was refluxed for 20 minutes, then diluted with water and concentrated in vacuo. The aqueous layer was extracted with dichloromethane and the solvent evaporated in vacuo to give 5-amino-4-[1-(3-fluoro-benzyl)-1H-indazol-5-ylamino]-thieno[2,3-d]pyrimidine-6-carboxylic acid ethyl ester ester Compound 4h (0.38 g, 95%) as a solid. ¹H NMR (400 MHz, DMSO) δ 9.06 (1H, br s), 8.38 (1H, br s), 8.15 (1H, br s), 7.91 (1H, br s), 7.75-7.70 (1H, m), 7.53-7.46 (1H, m), 7.40-7.28 (3H, m), 7.13-7.03 (3H, m), 5.70 (2H, s), 4.27 (2H, q), 1.29 (3H, t); MS (ES⁺) m/z 463.0 (MH⁺).

CDI (carbonyl diimidazole) (0.42 g, 2.60 mmol) was added to a suspension of Compound 4h (0.3 g, 0.65 mmol) in benzene (20 mL) at RT under nitrogen. The mixture was refluxed for 5 hours, then partitioned between ethyl acetate and water. The organic layer washed with brine and dried ($Na_2SO_4$), then filtered and the solvent evaporated in vacuo to yield Compound 78 (0.31 g, 99%) as a solid. ¹H NMR (400 MHz, DMSO) δ 8.61 (1H, s), 8.24 (1H, m), 7.88-7.85 (2H, m), 7.64 (1H, s), 7.41 (1H, dd, J=1.6 Hz & 8.9 Hz), 7.37-7.35 (1H, m), 7.15-7.09 (3H, m), 5.74 (2H, s), 4.37 (2H, q), 1.32 (3H, t); MS (ES⁺) m/z 489.0 (MH⁺).

Lithium hydroxide (LiOH) (0.05 g, 1.20 mmol) was added to a solution of Compound 78 (0.3 g, 0.61 mmol) in THF/methanol/water (10/4/4). The mixture was heated at 65° C. for 5 hours, then concentrated in vacuo. Neutralization of the aqueous layer with aqueous 1.0M HCl precipitated Compound 79 (0.28 g, 99%). ¹H NMR (400 MHz, $CD_3OD$) δ 8.45 (1H, s), 8.17 (1H, s), 7.93 (1H, s), 7.87 (1H, s), 7.70 (1H, d, J=8.9 Hz), 7.40 (1H, dd, J=1.7 Hz & 8.9 Hz), 7.35-7.29 (1H, m), 7.06-6.93 (3H, m), 5.72 (2H, s); MS (ES⁺) m/z 461.0 (MH⁺).

HATU (0.31 g, 0.81 mmol) and DIPEA (0.26 mL, 1.5 mmol) were added to a solution of Compound 79 (0.285 g, 0.62 mmol) in THF (10 mL) at RT under nitrogen. The mixture was stirred for 20 minutes, then 4-piperidin-1-ylmethyl-phenylamine Compound 1k (0.13 g, 0.68 mmol) was added. The reaction mixture was heated at 45° C. for 5 hours, kept at RT for 12 hours and then partitioned between ethyl acetate and water. The organic layer washed with brine and dried ($Na_2SO_4$), then filtered and the solvent evaporated in vacuo to yield a crude oil. Purification of the crude oil via flash chromatography (5% methanol/dichloromethane) yielded Compound 80 (0.204 g, 56%) as a solid. ¹H NMR (400 MHz, $CDCl_3$) δ 8.66 (1H, s), 8.14 (1H, s), 7.80-7.79 (1H, m), 7.63 (2H, d, J=8.4 Hz), 7.54 (1H, d, J=8.9 Hz), 7.35-7.28 (4H, m), 7.06-7.04 (1H, m), 6.98-6.94 (2H, m), 5.62 (2H, s), 3.62 (2H, s), 2.61-2.50 (4H, m), 1.65-1.63 (4H, m), 1.55-1.48 (2H, m); MS (ES⁺) m/z 633.0 (MH⁺).

Using the procedure of Example 4 and known appropriate reagents and starting materials, the following compounds of the invention were prepared:

| Cpd | Name | MS |
|---|---|---|
| 190 | 5-[2-(3-fluoro-benzyl)-3H-benzoimidazol-5-yl]-4-oxo-4,5-dihydro-3H-1-thia-3,5,6,8-tetraaza-acenaphthylene-2-carboxylic acid | 461 |
| 192 | 5-[2-(3-fluoro-benzyl)-3H-benzoimidazol-5-yl]-4-oxo-4,5-dihydro-3H-1-thia-3,5,6,8-tetraaza-acenaphthylene-2-carboxylic acid (4-piperidin-1-ylmethyl-phenyl)-amide | 633 |
| 193 | 5-[2-(3-fluoro-benzyl)-3H-benzoimidazol-5-yl]-4-oxo-4,5-dihydro-3H-1-thia-3,5,6,8-tetraaza-acenaphthylene-2-carboxylic acid (4-morpholin-4-ylmethyl-phenyl)-amide | 635 |
| 194 | 5-[2-(3-fluoro-benzyl)-3H-benzoimidazol-5-yl]-4-oxo-4,5-dihydro-3H-1-thia-3,5,6,8-tetraaza-acenaphthylene-2-carboxylic acid (1-methyl-piperidin-4-yl)-amide | 557 |
| 206 | 3-[4-({5-[2-(3-fluoro-benzyl)-3H-benzoimidazol-5-yl]-4-oxo-4,5-dihydro-3H-1-thia-3,5,6,8-tetraaza-acenaphthylene-2-carbonyl}-amino)-phenyl]-acrylic acid ethyl ester | 634 |
| 251 | 5-benzofuran-7-yl-4-oxo-4,5-dihydro-3H-1-thia-3,5,6,8-tetraaza-acenaphthylene-2-carboxylic acid [4-(2-piperidin-1-yl-ethyl)-phenyl]-amide | 539 |

EXAMPLE 5

5-[1-(3-fluoro-benzyl)-1H-indazol-5-yl]-4-oxo-4,5-dihydro-3H-1-thia-3,5, 6,8-tetraaza-acenaphthylene-2-carboxylic acid (4-morpholin-4-ylmethyl-phenyl)-amide (Cpd 175)

Using the procedure of Example 4, 4-morpholin-4-ylmethyl-phenylamine Compound 3e was used in place of 4-piperidin-1-ylmethyl-phenylamine Compound 1k to provide Compound 175. $^1$H NMR (300 MHz, CDCl$_3$) δ 8.70 (1H, s), 8.13 (1H, s), 7.78-7.77 (1H, m), 7.56-7.50 (2H, m), 7.36-7.27 (4H, m), 7.10-6.94 (4H, m), 5.61 (2H, s), 3.73-3.67 (6H, m), 2.41-2.40 (4H, m); MS (ES$^+$) m/z 635.2 (MH$^+$).

EXAMPLE 6

5-[1-(3-fluoro-benzyl)-1H-indazol-5-yl]-4-oxo-4,5-dihydro-3H-1-thia-3,5, 6,8-tetraaza-acenaphthylene-2-carboxylic acid (1-methyl-piperidin-4-yl)-amide (Cpd 177)

Using the procedure of Example 4, 1-methyl-piperidin-4-ylamine Compound 6a was used in place of 4-piperidin-1-ylmethyl-phenylamine Compound 1k to provide Compound 177. $^1$H NMR (300 MHz, CDCl$_3$) δ 8.66-8.65 (1H, m), 8.13 (1H, s), 7.76 (1H, s), 7.52 (1H, d, J=8.7 Hz), 7.31-7.27 (1H, m), 7.05-6.94 (4H, m), 5.61 (2H, s), 4.0-3.91 (1H, m), 2.91-2.85 (2H, m), 2.32 (3H, s), 2.19-2.11 (2H, m), 1.99-1.95 (2H, m), 1.70-1.60 (2H, m); MS (ES$^+$) m/z 557.2 (MH$^+$).

EXAMPLE 7

5-[1-(3-fluoro-benzyl)-1H-indol-5-yl]-4-oxo-4,5-dihydro-3H-1-thia-3,5, 6,8-tetraaza-acenaphthylene-2-carboxylic acid (Cpd 77)

5-[1-(3-fluoro-benzyl)-1H-indol-5-yl]-4-oxo-4,5-dihydro-3H-1-thia-3,5, 6,8-tetraaza-acenaphthylene-2-carboxylic acid (4-piperidin-1-ylmethyl-phenyl)-amide (Cpd 87)

Using the procedure of Example 4, 5-nitro-1H-indole Compound 7a was used in place of 5-nitro-1H-indazole Compound 4a to prepare 1-(3-fluoro-benzyl)-5-nitro-1H-indole Compound 7b. Using the procedure of Example 4, Compound 7b was used in place of 1-(3-fluoro-benzyl)-5-nitro-1H-indazole Compound 4c to prepare 1-(3-fluoro-benzyl)-1H-indol-5-ylamine Compound 7c. Using the procedure of Example 4, Compound 7c was used in place of 1-(3-fluoro-benzyl)-1H-indazol-5-ylamine Compound 4d to prepare 4-chloro-6-[1-(3-fluoro-benzyl)-1H-indol-5-ylamino]-pyrimidine-5-carbonitrile Compound 7d. Using the procedure of Example 4, Compound 7d was used in place of 4-chloro-6-[1-(3-fluoro-benzyl)-1H-indazol-5-ylamino]-pyrimidine-5-carbonitrile Compound 4e to prepare Compound 77. Using the procedure of Example 4, Compound 77 was used in place of Compound 79 to provide Compound 87. $^1$H NMR (400 MHz, CDCl$_3$) δ 8.67 (1H, s), 7.63-7.61 (2H, d, m), 7.42 (1H, d, J=8.4 Hz), 7.37-7.35 (2H, m), 7.32-7.27 (2H, m), 7.22 (1H, d, J=2.9 Hz), 7.11-7.09 (1H, m), 6.99-6.96 (2H, m), 6.88-6.85 (1H, m), 6.62 (1H, d, J=3.0 Hz), 5.34 (2H, s), 3.77 (2H, s), 2.71 (4H, br s), 1.69-1.67 (4H, m), 1.51-1.49 (2H, m); MS (ES$^+$) m/z 632 (MH$^+$).

EXAMPLE 8

4-({5-[1-(3-fluoro-benzyl)-1H-indol-5-yl]-4-oxo-4, 5-dihydro-3H-1-thia-3,5,6,8-tetraaza-acenaphthylene-2-carbonyl}-amino)-piperidine-1-carboxylic acid tert-butyl ester (Cpd 91)

Using the procedure of Example 4, Compound 77 was used in place of Compound 79 and 4-amino-piperidine-1-carboxylic acid tert-butyl ester Compound 8a was used in place of 4-piperidin-1-ylmethyl-phenylamine Compound 1k to provide Compound 91. $^1$H NMR (300 MHz, CDCl$_3$) δ 9.49 (1H, s), 8.70 (1H, s), 7.61 (1H, d, J=1.9 Hz), 7.42 (1H, d, J=8.7 Hz), 7.33-7.26 (1H, m), 7.22 (1H, d, J=3.1 Hz), 7.11-7.07 (1H, m), 7.01-6.95 (2H, m), 6.90-6.86 (1H, m), 6.63 (1H, d, J=2.7 Hz), 5.33 (2H, s), 4.15-4.08 (1H, m), 2.94-2.86 (4H, m), 2.05-2.01 (4H, m), 1.47 (9H, s); MS (ES$^+$) m/z 642 (MH$^+$).

EXAMPLE 9

5-[1-(3-fluoro-benzyl)-1H-indol-5-yl]-4-oxo-4,5-dihydro-3H-1-thia-3,5, 6,8-tetraaza-acenaphthylene-2-carboxylic acid (1-methyl-piperidin-4-yl)-amide (Cpd 92)

Using the procedure of Example 4, Compound 77 was used in place of Compound 79 and 1-methyl-piperidin-4-ylamine Compound 6a used in place of 4-piperidin-1-ylmethyl-phenylamine Compound 1k to provide Compound 92. ¹H NMR (300 MHz, CDCl₃) δ 8.65 (1H, s), 7.61 (1H, d, J=1.8 Hz), 7.43 (1H, d, J=8.5 Hz), 7.34-7.27 (1H, m), 7.25 (1H, d, J=3.4 Hz), 7.10-7.07 (1H, m), 7.0-6.98 (2H, m), 6.87-6.85 (1H, m), 6.64-6.63 (1H, m), 5.36 (2H, s), 4.21-4.016 (1H, m), 3.0-2.92 (2H, m), 2.85 (3H, s), 2.2-1.99 (6H, m); MS (ES⁺) m/z 556 (MH⁺)⁺.

EXAMPLE 10

5-[1-(3-fluoro-benzyl)-1H-indol-5-yl]-4-oxo-4,5-dihydro-3H-1-thia-3,5,6,8-tetraaza-acenaphthylene-2-carboxylic acid (2-morpholin-4-yl-ethyl)-amide (Cpd 93)

Using the procedure of Example 4, Compound 77 was used in place of Compound 79 and 2-morpholin-4-yl-ethylamine Compound 10a was used in place of 4-piperidin-1-ylmethyl-phenylamine Compound 1k to provide Compound 93. MS (ES⁺) m/z 572.1 (MH⁺).

EXAMPLE 11

5-[1-(3-fluoro-benzyl)-1H-indol-5-yl]-4-oxo-4,5-dihydro-3H-1-thia-3,5,6,8-tetraaza-acenaphthylene-2-carboxylic acid (3-morpholin-4-yl-propyl)-amide (Cpd 95)

Using the procedure of Example 4, Compound 77 was used in place of Compound 79 and 3-morpholin-4-yl-propylamine Compound 11a was used in place of 4-piperidin-1-ylmethyl-phenylamine Compound 1k to provide Compound 95. ¹H NMR (300 MHz, CD₃OD) δ 8.34 (1H, s), 7.55 (1H, d, J=1.9 Hz), 7.46 (1H, d, J=8.9 Hz), 7.41 (1H, d, J=3.1 Hz), 7.35-7.28 (2H, m), 7.07-6.97 (2H, m), 6.87-6.85 (1H, m), 6.62 (1H, m), 5.48 (2H, s), 3.72-3.69 (4H, m), 3.48-3.43 (2H, m), 2.51-2.46 (4H, m), 1.89-1.83 (2H, m), 1.34-1.28 (2H, m); MS (ES⁺) m/z 586.2 (M+H)⁺.

EXAMPLE 12

5-[1-(3-fluoro-benzyl)-1H-indol-5-yl]-4-oxo-4,5-dihydro-3H-1-thia-3,5, 6,8-tetraaza-acenaphthylene-2-carboxylic acid (4-morpholin-4-yl-phenyl)-amide (Cpd 94)

Using the procedure of Example 4, Compound 77 was used in place of Compound 79 and 4-morpholin-4-yl-phenylamine Compound 12a was used in place of 4-piperidin-1-ylmethyl-phenylamine Compound 1k to provide Compound 94. ¹H NMR (300 MHz, CDCl₃) δ 9.64 (1H, s), 8.72 (1H, s), 7.63 (1H, d, J=1.8 Hz), 7.53-7.50 (2H, m), 7.44-7.41 (1H, m), 7.33-7.27 (2H, m), 7.22 (1H, d, J=3.2 Hz), 7.12-7.09 (1H, m), 7.01-6.95 (2H, m), 6.89-6.87 (1H, m), 6.64 (1H, d, J=3.2 Hz), 5.34 (2H, s), 3.92-3.89 (4H, m), 3.26-3.19 (4H, m); MS (ES⁺) m/z 620.1 (MH⁺).

EXAMPLE 13

[3-({5-[1-(3-fluoro-benzyl)-1H-indol-5-yl]-4-oxo-4, 5-dihydro-3H-1-thia-3,5,6,8-tetraaza-acenaphthylene-2-carbonyl}-amino)-propyl]-carbamic acid tert-butyl ester (Cpd 141)

Using the procedure of Example 4, Compound 77 was used in place of Compound 79 and (3-amino-propyl)-carbamic acid tert-butyl ester Compound 13a was used in place of 4-piperidin-1-ylmethyl-phenylamine Compound 1k to provide Compound 141. MS (ES⁺) m/z 614.1 (MH⁺)⁺.

EXAMPLE 14

5-[1-(3-fluoro-benzyl)-1H-indol-5-yl]-4-oxo-4,5-dihydro-3H-1-thia-3,5,6,8-tetraaza-acenaphthylene-2-carboxylic acid (3-amino-propyl)-amide (Cpd 142)

Compound 141 (0.05 g, 0.08 mmol) was stirred under nitrogen at 0° C. in a 1:1 mixture of TFA:CH₂Cl₂ (3 mL) for 1 hour. The reaction mixture was partitioned between CH₂Cl₂ and aqueous 1.0M NaOH. The organic layer washed with brine and dried (Na₂SO₄), then filtered and concentrated in vacuo to yield a crude solid. Trituration of the solid with hexanes gave Compound 142 as a solid. MS (ES⁺) m/z 516 (MH⁺).

EXAMPLE 15

5-[1-(3-fluoro-benzyl)-1H-indol-5-yl]-3H,5H-1-thia-3,5,6,8-tetraaza-acenaphthylen-4-one (Cpd 152)

HATU (0.31 g, 0.81 mmol) and DIPEA (0.26 mL, 1.5 mmol) were added to a solution of Compound 77 (0.1 g, 0.21 mmol) in THF (10 mL) at RT under nitrogen. The mixture was heated at 90° C. for 12 hours and then partitioned between ethyl acetate and water. The organic layer was washed with brine and dried (Na₂SO₄), then filtered and concentrated in vacuo to yield a crude oil. Purification of the crude oil via flash chromatography (2% MeOH/DCM) yielded Compound 152 (0.08 g, 88%) as a solid. ¹H NMR (300 MHz, CDCl₃) δ 8.60 (1H, s), 8.52 (1H, br s), 7.62 (1H, d, J=1.8 Hz), 7.43 (1H, d, J=8.6 Hz), 7.33-7.28 (1H, m), 7.21 (1H, d, J=3.2 Hz), 7.13-7.10 (1H, m), 7.02-6.95 (2H, m), 6.91-6.88 (1H, m), 6.64-6.63 (1H, m), 5.99 (1H, s), 5.33 (2H, s); MS (ES⁺) m/z 416 (MH⁺).

EXAMPLE 16

5-[1-(3-fluoro-benzyl)-1H-indol-5-yl]-4-oxo-4,5-dihydro-3H-1-thia-3,5, 6,8-tetraaza-acenaphthylene-2-carboxylic acid (4-morpholin-4-ylmethyl-phenyl)-amide (Cpd 143)

Using the procedure of Example 4, Compound 77 was used in place of Compound 79 and 4-morpholin-4-ylmethyl-phenylamine Compound 3e was used in place of 4-piperidin-1-ylmethyl-phenylamine Compound 1k to prepare Compound 143. MS (ES⁺) m/z 634.2 (MH⁺).

EXAMPLE 17

5-(3-bromo-4-methyl-phenyl)-4-oxo-4,5-dihydro-3H-1-thia-3,5,6,8-tetraaza-acenaphthylene-2-carboxylic acid ethyl ester (Cpd 102)

5-(3-bromo-4-methyl-phenyl)-4-oxo-4,5-dihydro-3H-1-thia-3,5,6,8-tetraaza-acenaphthylene-2-carboxylic acid (4-morpholin-4-ylmethyl-phenyl)-amide (Cpd 108)

Using the procedure of Example 1, 3-bromo-4-methyl-phenylamine Compound 17a was used in place of 3-chloro-4-fluoro-phenylamine Compound 1e to provide 4-(3-bromo-4-methyl-phenylamino)-6-chloro-pyrimidine-5-carbonitrile Compound 17b. ¹H NMR (400 MHz, CDCl₃) δ 8.55 (1H, s), 7.83 (1H, d, J=2.0 Hz), 7.37 (1H, dd, J=2.0 & 8.15 Hz), 7.17 (1H, d, J=8.15 Hz), 2.26 (3H, s); MS (ES⁺) m/z 323.0 & 324.9 (MH⁺). Using the procedure of Example 4, Compound 17b (6.48 g, 20.0 mmol) was used in place of 4-chloro-6-[1-(3-fluoro-benzyl)-1H-indazol-5-ylamino]-pyrimidine-5-carbonitrile Compound 4e to provide Compound 102. $^1$H NMR (400 MHz, CDCl$_3$) δ 8.74 (1H, s), 7.55 (1H, d, J=2.1 Hz), 7.46-7.43 (1H, m), 7.22 (1H, dd, J=2.1 & 8.1 Hz), 4.43 (2H, q), 2.48 (3H, s), 1.42 (3H, t). MS (ES$^+$) m/z 432.9 & 434.9 (MH$^+$)$^+$.

Using the procedure of Example 4, Compound 102 was used in place of Compound 78 to provide 5-(3-bromo-4-methyl-phenyl)-4-oxo-4,5-dihydro-3H-1-thia-3,5,6,8-tetraaza-acenaphthylene-2-carboxylic acid Compound 17c. $^1$H NMR (300 MHz, DMSO) δ 10.83 (1H, s), 8.65 (1H, s), 7.71-7.69 (1H, m), 7.52 (1H, d, J=8.4 Hz), 7.36 (1H, dd, J=2.2 & 8.2 Hz), 2.34 (3H, s); MS (ES$^+$) m/z 405.0 & 407.0 (MH$^+$). Using the procedure of Example 1, Compound 17c was used in place of Compound 1 and 4-morpholin-4-ylmethyl-phenylamine Compound 3e was used in place of 4-piperidin-1-ylmethyl-phenylamine Compound 1k to provide Compound 108. $^1$H NMR (400 MHz, CDCl$_3$) δ 8.69 (1H, s), 7.61 (2H, d, J=8.6 Hz), 7.56 (1H, d, J=2.2 Hz), 7.45 (1H, d, J=8.0 Hz), 7.35-7.33 (2H, m), 7.23 (1H, dd, J=2.3 & 8.1 Hz), 3.73-3.71 (4H, m), 3.50-3.44 (2H, m), 2.49-2.41 (7H, m); MS (ES$^+$) m/z 579.0 & 581.0 (MH$^+$).

Using the procedure of Example 17 and known appropriate reagents and starting materials, the following compounds of the invention were prepared:

| Cpd | Name | MS |
| --- | --- | --- |
| 210 | 4-oxo-5-(4-phenylsulfanyl-phenyl)-4,5-dihydro-3H-1-thia-3,5,6,8-tetraaza-acenaphthylene-2-carboxylic acid ethyl ester | 449 |
| 222 | 5-[3-chloro-4-(furan-2-ylmethoxy)-phenyl]-4-oxo-4,5-dihydro-3H-1-thia-3,5,6,8-tetraaza-acenaphthylene-2-carboxylic acid ethyl ester | 471 |
| 223 | 5-[3-chloro-4-(thiophen-2-ylmethoxy)-phenyl]-4-oxo-4,5-dihydro-3H-1-thia-3,5,6,8-tetraaza-acenaphthylene-2-carboxylic acid ethyl ester | 487 |
| 241 | 5-(4-benzoylamino-phenyl)-4-oxo-4,5-dihydro-3H-1-thia-3,5,6,8-tetraaza-acenaphthylene-2-carboxylic acid ethyl ester | 460 |

EXAMPLE 18

5-(3-bromo-4-methyl-phenyl)-4-oxo-4,5-dihydro-3H-1-thia-3,5,6,8-tetraaza-acenaphthylene-2-carboxylic acid (1-methyl-piperidin-4-yl)-amide (Cpd 116)

Using the procedure of Example 1, 5-(3-bromo-4-methyl-phenyl)-4-oxo-4,5-dihydro-3H-1-thia-3,5,6,8-tetraaza-acenaphthylene-2-carboxylic acid Compound 17c was used in place of Compound 1 and 1-methyl-piperidin-4-ylamine Compound 6a was used in place of 4-piperidin-1-ylmethyl-phenylamine Compound 1k to provide Compound 116. $^1$H NMR (400 MHz, CDCl$_3$) δ 8.68 (1H, s), 7.54 (1H, d, J=2.2 Hz), 7.43 (1H, d, J=8.2 Hz), 7.21 (1H, dd, J=2.2 & 8.1 Hz), 4.01-3.95 (1H, m), 2.97-2.94 (2H, m), 2.47 (3H, s), 2.38 (3H, s), 2.26-2.20 (2H, m), 2.0-1.97 (2H, m), 1.71-1.61 (2H, m); MS (ES$^+$) m/z 501 & 503 (MH$^+$).

EXAMPLE 19

5-(3-bromo-4-methyl-phenyl)-4-oxo-4,5-dihydro-3H-1-thia-3,5,6,8-tetraaza-acenaphthylene-2-carboxylic acid (4-piperidin-1-ylmethyl-phenyl)-amide (Cpd 111)

Using the procedure of Example 1, 5-(3-bromo-4-methyl-phenyl)-4-oxo-4,5-dihydro-3H-1-thia-3,5,6,8-tetraaza-acenaphthylene-2-carboxylic acid Compound 17c was used in place of Compound 1 to provide Compound 111. $^1$H NMR (400 MHz, DMSO) δ 10.17 (1H, s), 9.26-9.22 (1H, br s), 8.67 (1H, s), 7.79 (2H, d, J=8.7 Hz), 7.73 (1H, d, J=1.4 Hz), 7.54 (1H, d, J=8.3 Hz), 7.49 (2H, d, J=8.7 Hz), 7.38-7.36 (1H, m), 4.25 (2H, s), 2.90-2.83 (2H, m), 2.43 (3H, s), 1.84-1.81 (2H, m), 1.72-1.58 (4H, m), 1.38-1.34 (2H, m); MS (ES$^+$) m/z 577.2 & 579.2 (MH$^+$).

EXAMPLE 20

5-(5-bromo-2-methyl-phenyl)-4-oxo-4,5-dihydro-3H-1-thia-3,5,6,8-tetraaza-acenaphthylene-2-carboxylic acid ethyl ester (Cpd 103)

5-(5-bromo-2-methyl-phenyl)-4-oxo-4,5-dihydro-3H-1-thia-3,5,6,8-tetraaza-acenaphthylene-2-carboxylic acid (4-morpholin-4-ylmethyl-phenyl)-amide (Cpd 109)

Using the procedure of Example 1, 5-bromo-2-methyl-phenylamine Compound 20a was used in place of 3-chloro-4-fluoro-phenylamine Compound 1e to provide 4-(5-bromo-2-methyl-phenylamino)-6-chloro-pyrimidine-5-carbonitrile Compound 20b. $^1$H NMR (400 MHz, CDCl$_3$) δ 8.55 (1H, s), 7.83 (1H, d, J=2.0 Hz), 7.37 (1H, dd, J=2.0 & 8.4 Hz), 7.23 (1H, br s), 7.17 (1H, d, J=8.0 Hz), 2.26 (3H, s); MS (ES$^+$) m/z 323.0 & 324.9 (MH$^+$).

Using the procedure of Example 4, Compound 20b was used in place of 4-chloro-6-[1-(3-fluoro-benzyl)-1H-indazol-5-ylamino]-pyrimidine-5-carbonitrile Compound 4e to provide Compound 103. $^1$H NMR (400 MHz, CDCl$_3$) δ 8.98 (1H, br s), 8.73 (1H, s), 7.57 (1H, dd, J=2.0 & 8.2 Hz), 7.4 (1H, d, J=2.0 Hz), 7.31 (1H, d, J=8.2 Hz), 4.41 (2H, q), 2.15 (3H, s), 1.42 (3H, t). MS (ES$^+$) m/z 433.0 & 434.9 (M+H)$^+$. Using the procedure of Example 4, Compound 103 was was used in place of Compound 78 and taken forward to provide 5-(5-bromo-2-methyl-phenyl)-4-oxo-4,5-dihydro-3H-1-thia-3,5,6,8-tetraaza-acenaphthylene-2-carboxylic acid Compound 20c. $^1$H NMR (400 MHz, CDCl$_3$) δ 8.66 (1H, s), 7.68 (1H, d, J=2.01 Hz), 7.60 (1H, dd, J=2.1 & 8.2 Hz), 7.38 (1H, d, J=8.2 Hz), 2.07 (3H, s); MS (ES$^+$) m/z 405 & 407 (MH$^+$). Using the procedure of Example 1, Compound 20c was used in place of Compound 1 and 4-morpholin-4-ylmethyl-phenylamine Compound 3e was used in place of 4-piperidin-1-ylmethyl-phenylamine Compound 1k to provide Compound 109. $^1$H NMR (400 MHz, CDCl$_3$) δ 8.74 (1H, s), 7.58-7.53 (3H, m), 7.41-7.36 (3H, m), 7.31-7.29 (1H, m), 3.73-3.68 (4H, m), 3.50-3.49 (2H, m), 2.46-2.44 (4H, m), 2.15 (3H, s); MS (ES$^+$) m/z 578.8 & 581 (M+H)$^+$.

EXAMPLE 21

5-(5-bromo-2-methyl-phenyl)-4-oxo-4,5-dihydro-3H-1-thia-3,5,6,8-tetraaza-acenaphthylene-2-carboxylic acid (1-methyl-piperidin-4-yl)-amide (Cpd 117)

Using the procedure of Example 1, 5-(5-bromo-2-methyl-phenyl)-4-oxo-4,5-dihydro-3H-1-thia-3,5,6,8-tetraaza-acenaphthylene-2-carboxylic acid Compound 20c was used in place of Compound 1 and 1-methyl-piperidin-4-ylamine Compound 6a was used in place of 4-piperidin-1-ylmethyl-phenylamine Compound 1k to provide Compound 117. $^1$H NMR (400 MHz, CDCl$_3$) δ 8.67 (1H, s), 7.56 (1H, dd, J=2.0 & 8.0 Hz), 7.40 (1H, d, J=2.0 Hz), 7.31-7.29 (1H, m), 4.01-3.96 (1H, m), 2.97-2.94 (2H, m), 2.37 (3H, s), 2.26-2.20 (2H, m), 2.13 (3H, s), 2.0-1.97 (2H, m), 1.72-1.62 (2H, m); MS (ES⁺) m/z 500.9 & 503 (MH⁺).

EXAMPLE 22

5-[4-(4-fluoro-phenoxy)-phenyl]-4-oxo-4,5-dihydro-3H-1-thia-3,5,6,8-tetraaza-acenaphthylene-2-carboxylic acid ethyl ester (Cpd 101)

5-[4-(4-fluoro-phenoxy)-phenyl]-4-oxo-4,5-dihydro-3H-1-thia-3,5,6,8-tetraaza-acenaphthylene-2-carboxylic acid (4-morpholin-4-ylmethyl-phenyl)-amide (Cpd 110)

Using the procedure of Example 1, 4-(4-fluoro-phenoxy)-phenylamine Compound 22a was used in place of 3-chloro-4-fluoro-phenylamine Compound 1e to provide 4-chloro-6-[4-(4-fluoro-phenoxy)-phenylamino]-pyrimidine-5-carbonitrile Compound 22b. ¹H NMR (400 MHz, DMSO) δ 10.23 (1H, s), 8.53 (1H, s), 7.49-7.47 (2H, m), 7.27-7.22 (2H, m), 7.10-7.07 (2H, m), 7.02-6.99 (2H, m); MS (ES⁺) m/z 341.1 (MH⁺). Using the procedure of Example 4, Compound 22b was used in place of 4-chloro-6-[1-(3-fluoro-benzyl)-1H-indazol-5-ylamino]-pyrimidine-5-carbonitrile Compound 4e to provide Compound 101. ¹H NMR (300 MHz, CDCl₃) δ 8.97 (1H, br s), 8.75 (1H, s), 7.30-7.27 (2H, m), 7.12-7.07 (6H, m), 4.42 (2H, q), 1.42 (3H, t). MS (ES⁺) m/z 451 (M+H)⁺.

Using the procedure of Example 4, Compound 101 was used in place of Compound 78 to provide 5-[4-(4-fluoro-phenoxy)-phenyl]-4-oxo-4,5-dihydro-3H-1-thia-3,5,6,8-tetraaza-acenaphthylene-2-carboxylic acid Compound 22c. ¹H NMR (400 MHz, acetone-d₆) δ 8.42 (1H, s), 7.48-7.37 (2H, m), 7.24-6.99 (6H, m); MS (ES⁺) m/z 421 (M–H⁺). Using the procedure of Example 1, Compound 22c was used in place of Compound 1 and 4-morpholin-4-ylmethyl-phenylamine Compound 3e was used in place of 4-piperidin-1-ylmethyl-phenylamine Compound k to provide Compound 110. ¹H NMR (400 MHz, CDCl₃) δ 8.75 (1H, s), 7.54 (2H, d, J=8.6 Hz), 7.36 (2H, d, J=8.4 Hz), 7.30-7.26 (2H, m), 7.10-7.08 (6H, m), 3.73-3.55 (6H, m), 2.46-2.40 (4H, m); MS (ES⁺) m/z 597 (MH⁺).

EXAMPLE 23

5-[4-(4-fluoro-phenoxy)-phenyl]-4-oxo-4,5-dihydro-3H-1-thia-3,5,6,8-tetraaza-acenaphthylene-2-carboxylic acid (1-methyl-piperidin-4-yl)-amide (Cpd 118)

Using the procedure of Example 1, 5-[4-(4-fluoro-phenoxy)-phenyl]-4-oxo-4,5-dihydro-3H-1-thia-3,5,6,8-tetraaza-acenaphthylene-2-carboxylic acid Compound 22c was used in place of Compound 1 and 1-methyl-piperidin-4-ylamine Compound 6a was used in place of 4-piperidin-1-ylmethyl-phenylamine Compound 1k to provide Compound 118. ¹H NMR (400 MHz, CDCl₃) δ 8.70 (1H, s), 7.29-7.26 (2H, m), 7.10-7.08 (6H, m), 4.02-3.96 (1H, m), 2.98-2.96 (2H, m), 2.39 (3H, s), 2.27-2.22 (2H, m), 2.02-1.99 (2H, m), 1.73-1.63 (2H, m); MS (ES⁺) m/z 519 (MH⁺).

EXAMPLE 24

5-(3-bromo-phenyl)-4-oxo-4,5-dihydro-3H-1-thia-3,5,6,8-tetraaza-acenaphthylene-2-carboxylic acid phenylamide (Cpd 130)

Using the procedure of Example 1, 3-bromo-phenylamine Compound 24a was used in place of 3-chloro-4-fluoro-phenylamine Compound 1e to prepare 4-(3-bromo-phenylamino)-6-chloro-pyrimidine-5-carbonitrile Compound 24b. Using the procedure of Example 4, Compound 24b was used in place of 4-chloro-6-[1-(3-fluoro-benzyl)-1H-indazol-5-ylamino]-pyrimidine-5-carbonitrile Compound 4e and 2-mercapto-N-phenyl-acetamide Compound 24c was used in place of ethyl thioglycolate Compound 4f to provide Compound 130. ¹H NMR (400 MHz, CDCl₃) δ 8.67 (1H, s), 7.67-7.63 (3H, m), 7.55-7.53 (1H, m), 7.48-7.44 (1H, m), 7.40-7.33 (3H, m), 7.20-7.16 (1H, m); MS (ES⁺) m/z 464 & 465.9 (M–H)⁺.

EXAMPLE 25

5-(4-morpholin-4-yl-phenyl)-4-oxo-4,5-dihydro-3H-1-thia-3,5,6,8-tetraaza-acenaphthylene-2-carboxylic acid (Cpd 107)

5-(4-morpholin-4-yl-phenyl)-4-oxo-4,5-dihydro-3H-1-thia-3,5,6,8-tetraaza-acenaphthylene-2-carboxylic acid (4-morpholin-4-ylmethyl-phenyl)-amide (Cpd 123)

Using the procedure of Example 1, 4-morpholin-4-yl-phenylamine Compound 12a was used in place of 3-chloro-4-fluoro-phenylamine Compound 1e to provide 4-chloro-6-(4-morpholin-4-yl-phenylamino)-pyrimidine-5-carbonitrile Compound 25a. ¹H NMR (300 MHz, CDCl₃) δ 8.51 (1H, s), 7.37 (2H, d, J=9.0 Hz), 6.94 (2H, d, J=9.0 Hz), 3.88-3.85 (4H, m), 3.20-3.17 (4H, m); MS (ES⁺) m/z 314.1 (M–H)⁺. Using the procedure of Example 1, Compound 25a was used in place of 4-chloro-6-(3-chloro-4-fluoro-phenylamino)-pyrimidine-5-carbonitrile Compound 1f to provide Compound 107. ¹H NMR (300 MHz, DMSO) δ 8.63 (1H, s), 7.23 (2H, d, J=8.9 Hz), 7.05 (2H, d, J=8.9 Hz), 3.78-3.75 (4H, m), 3.19-3.16 (4H, m); MS (ES⁺) m/z 398.0 (MH⁺). Using the procedure of Example 1, Compound 107 was used in place of Compound 1 and 4-morpholin-4-ylmethyl-phenylamine Compound 3e was used in place of 4-piperidin-1-ylmethyl-phenylamine Compound 1k to provide Compound 123. ¹H NMR (400 MHz, DMSO) δ 10.15 (1H, s), 9.85 (1H, br s), 8.65 (1H, s), 7.80 (2H, d, J=8.2 Hz), 7.49 (2H, d, J=8.2 Hz), 7.24 (2H, d, J=9.0 Hz), 7.06 (2H, d, J=9.0 Hz), 4.33 (2H, br s), 3.99-3.96 (2H, m), 3.78-3.76 (4H, m), 3.65-3.60 (2H, m), 3.29-3.26 (2H, m), 3.20-3.15 (4H, m), 3.12-3.06 (2H, m); MS (ES⁺) m/z 572.1 (MH⁺).

EXAMPLE 26

5-(4-morpholin-4-yl-phenyl)-4-oxo-4,5-dihydro-3H-1-thia-3,5,6,8-tetraaza-acenaphthylene-2-carboxylic acid (4-piperidin-1-ylmethyl-phenyl)-amide (Cpd 124)

Using the procedure of Example 1, 5-(4-morpholin-4-yl-phenyl)-4-oxo-4,5-dihydro-3H-1-thia-3,5,6,8-tetraaza-acenaphthylene-2-carboxylic acid Compound 107 was used in place of Compound 1 to provide Compound 124. MS (ES⁺) m/z 570 (MH⁺).

EXAMPLE 27

4-{[5-(4-morpholin-4-yl-phenyl)-4-oxo-4,5-dihydro-3H-1-thia-3,5,6,8-tetraaza-acenaphthylene-2-carbonyl]-amino}-piperidine-1-carboxylic acid tert-butyl ester (Cpd 126)

Using the procedure of Example 4, Compound 107 was used in place of Compound 79 and 4-amino-piperidine-1- carboxylic acid tert-butyl ester Compound 8a was used in place of 4-piperidin-1-ylmethyl-phenylamine Compound 1k to provide Compound 126. $^1$H NMR (400 MHz, CDCl$_3$) δ 8.72 (1H, s), 7.22 (2H, d, J=9.2 Hz), 7.04 (2H, d, J=9.2 Hz), 4.14-4.08 (1H, m), 3.88-3.86 (4H, m), 3.26-3.24 (4H, m), 2.92-2.84 (2H, m), 2.05-2.0 (2, m), 1.51-1.42 (13H, m); MS (ES$^+$) m/z 578.1 (M–H)$^+$.

EXAMPLE 28

5-(4-morpholin-4-yl-phenyl)-4-oxo-4,5-dihydro-3H-1-thia-3,5,6,8-tetraaza-acenaphthylene-2-carboxylic acid (4-morpholin-4-yl-phenyl)-amide (Cpd 125)

Using the procedure of Example 1, 5-(4-morpholin-4-yl-phenyl)-4-oxo-4,5-dihydro-3H-1-thia-3,5,6,8-tetraaza-acenaphthylene-2-carboxylic acid Compound 107 was used in place of Compound 1 and 4-morpholin-4-yl-phenylamine Compound 12a was used in place of 4-piperidin-1-ylmethyl-phenylamine Compound 1k to provide Compound 125. $^1$H NMR (400 MHz, CDCl$_3$) δ 8.73 (1H, s), 7.49-7.45 (2H, m), 7.23 (2H, d, J=9.0 Hz), 7.04 (2H, d, J=9.1 Hz), 6.93 (2H, d, J=9.0 Hz), 3.96-3.85 (8H, m), 3.26-3.23 (4H, m), 3.18-3.15 (4H, m); MS (ES$^+$) m/z 558 (MH$^+$).

EXAMPLE 29

5-(4-morpholin-4-yl-phenyl)-4-oxo-4,5-dihydro-3H-1-thia-3,5,6,8-tetraaza-acenaphthylene-2-carboxylic acid (furan-2-ylmethyl)-amide (Cpd 127)

Using the procedure of Example 1, 5-(4-morpholin-4-yl-phenyl)-4-oxo-4,5-dihydro-3H-1-thia-3,5,6,8-tetraaza-acenaphthylene-2-carboxylic acid Compound 107 was used in place of Compound 1 and C-furan-2-yl-methylamine Compound 29a was used in place of 4-piperidin-1-ylmethyl-phenylamine Compound 1k to provide Compound 127. MS (ES$^+$) m/z 475 (M–H)$^+$.

Using the procedure of Example 29 and known appropriate reagents and starting materials, the following compounds of the invention were prepared:

| Cpd | Name | MS |
|---|---|---|
| 217 | 4-oxo-5-(4-phenoxy-phenyl)-4,5-dihydro-3H-1-thia-3,5,6,8-tetraaza-acenaphthylene-2-carboxylic acid (2-pyridin-2-yl-ethyl)-amide | 509 |

EXAMPLE 30

5-(4-morpholin-4-yl-phenyl)-4-oxo-4,5-dihydro-3H-1-thia-3,5,6,8-tetraaza-acenaphthylene-2-carboxylic acid 3-fluoro-benzylamide (Cpd 128)

Using the procedure of Example 1, 5-(4-morpholin-4-yl-phenyl)-4-oxo-4,5-dihydro-3H-1-thia-3,5,6,8-tetraaza-acenaphthylene-2-carboxylic acid Compound 107 was used in place of Compound 1 and 2-fluoro-benzylamine Compound 30a was used in place of 4-piperidin-1-ylmethyl-phenylamine Compound 1k to provide Compound 128. $^1$H NMR (400 MHz, CDCl$_3$) δ 8.68 (1H, s), 7.45-7.41 (1H, m), 7.32-7.28 (1H, m), 7.23 (2H, d, J=9.0 Hz), 7.18-7.06 (4H, d, m), 4.65 (2H, s), 3.90-3.88 (4H, m), 3.28-3.25 (4H, m); MS (ES$^+$) m/z 503.1 (M–H)$^+$.

EXAMPLE 31

5-(4'-chloro-biphenyl-4-yl)-4-oxo-4,5-dihydro-3H-1-thia-3,5,6,8-tetraaza-acenaphthylene-2-carboxylic acid (4-morpholin-4-ylmethyl-phenyl)-amide (Cpd 140)

Using the procedure of Example 1, 4'-chloro-biphenyl-4-ylamine Compound 31a was used in place of 3-chloro-4-fluoro-phenylamine Compound 1e to provide 4-chloro-6-(4'-chloro-biphenyl-4-ylamino)-pyrimidine-5-carbonitrile Compound 31b. $^1$H NMR (300 MHz, CDCl$_3$) δ 8.56 (1H, s), 7.68-7.60 (4H, m), 7.58-7.50 (2H, m), 7.44-7.40 (2H, m); MS (ES$^+$) m/z 339 (M–H)$^+$. Using the procedure of Example 1, Compound 31b was used in place of 4-chloro-6-(3-chloro-4-fluoro-phenylamino)-pyrimidine-5-carbonitrile Compound 1f to provide 5-(4'-chloro-biphenyl-4-yl)-4-oxo-4,5-dihydro-3H-1-thia-3,5,6,8-tetraaza-acenaphthylene-2-carboxylic acid Compound 31c. $^1$H NMR (300 MHz, CDCl$_3$) δ 8.73 (1H, s), 7.78-7.73 (2H, m), 7.59-7.55 (2H, m), 7.49-7.41 (4H, m); MS (ES$^+$) m/z 421 (M–H)$^+$. Using the procedure of Example 1, Compound 31c was used in place of Compound 1 and 4-morpholin-4-ylmethyl-phenylamine Compound 3e was used in place of 4-piperidin-1-ylmethyl-phenylamine Compound 1k to provide Compound 140. $^1$H NMR (300 MHz, CDCl$_3$) δ 8.76 (1H, s), 7.58-7.54 (4H, m), 7.46-7.43 (4H, m), 7.38-7.35 (2H, m), 3.75-3.67 (6H, m), 2.49-2.46 (4H, m); MS (ES$^+$) m/z 596.9 (MH$^+$).

EXAMPLE 32

5-(4'-chloro-biphenyl-4-yl)-4-oxo-4,5-dihydro-3H-1-thia-3,5,6,8-tetraaza-acenaphthylene-2-carboxylic acid (4-piperidin-1-ylmethyl-phenyl)-amide (Cpd 139)

Using the procedure of Example 1, 5-(4'-chloro-biphenyl-4-yl)-4-oxo-4,5-dihydro-3H-1-thia-3,5,6,8-tetraaza-acenaphthylene-2-carboxylic acid Compound 31c was used in place of Compound 1 to provide Compound 139. $^1$H NMR (300 MHz, CDCl$_3$) δ 8.63 (1H, s), 7.75-7.67 (4H, m), 7.58-7.55 (2H, m), 7.45-7.38 (6H, m), 3.66-3.64 (2H, m), 2.61-2.50 (4H, m), 1.65-1.63 (4H, m), 1.55-1.48 (2H, m); MS (ES$^+$) m/z 595 (MH$^+$).

EXAMPLE 33

4-oxo-5-[(1R)-1-phenyl-ethyl]-4,5-dihydro-3H-1-thia-3,5,6,8-tetraaza-acenaphthylene-2-carboxylic acid (Cpd 170)

4-oxo-5-[(1R)-1-phenyl-ethyl]-4,5-dihydro-3H-1-thia-3,5,6,8-tetraaza-acenaphthylene-2-carboxylic acid (4-piperidin-1-ylmethyl-phenyl)-amide (Cpd 171)

Using the procedure of Example 1, 1R-1-phenyl-ethylamino (also referred to as (α$^1$R)-α-methyl-benzenemethanamine) Compound 33a was used in place of 3-chloro-4-fluoro-phenylamine Compound 1e to provide 4-chloro-6-[(1R)-1-phenyl-ethylamino]-pyrimidine-5-carbonitrile Compound 33b. $^1$H NMR (300 MHz, CDCl$_3$) δ 8.44 (1H, s), 7.39-7.27 (5H, m), 6.05-6.02 (1H, m), 5.49-5.40 (1H, m), 1.63 (3H, d, J=6.9 Hz); MS (ES$^+$) m/z 258 (M–H)$^+$. Using the procedure of Example 4, Compound 33b was used in place of 4-chloro-6-[1-(3-fluoro-benzyl)-1H-indazol-5-ylamino]-pyrimidine-5-carbonitrile Compound 4e to provide 4-oxo-5-

[(1R)-1-phenyl-ethyl]-4,5-dihydro-3H-1-thia-3,5,6,8-tetraaza-acenaphthylene-2-carboxylic acid Compound 170. $^1$H NMR (300 MHz, CDCl$_3$) δ 8.91 (1H, s), 8.77 (1H, s), 7.40-7.20 (5H, m), 6.37-6.30 (1H, m), 1.89 (3H, d, J=7.2 Hz); MS (ES$^+$) m/z 341 (M+H)$^+$. Using the procedure of Example 4, Compound 170 in place of Compound 79 to provide Compound 171. $^1$H NMR (300 MHz, CDCl$_3$) δ 8.75 (1H, s), 7.53-7.48 (4H, m), 7.34-7.23 (5H, m), 6.51-6.44 (1H, m), 3.72-3.69 (4H, m), 3.47 (2H, br s), 2.45-2.42 (4H, m), 2.0 (3H, d, J=7.2 Hz); MS (ES$^+$) m/z 515.1 (MH$^+$).

Using the procedure of Example 33 and known appropriate reagents and starting materials, the following compounds of the invention were prepared:

| Cpd | Name | MS |
|---|---|---|
| 179 | 5-[1-(4-bromo-phenyl)-ethyl]-4-oxo-4,5-dihydro-3H-1-thia-3,5,6,8-tetraaza-acenaphthylene-2-carboxylic acid ethyl ester | 447 |
| 185 | 5-[2-(3-fluoro-benzyl)-3H-benzoimidazol-5-yl]-4-oxo-4,5-dihydro-3H-1-thia-3,5,6,8-tetraaza-acenaphthylene-2-carboxylic acid ethyl ester | 489 |

EXAMPLE 34

4-oxo-5-[(1R)-1-phenyl-ethyl]-4,5-dihydro-3H-1-thia-3,5,6,8-tetraaza-acenaphthylene-2-carboxylic acid (4-morpholin-4-ylmethyl-phenyl)-amide (Cpd 172)

Using the procedure of Example 4, Compound 170 was used in place of Compound 79 and 4-morpholin-4-ylmethyl-phenylamine Compound 3e was used in place of 4-piperidin-1-ylmethyl-phenylamine Compound 1k to provide Compound 172. $^1$H NMR (300 MHz, CDCl$_3$) δ 8.74 (1H, s), 7.59-7.56 (2H, m), 7.50-7.48 (2H, m), 7.37-7.23 (5H, m), 6.52-6.45 (1H, m), 3.46 (2H, s), 2.28-2.08 (4H, m), 2.01 (3H, d, J=7.2 Hz), 1.45-1.39 (6, m); MS (ES$^+$) m/z 513.2 (MH$^+$).

EXAMPLE 35

4-oxo-5-[(1R)-1-phenyl-ethyl]-4,5-dihydro-3H-1-thia-3,5,6,8-tetraaza-acenaphthylene-2-carboxylic acid (1-methyl-piperidin-4-yl)-amide (Cpd 173)

Using the procedure of Example 4, Compound 170 was used in place of Compound 79 and 1-methyl-piperidin-4-ylamine Compound 6a was used in place of 4-piperidin-1-ylmethyl-phenylamine Compound 1k to provide Compound 173. $^1$H NMR (300 MHz, CDCl$_3$) δ 8.75 (1H, s), 7.49-7.47 (2H, m), 7.35-7.25 (3H, m), 6.50-6.44 (1H, m), 5.60-5.56 (1H, m), 3.94-3.92 (1H, m), 2.91-2.87 (2H, m), 2.33 (3H, s), 2.27-2.15 (2H, m), 2.01-1.98 (5H, m), 1.69-1.57 (2H, m); MS (ES$^+$) m/z 437.1 (MH$^+$).

EXAMPLE 36

5-(2-chloro-4-fluoro-phenyl)-4-oxo-4,5-dihydro-3H-1-thia-3,5,6,8-tetraaza-acenaphthylene-2-carboxylic acid [3-methoxy-4-(2-piperidin-1-yl-ethoxy)-phenyl]-amide (Cpd 144)

Using the procedure of Example 56, 1-(2-chloro-ethyl)-piperidine hydrochloride Compound 36b was used in place of Compound 56a and carried forward to give 3-methoxy-4-(2-piperidin-1-yl-ethoxy)-phenylamine Compound 36d. MS 251 (MH$^+$). (see, PCT Application WO04/046120). Using the procedure of Example 1, 5-(2-chloro-4-fluoro-phenyl)-4-oxo-4,5-dihydro-3H-1-thia-3,5,6,8-tetraaza-acenaphthylene-2-carboxylic acid Compound 264 was used in place of Compound 1 and Compound 36d was used in place of 4-piperidin-1-ylmethyl-phenylamine Compound 1k to give Compound 144. MS 597, 599 (MH$^+$).

EXAMPLE 37

5-(2-chloro-4-fluoro-phenyl)-4-oxo-4,5-dihydro-3H-1-thia-3,5,6,8-tetraaza-acenaphthylene-2-carboxylic acid (4-piperidin-1-ylmethyl-phenyl)-amide (Cpd 145)

Using the procedure of Example 1, Compound 264 was used in place of Compound 1 to give Compound 145. MS 537, 539 (MH$^+$).

EXAMPLE 38

5-(3-chloro-4-methoxy-phenyl)-4-oxo-4,5-dihydro-3H-1-thia-3,5,6,8-tetraaza-acenaphthylene-2-carboxylic acid [4-(2-piperidin-1-yl-ethyl)-phenyl]-amide (Cpd 120)

Using the procedure of Example 1, 3-chloro-4-methoxy-phenylamine Compound 38a was used in place of Compound 1e to prepare 4-chloro-6-(3-chloro-4-methoxy-phenylamino)-pyrimidine-5-carbonitrile Compound 38b. Compound 38b was used in place of 4-chloro-6-(3-chloro-4-fluoro-phenylamino)-pyrimidine-5-carbonitrile Compound 1f to prepare 5-(3-chloro-4-methoxy-phenyl)-4-oxo-4,5-dihydro-3H-1-thia-3,5,6,8-tetraaza-acenaphthylene-2-carboxylic acid Compound 38c. MS 377 (MH$^+$). Using the procedure of Example 1, 1-(2-bromo-ethyl)-4-nitro-benzene Compound 38d1 was used in place of 1-chloromethyl-4-nitro-benzene Compound 1i to prepare 4-(2-piperidin-1-yl-ethyl)-phenylamine Compound 38d. MS 205 (MH$^+$). Compound 38c was used in place of Compound 1 and 4-(2-piperidin-1-yl-ethyl)-phenylamine Compound 38d was used in place of 4-piperidin-1-ylmethyl-phenylamine Compound 1k to give Compound 120. MS 563, 565 (MH$^+$).

EXAMPLE 39

5-(3-chloro-4-fluoro-phenyl)-4-oxo-4,5-dihydro-3H-1-thia-3,5,6,8-tetraaza-acenaphthylene-2-carboxylic acid [4-(4-methyl-piperazin-1-ylmethyl)-phenyl]-amide (Cpd 14)

Using the procedure of Example 1, 1-methyl-piperazine was used in place of piperidine to prepare 1-methyl-4-(4-nitro-benzyl)-piperazine Compound 39a1. Using the procedure of Example 80, 1-methyl-4-(4-nitro-benzyl)-piperazine Compound 39a1 was used in place of 5-(2-chloro-4-nitro-phenoxy)-2-methyl-pyridine Compound 80c to prepare 4-(4-methyl-piperazin-1-ylmethyl)-phenylamine Compound 39a. MS 206 (MH$^+$). Using the procedure of Example 1, 4-(4-methyl-piperazin-1-ylmethyl)-phenylamine Compound 39a was used in place of 4-piperidin-1-ylmethyl-phenylamine Compound 1k to provide Compound 14. MS 552, 554 (MH$^+$).

EXAMPLE 40

5-(3-chloro-4-fluoro-phenyl)-4-oxo-4,5-dihydro-3H-1-thia-3,5,6,8-tetraaza-acenaphthylene-2-carboxylic acid [4-({[(2R)-tetrahydro-furan-2-ylmethyl]-amino}-methyl)-phenyl]-amide (Cpd 17)

Using the procedure of Example 1, (R)-(−)-tetrahydrofurfurylamine Compound 40a was used in place of piperidine to prepare (4-nitro-benzyl)-[(2R)-tetrahydro-furan-2-ylmethyl]-amine Compound 40b. 5% Rh/C (1.5 g) was added to a solution of Compound 40b (5.95 g, 25.2 mmol) in ethyl acetate (40 mL). The mixture was hydrogenated at 40 psi for a period of 2 hrs, then filtered through Celite. The filtrate was evaporated in vacuo to provide 4-({[(2R)-tetrahydro-furan-2-ylmethyl]-amino}-methyl)-phenylamine Compound 40c. MS 207 (MH$^+$). Using the procedure of Example 1, Compound 40c was used in place of 4-piperidin-1-ylmethyl-phenylamine Compound 1k to provide Compound 17. MS 553, 555 (MH$^+$).

EXAMPLE 41

5-(3-chloro-4-fluoro-phenyl)-4-oxo-4,5-dihydro-3H-1-thia-3,5,6,8-tetraaza-acenaphthylene-2-carboxylic acid (6-cyano-pyridin-3-yl)-amide (Cpd 18)

Using the procedure of Example 1, 5-amino-2-cyanopyridine Compound 41a was used in place of 4-piperidin-1-ylmethyl-phenylamine Compound 1k to provide Compound 18. MS 466,468 (MH$^+$).

EXAMPLE 42

5-(3-chloro-4-fluoro-phenyl)-4-oxo-4,5-dihydro-3H-1-thia-3,5,6,8-tetraaza-acenaphthylene-2-carboxylic acid (6-aminomethyl-pyridin-3-yl)-amide (Cpd 23)

Compound 18 (265 mg, 0.570 mmol) was combined with a 1:4 diluted solution of concentrated $H_2SO_4$:water (20 mL) and 10% Pd/C (200 mg) in a Parr shaker vessel. The mixture was placed under 50 PSI hydrogen for 2 hours and then filtered through Celite 545. The filter cake was rinsed with MeOH and the combined liquids evaporated down. The reaction yielded two products with the desired mass. The major product Compound 23 was isolated by reverse phase chromatography. MS 470, 472 (MH$^+$).

EXAMPLE 43

5-(2,4-dichloro-phenyl)-4-oxo-4,5-dihydro-3H-1-thia-3,5,6,8-tetraaza-acenaphthylene-2-carboxylic acid (4-morpholin-4-ylmethyl-phenyl)-amide (Cpd 29)

Using the procedure of Example 1, 2,4-dichloro-phenylamine Compound 43a was used in place of 3-chloro-4-fluoro-phenylamine Compound 1e to prepare 4-chloro-6-(2,4-dichloro-phenylamino)-pyrimidine-5-carbonitrile Compound 43b. Using the procedure of Example 1, Compound 43b was used in place of 4-chloro-6-(3-chloro-4-fluoro-phenylamino)-pyrimidine-5-carbonitrile Compound 1f to provide 5-(2,4-dichloro-phenyl)-4-oxo-4,5-dihydro-3H-1-thia-3,5,6,8-tetraaza-acenaphthylene-2-carboxylic acid Compound 43c. MS 381, 383 (MH$^+$). Using the procedure of Example 1, Compound 43c was used in place of Compound 1 and 4-morpholin-4-ylmethyl-phenylamine Compound 3e was used in place of 4-piperidin-1-ylmethyl-phenylamine Compound 1k to provide Compound 29. MS 555, 557, 559 (MH$^+$).

EXAMPLE 44

5-(5-chloro-benzo[1,3]dioxol-4-yl)-4-oxo-4,5-dihydro-3H-1-thia-3,5,6,8-tetraaza-acenaphthylene-2-carboxylic acid methyl ester (Cpd 54)

Using the procedure of Example 1, 5-chloro-benzo[1,3]dioxol-4-ylamine Compound 44a (prepared as described in J. Med. Chem., 2004, 47(4), 871-887) was used in place of 3-chloro-4-fluoro-phenylamine Compound 1e to prepare 4-chloro-6-(5-chloro-benzo[1,3]dioxol-4-ylamino)-pyrimidine-5-carbonitrile Compound 44b. Using the procedure of Example 3, Compound 44b was used in place of 4-chloro-6-(2-chloro-4-fluoro-phenylamino)-pyrimidine-5-carbonitrile Compound 3b and carried forward to provide Compound 54. MS 405, 407 (MH$^+$).

EXAMPLE 45

5-(5-chloro-benzo[1,3]dioxol-4-yl)-4-oxo-4,5-dihydro-3H-1-thia-3,5,6,8-tetraaza-acenaphthylene-2-carboxylic acid (4-morpholin-4-ylmethyl-phenyl)-amide (Cpd 62)

Compound 54 was hydrolyzed to prepare 5-(5-chloro-benzo[1,3]dioxol-4-yl)-4-oxo-4,5-dihydro-3H-1-thia-3,5,6,8-tetraaza-acenaphthylene-2-carboxylic acid Compound 45a. MS 389, 391 (M$^-$). Using the procedure of Example 1, Compound 45a was used in place of Compound 1 and 4-morpholin-4-ylmethyl-phenylamine Compound 3e was used in place of 4-piperidin-1-ylmethyl-phenylamine Compound 1k to give Compound 62. MS 565, 567 (MH$^+$).

EXAMPLE 46

5-(5-tert-butyl-2-p-tolyl-2H-pyrazol-3-yl)-4-oxo-4,5-dihydro-3H-1-thia-3,5, 6,8-tetraaza-acenaphthylene-2-carboxylic acid (4-morpholin-4-ylmethyl-phenyl)-amide (Cpd 76)

Using the procedure of Example 1, 5-tert-butyl-2-p-tolyl-2H-pyrazol-3-ylamine Compound 46a (prepared as described in J. Med. Chem., 2002, 45, 2994-3008) was used in place of 3-chloro-4-fluoro-phenylamine Compound 1e to prepare 4-(5-tert-butyl-2-p-tolyl-2H-pyrazol-3-ylamino)-6-chloro-pyrimidine-5-carbonitrile Compound 46b. MS 367, 369 (MH$^+$). Using the procedure of Example 3, Compound 46b was used in place of 4-chloro-6-(2-chloro-4-fluoro-phenylamino)-pyrimidine-5-carbonitrile Compound 3b to prepare 5-(5-tert-butyl-2-p-tolyl-2H-pyrazol-3-yl)-4-oxo-4,5-dihydro-3H-1-thia-3,5,6,8-tetraaza-acenaphthylene-2-carboxylic acid Compound 46c. MS 447 (M$^-$). Using the procedure of Example 1, Compound 46c was used in place of Compound 1 and 4-morpholin-4-ylmethyl-phenylamine Compound 3e was used in place of 4-piperidin-1-ylmethyl-phenylamine Compound 1k to provide Compound 76. MS 623 (MH$^+$).

EXAMPLE 47

5-(2,6-dichloro-phenyl)-4-oxo-4,5-dihydro-3H-1-thia-3,5,6,8-tetraaza-acenaphthylene-2-carboxylic acid (4-morpholin-4-ylmethyl-phenyl)-amide (Cpd 104)

Using the procedure of Example 1, 2,6-dichloro-phenylamine Compound 47a was used in place of 3-chloro-4-fluoro-phenylamine Compound 1e to prepare 4-chloro-6-(2,6-dichloro-phenylamino)-pyrimidine-5-carbonitrile Compound 47b. Using the procedure of Example 3, Compound 47b was used in place of 4-chloro-6-(2-chloro-4-fluoro-phenylamino)-pyrimidine-5-carbonitrile Compound 3b to prepare 5-(2,6-dichloro-phenyl)-4-oxo-4,5-dihydro-3H-1-thia-3,5, 6,8-tetraaza-acenaphthylene-2-carboxylic acid Compound 47c. MS 395, 397, 399 (MH$^+$). Using the procedure of Example 1, Compound 47c was used in place of Compound 1 and 4-morpholin-4-ylmethyl-phenylamine Compound 3e was used in place of 4-piperidin-1-ylmethyl-phenylamine Compound 1k to give Compound 104. MS 555, 557, 559 (MH+).

EXAMPLE 48

5-(2-chloro-6-methyl-phenyl)-4-oxo-4,5-dihydro-3H-1-thia-3,5,6,8-tetraaza-acenaphthylene-2-carboxylic acid (4-morpholin-4-ylmethyl-phenyl)-amide (Cpd 146)

Using the procedure of Example 1, 2-chloro-6-methyl-phenylamine Compound 48a was used in place of 3-chloro-4-fluoro-phenylamine Compound 1e to prepare 4-chloro-6-(2-chloro-6-methyl-phenylamino)-pyrimidine-5-carbonitrile Compound 48b. Using the procedure of Example 3, Compound 48b was used in place of 4-chloro-6-(2-chloro-4-fluoro-phenylamino)-pyrimidine-5-carbonitrile Compound 3b to prepare 5-(2-chloro-6-methyl-phenyl)-4-oxo-4,5-dihydro-3H-1-thia-3,5,6,8-tetraaza-acenaphthylene-2-carboxylic acid Compound 4&. MS 361, 363 (MH+). Using the procedure of Example 1, Compound 48c was used in place of Compound 1 and 4-morpholin-4-ylmethyl-phenylamine Compound 3e was used in place of 4-piperidin-1-ylmethyl-phenylamine Compound 1k to prepare Compound 146. MS 535, 537 (MH+).

EXAMPLE 49

5-(2-chloro-6-methyl-phenyl)-4-oxo-4,5-dihydro-3H-1-thia-3,5,6,8-tetraaza-acenaphthylene-2-carboxylic acid (4-piperidin-1-ylmethyl-phenyl)-amide (Cpd 147)

Using the procedure of Example 1, Compound 48c was used in place of Compound 1 to give Compound 147. MS 533, 535 (MH+).

EXAMPLE 50

5-(2-chloro-6-methyl-phenyl)-4-oxo-4,5-dihydro-3H-1-thia-3,5,6,8-tetraaza-acenaphthylene-2-carboxylic acid [4-(1-hydroxy-2-morpholin-4-yl-ethyl)-phenyl]-amide (Cpd 148)

Morpholine Compound 50b (1.41 mL, 16.2 mmol) was added dropwise to a solution of 2-bromo-1-(4-nitro-phenyl)-ethanone Compound 50a (4.15 g, 16.2 mmol) in THF (50 mL) and DIPEA (3.1 mL, 17.8 mmol). The reaction was stirred for 3 hours and then extracted from 0.5 M NaH$_2$PO$_4$ with EtOAc. The combined extracts were dried over MgSO$_4$, filtered and evaporated down. The residue was recrystallized from EtOAc and hexanes to give 2-morpholin-4-yl-1-(4-nitro-phenyl)-ethanone Compound 50c (2.55 g) as a yellow solid. MS 251 (MH+).

Compound 50c (1.36 g, 5.44 mmol) was dissolved in EtOAc (15 mL) containing 10% Pd/C (270 mg). The reaction mixture was placed under 50 PSI of hydrogen in a Parr apparatus for 1 hr. The mixture was then filtered through a celite plug, washed with EtOAc and evaporated down to give a white solid (1.25 g). MS 221 (MH+). The solid (1.07 g, 4.86 mmol) was then taken up in MeOH (15 mL) and cooled to 0° C. NaBH$_4$ (184 mg, 4.86 mmol) was added portionwise to the mixture. After 3 hrs, the reaction mixture was diluted with water and extracted with EtOAc. The combined extracts were dried (MgSO$_4$), filtered and evaporated to give a residue. The residue was recrystallized from EtOAc and hexanes to give 1-(4-amino-phenyl)-2-morpholin-4-yl-ethanol Compound 50d (452 mg) as a white solid. MS 223 (MH+).

Using the procedure of Example 1, 5-(2-chloro-6-methyl-phenyl)-4-oxo-4,5-dihydro-3H-1-thia-3,5,6,8-tetraaza-acenaphthylene-2-carboxylic acid Compound 48c was used in place of Compound 1 and Compound 50d was used in place of 4-piperidin-1-ylmethyl-phenylamine Compound 1k to give Compound 148. MS 565, 567 (MH+).

EXAMPLE 51

5-(2-chloro-phenyl)-4-oxo-4,5-dihydro-3H-1-thia-3,5,6,8-tetraaza-acenaphthylene-2-carboxylic acid (4-morpholin-4-ylmethyl-phenyl)-amide (Cpd 149)

Using the procedure of Example 1, 2-chloro-phenylamine Compound 51a was used in place of Compound 1e to prepare 4-chloro-6-(2-chloro-phenylamino)-pyrimidine-5-carbonitrile Compound 51b. Using the procedure of Example 1, Compound 51b was used in place of Compound 1f to prepare 5-(2-chloro-phenyl)-4-oxo-4,5-dihydro-3H-1-thia-3,5,6,8-tetraaza-acenaphthylene-2-carboxylic acid Compound 51c. MS 347, 349 (MH+). Using the procedure of Example 1, Compound 51c was used in place of Compound 1 and Compound 3e was used in place of Compound 1k to provide Compound 149. MS 521, 523 (MH+).

EXAMPLE 52

5-(2-chloro-phenyl)-4-oxo-4,5-dihydro-3H-1-thia-3,5,6,8-tetraaza-acenaphthylene-2-carboxylic acid (4-piperidin-1-ylmethyl-phenyl)-amide (Cpd 150)

Using the procedure of Example 1, Compound 51c was used in place of Compound 1 to give Compound 150. MS 519, 521 (MH+).

EXAMPLE 53

5-(2-chloro-phenyl)-4-oxo-4,5-dihydro-3H-1-thia-3,5,6,8-tetraaza-acenaphthylene-2-carboxylic acid [4-(4-methyl-piperazin-1-ylmethyl)-phenyl]-amide (Cpd 151)

Using the procedure of Example 1, 5-(2-chloro-phenyl)-4-oxo-4,5-dihydro-3H-1-thia-3,5, 6,8-tetraaza-acenaphthylene-2-carboxylic acid Compound 51c was used in place of Compound 1 and 4-(4-methyl-piperazin-1-ylmethyl)-phenylamine Compound 39a was used in place of Compound 1k to give Compound 151. MS 534, 536 (MH+).

EXAMPLE 54

5-(3-ethynyl-phenyl)-4-oxo-4,5-dihydro-3H-1-thia-3,5,6,8-tetraaza-acenaphthylene-2-carboxylic acid (4-pyrrolidin-1-ylmethyl-phenyl)-amide (Cpd 15)

Using the procedure of Example 1, 3-ethynyl-phenylamine Compound 54a was used in place of 3-chloro-4-fluoro-phenylamine Compound 1e to prepare 4-chloro-6-(3-ethynyl-phenylamino)-pyrimidine-5-carbonitrile Compound 54b. MS 255 (MH+). Using the procedure of Example 1, Compound 54b was used in place of Compound 1f to prepare 5-(3-ethynyl-phenyl)-4-oxo-4,5-dihydro-3H-1-thia-3,5,6,8-tetraaza-acenaphthylene-2-carboxylic acid Compound 54c.

MS 335 (M⁻). Using the procedure of Example 1, pyrrolidine was used in place of piperidine and combined with 1-chloromethyl-4-nitro-benzene Compound 1i and taken forward to provide 4-pyrrolidin-1-ylmethyl-phenylamine Compound 54e. MS 177 (MH⁺). Using the procedure of Example 2, Compound 54c was used in place of Compound 40 and Compound 54e was used in place of 3,4-dimethoxy-phenylamine Compound 2c to give Compound 15. MS 495 (MH⁺).

EXAMPLE 55

5-(3-ethynyl-phenyl)-4-oxo-4,5-dihydro-3H-1-thia-3,5,6,8-tetraaza-acenaphthylene-2-carboxylic acid [4-(piperidin-4-ylaminomethyl)-phenyl]-amide (Cpd 24)

4-nitro-benzaldehyde Compound 55a (9.1 g, 45.4 mmol) and 4-amino-piperidine-1-carboxylic acid tert-butyl ester Compound 8a (6.9 g, 45.4 mmol) were dissolved in toluene (100 mL) and treated with AcOH (1 mL). The mixture was stirred for 10 min and concentrated to dryness. The residue was dissolved in MeOH (100 mL) and cooled to 0° C. Sodium borohydride was added and the mixture was warmed to rt. After 30 min, the mixture was poured into EtOAc and extracted with sodium bicarbonate, water and brine. The organic layer was dried over Na₂SO₄, filtered and concentrated. The residue was dissolved in THF (60 mL) and treated with Boc₂O (19.5 g, 90 mmol) and Et₃N (21 mL, 149.25 mmol). The mixture was stirred for 1 hr, poured into EtOAc and washed with sodium bicarbonate, water and brine. The residue was purified via flash chromatography using gradient elution (20% ethyl acetate/80% hexane to 50% ethyl acetate/50% hexane) to yield 4-[tert-butoxycarbonyl-(4-nitro-benzyl)-amino]-piperidine-1-carboxylic acid tert-butyl ester Compound 55b.

10% Pd/C (1.0 g) was added to a solution of Compound 55b (5.0 g, 11.5 mmol) in EtOAc (100 mL). The mixture was hydrogenated at 50 PSI for a period of 2 hrs and filtered through Celite. The filtrate was evaporated to yield 4-[(4-amino-benzyl)-tert-butoxycarbonyl-amino]-piperidine-1-carboxylic acid tert-butyl ester Cpd 55c. MS 406 (MH⁺).

HATU (2.25 g, 5.9 mmol), DIPEA (3.1 mL, 17.8 mmol) and Compound 55c (2.4 g, 5.9 mmol) were added to a suspension of 5-(3-ethynyl-phenyl)-4-oxo-4,5-dihydro-3H-1-thia-3,5,6,8-tetraaza-acenaphthylene-2-carboxylic acid Compound 54c (2.0 g, 5.9 mmol) in THF (100 mL). The dark solution was stirred for 5 hrs at 50° C., then the reaction was quenched with 10% aq. NH₄Cl (100 mL) and extracted with EtOAc. The organic layers were combined, dried (Na₂SO₄), filtered and concentrated to a 100 mL volume. The dark solution was treated with Et₂O and filtered. The precipitate was dissolved in MeOH and treated with 2N HCl in Et₂O (5.0 mL). The solution was filtered to yield Compound 24 (1.8 g, 56%). MS 524 (MH⁺).

EXAMPLE 56

5-(4-bromo-2-fluoro-phenyl)-4-oxo-4,5-dihydro-3H-1-thia-3,5,6,8-tetraaza-acenaphthylene-2-carboxylic acid [3-methoxy-4-(2-morpholin-4-yl-ethoxy)-phenyl]-amide (Cpd 39)

A mixture of 2-methoxy-4-nitro-phenol Compound 36a (0.92 g, 5.4 mmol), potassium carbonate (1.5 g, 10.8 mmol) and 4-(2-chloro-ethyl)-morpholine hydrochloride Compound 56a (1.04 g, 5.65 mmol) in DMF (10 mL) was heated under microwave conditions to 140° C. for 30 minutes. The reaction mixture was filtered, diluted with EtOAc and subsequently washed with water, then brine. The organic layer was dried over sodium sulfate and concentrated to yield 4-[2-(2-methoxy-4-nitro-phenoxy)-ethyl]-morpholine Compound 56b (1.46 g). ¹H NMR (400 MHz, CDCl₃) δ 7.90 (dd, 1H); 7.77 (d, 1H); 6.93 (d, 1H); 4.26 (t, 2H); 3.97 (s, 3H); 3.79-3.69 (m, 4H); 2.91 (t, 2H); 2.66-2.55 (m, 4H). MS 283 (MH⁺).

10% Pd/C (0.50 g) was added to a solution of 1-[2-(2-methoxy-4-nitro-phenoxy)-ethyl]-morpholine Compound 56b (2.96 g, 10.5 mmol) in EtOAc (50 mL). The solution was exposed to 40 PSI of hydrogen gas for a period of 1 hr. The catalyst was removed by filtration through Celite 545 and the solvent was removed to give 3-methoxy-4-(2-morpholin-4-yl-ethoxy)-phenylamine Compound 56c (2.78 g). MS 253 (MH⁺). Using the procedure of Example 2, 3-methoxy-4-(2-morpholin-4-yl-ethoxy)-phenylamine Compound 56c was used in place of 3,4-dimethoxy-phenylamine Compound 2c to give Compound 39. MS 641, 643 (M⁻).

EXAMPLE 57

5-(4-bromo-2-fluoro-phenyl)-4-oxo-4,5-dihydro-3H-1-thia-3,5,6,8-tetraaza-acenaphthylene-2-carboxylic acid (4-morpholin-4-ylmethyl-phenyl)-amide (Cpd 53)

Using the procedure of Example 2, 4-morpholin-4-ylmethyl-phenylamine Compound 3e was used in place of 3,4-dimethoxy-phenylamine Compound 2c to give Compound 53. MS 581, 583 (M⁻).

EXAMPLE 58

5-(4-bromo-2-fluoro-phenyl)-4-oxo-4,5-dihydro-3H-1-thia-3,5,6,8-tetraaza-acenaphthylene-2-carboxylic acid [4-(4-methyl-piperazin-1-ylmethyl)-phenyl]-amide (Cpd 70)

Using the procedure of Example 2, 4-(4-methyl-piperazin-1-ylmethyl)-phenylamine Compound 39a was used in place of 3,4-dimethoxy-phenylamine Compound 2c to give Compound 70. MS 594, 596 (M⁻).

EXAMPLE 59

5-(4-bromo-2-fluoro-phenyl)-4-oxo-4,5-dihydro-3H-1-thia-3,5,6,8-tetraaza-acenaphthylene-2-carboxylic acid [6-(3-morpholin-4-yl-propylamino)-pyridin-3-yl]-amide (Cpd 71)

2-chloro-5-nitro-pyridine Compound 59a (6.06 g, 38.2 mmol) and 3-morpholin-4-yl-propylamine Compound 11a (6.27 mL, 42.1 mmol) were combined in DMSO (100 mL) and heated to 50° C. for 2.5 hrs. The reaction mixture was diluted with 0.5 M HCl and washed with ethyl ether. The pH of the aqueous layer was adjusted to 11 with NaOH and extracted with EtOAc. The combined organic layers were dried over MgSO₄ and concentrated to prepare (3-morpholin-4-yl-propyl)-(5-nitro-pyridin-2-yl)-amine Compound 59b.

Compound 59b was then taken up in AcOH (30 mL) and 10% Pd/C (3.1 g) was added. The mixture was hydrogenated at 50 psi for 2 hrs; then filtered through Celite. The filtrate was evaporated down and the residue was dissolved in aqueous 10% NH₄Cl and washed with ethyl ether. The aqueous layer was adjusted to pH 10 with NaOH and extracted with EtOAc. The combined organic layers are dried over MgSO₄, then filtered and evaporated down in vacuo to prepare N²-(3-morpholin-4-yl-propyl)-pyridine-2,5-diamine Compound 59c (5.0 g). $^1$H NMR (CDCl$_3$) δ 7.67 (d, J=3.0 Hz, 1H); 6.95 (dd, J=8.6, 3.0 Hz, 1H); 6.31 (d, J=8.6 Hz, 1H); 3.77-3.66 (m, 4H); 2.52-2.38 (m, 8H); 2.08 (p, J=6.8 Hz, 2H). MS 237 (MH$^+$). Using the procedure of Example 2, Compound 59c was used in place of 3,4-dimethoxy-phenylamine Compound 2c to give Compound 71. MS 625, 627 (M$^-$).

EXAMPLE 60

5-(2-chloro-5-methoxy-phenyl)-4-oxo-4,5-dihydro-3H-1-thia-3,5,6,8-tetraaza-acenaphthylene-2-carboxylic acid (Cpd 47)

Using the procedure of Example 1, 2-chloro-5-methoxy-phenylamine Compound 60a was used in place of Compound 1e to prepare 4-chloro-6-(2-chloro-5-methoxy-phenylamino)-pyrimidine-5-carbonitrile Compound 60b. Using the procedure of Example 1, Compound 60b was carried forward in place of 4-chloro-6-(3-chloro-4-fluoro-phenylamino)-pyrimidine-5-carbonitrile Compound 1f to prepare Compound 47. MS 377 (MH$^+$).

EXAMPLE 61

5-(2-chloro-5-methoxy-phenyl)-4-oxo-4,5-dihydro-3H-1-thia-3,5,6,8-tetraaza-acenaphthylene-2-carboxylic acid (3,4-dimethoxy-phenyl)-amide (Cpd 49)

Using the procedure of Example 1, Compound 47 was used in place of Compound 1 and 3,4-dimethoxy-phenylamine Compound 2c was used in place of Compound 1k to give Compound 49 (0.072 g, 52%). MS 512 (MH$^+$).

EXAMPLE 62

5-(2-chloro-5-methoxy-phenyl)-4-oxo-4,5-dihydro-3H-1-thia-3,5,6,8-tetraaza-acenaphthylene-2-carboxylic acid [3-methoxy-4-(2-morpholin-4-yl-ethoxy)-phenyl]-amide (Cpd 50)

Using the procedure of Example 1, Compound 47 was used in place of Compound 1 and 3-methoxy-4-(2-morpholin-4-yl-ethoxy)-phenylamine Compound 56c was used in place of Compound 1k to provide Compound 50. MS 611, 613 (MH$^+$).

EXAMPLE 63

5-(2-chloro-5-methoxy-phenyl)-4-oxo-4,5-dihydro-3H-1-thia-3,5,6,8-tetraaza-acenaphthylene-2-carboxylic acid (4-morpholin-4-ylmethyl-phenyl)-amide (Cpd 51)

Using the procedure of Example 1, Compound 47 was used in place of Compound 1 and 4-morpholin-4-ylmethyl-phenylamine Compound 3e was used in place of Compound 1k to provide Compound 51. MS 551, 553 (MH$^+$).

EXAMPLE 64

5-(2-chloro-5-methoxy-phenyl)-4-oxo-4,5-dihydro-3H-1-thia-3,5,6,8-tetraaza-acenaphthylene-2-carboxylic acid [3-methoxy-4-(2-piperidin-1-yl-ethoxy)-phenyl]-amide (Cpd 88)

Using the procedure of Example 1, Compound 47 was used in place of Compound 1 and 3-methoxy-4-(2-piperidin-1-yl-ethoxy)-phenylamine Compound 36d was used in place of Compound 1k to provide Compound 88. MS 609, 611 (MH$^+$).

EXAMPLE 65

5-[3-chloro-4-(pyridin-2-ylmethoxy)-phenyl]-4-oxo-4,5-dihydro-3H-1-thia-3,5,6,8-tetraaza-acenaphthylene-2-carboxylic acid (Cpd 38)

Using the procedure of Example 1, 3-chloro-4-(pyridin-2-ylmethoxy)-phenylamine Compound 65a (prepared according to the procedure described in WO04/046101) was used in place of Compound 1e to prepare 4-chloro-6-[3-chloro-4-(pyridin-2-ylmethoxy)-phenylamino]-pyrimidine-5-carbonitrile Compound 65b. Using the procedure of Example 1, Compound 65b was used in place of 4-chloro-6-(3-chloro-4-fluoro-phenylamino)-pyrimidine-5-carbonitrile Compound 1f and carried forward to prepare Compound 38. MS 452 (M$^-$).

EXAMPLE 66

5-[3-chloro-4-(pyridin-2-ylmethoxy)-phenyl]-4-oxo-4,5-dihydro-3H-1-thia-3,5,6,8-tetraaza-acenaphthylene-2-carboxylic acid (3,4-dimethoxy-phenyl)-amide (Cpd 48)

Using the procedure of Example 1, Compound 38 was used in place of Compound 1 and 3,4-dimethoxy-phenylamine Compound 2c was used in place of Compound 1k to give Compound 48. MS 587 (M$^-$).

EXAMPLE 67

5-[3-chloro-4-(pyridin-2-ylmethoxy)-phenyl]-4-oxo-4,5-dihydro-3H-1-thia-3,5,6,8-tetraaza-acenaphthylene-2-carboxylic acid [3-methoxy-4-(2-morpholin-4-yl-ethoxy)-phenyl]-amide (Cpd 86)

Using the procedure of Example 1, Compound 38 was used in place of Compound 1 and 3-methoxy-4-(2-morpholin-4-yl-ethoxy)-phenylamine Compound 56c was used in place of Compound 1k to give Compound 86. MS 686 (M$^-$).

EXAMPLE 68

5-[3-chloro-4-(pyridin-2-ylmethoxy)-phenyl]-4-oxo-4,5-dihydro-3H-1-thia-3,5,6,8-tetraaza-acenaphthylene-2-carboxylic acid (4-morpholin-4-ylmethyl-phenyl)-amide (Cpd 52)

Using the procedure of Example 1, Compound 38 was used in place of Compound 1 and 4-morpholin-4-ylmethyl-phenylamine Compound 3e was used in place of Compound 1k to give Compound 52. MS 626 (M$^-$).

EXAMPLE 69

5-[3-chloro-4-(pyridin-2-ylmethoxy)-phenyl]-4-oxo-4,5-dihydro-3H-1-thia-3,5,6,8-tetraaza-acenaphthylene-2-carboxylic acid (4-piperidin-1-ylmethyl-phenyl)-amide (Cpd 89)

Using the procedure of Example 1, Compound 38 was used in place of Compound 1 to give Compound 89. MS 624 (M$^-$).

EXAMPLE 70

5-[3-chloro-4-(pyridin-2-ylmethoxy)-phenyl]-4-oxo-4,5-dihydro-3H-1-thia-3,5,6,8-tetraaza-acenaphthylene-2-carboxylic acid [4-(4-methyl-piperazin-1-ylmethyl)-phenyl]-amide (Cpd 90)

Using the procedure of Example 1, Compound 38 was used in place of Compound 1 and 4-(4-methyl-piperazin-1-ylmethyl)-phenylamine Compound 39a was used in place of Compound 1k to give Compound 90. MS 639 (M⁻).

EXAMPLE 71

5-(3-bromo-phenyl)-4-oxo-4,5-dihydro-3H-1-thia-3, 5,6,8-tetraaza-acenaphthylene-2-carboxylic acid (4-morpholin-4-ylmethyl-phenyl)-amide (Cpd 36)

Using the procedure of Example 1, 4-(3-bromo-phenylamino)-6-chloro-pyrimidine-5-carbonitrile Compound 24b was used in place of 4-chloro-6-(3-chloro-4-fluoro-phenylamino)-pyrimidine-5-carbonitrile Compound 1f to prepare 5-(3-bromo-phenyl)-4-oxo-4,5-dihydro-3H-1-thia-3,5,6,8-tetraaza-acenaphthylene-2-carboxylic acid Compound 71a. MS 389, 391 (M⁻). Using the procedure of Example 1, Compound 71a was used in place of Compound 1 and 4-morpholin-4-ylmethyl-phenylamine Compound 3e was used in place of Compound 1k to give Compound 36. MS 563, 565 (M⁻).

EXAMPLE 72

5-(3-bromo-phenyl)-4-oxo-4,5-dihydro-3H-1-thia-3, 5,6,8-tetraaza-acenaphthylene-2-carboxylic acid [3-methoxy-4-(2-piperidin-1-yl-ethoxy)-phenyl]-amide (Cpd 63)

Using the procedure of Example 1, 5-(3-bromo-phenyl)-4-oxo-4,5-dihydro-3H-1-thia-3,5, 6,8-tetraaza-acenaphthylene-2-carboxylic acid Compound 71a was used in place of Compound 1 and 3-methoxy-4-(2-piperidin-1-yl-ethoxy)-phenylamine Compound 36d was used in place of Compound 1k to give Compound 63. MS 621, 623 (M⁻).

EXAMPLE 73

5-(3-bromo-phenyl)-4-oxo-4,5-dihydro-3H-1-thia-3, 5,6,8-tetraaza-acenaphthylene-2-carboxylic acid [6-(3-morpholin-4-yl-propylamino)-pyridin-3-yl]-amide (Cpd 64)

Using the procedure of Example 1, 5-(3-bromo-phenyl)-4-oxo-4,5-dihydro-3H-1-thia-3,5, 6,8-tetraaza-acenaphthylene-2-carboxylic acid Compound 71a was used in place of Compound 1 and $N^2$-(3-morpholin-4-yl-propyl)-pyridine-2,5-diamine Compound 59c was used in place of Compound 1k to give Compound 64. MS 607, 609 (M⁻).

EXAMPLE 74

5-(2-fluoro-4-methoxy-phenyl)-4-oxo-4,5-dihydro-3H-1-thia-3,5,6,8-tetraaza-acenaphthylene-2-carboxylic acid (4-morpholin-4-ylmethyl-phenyl)-amide (Cpd 65)

Using the procedure of Example 1, 2-fluoro-4-methoxy-phenylamine Compound 74a was used in place of Compound 1e to prepare 4-chloro-6-(2-fluoro-4-methoxy-phenylamino)-pyrimidine-5-carbonitrile Compound 74b. MS 279 (M⁻). Using the procedure of Example 1, Compound 74b was carried forward in place of 4-chloro-6-(3-chloro-4-fluoro-phenylamino)-pyrimidine-5-carbonitrile Compound 1f to prepare 5-(2-fluoro-4-methoxy-phenyl)-4-oxo-4,5-dihydro-3H-1-thia-3,5,6,8-tetraaza-acenaphthylene-2-carboxylic acid Compound 74c. MS 359 (M⁻). Using the procedure of Example 1, Compound 74c was used in place of Compound 1 and 4-morpholin-4-ylmethyl-phenylamine Compound 3e was used in place of Compound 1k to give Compound 65. MS 533 (M⁻).

EXAMPLE 75

5-(2-fluoro-4-methoxy-phenyl)-4-oxo-4,5-dihydro-3H-1-thia-3,5,6,8-tetraaza-acenaphthylene-2-carboxylic acid (4-piperidin-1-ylmethyl-phenyl)-amide (Cpd 66)

Using the procedure of Example 1, 5-(2-fluoro-4-methoxy-phenyl)-4-oxo-4,5-dihydro-3H-1-thia-3,5,6,8-tetraaza-acenaphthylene-2-carboxylic acid Compound 74c was used in place of Compound 1 to give Compound 66. MS 531 (M⁻).

EXAMPLE 76

5-(2-fluoro-4-methoxy-phenyl)-4-oxo-4,5-dihydro-3H-1-thia-3,5,6,8-tetraaza-acenaphthylene-2-carboxylic acid [3-methoxy-4-(2-morpholin-4-yl-ethoxy)-phenyl]-amide (Cpd 67)

Using the procedure of Example 1, 5-(2-fluoro-4-methoxy-phenyl)-4-oxo-4,5-dihydro-3H-1-thia-3,5,6,8-tetraaza-acenaphthylene-2-carboxylic acid Compound 74c was used in place of Compound 1 and 3-methoxy-4-(2-morpholin-4-yl-ethoxy)-phenylamine Compound 56c was used in place of Compound 1k to give Compound 67. MS 593 (M⁻).

EXAMPLE 77

5-(2-fluoro-4-methoxy-phenyl)-4-oxo-4,5-dihydro-3H-1-thia-3,5,6,8-tetraaza-acenaphthylene-2-carboxylic acid [3-methoxy-4-(tetrahydro-pyran-2-ylmethoxy)-phenyl]-amide (Cpd 68)

Using the procedure of Example 56, 2-chloromethyl-tetrahydro-pyran Compound 77a was used in place of 4-(2-chloro-ethyl)-morpholine hydrochloride Compound 56a to prepare 2-(2-methoxy-4-nitro-phenoxymethyl)-tetrahydro-pyran Compound 77b. MS 268 (MH⁺). Using the procedure of Example 56, Compound 77b was used in place of 4-[2-(2-methoxy-4-nitro-phenoxy)-ethyl]-morpholine Compound 56b to prepare 3-methoxy-4-(tetrahydro-pyran-2-ylmethoxy)-phenylamine Compound 77c. MS 238 (MH⁺). Using the procedure of Example 1, 5-(2-fluoro-4-methoxy-phenyl)-4-oxo-4,5-dihydro-3H-1-thia-3,5,6,8-tetraaza-acenaphthylene-2-carboxylic acid Compound 74c was used in place of Compound 1 and Compound 77c was used in place of Compound 1k to give Compound 68. MS 578 (M⁻).

EXAMPLE 78

5-(2-fluoro-4-methoxy-phenyl)-4-oxo-4,5-dihydro-3H-1-thia-3,5,6,8-tetraaza-acenaphthylene-2-carboxylic acid (3,4-dimethoxy-phenyl)-amide (Cpd 69)

Using the procedure of Example 1, 5-(2-fluoro-4-methoxy-phenyl)-4-oxo-4,5-dihydro-3H-1-thia-3,5,6,8-tetraaza-acenaphthylene-2-carboxylic acid Compound 74c was used in place of Compound 1 and Compound 2c was used in place of Compound 1k to give Compound 69. MS 494 (M⁻).

EXAMPLE 79

5-[3-methyl-4-(6-methyl-pyridin-3-yloxy)-phenyl]-4-oxo-4,5-dihydro-3H-1-thia-3,5,6,8-tetraaza-acenaphthylene-2-carboxylic acid (4-morpholin-4-ylmethyl-phenyl)-amide (Cpd 119)

Using the procedure of Example 1, 3-methyl-4-(6-methyl-pyridin-3-yloxy)-phenylamine Compound 79a (prepared according to the procedure described in WO04/046101) was used in place of Compound 1e to prepare 4-chloro-6-[3-methyl-4-(6-methyl-pyridin-3-yloxy)-phenylamino]-pyrimidine-5-carbonitrile Compound 79b. MS 350 (M−). Using the procedure of Example 1, Compound 79b was carried forward in place of 4-chloro-6-(3-chloro-4-fluoro-phenylamino)-pyrimidine-5-carbonitrile Compound 1f to prepare 5-[3-methyl-4-(6-methyl-pyridin-3-yloxy)-phenyl]-4-oxo-4,5-dihydro-3H-1-thia-3,5,6,8-tetraaza-acenaphthylene-2-carboxylic acid Compound 79c. MS 432 (M−). Using the procedure of Example 1, Compound 79c was used in place of Compound 1 and 4-morpholin-4-ylmethyl-phenylamine Compound 3e was used in place of Compound 1k to give Compound 119. MS 606 (M−).

EXAMPLE 80

5-[3-chloro-4-(6-methyl-pyridin-3-yloxy)-phenyl]-4-oxo-4,5-dihydro-3H-1-thia-3,5,6,8-tetraaza-acenaphthylene-2-carboxylic acid (4-morpholin-4-ylmethyl-phenyl)-amide (Cpd 129)

6-methyl-pyridin-3-ol Compound 80b (3.10 g, 28.4 mmol) and potassium carbonate (7.80 g, 56.8 mmol) were added to a solution of 2-chloro-1-fluoro-4-nitro-benzene Compound 80a (5.0 g, 28.4 mmol) in acetone (50 mL). The suspension was refluxed for 20 hrs and then cooled to 25° C. The reaction mixture was diluted with EtOAc and washed with water and brine. The organic solution was dried over $Na_2SO_4$, then filtered and concentrated to yield 5-(2-chloro-4-nitro-phenoxy)-2-methyl-pyridine Compound 80c (5.6 g, 80%). MS 350 (M−).

$NiCl_2.6H_2O$ (14.0 g, 59.0 mmol) was added to a solution of Compound 80c (7.8 g, 29.5 mmol) in MeOH (220 mL). The green solution was cooled to 0° C. and then $NaBH_4$ (4.5 g, 118.0 mmol) was added in portions over 30 min. The black solution was stirred an additional 30 min at 0° C. and then warmed to 25° C. The reaction was concentrated and then dissolved into 6N HCl. The reaction was adjusted to pH 8 using ammonium hydroxide and extracted with EtOAc. The organic layers were combined, washed with brine, dried over $Na_2SO_4$, then filtered and concentrated to yield (5.7 g, 83%) 3-chloro-4-(6-methyl-pyridin-3-yloxy)-phenylamine Compound 80d. MS 233 (M−)

Using the procedure of Example 1, Compound 80d was used in place of Compound 1e to prepare 4-chloro-6-[3-chloro-4-(6-methyl-pyridin-3-yloxy)-phenylamino]-pyrimidine-5-carbonitrile Compound 80e. MS 370 (M−). Compound 80e was used in place of 4-chloro-6-(3-chloro-4-fluoro-phenylamino)-pyrimidine-5-carbonitrile Compound 1f to provide 5-[3-chloro-4-(6-methyl-pyridin-3-yloxy)-phenyl]-4-oxo-4,5-dihydro-3H-1-thia-3,5,6,8-tetraaza-acenaphthylene-2-carboxylic acid, Compound 80f. MS 452 (M−). Using the procedure of Example 1, Compound 8 of was used in place of Compound 1 and 4-morpholin-4-ylmethyl-phenylamine Compound 3e was used in place of Compound 1k to give Compound 129. MS 626 (M−).

EXAMPLE 81

5-(3-bromo-4-fluoro-phenyl)-4-oxo-4,5-dihydro-3H-1-thia-3,5,6,8-tetraaza-acenaphthylene-2-carboxylic acid (4-morpholin-4-ylmethyl-phenyl)-amide (Cpd 153)

Using the procedure of Example 1, 3-bromo-4-fluoro-phenylamine Compound 81a was used in place of Compound 1e to prepare 4-(3-bromo-4-fluoro-phenylamino)-6-chloro-pyrimidine-5-carbonitrile Compound 81b. MS 325, 327 (M−). Using the procedure of Example 1, Compound 81b was then carried forward in place of 4-chloro-6-(3-chloro-4-fluoro-phenylamino)-pyrimidine-5-carbonitrile Compound 1f to prepare 5-(3-bromo-4-fluoro-phenyl)-4-oxo-4,5-dihydro-3H-1-thia-3,5,6,8-tetraaza-acenaphthylene-2-carboxylic acid Compound 81c. MS 407, 409 (M−). Using the procedure of Example 1, Compound 81c was used in place of Compound 1 and 4-morpholin-4-ylmethyl-phenylamine Compound 3e was used in place of Compound 1k to give Compound 153. MS 581, 583 (M−).

EXAMPLE 82

5-(3-bromo-4-fluoro-phenyl)-4-oxo-4,5-dihydro-3H-1-thia-3,5,6,8-tetraaza-acenaphthylene-2-carboxylic acid (3-hydroxy-propyl)-amide (Cpd 154)

Using the procedure of Example 1, 5-(3-bromo-4-fluoro-phenyl)-4-oxo-4,5-dihydro-3H-1-thia-3,5,6,8-tetraaza-acenaphthylene-2-carboxylic acid Compound 81c was used in place of Compound 1 and 3-amino-propan-1-ol Compound 82a was used in place of Compound 1k to give Compound 154. MS 464, 466 (M−). Using the procedure of Example 82 and known appropriate reagents and starting materials, the following compounds of the invention were prepared:

| Cpd | Name | MS |
| --- | --- | --- |
| 212 | 4-oxo-5-(4-phenylsulfanyl-phenyl)-4,5-dihydro-3H-1-thia-3,5,6,8-tetraaza-acenaphthylene-2-carboxylic acid (3-dimethylamino-propyl)-amide | 505 |

EXAMPLE 83

5-(3-bromo-4-fluoro-phenyl)-4-oxo-4,5-dihydro-3H-1-thia-3,5,6,8-tetraaza-acenaphthylene-2-carboxylic acid (4-piperidin-1-ylmethyl-phenyl)-amide (Cpd 155)

Using the procedure of Example 1, 5-(3-bromo-4-fluoro-phenyl)-4-oxo-4,5-dihydro-3H-1-thia-3,5,6,8-tetraaza-acenaphthylene-2-carboxylic acid Compound 81c was used in place of Compound 1 to give Compound 155. MS 579, 581 (M−).

EXAMPLE 84

5-(3-chloro-4-fluoro-phenyl)-2-phenyl-3H,5H-1-thia-3,5,6,8-tetraaza-acenaphthylen-4-one (Cpd 8)

DBU (0.88 mL, 5.9 mmol) was added to a solution of [6-(3-chloro-4-fluoro-phenylamino)-5-cyano-pyrimidin-4-ylsulfanyl]-acetic acid Compound 1h (2.0 g, 5.9 mmol) in THF (50 mL). The solution was heated to reflux for 24 hrs and then cooled to room temperature. The mixture was partitioned between EtOAc and 1 N $NH_4Cl$. The organic layer washed twice with 1 N $NH_4Cl$ and once with brine. The organic solution was dried over $Na_2SO_4$, filtered and concentrated to dryness. The residue was purified by flash chromatography using gradient elution (20% EtOAc/80% Hexanes to 50% EtOAc/50% Hexanes) to yield N-(3-chloro-4-fluoro-phenyl)-thieno[2,3-d]pyrimidine-4,5-diamine Compound 84a (606 mg, 32%). MS 295 (M+H).

CDI (2.45 g, 15.1 mmol) and DIEA (2.6 mL, 15.1 mmol) were added to a solution of Compound 84a (1.4 g, 4.7 mmol) in THF (50 mL). The solution was stirred for 12 hrs and filtered. The precipitate washed with hexanes to yield (1.2 g, 78%) 5-(3-chloro-4-fluoro-phenyl)-3H,5H-1-thia-3,5,6,8-tetraaza-acenaphthylen-4-one, Compound 84b. MS 319 (M−).

NBS (0.14 g, 0.78 mmol) was added to a solution of Compound 84b (0.25 g, 0.78 mmol) in THF (30 mL) and AcOH (5 mL). The solution was stirred for 15 min and concentrated to dryness. The residue was purified by flash chromatography using gradient elution (20% EtOAc/80% Hexanes to 80% EtOAc/20% Hexanes) to yield 2-bromo-5-(3-chloro-4-fluoro-phenyl)-3H,5H-1-thia-3,5,6,8-tetraaza-acenaphthylen-4-one Compound 84c (0.25 g, 80%). MS 397, 399 (M−).

KF (44 mg, 0.75 mmol) and bis(tri-t-butylphosphine)palladium(0) (0.026 g, 0.05 mmol) were added to a solution of Compound 84c (0.10 g, 0.25 mmol) and phenylboronic acid Compound 84d (0.031 g, 0.25 mmol) in THF (2 mL). The reaction mixture was stirred for 12 hrs. The solution was partitioned between EtOAc and water and the aqueous layer was extracted twice with EtOAc. The organic layers were combined, dried over $Na_2SO_4$, then filtered and concentrated. The residue was purified by reverse phase HPLC using gradient elution (60% $CH_3CN$/40% $H_2O$ to 100% $CH_3CN$ spiked with 0.05% TFA) to yield Compound 8 (0.018 g, 18%). MS 395 (M−).

EXAMPLE 85

5-(3-chloro-4-fluoro-phenyl)-2-(3,4-dimethoxy-phenyl)-3H,5H-1-thia-3,5,6,8-tetraaza-acenaphthylen-4-one (Cpd 9)

Using the procedure of Example 84, 3,4-dimethoxyphenylboronic acid Compound 85a was used in place of phenylboronic acid Compound 84d to yield Compound 9. MS 455 (M−).

EXAMPLE 86

5-(3-chloro-4-fluoro-phenyl)-2-nitro-3H,5H-1-thia-3,5,6,8-tetraaza-acenaphthylen-4-one (Cpd 156)

$KNO_3$ (0.40 g, 0.40 mmol) was added to a solution of Compound 84b (0.16 g, 0.40 mmol) in $H_2SO_4$ (3 mL). The solution was stirred for 12 hrs at ambient temperature. The reaction mixture was diluted with EtOAc and washed with water, then saturated aqueous $NaHCO_3$ and brine. The organic layer was dried over $Na_2SO_4$, then filtered and concentrated. The residue was purified by flash chromatography using gradient elution (20% EtOAc/80% Hexanes to 80% EtOAc/20% Hexanes) to yield Compound 156 (0.15 g, 86%). MS 364 (M−).

EXAMPLE 87

2-amino-5-(3-chloro-4-fluoro-phenyl)-3H,5H-1-thia-3,5,6,8-tetraaza-acenaphthylen-4-one (Cpd 157)

A suspension of 5-(3-chloro-4-fluoro-phenyl)-2-nitro-3H,5H-1-thia-3,5,6,8-tetraaza-acenaphthylen-4-one Compound 156 (0.50 g, 1.40 mmol) in EtOAc (100 mL) was hydrogenated for 12 hrs at 50 psi. The resulting dark solution was filtered through a celite pad, rinsed with EtOAc and concentrated to yield Compound 157 (0.335 g, 76%). MS 336 (M+H).

EXAMPLE 88

N-[5-(3-chloro-4-fluoro-phenyl)-4-oxo-4,5-dihydro-3H-1-thia-3,5,6,8-tetraaza-acenaphthylen-2-yl]-2-(3,4-dimethoxy-phenyl)-acetamide (Cpd 158)

$Et_3N$ (0.167 mL, 1.20 mmol) and (3,4-dimethoxy-phenyl)-acetyl chloride Compound 88a (0.129 g, 0.60 mmol) were added to a solution of 2-amino-5-(3-chloro-4-fluoro-phenyl)-3H,5H-1-thia-3,5,6,8-tetraaza-acenaphthylen-4-one Compound 157 (0.200 g, 0.60 mmol) in THF (10 mL) at 0° C. The reaction mixture was stirred for 2 hrs at 0° C., then warmed to ambient temperature and stirred overnight. The mixture was diluted with EtOAc and washed with water and brine. The organic layer was dried over $Na_2SO_4$, then filtered and concentrated. The residue was purified by reverse phase HPLC using gradient elution (60%:40% $CH_3CN$:$H_2O$ to 100% $CH_3CN$ spiked with 0.05% TFA) to yield Compound 158. MS 512 (M−).

EXAMPLE 89

N-[5-(3-chloro-4-fluoro-phenyl)-4-oxo-4,5-dihydro-3H-1-thia-3,5,6,8-tetraaza-acenaphthylen-2-yl]-3,4-dimethoxy-benzamide (Cpd 159)

Using the procedure of Example 88, 3,4-dimethoxy-benzoyl chloride Compound 89a was used in place of (3,4-dimethoxy-phenyl)-acetyl chloride Compound 88a to yield Compound 159. MS 498 (M−)

EXAMPLE 90

5-(3-chloro-4-fluoro-phenyl)-4-oxo-4,5-dihydro-3H-1-thia-3,5,6,8-tetraaza-acenaphthylene-2-carboxylic acid (3,4-dimethoxy-phenyl)-amide (Cpd 2)

Using the procedure of Example 1, Compound 2c was used in place of Compound 1k and carried forward to prepare Compound 2. MS 501 (MH+).

EXAMPLE 91

5-(3-chloro-4-fluoro-phenyl)-4-oxo-4,5-dihydro-3H-1-thia-3,5,6,8-tetraaza-acenaphthylene-2-carboxylic acid thiazol-2-ylamide (Cpd 4)

Using the procedure of Example 1, thiazol-2-ylamine Compound 91a was used in place of Compound 1k to prepare Compound 4. MS 447, 449 (MH+).

EXAMPLE 92

5-(3-chloro-4-fluoro-phenyl)-4-oxo-4,5-dihydro-3H-1-thia-3,5,6,8-tetraaza-acenaphthylene-2-carboxylic acid pyridin-3-ylamide (Cpd 5)

Using the procedure of Example 1, pyridine-3-ylamine Compound 92a was used in place of Compound 1k to prepare Compound 5. MS 439 (M−).

EXAMPLE 93

5-(3-chloro-4-fluoro-phenyl)-4-oxo-4,5-dihydro-3H-1-thia-3,5,6,8-tetraaza-acenaphthylene-2-carboxylic acid [6-(3-morpholin-4-yl-propylamino)-pyridin-3-yl]-amide (Cpd 6)

Using the procedure of Example 1, $N^2$-(3-morpholin-4-yl-propyl)-pyridine-2,5-diamine Compound 59c was used in place of Compound 1k to prepare Compound 6. MS 583, 585 (MH+).

EXAMPLE 94

5-(3-chloro-4-fluoro-phenyl)-4-oxo-4,5-dihydro-3H-1-thia-3,5,6,8-tetraaza-acenaphthylene-2-carboxylic acid (4-pyrrolidin-1-ylmethyl-phenyl)-amide (Cpd 7)

Using the procedure of Example 1, 4-pyrrolidin-1-ylmethyl-phenylamine Compound 54e was used in place of Compound 1k to give Compound 7. MS 523, 525 (MH$^+$).

EXAMPLE 95

5-(3-chloro-4-fluoro-phenyl)-4-oxo-4,5-dihydro-3H-1-thia-3,5,6,8-tetraaza-acenaphthylene-2-carboxylic acid (4-amino-benzyl)-(2-isopropoxy-ethyl)-amide (Cpd 10)

Using the procedure of Example 1, 4-[(2-isopropoxy-ethylamino)-methyl]-phenylamine Compound 95a was used in place of Compound 1k to give Compound 10. MS 555, 557 (MH$^+$).

Using the procedure of Example 95 and known appropriate reagents and starting materials, the following compounds of the invention were prepared:

| Cpd | Name | MS |
|---|---|---|
| 198 | 4-oxo-5-(3-phenoxy-phenyl)-4,5-dihydro-3H-1-thia-3,5,6,8-tetraaza-acenaphthylene-2-carboxylic acid methyl-(4-morpholin-4-ylmethyl-phenyl)-amide | 593 |

EXAMPLE 96

5-(3-chloro-4-fluoro-phenyl)-4-oxo-4,5-dihydro-3H-1-thia-3,5,6,8-tetraaza-acenaphthylene-2-carboxylic acid (4-hydroxy-3-methoxy-phenyl)-amide (Cpd 19)

Using the procedure of Example 1, 4-amino-2-methoxy-phenol Compound 96a was used in place of Compound 1k to give Compound 19. MS 484 (MH−).

EXAMPLE 97

5-(3-chloro-4-fluoro-phenyl)-4-oxo-4,5-dihydro-3H-1-thia-3,5,6,8-tetraaza-acenaphthylene-2-carboxylic acid 4-dimethylaminomethyl-phenyl-amide (Cpd 12)

Using the procedure of Example 1, dimethylamine Compound 97a was used in place of piperidine to provide 4-dimethylaminomethyl-phenylamine Compound 97c. Using the procedure of Example 1, Compound 97c was used in place of Compound 1k to give Compound 12. MS 497, 499 (MH$^+$).

EXAMPLE 98

5-(3-chloro-4-fluoro-phenyl)-4-oxo-4,5-dihydro-3H-1-thia-3,5,6,8-tetraaza-acenaphthylene-2-carboxylic acid (4-morpholin-1-ylmethyl-phenyl)-amide (Cpd 13)

Using the procedure of Example 1, 4-morpholin-4-ylmethyl-phenylamine Compound 3e was used in place of 4-piperidin-1-ylmethyl-phenylamine Compound 1k to give Compound 13. MS 539, 541 (MH$^+$).

EXAMPLE 99

5-(3-chloro-4-fluoro-phenyl)-4-oxo-4,5-dihydro-3H-1-thia-3,5,6,8-tetraaza-acenaphthylene-2-carboxylic acid (3-hydroxy-4-methoxy-phenyl)-amide (Cpd 11)

Using the procedure of Example 1, 5-amino-2-methoxy-phenol Compound 99a was used in place of 4-piperidin-1-ylmethyl-phenylamine Compound 1k to give Compound 11. MS 484 (MH$^−$).

EXAMPLE 100

5-(3-chloro-4-fluoro-phenyl)-4-oxo-4,5-dihydro-3H-1-thia-3,5,6,8-tetraaza-acenaphthylene-2-carboxylic acid [3-methoxy-4-(2-morpholin-4-yl-ethoxy)-phenyl]-amide (Cpd 20)

Using the procedure of Example 1, 3-methoxy-4-(2-morpholin-4-yl-ethoxy)-phenylamine Compound 56c was used in place of 4-piperidin-1-ylmethyl-phenylamine Compound 1k to give Compound 20. MS 599, 601 (MH$^+$).

EXAMPLE 101

5-(3-chloro-4-fluoro-phenyl)-4-oxo-4,5-dihydro-3H-1-thia-3,5,6,8-tetraaza-acenaphthylene-2-carboxylic acid [3-methoxy-4-(3-piperidin-1-yl-propoxy)-phenyl]-amide (Cpd 21)

Using the procedure of Example 56, 1-(3-chloro-propyl)-piperidine Compound 101a was used in place of Compound 56a and carried forward to provide 3-methoxy-4-(3-piperidin-1-yl-propoxy)-phenylamine Compound 101c. Using the procedure of Example 1, Compound 101c was used in place of 4-piperidin-1-ylmethyl-phenylamine Compound 1k to give Compound 21. MS 611, 613 (MH$^+$).

EXAMPLE 102

5-(3-chloro-4-fluoro-phenyl)-4-oxo-4,5-dihydro-3H-1-thia-3,5,6,8-tetraaza-acenaphthylene-2-carboxylic acid [3-methoxy-4-(2-piperidin-4-yl-ethoxy)-phenyl]-amide (Cpd 22)

Using the procedure of Example 1, 3-methoxy-4-(2-piperidin-4-yl-ethoxy)-phenylamine Compound 36d was used in place of 4-piperidin-1-ylmethyl-phenylamine Compound 1k to give Compound 22. MS 597, 599 (MH$^+$).

EXAMPLE 103

5-(2,4-dichloro-phenyl)-4-oxo-4,5-dihydro-3H-1-thia-3,5,6,8-tetraaza-acenaphthylene-2-carboxylic acid (4-piperidin-1-ylmethyl-phenyl)-amide (Cpd 25)

Using the procedure of Example 1, 5-(2,4-dichloro-phenyl)-4-oxo-4,5-dihydro-3H-1-thia-3,5,6,8-tetraaza-acenaphthylene-2-carboxylic acid Compound 43c was used in place of Compound 1 to prepare Compound 25. MS 553, 555, 557 (MH$^+$).

EXAMPLE 104

5-(2,4-dichloro-phenyl)-4-oxo-4,5-dihydro-3H-1-thia-3,5,6,8-tetraaza-acenaphthylene-2-carboxylic acid [4-(1-methyl-piperidin-3-ylmethoxy)-phenyl]-amide (Cpd 32)

Using the procedure of Example 56, 4-nitro-phenol Compound 104a was used in place of Compound 36a and 3-chloromethyl-1-methyl-piperidine Compound 104b was used in place of Compound 56a and carried forward to provide 4-(1-methyl-piperidin-3-ylmethoxy)-phenylamine Compound 104d. MS 221 (MH$^+$). Using the procedure of Example 1, 5-(2,4-dichloro-phenyl)-4-oxo-4,5-dihydro-3H-1-thia-3,5,6,8-tetraaza-acenaphthylene-2-carboxylic acid Compound 43c was used in place of Compound 1 and Compound 104d was used in place of 4-piperidin-1-ylmethyl-phenylamine Compound 1k to give Compound 32. MS 583, 585, 587 (MH$^+$).

EXAMPLE 105

5-(2-chloro-3,4,5-trimethoxy-phenyl)-4-oxo-4,5-dihydro-3H-1-thia-3,5,6,8-tetraaza-acenaphthylene-2-carboxylic acid (4-piperidin-1-ylmethyl-phenyl)-amide (Cpd 26)

Using the procedure of Example 107, Compound 26 was isolated as a byproduct. MS 609, 611 (MH$^+$).

EXAMPLE 106

4-oxo-5-(3,4,5-trimethoxy-phenyl)-4,5-dihydro-3H-1-thia-3,5,6,8-tetraaza-acenaphthylene-2-carboxylic acid (Cpd 42)

4-oxo-5-(3,4,5-trimethoxy-phenyl)-4,5-dihydro-3H-1-thia-3,5,6,8-tetraaza-acenaphthylene-2-carboxylic acid [3-methoxy-4-(2-morpholin-4-yl-ethoxy)-phenyl]-amide(Cpd 27)

Using the procedure of Example 1, 3,4,5-trimethoxy-phenylamine Compound 106a was used in place of Compound 1e to prepare 4-chloro-6-(3,4,5-trimethoxy-phenylamino)-pyrimidine-5-carbonitrile Compound 106b. Using the procedure of Example 1, Compound 106b, was carried forward in place of 4-chloro-6-(3-chloro-4-fluoro-phenylamino)-pyrimidine-5-carbonitrile Compound 1f to prepare Compound 42. MS 401 (M$^-$). Using the procedure of Example 1, Compound 42 was used in place of Compound 1 and 3-methoxy-4-(2-morpholin-4-yl-ethoxy)-phenylamine Compound 56c was used in place of 4-piperidin-1-ylmethyl-phenylamine Compound 1k to give Compound 27. MS 637 (MH$^+$).

EXAMPLE 107

5-(3,4,5-trimethoxy-phenyl)-4-oxo-4,5-dihydro-3H-1-thia-3,5,6,8-tetraaza-acenaphthylene-2-carboxylic acid (4-piperidin-1-ylmethyl-phenyl)-amide (Cpd 28)

Using the procedure of Example 1, Compound 42 was used in place of Compound 1 to give Compound 28. MS 575 (MH$^+$).

EXAMPLE 108

5-(2-chloro-3,4,5-trimethoxy-phenyl)-4-oxo-4,5-dihydro-3H-1-thia-3,5, 6,8-tetraaza-acenaphthylene-2-carboxylic acid [3-methoxy-4-(tetrahydro-pyran-2-ylmethoxy)-phenyl]-amide (Cpd 30)

Using the procedure of Example 109, Compound 30 was isolated as a byproduct. MS 656, 658 (MH$^+$).

EXAMPLE 109

5-(3,4,5-trimethoxy-phenyl)-4-oxo-4,5-dihydro-3H-1-thia-3,5,6,8-tetraaza-acenaphthylene-2-carboxylic acid [3-methoxy-4-(tetrahydro-pyran-2-ylmethoxy)-phenyl]-amide (Cpd 31)

Using the procedure of Example 1, Compound 42 was used in place of Compound 1 and 3-methoxy-4-(tetrahydro-pyran-2-ylmethoxy)-phenylamine Compound 77c was used in place of 4-piperidin-1-ylmethyl-phenylamine Compound 1k to give Compound 31. MS 622 (MH$^+$).

EXAMPLE 110

5-(2,4-dichloro-5-methoxy-phenyl)-4-oxo-4,5-dihydro-3H-1-thia-3,5,6,8-tetraaza-acenaphthylene-2-carboxylic acid (Cpd 41)

5-(2,4-dichloro-5-methoxy-phenyl)-4-oxo-4,5-dihydro-3H-1-thia-3,5,6,8-tetraaza-acenaphthylene-2-carboxylic acid (4-piperidin-1-ylmethyl-phenyl)-amide (Cpd 33)

Using the procedure of Example 1, 2,4-dichloro-5-methoxy-phenylamine Compound 110a was used in place of Compound 1e to prepare 4-chloro-6-(2,4-dichloro-5-methoxy-phenylamino)-pyrimidine-5-carbonitrile Compound 110b. Using the procedure of Example 1, Compound 110b was carried forward in place of 4-chloro-6-(3-chloro-4-fluoro-phenylamino)-pyrimidine-5-carbonitrile Compound 1f to prepare Compound 41. MS 411 (M$^-$). Using the procedure of Example 1, Compound 41 was carried forward in place of Compound 1 to give Compound 33. MS 583, 585, 587 (MH$^+$).

EXAMPLE 111

5-(2,4-dichloro-5-methoxy-phenyl)-4-oxo-4,5-dihydro-3H-1-thia-3,5,6,8-tetraaza-acenaphthylene-2-carboxylic acid [3-methoxy-4-(2-morpholin-4-yl-ethoxy)-phenyl]-amide (Cpd 34)

Using the procedure of Example 1, Compound 41 was used in place of Compound 1 and 3-methoxy-4-(2-morpholin-4-yl-ethoxy)-phenylamine Compound 56c was used in place of 4-piperidin-1-ylmethyl-phenylamine Compound 1k to give Compound 34. MS 645, 647, 649 (MH$^+$).

EXAMPLE 112

5-(2,4-dichloro-5-methoxy-phenyl)-4-oxo-4,5-dihydro-3H-1-thia-3,5,6,8-tetraaza-acenaphthylene-2-carboxylic acid (3,4-dimethoxy-phenyl)-amide (Cpd 35)

Using the procedure of Example 1, Compound 41 was used in place of Compound 1 and 3,4-dimethoxy-phenylamine Compound 2c was used in place of 4-piperidin-1-ylmethyl-phenylamine Compound 1k to give Compound 35. MS 546, 548, 550 (MH$^+$).

EXAMPLE 113

5-(2,4-dichloro-5-methoxy-phenyl)-4-oxo-4,5-dihydro-3H-1-thia-3,5,6,8-tetraaza-acenaphthylene-2-carboxylic acid (4-pyrrolidin-1-ylmethyl-phenyl)-amide (Cpd 43)

Using the procedure of Example 1, Compound 41 was used in place of Compound 1 and 4-pyrrolidin-1-ylmethyl-phenylamine Compound 54e was used in place of 4-piperidin-1-ylmethyl-phenylamine Compound 1k to give Compound 43. MS 569, 571, 573 (MH$^+$).

EXAMPLE 114

5-(2,4-dichloro-5-methoxy-phenyl)-4-oxo-4,5-dihydro-3H-1-thia-3,5,6,8-tetraaza-acenaphthylene-2-carboxylic acid (4-morpholin-1-ylmethyl-phenyl)-amide (Cpd 44)

Using the procedure of Example 1, Compound 41 was used in place of Compound 1 and 4-morpholin-4-ylmethyl-phenylamine Compound 3e was used in place of 4-piperidin-1-ylmethyl-phenylamine Compound 1k to give Compound 44. MS 585, 587, 589 (MH$^+$).

EXAMPLE 115

5-(2,4-dichloro-5-methoxy-phenyl)-4-oxo-4,5-dihydro-3H-1-thia-3,5,6,8-tetraaza-acenaphthylene-2-carboxylic acid [3-methoxy-4-(tetrahydro-pyran-2-ylmethoxy)-phenyl]-amide (Cpd 45)

Using the procedure of Example 1, Compound 41 was used in place of Compound 1 and 3-methoxy-4-(tetrahydro-pyran-2-ylmethoxy)-phenylamine Compound 77c was used in place of 4-piperidin-1-ylmethyl-phenylamine Compound 1k to give Compound 45. MS 630, 632, 634 (MH$^+$).

EXAMPLE 116

5-(2,4-dichloro-5-methoxy-phenyl)-2-(pyrrolidine-1-carbonyl)3H,5H-1-thia-3,5,6,8-tetraaza-acenaphthylen-4-one (Cpd 46)

Using the procedure of Example 1, 5-(2,4-dichloro-5-methoxy-phenyl)-4-oxo-4,5-dihydro-3H-1-thia-3,5,6,8-tetraaza-acenaphthylene-2-carboxylic acid Compound 41 was used in place of Compound 1 and pyrrolidine was used in place of 4-piperidin-1-ylmethyl-phenylamine Compound 1k to give Compound 46. MS 464, 466, 468 (MH$^+$).

Using the procedure of Example 116 and known appropriate reagents and starting materials, the following compounds of the invention were prepared:

| Cpd | Name | MS |
|---|---|---|
| 213 | 2-[4-(2-morpholin-4-yl-ethyl)-piperazine-1-carbonyl]-5-(4-phenoxy-phenyl)-3H,5H-1-thia-3,5,6,8-tetraaza-acenaphthylen-4-one | 586 |
| 214 | 2-(4-methyl-[1,4]diazepane-1-carbonyl)-5-(4-phenoxy-phenyl)-3H,5H-1-thia-3,5,6,8-tetraaza-acenaphthylen-4-one | 501 |
| 216 | 2-(4-methyl-piperazine-1-carbonyl)-5-(4-phenoxy-phenyl)-3H,5H-1-thia-3,5,6,8-tetraaza-acenaphthylen-4-one | 487 |

EXAMPLE 117

5-(2,4-dichloro-5-methoxy-phenyl)-4-oxo-4,5-dihydro-3H-1-thia-3,5,6,8-tetraaza-acenaphthylene-2-carboxylic acid [4-(4-methyl-piperazin-1-ylmethyl-phenyl)-amide (Cpd 60)

Using the procedure of Example 1, 5-(2,4-dichloro-5-methoxy-phenyl)-4-oxo-4,5-dihydro-3H-1-thia-3,5,6,8-tetraaza-acenaphthylene-2-carboxylic acid Compound 41 was used in place of Compound 1 and 4-(4-methyl-piperazin-1-ylmethyl)-phenylamine Compound 39a was used in place of 4-piperidin-1-ylmethyl-phenylamine Compound 1k to give Compound 60. MS 598, 600, 602 (MH$^+$).

EXAMPLE 118

4-oxo-5-(4-phenoxy-phenyl)-4,5-dihydro-3H-1-thia-3,5,6,8-tetraaza-acenaphthylene-2-carboxylic acid (Cpd 168)

4-oxo-5-(4-phenoxy-phenyl)-4,5-dihydro-3H-1-thia-3,5,6,8-tetraaza-acenaphthylene-2-carboxylic acid (4-piperidin-1-ylmethyl-phenyl)-amide (Cpd 96)

Using the procedure of Example 1, 4-phenoxy-phenylamine Compound 118a was used in place of Compound 1e to prepare 4-chloro-6-(4-phenoxy-phenylamino)-pyrimidine-5-carbonitrile Compound 118b. Using the procedure of Example 1, Compound 118b was carried forward in place of 4-chloro-6-(3-chloro-4-fluoro-phenylamino)-pyrimidine-5-carbonitrile Compound 1f to prepare Compound 168. MS 403 (M$^-$). Using the procedure of Example 1, Compound 168 was carried forward in place of Compound 1 to give Compound 96. MS 577 (MH$^+$).

EXAMPLE 119

4-oxo-5-(4-phenoxy-phenyl)-4,5-dihydro-3H-1-thia-3,5,6,8-tetraaza-acenaphthylene-2-carboxylic acid [4-(4-methyl-piperazin-1-ylmethyl)-phenyl]-amide (Cpd 98)

Using the procedure of Example 1, Compound 168 was used in place of Compound 1 and 4-(4-methyl-piperazin-1-ylmethyl)-phenylamine Compound 39a was used in place of 4-piperidin-1-ylmethyl-phenylamine Compound 1k to give Compound 98. MS 592 (MH$^+$).

EXAMPLE 120

4-oxo-5-(4-phenoxy-phenyl)-4,5-dihydro-3H-1-thia-3,5,6,8-tetraaza-acenaphthylene-2-carboxylic acid (3,4-dimethoxy-phenyl)-amide (Cpd 99)

Using the procedure of Example 1, Compound 168 was used in place of Compound 1 and 3,4-dimethoxy-phenylamine Compound 2c was used in place of 4-piperidin-1-ylmethyl-phenylamine Compound 1k to give Compound 99. MS 540 (MH$^+$).

EXAMPLE 121

4-oxo-5-(4-phenoxy-phenyl)-4,5-dihydro-3H-1-thia-3,5,6,8-tetraaza-acenaphthylene-2-carboxylic acid (4-morpholin-4-ylmethyl-phenyl)-amide (Cpd 97)

Using the procedure of Example 1, Compound 168 was used in place of Compound 1 and 4-morpholin-4-ylmethylphenylamine Compound 3e was used in place of 4-piperidin-1-ylmethyl-phenylamine Compound 1k to give Compound 97. MS 579 (MH$^+$).

EXAMPLE 122

4-oxo-5-(4-phenoxy-phenyl)-4,5-dihydro-3H-1-thia-3,5,6,8-tetraaza-acenaphthylene-2-carboxylic acid [3-methoxy-4-(2-piperidin-1-yl-ethoxy)-phenyl]-amide (Cpd 100)

Using the procedure of Example 1, Compound 168 was used in place of Compound 1 and 3-methoxy-4-(2-piperidin-1-yl-ethoxy)-phenylamine Compound 36d was used in place of 4-piperidin-1-ylmethyl-phenylamine Compound 1k to give Compound 100. MS 637 (MH$^+$).

EXAMPLE 123

4-oxo-5-(4-phenoxy-phenyl)-4,5-dihydro-3H-1-thia-3,5,6,8-tetraaza-acenaphthylene-2-carboxylic acid (2-morpholin-4-yl-ethyl)-amide (Cpd 105)

Using the procedure of Example 1, Compound 168 was used in place of Compound 1 and 2-morpholin-4-yl-ethylamine Compound 10a was used in place of 4-piperidin-1-ylmethyl-phenylamine Compound 1k to give Compound 105. MS 517 (MH$^+$).

EXAMPLE 124

4-oxo-5-(4-phenoxy-phenyl)-4,5-dihydro-3H-1-thia-3,5,6,8-tetraaza-acenaphthylene-2-carboxylic acid [4-(1-hydroxy-2-morpholin-4-yl-ethyl)-phenyl]-amide (Cpd 174)

Using the procedure of Example 1, Compound 168 was used in place of Compound 1 and 1-(4-amino-phenyl)-2-morpholin-4-yl-ethanol Compound 50d was used in place of 4-piperidin-1-ylmethyl-phenylamine Compound 1k to give Compound 174. MS 609 (MH$^+$).

EXAMPLE 125

4-oxo-5-(4-phenoxy-phenyl)-4,5-dihydro-3H-1-thia-3,5,6,8-tetraaza-acenaphthylene-2-carboxylic acid [3-methoxy-4-(2-morpholin-4-yl-ethoxy)-phenyl]-amide (Cpd 167)

Using the procedure of Example 1, Compound 168 was used in place of Compound 1 and 3-methoxy-4-(2-morpholin-4-yl-ethoxy)-phenylamine Compound 56c was used in place of 4-piperidin-1-ylmethyl-phenylamine Compound 1k to give Compound 167. MS 639 (MH$^+$).

EXAMPLE 126

4-oxo-5-(4-phenoxy-phenyl)-4,5-dihydro-3H-1-thia-3,5,6,8-tetraaza-acenaphthylene-2-carboxylic acid [4-(2-piperidin-1-yl-ethyl)-phenyl]-amide (Cpd 166)

Using the procedure of Example 1, Compound 168 was used in place of Compound 1 and Compound 38d was used in place of 4-piperidin-1-ylmethyl-phenylamine Compound 1k to give Compound 166. MS 591 (MH$^+$).

EXAMPLE 127

4-oxo-5-(4-phenoxy-phenyl)-4,5-dihydro-3H-1-thia-3,5,6,8-tetraaza-acenaphthylene-2-carboxylic acid (3-methoxy-4-morpholin-4-ylmethyl-phenyl)-amide (Cpd 176)

2-methoxy-4-nitro-benzoic acid Compound 127a (11.0 g, 55.8 mmol) was refluxed in SOCl$_2$ (50 mL) for 1 hr, then cooled to ambient temperature and evaporated down. The oil was resuspended in DCM and evaporated down a second time. The residue was then taken up in THF (150 mL) and cooled to 0° C. A mixture of morpholine Compound 50b (4.85 mL, 55.8 mmol) and DIEA (29.2 mL, 167 mmol) in THF (50 mL) was added dropwise. The reaction was stirred for 2 hrs before diluting with 1N HCl and extracting with ethyl acetate. The combined organic layer was separated and dried (MgSO$_4$), then filtered and concentrated to give (2-methoxy-4-nitro-phenyl)-morpholin-4-yl-methanone Compound 127b (13.1 g). MS 267 (MH$^+$). Borane dimethyl-sulfide (9.3 mL, 97.7 mmol) was combined with Compound 127b (13 g, 48.9 mmol) in THF (260 mL) and refluxed for 2 hrs. The reaction was chilled in ice and MeOH (25 mL) was carefully added. The mixture was subsequently diluted with 1N HCl, then stirred for 1 hr before adjusting the pH to 10 with 1N NaOH and extracted with ethyl acetate. The organic extracts were dried over Na$_2$SO$_4$ and evaporated down to give 4-(2-methoxy-4-nitro-benzyl)-morpholine Compound 127c (10 g). MS 253 (MH$^+$). Using the procedure of Example 80, Compound 127c was used in place of 5-(2-chloro-4-nitro-phenoxy)-2-methyl-pyridine Compound 80c to give 3-methoxy-4-morpholin-4-ylmethyl-phenylamine Compound 127d. $^1$H NMR (400 MHz, CDCl$_3$) δ 6.83 (1H, J=8.3 Hz, d), 6.19 (1H, J=2.0 Hz, d), 6.10 (1H, J=8.3 Hz, 2.0 Hz, dd), 3.66 (3H, s), 3.53 (4H, m), 3.28 (2H, s), 2.30 (4H, m). MS 223 (MH$^+$). Using the procedure of Example 1, Compound 168 was used in place of Compound 1 and Compound 127d was used in place of 4-piperidin-1-ylmethyl-phenylamine Compound 1k to give Compound 176 as a HCl salt. $^1$H NMR (400 MHz, CDCl$_3$) δ 10.65 (1H, br s), 10.24 (1H, s), 8.69 (1H, s), 7.62-7.39 (8H, m), 7.22 (1H, t), 7.13 (4H, d), 4.25 (2H, br s), 3.99-3.72 (7H, m), 3.32-3.21 (2H, m), 3.16-3.00 (2H, m). MS 609 (MH$^+$).

EXAMPLE 128

5-[4-(3-fluoro-phenoxy)-phenyl]-4-oxo-4,5-dihydro-3H-1-thia-3,5,6,8-tetraaza-acenaphthylene-2-carboxylic acid (4-piperidin-1-ylmethyl-phenyl)-amide (Cpd 131)

Using the procedure of Example 1, 4-(3-fluoro-phenoxy)-phenylamine Compound 128a was used in place of Compound 1e to prepare 4-chloro-6-[4-(3-fluoro-phenoxy)-phenylamino]-pyrimidine-5-carbonitrile Compound 128b. Using the procedure of Example 1, Compound 128b was carried forward in place of 4-chloro-6-(3-chloro-4-fluoro-phenylamino)-pyrimidine-5-carbonitrile Compound 1f to prepare 5-[4-(3-fluoro-phenoxy)-phenyl]-4-oxo-4,5-dihydro-3H-1-thia-3,5,6,8-tetraaza-acenaphthylene-2-carboxylic acid Compound 128c. MS 423 (MH$^+$). Using the procedure of Example 1, Compound 128c was carried forward in place of Compound 1 to give Compound 131. MS 595 (MH$^+$).

EXAMPLE 129

5-[4-(3-fluoro-phenoxy)-phenyl]-4-oxo-4,5-dihydro-3H-1-thia-3,5,6,8-tetraaza-acenaphthylene-2-carboxylic acid [4-(2-piperidin-1-yl-ethyl)-phenyl]-amide (Cpd 132)

Using the procedure of Example 1, 5-[4-(3-fluoro-phenoxy)-phenyl]-4-oxo-4,5-dihydro-3H-1-thia-3,5,6,8-tetraaza-acenaphthylene-2-carboxylic acid Compound 128c was used in place of Compound 1 and 4-(2-piperidin-1-yl-ethyl)-phenylamine Compound 38d was used in place of 4-piperidin-1-ylmethyl-phenylamine Compound 1k to give Compound 132. MS 609 (MH$^+$).

EXAMPLE 130

5-[4-(3-fluoro-phenoxy)-phenyl]-4-oxo-4,5-dihydro-3H-1-thia-3,5,6,8-tetraaza-acenaphthylene-2-carboxylic acid (4-morpholin-4-ylmethyl-phenyl)-amide (Cpd 134)

Using the procedure of Example 1, 5-[4-(3-fluoro-phenoxy)-phenyl]-4-oxo-4,5-dihydro-3H-1-thia-3,5,6,8-tetraaza-acenaphthylene-2-carboxylic acid Compound 128c was used in place of Compound 1 and 4-morpholin-4-ylmethyl-phenylamine Compound 3e was used in place of 4-piperidin-1-ylmethyl-phenylamine Compound 1k to give Compound 134. MS 597 (MH$^+$).

EXAMPLE 131

5-[4-(3-fluoro-phenoxy)-phenyl]-4-oxo-4,5-dihydro-3H-1-thia-3,5,6,8-tetraaza-acenaphthylene-2-carboxylic acid (3-hydroxy-propyl)-amide (Cpd 133)

Using the procedure of Example 1, 5-[4-(3-fluoro-phenoxy)-phenyl]-4-oxo-4,5-dihydro-3H-1-thia-3,5,6,8-tetraaza-acenaphthylene-2-carboxylic acid Compound 128c was used in place of Compound 1 and 3-amino-propan-1-ol Compound 82a was used in place of 4-piperidin-1-ylmethyl-phenylamine Compound 1k to give Compound 133. MS 480 (MH$^+$).

EXAMPLE 132

5-(3-fluoro-4-phenoxy-phenyl)-4-oxo-4,5-dihydro-3H-1-thia-3,5,6,8-tetraaza-acenaphthylene-2-carboxylic acid (Cpd 112)

5-(3-fluoro-4-phenoxy-phenyl)-4-oxo-4,5-dihydro-3H-1-thia-3,5,6,8-tetraaza-acenaphthylene-2-carboxylic acid (4-morpholin-4-ylmethyl-phenyl)-amide (Cpd 113)

1,2-difluoro-4-nitro-benzene Compound 132a (1.3 g, 8.2 mmol), K$_2$CO$_3$ (1.2 g, 9.0 mmol) and phenol Compound 132b (0.84 g, 9.0 mmol.) were combined with 10 mL of NMP in a sealed pressure tube. The reaction was heated in a microwave at 140° C. for 50 min. The reaction mixture was diluted with ethyl acetate and washed with water and brine. The organic layer was dried over NaSO$_4$, then filtered and concentrated down to an oil. The crude oil in ethyl acetate (25 mL) was added to 10% Pd/C (1.3 g) and placed under 40 psi of hydrogen in a Parr apparatus for 1 hr. The solution was then filtered through Celite and concentrated to give 3-fluoro-4-phenoxy-phenylamine Compound 132c (1.9 g). MS 204 (MH$^+$). An alternative procedure for making Compound 132c is described in U.S. Pat. No. 3,652,665. Using the procedure of Example 1, 3-fluoro-4-phenoxy-phenylamine Compound 132c was used in place of Compound 1e to prepare 4-chloro-6-(3-fluoro-4-phenoxy-phenylamino)-pyrimidine-5-carbonitrile Compound 132d. Using the procedure of Example 1, Compound 132d was carried forward in place of 4-chloro-6-(3-chloro-4-fluoro-phenylamino)-pyrimidine-5-carbonitrile Compound 1f to prepare 5-(3-fluoro-4-phenoxy-phenyl)-4-oxo-4,5-dihydro-3H-1-thia-3,5,6,8-tetraaza-acenaphthylene-2-carboxylic acid Compound 112. MS 423 (MH$^+$). Compound 112 was carried forward in place of Compound 1 and 4-morpholin-4-ylmethyl-phenylamine Compound 3e was used in place of 4-piperidin-1-ylmethyl-phenylamine Compound 1k to give Compound 113. MS 597 (MH$^+$).

EXAMPLE 133

5-(3-fluoro-4-phenoxy-phenyl)-4-oxo-4,5-dihydro-3H-1-thia-3,5,6,8-tetraaza-acenaphthylene-2-carboxylic acid [4-(4-methyl-piperazin-1-ylmethyl)-phenyl]-amide (Cpd 115)

Using the procedure of Example 1, Compound 112 was used in place of Compound 1 and 4-(4-methyl-piperazin-1-ylmethyl)-phenylamine Compound 39a was used in place of 4-piperidin-1-ylmethyl-phenylamine Compound 1k to give Compound 115. MS 610 (MH$^+$).

EXAMPLE 134

5-(3-fluoro-4-phenoxy-phenyl)-4-oxo-4,5-dihydro-3H-1-thia-3,5,6,8-tetraaza-acenaphthylene-2-carboxylic acid [4-(2-piperidin-1-yl-ethyl)-phenyl]-amide (Cpd 114)

Using the procedure of Example 1, Compound 112 was used in place of Compound 1 and 4-(2-piperidin-1-yl-ethyl)-phenylamine Compound 38d was used in place of 4-piperidin-1-ylmethyl-phenylamine Compound 1k to give Compound 114. MS 609 (MH$^+$).

EXAMPLE 135

5-(3-chloro-4-phenoxy-phenyl)-4-oxo-4,5-dihydro-3H-1-thia-3,5,6,8-tetraaza-acenaphthylene-2-carboxylic acid (4-piperidin-1-ylmethyl-phenyl)-amide (Cpd 135)

Using the procedure from Example 132, 2-chloro-1-fluoro-4-nitro-benzene Compound 135a was used in place of Compound 132a and carried forward to give Compound 135b. MS 220 (MH$^+$). Using the procedure of Example 1, 3-chloro-4-phenoxy-phenylamine Compound 135b was used in place of Compound 1e to prepare 4-chloro-6-(3-chloro-4-phenoxy-phenylamino)-pyrimidine-5-carbonitrile Compound 135c. Compound 135c was carried forward in place of 4-chloro-6-(3-chloro-4-fluoro-phenylamino)-pyrimidine-5-carbonitrile Compound 1f to prepare 5-(3-chloro-4-phenoxy-phenyl)-4-oxo-4,5-dihydro-3H-1-thia-3,5,6,8-tetraaza-acenaphthylene-2-carboxylic acid Compound 135d. MS 439

EXAMPLE 136

5-(3-chloro-4-phenoxy-phenyl)-4-oxo-4,5-dihydro-3H-1-thia-3,5,6,8-tetraaza-acenaphthylene-2-carboxylic acid (4-morpholin-4-ylmethyl-phenyl)-amide (Cpd 138)

Using the procedure of Example 1, 5-(3-chloro-4-phenoxy-phenyl)-4-oxo-4,5-dihydro-3H-1-thia-3,5,6,8-tetraaza-acenaphthylene-2-carboxylic acid Compound 135d was used in place of Compound 1 and 4-morpholin-4-ylmethyl-phenylamine Compound 3e was used in place of 4-piperidin-1-ylmethyl-phenylamine Compound 1k to give Compound 138. MS 613, 615 (MH$^+$).

EXAMPLE 137

5-(3-chloro-4-phenoxy-phenyl)-4-oxo-4,5-dihydro-3H-1-thia-3,5,6,8-tetraaza-acenaphthylene-2-carboxylic acid (3-hydroxy-propyl)-amide (Cpd 137)

Using the procedure of Example 1, 5-(3-chloro-4-phenoxy-phenyl)-4-oxo-4,5-dihydro-3H-1-thia-3,5,6,8-tetraaza-acenaphthylene-2-carboxylic acid Compound 135d was used in place of Compound 1 and 3-amino-propan-1-ol Compound 82a was used in place of 4-piperidin-1-ylmethyl-phenylamine Compound 1k to give Compound 137. MS 496, 498 (MH$^+$).

EXAMPLE 138

5-(3-chloro-4-phenoxy-phenyl)-4-oxo-4,5-dihydro-3H-1-thia-3,5,6,8-tetraaza-acenaphthylene-2-carboxylic acid [4-(2-piperidin-1-yl-ethyl)-phenyl]-amide (Cpd 136)

Using the procedure of Example 1, 5-(3-chloro-4-phenoxy-phenyl)-4-oxo-4,5-dihydro-3H-1-thia-3,5,6,8-tetraaza-acenaphthylene-2-carboxylic acid Compound 135d was used in place of Compound 1 and 4-(2-piperidin-1-yl-ethyl)-phenylamine Compound 38d was used in place of 4-piperidin-1-ylmethyl-phenylamine Compound 1k to give Compound 136. MS 625, 627 (MH$^+$).

EXAMPLE 139

5-[3-chloro-4-(3-fluoro-phenoxy)-phenyl]-4-oxo-4,5-dihydro-3H-1-thia-3,5,6,8-tetraaza-acenaphthylene-2-carboxylic acid (4-piperidin-1-ylmethyl-phenyl)-amide (Cpd 160)

Using the procedure of Example 132, 2-chloro-1-fluoro-4-nitro-benzene Compound 139a was used in place of 1,2-difluoro-4-nitro-benzene Compound 132a to prepare 3-chloro-4-phenoxy-phenylamine Compound 139b. (see also, PCT Application WO 98/02434 and WO 03/040108). Using the procedure of Example 1, Compound 139b was used in place of Compound 1e to prepare 4-chloro-6-[3-chloro-4-(3-fluoro-phenoxy)-phenylamino]-pyrimidine-5-carbonitrile Compound 139c. Using the procedure of Example 1, Compound 139c was carried forward in place of 4-chloro-6-(3-chloro-4-fluoro-phenylamino)-pyrimidine-5-carbonitrile Compound 1f to prepare 5-[3-chloro-4-(3-fluoro-phenoxy)-phenyl]-4-oxo-4,5-dihydro-3H-1-thia-3,5,6,8-tetraaza-acenaphthylene-2-carboxylic acid Compound 139d. MS 457 (MH$^+$). Using the procedure of Example 1, Compound 139d was used in place of Compound 1 to give Compound 160. MS 629, 631 (MH$^+$).

EXAMPLE 140

5-[3-chloro-4-(3-fluoro-phenoxy)-phenyl]-4-oxo-4,5-dihydro-3H-1-thia-3,5, 6,8-tetraaza-acenaphthylene-2-carboxylic acid (4-morpholin-4-ylmethyl-phenyl)-amide (Cpd 162)

Using the procedure of Example 1, 5-[3-chloro-4-(3-fluoro-phenoxy)-phenyl]-4-oxo-4,5-dihydro-3H-1-thia-3,5,6,8-tetraaza-acenaphthylene-2-carboxylic acid Compound 139d was used in place of Compound 1 and 4-morpholin-4-ylmethyl-phenylamine Compound 3e was used in place of 4-piperidin-1-ylmethyl-phenylamine Compound 1k to give Compound 162. MS 631, 633 (MH$^+$).

EXAMPLE 141

5-[3-chloro-4-(3-fluoro-phenoxy)-phenyl]-4-oxo-4,5-dihydro-3H-1-thia-3,5, 6,8-tetraaza-acenaphthylene-2-carboxylic acid [3-methoxy-4-(2-piperidin-1-yl-ethoxy)-phenyl]-amide (Cpd 161)

Using the procedure of Example 1, 5-[3-chloro-4-(3-fluoro-phenoxy)-phenyl]-4-oxo-4,5-dihydro-3H-1-thia-3,5,6,8-tetraaza-acenaphthylene-2-carboxylic acid Compound 139d was used in place of Compound 1 and 3-methoxy-4-(2-piperidin-1-yl-ethoxy)-phenylamine Compound 36d was used in place of 4-piperidin-1-ylmethyl-phenylamine Compound 1k to give Compound 161. MS 689, 691 (MH$^+$).

EXAMPLE 142

5-(4-bromo-3-methoxy-phenyl)-4-oxo-4,5-dihydro-3H-1-thia-3,5,6,8-tetraaza-acenaphthylene-2-carboxylic acid (4-piperidin-1-ylmethyl-phenyl)-amide (Cpd 81)

Using the procedure of Example 1, 4-bromo-3-methoxy-phenylamine Compound 142a was used in place of Compound 1e to prepare 4-(4-bromo-3-methoxy-phenylamino)-6-chloro-pyrimidine-5-carbonitrile Compound 142b. MS 340 (MH$^+$). Compound 142b was carried forward in place of 4-chloro-6-(3-chloro-4-fluoro-phenylamino)-pyrimidine-5-carbonitrile Compound 1f to prepare 5-(4-bromo-3-methoxy-phenyl)-4-oxo-4,5-dihydro-3H-1-thia-3,5,6,8-tetraaza-acenaphthylene-2-carboxylic acid Compound 142c. MS 422 (MH$^+$). Compound 142c was carried forward in place of Compound 1 to give Compound 81. MS 593, 595 (MH$^+$).

EXAMPLE 143

5-(4-bromo-3-methoxy-phenyl)-4-oxo-4,5-dihydro-3H-1-thia-3,5,6,8-tetraaza-acenaphthylene-2-carboxylic acid (3,4-dimethoxy-phenyl)-amide (Cpd 82)

Using the procedure of Example 1, 5-(4-bromo-3-methoxy-phenyl)-4-oxo-4,5-dihydro-3H-1-thia-3,5,6,8-tetraaza-acenaphthylene-2-carboxylic acid Compound 142c was used in place of Compound 1 and 3,4-dimethoxy-phenylamine Compound 2c was used in place of 4-piperidin-1-ylmethyl-phenylamine Compound 1k to give Compound 82. MS 556, 558 (MH$^+$).

EXAMPLE 144

5-(4-bromo-3-methoxy-phenyl)-4-oxo-4,5-dihydro-3H-1-thia-3,5,6,8-tetraaza-acenaphthylene-2-carboxylic acid dimethylamide (Cpd 83)

Using the procedure of Example 1, 5-(4-bromo-3-methoxy-phenyl)-4-oxo-4,5-dihydro-3H-1-thia-3,5,6,8-tetraaza-acenaphthylene-2-carboxylic acid Compound 142c was used in place of Compound 1 and dimethylamine Compound 144a was used in place of 4-piperidin-1-ylmethyl-phenylamine Compound 1k to give Compound 83. MS 448, 450 (MH$^+$).

EXAMPLE 145

5-(4-bromo-3-methoxy-phenyl)-4-oxo-4,5-dihydro-3H-1-thia-3,5,6,8-tetraaza-acenaphthylene-2-carboxylic acid (4-morpholin-4-ylmethyl-phenyl)-amide (Cpd 84)

Using the procedure of Example 1, 5-(4-bromo-3-methoxy-phenyl)-4-oxo-4,5-dihydro-3H-1-thia-3,5,6,8-tetraaza-acenaphthylene-2-carboxylic acid Compound 142c was used in place of Compound 1 and 4-morpholin-4-ylmethyl-phenylamine Compound 3e was used in place of 4-piperidin-1-ylmethyl-phenylamine Compound 1k to give Compound 84. MS 595, 597 (MH$^+$).

EXAMPLE 146

5-(4-bromo-3-methoxy-phenyl)-4-oxo-4,5-dihydro-3H-1-thia-3,5,6,8-tetraaza-acenaphthylene-2-carboxylic acid [4-(4-methyl-piperazin-1-ylmethyl)-phenyl]-amide (Cpd 85)

Using the procedure of Example 1, 5-(4-bromo-3-methoxy-phenyl)-4-oxo-4,5-dihydro-3H-1-thia-3,5,6,8-tetraaza-acenaphthylene-2-carboxylic acid Compound 142c was used in place of Compound 1 and 4-(4-methyl-piperazin-1-ylmethyl)-phenylamine Compound 39a was used in place of 4-piperidin-1-ylmethyl-phenylamine Compound 1k to give Compound 85. MS 608, 610 (MH$^+$).

EXAMPLE 147

5-(5-chloro-2-methoxy-phenyl)-4-oxo-4,5-dihydro-3H-1-thia-3,5,6,8-tetraaza-acenaphthylene-2-carboxylic acid (4-piperidin-1-ylmethyl-phenyl)-amide (Cpd 72)

Using the procedure of Example 1, 5-chloro-2-methoxy-phenylamine Compound 147a was used in place of Compound 1e to prepare 4-chloro-6-(5-chloro-2-methoxy-phenylamino)-pyrimidine-5-carbonitrile Compound 147b. MS 295 (MH$^+$). Compound 147b was carried forward in place of 4-chloro-6-(3-chloro-4-fluoro-phenylamino)-pyrimidine-5-carbonitrile Compound 1f to prepare 5-(5-chloro-2-methoxy-phenyl)-4-oxo-4,5-dihydro-3H-1-thia-3,5,6,8-tetraaza-acenaphthylene-2-carboxylic acid Compound 147c. MS 377 (MH$^+$). Compound 147c was carried forward in place of Compound 1 to give Compound 72. MS 549, 551 (MH$^+$).

EXAMPLE 148

5-(5-chloro-2-methoxy-phenyl)-4-oxo-4,5-dihydro-3H-1-thia-3,5,6,8-tetraaza-acenaphthylene-2-carboxylic acid (3,4-dimethoxy-phenyl)-amide (Cpd 73)

Using the procedure of Example 1, 5-(5-chloro-2-methoxy-phenyl)-4-oxo-4,5-dihydro-3H-1-thia-3,5,6,8-tetraaza-acenaphthylene-2-carboxylic acid Compound 147c was used in place of Compound 1 and 3,4-dimethoxy-phenylamine Compound 2c was used in place of 4-piperidin-1-ylmethyl-phenylamine Compound 1k to give Compound 73. MS 512, 514 (MH$^+$).

EXAMPLE 149

5-(5-chloro-2-methoxy-phenyl)-4-oxo-4,5-dihydro-3H-1-thia-3,5,6,8-tetraaza-acenaphthylene-2-carboxylic acid [3-methoxy-4-(2-piperidin-1-yl-ethoxy)-phenyl]-amide (Cpd 74)

Using the procedure of Example 1, 5-(5-chloro-2-methoxy-phenyl)-4-oxo-4,5-dihydro-3H-1-thia-3,5,6,8-tetraaza-acenaphthylene-2-carboxylic acid Compound 147c was used in place of Compound 1 and 3-methoxy-4-(2-piperidin-1-yl-ethoxy)-phenylamine Compound 36d was used in place of 4-piperidin-1-ylmethyl-phenylamine Compound 1k to give Compound 74. MS 609, 611 (MH$^+$).

EXAMPLE 150

5-(5-chloro-2-methoxy-phenyl)-4-oxo-4,5-dihydro-3H-1-thia-3,5,6,8-tetraaza-acenaphthylene-2-carboxylic acid [4-({methyl-[(2R)-tetrahydro-furan-2-ylmethyl]-amino}-methyl)-phenyl]-amide (Cpd 75)

Methyl iodide (0.728 mL, 11.7 mmol) was added to (4-nitro-benzyl)-[(2R)-tetrahydro-furan-2-ylmethyl]-amine Compound 40b (1.84 g, 7.80 mmol) and potassium carbonate (3.23 g, 23.4 mmol) in DMF (30 mL). After 4 hrs, the reaction is was diluted with water and extracted with ethyl ether. The combined extracts are were washed with water, dried over MgSO$_4$, and evaporated to prepare 1.43 g of methyl-(4-nitro-benzyl)-[(2R)-tetrahydro-furan-2-ylmethyl]-amine Compound 150a. Using the procedure of Example 40, Compound 150a was used in place of (4-nitro-benzyl)-[(2R)-tetrahydro-furan-2-ylmethyl]-amine Compound 40b and carried forward to provide 4-({methyl-[(2R)-tetrahydro-furan-2-ylmethyl]-amino}-methyl)-phenylamine Compound 150b. Using the procedure of Example 1, 5-(5-chloro-2-methoxy-phenyl)-4-oxo-4,5-dihydro-3H-1-thia-3,5, 6,8-tetraaza-acenaphthylene-2-carboxylic acid Compound 147c was used in place of Compound 1 and Compound 150b was used in place of 4-piperidin-1-ylmethyl-phenylamine Compound 1k to give Compound 75. MS 579, 581 (MH$^+$).

EXAMPLE 151

5-(4-benzyl-phenyl)-4-oxo-4,5-dihydro-3H-1-thia-3, 5,6,8-tetraaza-acenaphthylene-2-carboxylic acid [3-methoxy-4-(2-piperidin-1-yl-ethoxy)-phenyl]-amide (Cpd 163)

Using the procedure of Example 1, 4-benzyl-phenylamine Compound 151a is used in place of Compound 1e to prepare 4-(4-benzyl-phenylamino)-6-chloro-pyrimidine-5-carbonitrile Compound 151b. MS 321 (MH$^+$). Compound 151b was carried forward in place of 4-chloro-6-(3-chloro-4-fluoro-phenylamino)-pyrimidine-5-carbonitrile Compound 1f to prepare 5-(4-benzyl-phenyl)-4-oxo-4,5-dihydro-3H-1-thia-3,5,6,8-tetraaza-acenaphthylene-2-carboxylic acid Compound 151c. MS 403 (MH$^+$). Compound 151c was carried forward in place of Compound 1 and 3-methoxy-4-(2-piperidin-1-yl-ethoxy)-phenylamine Compound 36d was used in place of 4-piperidin-1-ylmethyl-phenylamine Compound 1k to give Compound 163. MS 635 (MH$^+$).

EXAMPLE 152

5-(4-benzyl-phenyl)-4-oxo-4,5-dihydro-3H-1-thia-3,5,6,8-tetraaza-acenaphthylene-2-carboxylic acid (4-piperidin-1-ylmethyl-phenyl)-amide (Cpd 164)

Using the procedure of Example 1, 5-(4-benzyl-phenyl)-4-oxo-4,5-dihydro-3H-1-thia-3,5,6,8-tetraaza-acenaphthylene-2-carboxylic acid Compound 151c was used in place of Compound 1 to give Compound 164. MS 575 (MH$^+$).

EXAMPLE 153

5-(4-benzyl-phenyl)-4-oxo-4,5-dihydro-3H-1-thia-3,5,6,8-tetraaza-acenaphthylene-2-carboxylic acid (4-morpholin-4-ylmethyl-phenyl)-amide (Cpd 165)

Using the procedure of Example 1, 5-(4-benzyl-phenyl)-4-oxo-4,5-dihydro-3H-1-thia-3,5,6,8-tetraaza-acenaphthylene-2-carboxylic acid Compound 151c was used in place of Compound 1 and 4-morpholin-4-ylmethyl-phenylamine Compound 3e was used in place of 4-piperidin-1-ylmethyl-phenylamine Compound 1k to give Compound 165. MS 577 (MH$^+$).

EXAMPLE 154

5-[2,4-dichloro-5-(3-fluoro-benzyloxy)-phenyl]-4-oxo-4,5-dihydro-3H-1-thia-3,5,6,8-tetraaza-acenaphthylene-2-carboxylic acid (Cpd 58)

5-[2,4-dichloro-5-(3-fluoro-benzyloxy)-phenyl]-4-oxo-4,5-dihydro-3H-1-thia-3,5,6,8-tetraaza-acenaphthylene-2-carboxylic acid (4-pyrrolidin-1-ylmethyl-phenyl)-amide (Cpd 55)

Using the procedure of Example 132, 1,5-dichloro-2-fluoro-4-nitro-benzene Compound 154a was used in place of 1,2-difluoro-4-nitro-benzene Compound 132a and (3-fluoro-phenyl)-methanol Compound 154b was used in place of phenol Compound 132b to prepare 2,4-dichloro-5-(3-fluoro-benzyloxy)-phenylamine Compound 154c. Using the procedure of Example 1, Compound 154c was used in place of Compound 1e to prepare 4-chloro-6-[2,4-dichloro-5-(3-fluoro-benzyloxy)-phenylamino]-pyrimidine-5-carbonitrile Compound 154d. Using the procedure of Example 1, Compound 154d was used in place of 4-chloro-6-(3-chloro-4-fluoro-phenylamino)-pyrimidine-5-carbonitrile Compound 1f to prepare Compound 58. MS 478 (MH$^+$). Using the procedure of Example 1, Compound 58 was carried forward in place of Compound 1 and 4-pyrrolidin-1-ylmethyl-phenylamine Compound 54e was used in place of 4-piperidin-1-ylmethyl-phenylamine Compound 1k to give Compound 55. MS 663, 665, 667 (MH$^+$).

EXAMPLE 155

5-[2,4-dichloro-5-(3-fluoro-benzyloxy)-phenyl]-4-oxo-4,5-dihydro-3H-1-thia-3,5,6,8-tetraaza-acenaphthylene-2-carboxylic acid [3-methoxy-4-(2-piperidin-1-yl-ethoxy)-phenyl]-amide (Cpd 56)

Using the procedure of Example 1, Compound 58 was used in place of Compound 1 and 3-methoxy-4-(2-piperidin-1-yl-ethoxy)-phenylamine Compound 36d was used in place of 4-piperidin-1-ylmethyl-phenylamine Compound 1k to give Compound 56. MS 737, 739, 741 (MH$^+$).

EXAMPLE 156

5-[2,4-dichloro-5-(3-fluoro-benzyloxy)-phenyl]-4-oxo-4,5-dihydro-3H-1-thia-3,5,6,8-tetraaza-acenaphthylene-2-carboxylic acid (4-piperidin-1-ylmethyl-phenyl)-amide (Cpd 57)

Using the procedure of Example 1, Compound 58 was used in place of Compound 1 to give Compound 57. MS 677, 679, 681 (MH$^+$).

EXAMPLE 157

5-[2,4-dichloro-5-(3-fluoro-benzyloxy)-phenyl]-4-oxo-4,5-dihydro-3H-1-thia-3,5,6,8-tetraaza-acenaphthylene-2-carboxylic acid [4-({methyl-[(2R)-tetrahydro-furan-2-ylmethyl]-amino}-methyl)-phenyl]-amide (Cpd 59)

Using the procedure of Example 1, Compound 58 was used in place of Compound 1 and 4-({methyl-[(2R)-tetrahydro-furan-2-ylmethyl]-amino}-methyl)-phenylamine Compound 151b was used in place of 4-piperidin-1-ylmethyl-phenylamine Compound 1k to give Compound 59. MS 707, 709, 711 (MH$^+$).

EXAMPLE 158

5-[2,4-dichloro-5-(3-fluoro-benzyloxy)-phenyl]-4-oxo-4,5-dihydro-3H-1-thia-3,5,6,8-tetraaza-acenaphthylene-2-carboxylic acid [4-(4-methyl-piperazin-1-ylmethyl)-phenyl]-amide (Cpd 61)

Using the procedure of Example 1, Compound 58 was used in place of Compound 1 and 4-(4-methyl-piperazin-1-ylmethyl)-phenylamine Compound 39a was used in place of 4-piperidin-1-ylmethyl-phenylamine Compound 1k to give Compound 61. MS 692, 694 (MH$^+$).

EXAMPLE 159

5-(3-chloro-4-methoxy-phenyl)-4-oxo-4,5-dihydro-3H-1-thia-3,5,6,8-tetraaza-acenaphthylene-2-carboxylic acid (4-piperidin-1-ylmethyl-phenyl)-amide (Cpd 121)

Using the procedure of Example 1, 5-(3-chloro-4-methoxy-phenyl)-4-oxo-4,5-dihydro-3H-1-thia-3,5,6,8-tetraaza-acenaphthylene-2-carboxylic acid Compound 38c was used in place of Compound 1 to give Compound 121. MS 549, 551 (MH$^+$).

EXAMPLE 160

5-(3-chloro-4-methoxy-phenyl)-4-oxo-4,5-dihydro-3H-1-thia-3,5,6,8-tetraaza-acenaphthylene-2-carboxylic acid (4-morpholin-1-ylmethyl-phenyl)-amide (Cpd 122)

Using the procedure of Example 1, 5-(3-chloro-4-methoxy-phenyl)-4-oxo-4,5-dihydro-3H-1-thia-3,5,6,8-tetraaza-acenaphthylene-2-carboxylic acid Compound 38c was used in place of Compound 1 and 4-morpholin-4-ylmethyl-phenylamine Compound 3e was used in place of 4-piperidin-1-ylmethyl-phenylamine Compound 1k to give Compound 122. MS 551, 553 (MH$^+$).

EXAMPLE 161

4-oxo-5-(4-phenylsulfanyl-phenyl)-4,5-dihydro-3H-1-thia-3,5,6,8-tetraaza-acenaphthylene-2-carboxylic acid (4-piperidin-1-ylmethyl-phenyl)-amide (Cpd 169)

Nickel chloride hexahydrate (41 g, 172.5 mmol), then sodium borohydride (19.5 g, 0.516 mmol) were added to a solution of 4-nitrophenyl phenyl sulfide Compound 161a (20 g, 86.5 mmol) in a mixture of MeOH (200 mL) and THF (75 mL) at 0° C. under nitrogen over a period of 1 hr. The mixture was stirred for 30 mins at 0° C. and the reaction was quenched slowly with aqueous 10% NH$_4$Cl, neutralized with ammonium hydroxide and partitioned between ethyl acetate and water. The organic layer was dried (Na$_2$SO$_4$), then filtered and the solvent evaporated in vacuo to yield 4-phenylsulfanyl-phenylamine Compound 161b (15.08 g, 87%), as a solid. MS (ES$^+$) m/z 202.1 (M+H$^+$). $^1$H NMR (400 MHz, CDCl$_3$) δ 7.32-7.29 (2H, m), 7.22-7.18 (2H, m), 7.13-7.09 (3H, m), 6.68-6.66 (2H, m), 3.79 (2H, br s)

Using the procedure of Example 1, Compound 161b (10.0 g, 49.8 mmol) in THF (30 mL) was used in place of Compound 1e and added dropwise to a solution containing 4,6-dichloro-2-methylsulfanyl-pyrimidine-5-carbonitrile Compound 1d (8.6 g, 49.8 mmol) in THF (20 mL) and DIPEA (10.0 mL, 57.4 mmol) at room temperature. After 5 hrs, the reaction mixture was partitioned between ethyl acetate and aqueous 10% NH$_4$Cl. The organic layer was dried (Na$_2$SO$_4$), then filtered and concentrated. The resulting solid was triturated with an ethyl acetate/hexane mixture to give 4-chloro-6-(4-phenylsulfanyl-phenylamino)-pyrimidine-5-carbonitrile Compound 161c (14.72 g, 88%) as a solid. MS (ES$^+$) m/z 339.1 (M+H$^+$); $^1$H NMR (400 MHz, CDCl$_3$) δ 8.57 (1H, s), 7.51-7.48 (2H, m), 7.39-7.28 (7H, m).

Using the procedure of Example 4, ethyl thioglycolate Compound 4f (1.01 g, 8.4 mmol) was added to a solution of Compound 161c (2.38 g, 7.02 mmol) used in place of Compound 4f in pyridine (12 mL) at room temperature under nitrogen. The mixture was refluxed for 5 hrs, then partitioned between ethyl acetate and water. The organic layer washed sequentially with aqueous 1.0M HCl, water and brine, then dried (Na$_2$SO$_4$), filtered and the solvent evaporated in vacuo. The resulting solid was recrystallized with a mixture of ethyl acetate in hexanes to provide [5-cyano-6-(4-phenylsulfanyl-phenylamino)-pyrimidin-4-ylsulfanyl]-acetic acid ethyl ester Compound 161d (1.92 g, 65%) as a solid. MS (ES$^+$) m/z 423.0 (M+H$^+$); $^1$H NMR (400 MHz, DMSO) δ 9.99 (1H, s), 8.51 (1H, s), 7.58-7.56 (2H, m), 7.39-7.35 (4H, m), 7.29-7.26 (3H, m), 4.15-4.10 (4H, m), 1.19 (3H, t). Using the procedure of Example 4, Compound 161d was used in place of Compound 4g to give 5-amino-4-(4-phenylsulfanyl-phenylamino)-thieno[2,3-d]pyrimidine-6-carboxylic acid ethyl ester Compound 161e in a mixture with pentane. MS (ES$^+$) m/z 423.1 (M+H$^+$); $^1$H NMR (300 MHz, CDCl$_3$) δ 8.59 (1H, s), 8.04 (1H, br s), 7.64-7.62 (2H, m), 7.43-7.40 (2H, m), 7.34-7.22 (5H, m), 5.50 (2H, br s), 4.42-4.35 (2H, q), 1.19 (3H, t).

Using the procedure of Example 4, Compound 161e was used in place of Compound 4h to give 4-oxo-5-(4-phenylsulfanyl-phenyl)-4,5-dihydro-3H-1-thia-3,5,6,8-tetraaza-acenaphthylene-2-carboxylic acid ethyl ester Compound 161f. MS (ES$^+$) m/z 449.1 (M+H$^+$); $^1$H NMR (300 MHz, CDCl$_3$) δ 11.6 (1H, br s), 8.65 (1H, s), 7.52-7.40 (9H, m), 4.39-4.33 (2H, q), 1.31 (3H, t). Using the procedure of Example 4, Compound 161f was used in place of Compound 78 to give 4-oxo-5-(4-phenylsulfanyl-phenyl)-4,5-dihydro-3H-1-thia-3,5,6,8-tetraaza-acenaphthylene-2-carboxylic acid Compound 161g. MS (ES$^+$) m/z 421.0 (M+H$^+$); $^1$H NMR (300 MHz, DMSO) δ 10.77 (1H, br s), 8.64 (1H, s), 7.51-7.37 (9H, m). Using the procedure of Example 4, Compound 161g was used in place of Compound 79 to give Compound 169. MS (ES$^+$) m/z 593.1 (M+H$^+$); $^1$H NMR (400 MHz, DMSO) δ 10.18 (1H, s), 9.81 (1H, br s), 8.66 (1H, s), 7.79-7.77 (2H, m), 7.54-7.38 (11H, m), 4.24-4.22 (2H, m), 3.32-3.28 (2H, m), 2.88-2.80 (2H, m), 1.82-1.65 (3H, m).

EXAMPLE 162

4-oxo-5-(4-phenylsulfanyl-phenyl)-4,5-dihydro-3H-1-thia-3,5,6,8-tetraaza-acenaphthylene-2-carboxylic acid (4-morpholin-4-ylmethyl-phenyl)-amide (Cpd 178)

Using the procedure of Example 4, 4-morpholin-4-ylmethyl-phenylamine Compound 3e was used in place of Compound 79 to provide Compound 178. MS (ES$^+$) m/z 595.2 (M+H$^+$); $^1$H NMR (400 MHz, DMSO) δ 10.81 (1H, br s), 10.20 (1H, s), 8.66 (1H, s), 7.80-7.78 (2H, m), 7.57-7.55 (2H, m), 7.52-7.38 (9H, m), 3.59-3.52 (6H, m), 2.46-2.40 (4H, m).

EXAMPLE 163

4-oxo-5-(4-phenoxy-phenyl)-4,5-dihydro-3H-1-thia-3,5,6,8-tetraaza-acenaphthylene-2-carboxylic acid (3-hydroxy-propyl)-amide (Cpd 106)

Using the procedure of Example 1, Compound 168 was used in place of Compound 1 and 3-amino-propan-1-ol Compound 82a was used in place of 4-piperidin-1-ylmethyl-phenylamine Compound 1k to give Compound 106. MS 462 (MH$^+$).

BIOLOGICAL EXAMPLES

The ability of the compounds to treat or ameliorate protein kinase mediated disorders was determined using the following procedures.

Example 169 and 171 are intended as prophetic examples and are expected to demonstrate that said compounds are useful in treating or ameliorating a protein kinase mediated disorder as an inhibitor in the indicated assay.

EXAMPLE 164

EGFR Kinase Assay

The EGFR kinase used was a fusion of Glutathione-S-Transferase (GST) and a PCR amplified intracellular portion of EGFR (Accession Number NM_005228). The intracellular portion of EGFR started at nucleotide 2189 (corresponding to amino acid 667) and ended at the termination codon. The portion was PCR amplified with primers that added the lambda attB sequences to each end, recombined into an entry vector, then into a GST destination vector (as described in Gateway Technologies Manual by Invitrogen Corporation, Carlsbad, Calif.).

The destination vector was recombined in the DH10BAC strain of bacteria to produce a bacmid. The bacmid was transfected into Sf9 cells and the supernatant containing the baculovirus was collected. The GSTEGFR protein was purified using large cultures of Sf 9 cells infected with stock virus. After an appropriate period of time, the cells were collected and lysed. The GSTEGFR was then purified from the lysate on Glutathione-Sepharose columns (as described by Amersham Biosciences, Buckinghamshire, United Kingdom).

The EGFR substrate was prepared by biotinylating polyGluTyr (128 mg) (Sigma, St. Louis, Mo.) in a 1×PBS buffer incubated together with a 12-fold molar excess of Sulfo-NHS-LC-Biotin on ice for at least 2 hrs. The free biotin was separated from the biotinylated polyGluTyr on a gel filtration column.

A mixture of a 10× kinase buffer (500 mM Tris at pH 8.0, 100 mM Magnesium Chloride and 1 mM Sodium Vanadate), DTT (1 mM final from 500 mM stock), ATP (5 µM final from 10 mM stock), biotinylated polyGluTyr (10 µg/µL stock), $\gamma$-$^{33}$PATP (10 µCl/µL stock) and water was added to each well (for a total of 90 µL/well) of a Streptavidin Flashplate (Perkin Elmer, Wellesley, Mass.).

Test compound in 100% DMSO (2 µL) was added to the appropriate wells. Diluted GSTEGFR (1:300 dilution in 50 mM Tris at pH 8.0 and 0.1% bovine serum albumin) (10 µL) was added to the wells to initiate the reactions.

The plates were incubated at 30° C. for 1 hr with shaking. The reacted contents were removed and the plates were sequentially washed three times with a 1×PBS stop buffer (300 µL without Magnesium and Calcium) and 100 mM EDTA. After the final wash, the same stop buffer (200 µL) was added to the wells. The plates were then sealed and read on the TopCount scintillation counter.

Test compounds were assayed in triplicate at 16 concentrations at half-log dilutions starting at 200 uM. A maximum and minimum signal for the assay was determined on each plate. The percent inhibition of a test compound was calculated according to the formula:

$$\left[\frac{(\text{max signal} - \text{test compound})}{(\text{max signal} - \text{min signal})}\right](100) = \% \text{ inhibition}$$

For a series of test concentrations, the $IC_{50}$ was derived by graphing percent inhibition against the log of the concentrations tested for a given compound. The EGFR $IC_{50}$ results are shown in Table 1. For those compounds without an $IC_{50}$, the inhibition values in percent are shown at a test concentration of 2 µM. For compounds with multiple values, each value represents a separate assay result.

TABLE 1

| Cpd | IC$_{50}$ |
|---|---|
| 1 | 1.70 |
| 2 | 0.037 |
| 3 | 0.009 |
| 4 | 0.072 |
| 5 | 0.069 |
| 6 | 0.083 |
| 7 | 0.007 |
| 8 | 0.542 |
| 9 | 1.03 |
| 13 | 0.041 |
| 14 | 0.043 |
| 15 | 0.026 |
| 16 | 0.223 |
| 17 | 0.044 |
| 18 | 0.116 |
| 19 | 0.043 |
| 20 | 0.030 |
| 21 | 0.027 |
| 22 | 0.042 |
| 23 | 0.027 |
| 24 | 0.126 |
| 25 | 0.168 |
| 26 | 9.26 |
| 27 | 41.5 |
| 28 | 15% |
| 29 | 0.873 |
| 30 | 19.15 |
| 31 | 42.71 |
| 32 | 0.580 |
| 33 | 1.89 |
| 34 | 5.37 |
| 35 | 5.71 |
| 36 | 0.184 |
| 37 | 0.49 |
| 38 | 0.92 |
| 39 | 0.41 |
| 40 | 7.43 |
| 41 | 11% |
| 42 | −3% |
| 43 | 47% |
| 44 | 26% |
| 45 | 14% |
| 46 | 1% |
| 47 | 5% |
| 48 | 0.061 |
| 49 | 25% |
| 50 | 30% |
| 51 | 53% |
| 52 | 0.051 |
| 53 | 34% |
| 54 | 25% |
| 55 | 14% |
| 56 | 20% |
| 57 | 12% |
| 58 | 16% |
| 59 | 20% |
| 60 | 29% |
| 61 | 9% |
| 62 | 0.356 |
| 63 | 0.104 |
| 64 | 0.159 |
| 65 | 0.120 |
| 66 | 0.524 |
| 67 | 0.103 |
| 68 | 0.69 |
| 69 | 0.97 |
| 70 | 0.33 |
| 71 | 0.85 |
| 72 | 57% |
| 73 | 51% |
| 74 | 56% |
| 75 | 46% |
| 76 | 7% |
| 77 | 0.164 |
| 78 | 2.222 |
| 79 | 0.302 |
| 80 | 0.036 |
| 81 | 0.498 |
| 82 | 30% |
| 83 | −2% |
| 84 | 0.776 |
| 85 | 36% |
| 86 | 0.083 |
| 87 | 0.113 |
| 89 | 0.034 |
| 90 | 0.112 |
| 91 | 0.168 |
| 92 | 0.045 |
| 93 | 0.07 |
| 94 | 0.264 |
| 95 | 0.069 |
| 96 | 0.010 |
| 97 | 0.013 |
| 98 | 0.022 |

TABLE 1-continued

| Cpd | IC$_{50}$ |
|---|---|
| 99 | 0.027 |
| 100 | 0.015 |
| 101 | 18% |
| 102 | 17% |
| 103 | 21% |
| 104 | 41% |
| 105 | 0.11 |
| 106 | 0.042 |
| 108 | 0.043 |
| 109 | 0.344 |
| 110 | 0.034 |
| 111 | 0.029 |
| 112 | 1.03 |
| 113 | 0.021 |
| 114 | 0.025 |
| 115 | 0.042 |
| 116 | 0.146 |
| 117 | 1.78 |
| 118 | 0.132 |
| 119 | 1.80 |
| 120 | 1.08 |
| 121 | 0.344 |
| 122 | 0.222 |
| 123 | 11% |
| 124 | 9% |
| 125 | 20% |
| 126 | 3% |
| 127 | 0.5% |
| 128 | 0% |
| 129 | 0.154 |
| 130 | 0.191 |
| 131 | 0.010 |
| 132 | 0.015 |
| 133 | 0.034 |
| 134 | 0.021 |
| 135 | 0.018 |
| 136 | 0.031 |
| 137 | 0.030 |
| 138 | 0.059 |
| 139 | 18% |
| 140 | 20% |
| 141 | 0.346 |
| 142 | 0.011 |
| 144 | 0.330 |
| 145 | 0.166 |
| 146 | 37% |
| 147 | 43% |
| 148 | 38% |
| 149 | 0.187 |
| 150 | 0.170 |
| 151 | 0.603 |
| 152 | 0.333 |
| 153 | 0.159 |
| 154 | 0.592 |
| 155 | 0.028 |
| 156 | 1.37 |
| 157 | 0.371 |
| 158 | 2.43 |
| 159 | 1.04 |
| 160 | 0.023 |
| 161 | 0.023 |
| 162 | 0.026 |
| 163 | 0.018 |
| 164 | 0.011 |
| 165 | 0.023 |
| 166 | 0.021 |
| 167 | 0.020 |
| 168 | 0.452 |
| 169 | 0.029 |
| 170 | 11% |
| 171 | 13% |
| 172 | 2% |
| 173 | −3% |
| 174 | 0.018 |
| 175 | 0.130 |
| 176 | 0.022 |
| 177 | 0.075 |

TABLE 1-continued

| Cpd | IC$_{50}$ |
|---|---|
| 178 | 0.077 |
| 179 | 0.7% |
| 180 | 0.095 |
| 181 | 0.887 |
| 182 | 0.880 |
| 183 | 0.420 |
| 184 | 0.017 |
| 187 | 0.121 |
| 188 | 0.049 |
| 189 | 0.083 |
| 191 | 0.018 |
| 192 | 0.41 |
| 193 | 0.704 |
| 194 | 31% |
| 195 | 0.097 |
| 196 | 0.206 |
| 197 | 0.039 |
| 198 | 45% |
| 199 | 0.155 |
| 200 | 0.089 |
| 201 | 0.106 |
| 202 | 31% |
| 203 | 0.035 |
| 204 | 0.133 |
| 205 | 0.689 |
| 206 | 12% |
| 207 | 0.016 |
| 208 | 0.133 |
| 209 | 0.101 |
| 210 | 0.615 |
| 211 | 0.063 |
| 212 | 0.036 |
| 213 | 48% |
| 214 | 1.30 |
| 215 | 0.121 |
| 216 | 0.780 |
| 217 | 0.225 |
| 218 | 0.014 |
| 219 | 0.127 |
| 220 | 0.141 |
| 221 | 0.085 |
| 222 | 4% |
| 223 | 5% |
| 224 | 0.014 |
| 226 | 0.033 |
| 227 | 0.019 |
| 228 | 0.017 |
| 229 | 0.033 |
| 230 | 0.109 |
| 231 | 0.314 |
| 232 | 0.041 |
| 233 | 0.017 |
| 234 | 0.052 |
| 236 | 0.108 |
| 237 | 0.090 |
| 238 | 0.132 |
| 239 | 0.114 |
| 240 | 0.031 |
| 241 | −2% |
| 242 | 0.022 |
| 243 | 0.016 |
| 244 | 0.023 |
| 245 | 0.024 |
| 246 | 0.022 |
| 247 | 0.249 |
| 248 | 8% |
| 249 | 9% |
| 250 | 0.037 |
| 251 | 0.141 |
| 252 | 0.161 |
| 253 | 0.12 |
| 254 | 0.026 |
| 255 | 0.041 |
| 256 | 0.321 |
| 257 | 0.096 |
| 258 | 0.053 |
| 259 | 0.021 |

TABLE 1-continued

| Cpd | IC$_{50}$ |
|---|---|
| 260 | 0.037 |
| 261 | 0.018 |
| 262 | 0.035 |
| 263 | 83% |

EXAMPLE 165 c-Src Kinase Assay

A mixture of a 10× kinase buffer (80 mM MOPS at pH 7.0, 2 mM EDTA and 100 mM Magnesium Chloride), ATP (5 μM final from a 10 mM stock), a Cdc2 peptide KVEKIGEG-TYGVVYK (100 μM final from a 2.5 mM stock), γ-$^{33}$P ATP (10 μCi/μL stock) and water (for a total of 20 μL/well) was added to each well of a Streptavidin Flashplate.

Test compound in 100% DMSO (0.5 μL) was added to the appropriate wells. Diluted c-Src kinase (human) (Accession Number SWISS-PROT P12931) (Upstate Biotechnology, Lake Placid, N.Y.) (diluted in a buffer consisting of 20 mM MOPS at pH 7.0, 1 mM EDTA, β-mercaptoethanol (0.1%), Brij-35 (0.01%), glycerol (5%), and 1 mg/mL bovine serum albumin) (2.5 μL) was added to the wells to initiate the reactions. The reaction plates were incubated at 30° C. for 40 min. The reaction was terminated by the addition of a 3% phosphoric acid solution (5 μL). The reaction product (10 μL) was spotted onto a P30 filtermat and washed for 5 minutes in phosphoric acid (75 mM). The wash sequence was repeated two more times, followed with one final wash in methanol. The plates were then dried, sealed and read on the TopCount scintillation counter after adding 30 μL scintillation fluid.

The c-Src inhibition values were derived using the percent inhibition formula provided in Example 164 and are shown as percent in Table 2 at a test concentration of 2 μM. For those compounds with an IC$_{50}$, the IC$_{50}$ value in μM is shown in parentheses. For compounds with multiple test values, each value represents a separate assay result.

TABLE 2

| Cpd | % Inhibition (IC$_{50}$) |
|---|---|
| 9 | 26 |
| 16 | 52 |
| 30 | 1 |
| 31 | 8 |
| 32 | 32 |
| 33 | 32 |
| 34 | 23 |
| 35 | 7 |
| 36 | −3, 17, 21 (>20) |
| 37 | 11 |
| 38 | 7 |
| 39 | 16 |
| 40 | 3 |
| 41 | 18 |
| 42 | 8 |
| 43 | 53 (4.15) |
| 44 | 45 |
| 45 | 17 |
| 46 | 30 |
| 47 | 9 |
| 48 | 7 |
| 49 | 23 (>200) |
| 50 | 20 (8.09) |
| 51 | 33 (6.58) |
| 52 | 1 |
| 53 | 11 |
| 54 | 42 (1.49) |
| 55 | −16 |
| 56 | −22 |
| 57 | −16 |
| 58 | −48 |
| 59 | −13 |
| 60 | 38 (7.94) |
| 61 | −2 |
| 62 | 83 (0.075) |
| 64 | −14 |
| 65 | −9 |
| 67 | −17 |
| 70 | 43 |
| 71 | 44 |
| 73 | −17 |
| 76 | 43 |
| 77 | 44 (>200) |
| 78 | (>200) |
| 79 | −17 (>200) |
| 80 | (>200) |
| 82 | 43 |
| 83 | 44 |
| 85 | −17 |
| 87 | (>200) |
| 88 | 43 |
| 89 | 44 |
| 90 | 8, 4 |
| 91 | −37 |
| 92 | 65, 45 (0.431) |
| 93 | 41 |
| 94 | −39 |
| 95 | −15 |
| 96 | 53, 24 (>200) |
| 97 | 71, 32 (~2) |
| 98 | 63, 41 (0.592) |
| 99 | −9 |
| 100 | 26, 58 (>200) |
| 101 | 29, 14 |
| 102 | 3, 12 |
| 103 | 14, 18 |
| 104 | 55, 60 (1.84) |
| 105 | 12 |
| 106 | 30 |
| 108 | 19 |
| 109 | 31 |
| 110 | 16 |
| 112 | −16 |
| 113 | 68, 54 |
| 114 | 35, −11 |
| 115 | −1 |
| 116 | −7 |
| 117 | 25 |
| 118 | 15 |
| 119 | −17 |
| 120 | −5 |
| 121 | −1 |
| 122 | −9 |
| 123 | 77 (0.545) |
| 124 | 30 |
| 125 | 5 |
| 126 | −4 |
| 127 | −2 |
| 128 | −18 |
| 129 | −3 |
| 130 | −3 |
| 131 | 36 |
| 132 | 32 |
| 133 | 16 |
| 134 | 49 |
| 135 | 12 |
| 136 | −41 |
| 137 | 26 |
| 138 | 39 |
| 139 | 28 |
| 140 | 25 |
| 141 | 26 |
| 142 | 10 |

TABLE 2-continued

| Cpd | % Inhibition (IC$_{50}$) |
|---|---|
| 144 | 67 |
| 145 | 50 |
| 146 | 45 |
| 147 | 61 |
| 148 | 53 |
| 149 | 54 |
| 150 | 52 |
| 151 | 53 |
| 152 | −6 |
| 153 | 16 |
| 154 | 8 |
| 155 | 18 |
| 163 | 26 |
| 164 | 25 |
| 165 | 29 |
| 166 | 22 |
| 167 | 35 |
| 168 | −21 |
| 170 | 4 |
| 171 | 7 |
| 172 | −2 |
| 173 | −8 |
| 175 | −1 |

EXAMPLE 166

Lyn Kinase Assay

A mixture of a 10× kinase buffer (500 mM MOPS at pH 7.5, 1 mM EGTA, 1 mM Sodium Vanadate, 1% β-mercaptoethanol and 100 mM Magnesium Acetate), ATP (5 μM final from a 10 mM stock), polyGluTyr (0.1 mg/mL final from a 1 mg/mL stock), γ-$^{33}$P ATP (10 μCi/μL stock) and water (for a total of 20 μL/well) was added to each well of a Streptavidin Flashplate.

Test compound in 100% DMSO (0.5 μL) was added to the appropriate wells. Diluted Lyn kinase (human)(Accession Number EMBL M16038) (Upstate Biotechnology, Lake Placid, N.Y.) (diluted in a buffer consisting of 50 mM Tris at pH 7.5, 0.1 mM EGTA, Sodium Vanadate (0.1 mM), β-mercaptoethanol (0.1%) and 1 mg/mL bovine serum albumin) (2.5 μL) was added to the wells to initiate the reactions.

The reaction plates were incubated at 30° C. for 40 min. The reaction was terminated by the addition of a 3% phosphoric acid solution (5 μL). The reaction product (10 μL) was spotted onto a P30 filtermat and washed for 5 minutes in phosphoric acid (75 mM). The wash sequence was repeated two more times, followed with one final wash in methanol. The plates were then dried, sealed and read on the TopCount scintillation counter after adding 30 μL scintillation fluid.

The Lyn inhibition values were derived according to the procedure described in Example 164 and are shown as percent in Table 3 at a test concentration of 2 μM. For those compounds with an IC$_{50}$, the IC$_{50}$ value in μM is shown in parentheses. For compounds with multiple test values, each value represents a separate assay result.

TABLE 3

| Cpd | % Inhibition (IC$_{50}$) |
|---|---|
| 9 | −7 |
| 16 | 68 |
| 30 | −6 |
| 31 | −7 |
| 32 | 38 |
| 33 | 36 |

TABLE 3-continued

| Cpd | % Inhibition (IC$_{50}$) |
|---|---|
| 34 | 10 |
| 35 | −11 |
| 36 | 43, 57, 15 |
| 37 | −13 |
| 38 | −16 |
| 39 | 11 |
| 40 | −5 |
| 41 | 29 |
| 42 | 24 |
| 43 | 71 |
| 44 | 49 |
| 45 | 29 |
| 46 | 40 |
| 47 | 28 |
| 48 | 14 |
| 49 | 50 |
| 50 | 60 |
| 51 | 70 |
| 52 | 16.2 |
| 53 | 17 |
| 54 | 52 |
| 55 | 3 |
| 56 | 7 |
| 57 | 1 |
| 58 | 6 |
| 59 | 8 |
| 60 | 50 |
| 61 | 30 |
| 62 | 92 |
| 64 | 26 |
| 65 | 17.82 |
| 67 | 22.5 |
| 89 | 4, 0.5 |
| 90 | −8.1 |
| 91 | 7 |
| 92 | 25, 10 |
| 93 | 16 |
| 94 | 3 |
| 95 | 18 |
| 96 | 27, 16.8 |
| 97 | 36.5, 26.6 |
| 98 | 30.7, 50.0 |
| 99 | 22, −4 |
| 100 | 40, 50 |
| 101 | 3, 6 |
| 102 | 8, 13 |
| 103 | 15, −2 |
| 104 | 70, 69 |
| 105 | −3 |
| 106 | 27 |
| 108 | 69 |
| 109 | 75 |
| 110 | 21 |
| 112 | 30 |
| 113 | 60, 55 |
| 114 | 40, 48.5 |
| 115 | 51.2 |
| 116 | −2 |
| 117 | 12 |
| 118 | 12 |
| 119 | −47 |
| 120 | 0 |
| 121 | −13 |
| 122 | 3 |
| 123 | 55 (1.44) |
| 124 | 18 |
| 125 | 21 |
| 126 | 19 |
| 127 | 25 |
| 128 | 19 |
| 129 | 10 |
| 130 | 32 |
| 131 | 41 |
| 132 | 33 |
| 133 | 20 |
| 134 | 48 |
| 135 | 46 |

TABLE 3-continued

| Cpd | % Inhibition (IC$_{50}$) |
|---|---|
| 136 | 43 |
| 137 | 43 |
| 138 | 50 |
| 139 | 34 |
| 140 | 43 |
| 141 | 37 |
| 142 | 39 |
| 144 | 84 |
| 145 | 83 |
| 146 | 65 |
| 147 | 76 |
| 148 | 59 |
| 149 | 72 |
| 150 | 77 |
| 151 | 61 |
| 152 | 7 |
| 153 | −4 |
| 154 | 7 |
| 155 | 41 |
| 163 | 55 |
| 164 | 35 |
| 165 | 39 |
| 166 | 51 |
| 167 | 51 |
| 168 | 28 |
| 170 | 12 |
| 171 | 28 |
| 172 | 2 |
| 173 | −5 |
| 175 | 0 |

EXAMPLE 167

HER-2 Kinase Assay

The HER-2 kinase used was purified at Proqinase (Freiburg, Germany) from a construct that consisted of a fusion of GST (Glutathione-S-Transferase), HIS6-Thrombin and the nucleotides encoding amino acids 679 to 1255 of HER-2 (Accession Number M11730).

A mixture of a 10× kinase reaction buffer (600 mM Hepes at pH 7.5, 30 mM Magnesium Chloride, 0.03 mM Sodium Vanadate and 500 µg/mL PEG 20,000), DTT (1.2 mM final from a 10 mM stock), APT (1 µM from a 10 mM stock), biotinylated polyGluTyr (1.5 ng/µL final from stock of 1 µg/µL) prepared by Upstate Biotechnologies, Lake Placid, N.Y.), Manganese Chloride (3 mM final from a 1 M stock), γ-$^{33}$P-ATP (10 µCI/µL stock) and water (70 µL/well) was added to each well of a Streptavidin Flashplate (Cat. # SMP103, NEN, Boston, Mass.).

Test compound stock (1 µL) was added to the appropriate wells. Diluted GSTHER2 kinase (6.7 ng/µL diluted into 50 mM Tris-HCl at pH 8.0 and 0.1% bovine serum albumin) (30 µL) was added (total volume of 200 ng/well) to initiate the reactions.

The reaction plates were incubated at 30° C. for 1 hr. The reaction was terminated by aspirating the reaction mixture from the plate wells and washing the wells three times with a 1×PBS stop buffer (300 µL) and 100 mM EDTA. After the final wash, the same stop buffer (200 µL) was again added to the wells. The plates were then sealed and read on the TopCount scintillation counter.

The Her-2 inhibition values were derived according to the procedure described in Example 164 and are shown as percent in Table 4 at a test concentration of 1 µM. For those compounds with an IC$_{50}$, the IC$_{50}$ value in µM is shown in parentheses. For compounds with multiple test values, each value represents a separate assay result.

TABLE 4

| Cpd | % Inhibition (IC$_{50}$) |
|---|---|
| 3 | 59 |
| 7 | 69 |
| 13 | 40 (0.804) |
| 14 | −1 |
| 15 | 21 |
| 16 | 54 (5.44) |
| 25 | (0.768) |
| 26 | (10) |
| 27 | (100) |
| 28 | (10) |
| 29 | (0.884) |
| 30 | 19 |
| 31 | 1 |
| 32 | 33 |
| 33 | 14 |
| 34 | −14 |
| 35 | −12 |
| 36 | 60 (0.295) |
| 37 | 1 |
| 38 | −7 |
| 39 | 24 |
| 40 | −19 |
| 41 | −17 |
| 42 | −36 |
| 43 | 21 |
| 44 | 21 |
| 45 | −25 |
| 46 | 0 |
| 47 | −28 |
| 48 | 45 |
| 49 | −5 |
| 50 | −5 |
| 51 | 28 |
| 52 | 95 (0.246) |
| 53 | −13 |
| 54 | 3 |
| 55 | −22 |
| 56 | −6 |
| 57 | −20 |
| 58 | −27 |
| 59 | −18 |
| 60 | 22 |
| 61 | −11 |
| 62 | (0.528) |
| 63 | 45 |
| 64 | 57 (0.447) |
| 65 | 58 (0.643) |
| 66 | 11 |
| 67 | 51 (0.965) |
| 68 | −8 |
| 69 | −3 |
| 70 | (1.025) |
| 71 | (1.761) |
| 72 | 4 |
| 73 | −14 |
| 74 | 4 |
| 75 | 2 |
| 76 | −11 |
| 77 | (1.373) |
| 78 | (>100) |
| 79 | (>10) |
| 80 | (0.121) |
| 81 | (0.695) |
| 82 | (>10) |
| 83 | (>10) |
| 84 | (0.518) |
| 85 | (4.38) |
| 86 | (0.35) |
| 87 | (0.15) |
| 89 | 93 (0.069) |
| 90 | 82 (0.503) |
| 91 | (2.185) |
| 92 | (0.360) |
| 93 | (0.779) |
| 94 | (~10) |
| 95 | (0.350) |
| 96 | 98 (0.041) |

TABLE 4-continued

| Cpd | % Inhibition (IC$_{50}$) |
|---|---|
| 97 | 97 (0.027) |
| 98 | 95 (0.088) |
| 99 | 60 (0.915) |
| 100 | 95 (0.111) |
| 101 | (>100) |
| 102 | (>100) |
| 103 | (>100) |
| 104 | (7.07) |
| 105 | (3.15) |
| 106 | (0.771) |
| 108 | (0.148) |
| 109 | (0.684) |
| 110 | (0.161) |
| 111 | (0.325) |
| 112 | (5.06) |
| 113 | 83 (0.089) |
| 114 | 60 (0.536) |
| 115 | (0.182) |
| 116 | (1.70) |
| 117 | (12.96) |
| 118 | (~100) |
| 119 | (1.09) |
| 120 | (11.74) |
| 121 | (3.52) |
| 122 | (1.44) |
| 123 | (>100) |
| 124 | (>100) |
| 125 | (>100) |
| 126 | (>100) |
| 127 | (>100) |
| 128 | (>100) |
| 129 | 63 (0.515) |
| 130 | (>100) |
| 131 | 91 (0.084) |
| 132 | 76 (0.495) |
| 133 | 0 (>10) |
| 134 | 35 (0.087) |
| 135 | 85 (0.090) |
| 136 | 70 (0.222) |
| 137 | 48 (1.63) |
| 138 | (0.178) |
| 139 | (>100) |
| 140 | (>100) |
| 141 | (~100) |
| 142 | (0.381) |
| 144 | 18 |
| 145 | 54 (4.23) |
| 146 | 21 |
| 147 | 17 |
| 148 | 30 |
| 149 | 53 (2.54) |
| 150 | 18 |
| 151 | 29 |
| 152 | (3.72) |
| 153 | 70 (0.294) |
| 154 | 12 (>10) |
| 155 | 88 (0.327) |
| 160 | (0.155) |
| 161 | (0.699) |
| 162 | (0.082) |
| 163 | (0.278) |
| 164 | (0.103) |
| 165 | (0.157) |
| 166 | (0.171) |
| 167 | (0.129) |
| 168 | (12.19) |
| 169 | (0.026) |
| 170 | (>100) |
| 171 | (>100) |
| 172 | (~100) |
| 173 | (>100) |
| 174 | (0.818) |
| 175 | (0.515) |
| 176 | (0.012) |
| 177 | (1.498) |
| 178 | (0.056) |
| 179 | (>100) |
| 180 | (0.112) |
| 181 | (2.191) |
| 182 | (1.677) |
| 183 | (0.980) |
| 184 | (0.079) |
| 187 | (0.248) |
| 188 | (0.083) |
| 189 | (0.072) |
| 191 | (0.062) |
| 192 | (>1) |
| 193 | (>1) |
| 194 | (5.774) |
| 195 | (0.094) |
| 196 | (0.122) |
| 197 | (0.175) |
| 198 | (>10) |
| 199 | (0.613) |
| 200 | (0.130) |
| 201 | (0.092) |
| 202 | (>100) |
| 203 | (0.060) |
| 204 | (2.864) |
| 205 | (1.435) |
| 206 | (~100) |
| 207 | (0.015) |
| 208 | (0.057) |
| 209 | (0.072) |
| 210 | (>10) |
| 211 | (0.518) |
| 212 | (0.168) |
| 213 | (>10) |
| 214 | (>10) |
| 215 | (4.457) |
| 216 | (~100) |
| 217 | (>100) |
| 218 | (0.073) |
| 219 | (0.058) |
| 220 | (0.355) |
| 221 | (0.111) |
| 222 | (>100) |
| 223 | (>100) |
| 224 | (0.027) |
| 226 | (0.027) |
| 227 | (0.033) |
| 228 | (0.033) |
| 229 | (0.017) |
| 230 | (0.367) |
| 231 | (1.049) |
| 232 | (0.028) |
| 233 | (0.009) |
| 234 | (0.034) |
| 236 | (0.454) |
| 237 | (0.454) |
| 238 | (1.046) |
| 239 | (0.414) |
| 240 | (0.227) |
| 241 | (>100) |
| 242 | (0.042) |
| 243 | (0.083) |
| 244 | (0.085) |
| 245 | (0.048) |
| 246 | (0.047) |
| 247 | (1.188) |
| 248 | (>100) |
| 249 | (>100) |
| 250 | (0.026) |
| 251 | (0.285) |
| 252 | (0.610) |
| 253 | (0.344) |
| 254 | (0.068) |
| 255 | (0.024) |
| 256 | (0.450) |
| 257 | (0.024) |
| 258 | (0.058) |
| 259 | (0.011) |
| 260 | (0.028) |
| 261 | (0.011) |

TABLE 4-continued

| Cpd | % Inhibition (IC$_{50}$) |
|---|---|
| 262 | (0.019) |
| 263 | (0.523) |

EXAMPLE 168

HER-4 Kinase Assay

The HER-4 kinase used was purified at Proqinase (Freiburg, Germany) from a construct that consisted of a fusion of GST (Glutathione-S-Transferase), HIS6-Thrombin and the nucleotides encoding amino acids 676 to 1307 of HER-4 (Accession NM 005235).

A mixture of a 10× kinase reaction buffer (600 mM Hepes at pH 7.5, 30 mM Magnesium Chloride, 0.03 mM Sodium Vanadate and 500 µg/mL PEG 20,000), DTT (1.2 mM final from a 10 mM) stock), ATP (1 µM from a 10 mM stock), biotinylated polyGluTyr (1.5 ng/µL final from stock of 1 µg/µL) prepared by Upstate Biotechnologies, Lake Placid, N.Y.), Manganese Chloride (3 mM final from a 1 M stock), γ-$^{33}$P-ATP (10 µCi/mL stock) and water (70 µL/well) was added to each well of a Streptavidin Flashplate (Cat. # SMP103, NEN, Boston, Mass.).

Test compound stock (1 µL) was added to the appropriate wells. Diluted GST HER-4 kinase (6.7 ng/µL diluted into 50 mM Tris-HCl at pH 8.0 and 0.1% bovine serum albumin) (30 µL) was added (total volume of 200 ng/well) to initiate the reactions.

The reaction plates were incubated at 30° C. for 1 hr. The reaction was terminated by aspirating the reaction mixture from the plate wells and washing the wells three times with a 1×PBS stop buffer (300 µL) and 100 mM EDTA. After the final wash, the same stop buffer (200 µL) was again added to the wells. The plates were then sealed and read on the Top-Count scintillation counter.

For a series of test concentrations, the IC$_{50}$ was derived by graphing percent inhibition against the log of the concentrations tested for a given compound. The Her-4 IC$_{50}$ results are shown in Table 5.

TABLE 5

| Cpd | IC$_{50}$ |
|---|---|
| 96 | 0.018 |
| 97 | 0.099 |
| 98 | 0.081 |
| 169 | 0.030 |
| 176 | 0.047 |
| 178 | 0.126 |
| 233 | 0.009 |
| 234 | 0.059 |
| 245 | 0.227 |
| 250 | 0.033 |

EXAMPLE 169 c-Abl Kinase Assay

A mixture of a 10× kinase buffer (80 mM MOPS at pH 7.0, 2 mM EDTA and 100 mM Magnesium Acetate), ATP (5 µM final from a 10 mM stock), a peptide EAIYAAPFAKKK (50 µM final from a 0.5 mM stock), γ-$^{33}$P ATP (10 µCi/µL stock) and water is added to each well (for a total of 20 µL/well) of a Streptavidin Flashplate.

Test compound in 100% DMSO (0.5 µL) is added to the appropriate wells. Diluted c-Abl kinase (human) (Accession Number U07563) (Upstate Biotechnology, Lake Placid, N.Y.) (diluted in a buffer consisting of 20 mM MOPS at pH 7.0, 1 mM EDTA, β-mercaptoethanol (0.1%), Brij-35 (0.01%), glycerol (5%) and 1 mg/mL bovine serum albumin) (2.5 µL) is added to the wells to initiate the reactions.

The reaction plates are incubated at 30° C. for 40 min. The reaction is terminated by the addition of a 3% phosphoric acid solution (5 µL). The reaction product (10 µL) is spotted onto a P30 filtermat and is washed for 5 minutes in phosphoric acid (75 mM). The wash sequence is repeated two more times and is followed with one final wash in methanol. The plates are then dried, sealed and read on the TopCount scintillation counter after 30 µL scintillation fluid is added.

EXAMPLE 170

Cell Proliferation Inhibition Assay

The ability of a test compound to inhibit unregulated cell proliferation may be determined by measuring incorporation of $^{14}$C-labelled thymidine into newly synthesized DNA within cell lines derived from carcinomas originating from several tissues. Accordingly, the effect of a test compound on proliferation of cells with a variety of phenotypes may be determined.

Carcinoma cell lines used include the HeLa cervical adenocarcinoma from the American Type Culture Collection (ATCC Cat. #CCL2), A375 malignant melanoma (ATCC Cat. #CRL-1619), HCT-116 colon carcinoma (ATCC Cat. #CCL-247), SKBR3 breast carcinoma (ATCC Cat. #HTB-30) and BT474 breast carcinoma (ATCC Cat. #HTB-20).

The carcinoma cells were trypsinized and counted. The cells (3000-8000 count) were added to each well of a 96-well CytoStar tissue culture treated scintillating microplate (Amersham #RPNQ0160) in complete medium (100 µL) and the plate was then incubated in complete medium for 24 hrs at 37° C. in an inert atmosphere containing 5% CO$_2$.

Test compound (1 µL) in 100% DMSO was added to the plate test-wells with DMSO only added to control-wells. The plate was incubated in complete medium for a second 24 hr period at 37° C. in an atmosphere containing 5% CO$_2$.

An aliquot of a solution of Methyl $^{14}$C-thymidine (56 mC/mmol) (NEN #NEC568 or AMersham #CFA532) and complete medium (20 uL to provide 0.2 µCi/well) was then added to each well and the plate was incubated for a third 24 hr period at 37° C. in an atmosphere containing 5% CO$_2$.

The plate contents were then discarded, the plate washed twice with PBS (200 µL) and then PBS (200 µL) was added to each well. The plate was sealed and the degree of methyl $^{14}$C-thymidine incorporation was quantified on a Packard Top Count.

Cell proliferation of the Hela cell line was measured using the ATP-Lite method as described in the ATP Lite Kit (Perkin-Elmer Kit Number 6106941) or the C$^{14}$ method as described above. Cell proliferation of the other cell lines was measured using the C$^{14}$ method.

TABLE 6

| | (IC$_{50}$) | | |
|---|---|---|---|
| Cpd | BT474 | Hela (ATP Lite) | SKBR3 |
| 3 | 9.576 | 42.64 | 9.719 |
| 36 | 100 | 100 | 100 |

TABLE 6-continued (IC$_{50}$)

| Cpd | BT474 | Hela (ATP Lite) | SKBR3 |
|---|---|---|---|
| 38 | 100 | 100 | 100 |
| 48 | 10 | 100 | 100 |
| 52 | 5.98 | 26.96 | 2.61 |
| 63 | 10 | 59.01 | 26.88 |
| 64 | 10 | 10 | 100 |
| 169 | 0.383 | 4.283 | 0.144 |
| 178 | 0.158 | 53.35 | 0.292 |

TABLE 7

(IC$_{50}$)

| Cpd | Hela | HCT-116 | A375 |
|---|---|---|---|
| 36 | 10 | 67.92 | 10 |
| 38 | 100 | 100 | 100 |
| 48 | 10 | 30.41 | 17.22 |
| 52 | 100 | 100 | 100 |
| 77 | 100 | 100 | 100 |
| 78 | 100 | 100 | 100 |
| 79 | 100 | 100 | 100 |
| 80 | 5.14 | 14.02 | 10.14 |
| 87 | 3.19 | 3.69 | 6.79 |
| 91 | 1 | 10 | 10 |
| 92 | 4.30 | 4.36 | 4.89 |
| 93 | 10 | 10 | 10 |
| 94 | 100 | 100 | 100 |
| 95 | 10 | 10 | 10 |
| 101 | 100 | 100 | 100 |
| 102 | 100 | 100 | 100 |
| 103 | 100 | 100 | 100 |
| 108 | 100 | 100 | 100 |
| 109 | 10 | 10 | 10 |
| 110 | 15.5 | 10 | 100 |
| 116 | 10 | 10 | 10 |
| 117 | 100 | 100 | 100 |
| 118 | 10 | 10 | 10 |

EXAMPLE 171

In Vivo Models—Inhibition of Tumor Growth

The ability of test compounds to inhibit unregulated growth of human tumor cells in vivo was evaluated by implanting human tumor cells into the hindflank of athymic mice, administering a test compound and then quantifying any change in tumor size.

Human epidermoid A431 carcinoma, N87 cells and BT474 cells were implanted subcutaneously into the hindflank of female athymic mice (Charles River) and allowed to grow for 6-10 days. After a measurable tumor was established (as determined by baseline caliper measurement), the animal was administered an oral dose of the test compound daily for a period of 30 days. Tumor size was measured every five days and the degree of inhibition was determined by comparing drug-treated animals to vehicle-treated animals.

Variations of this method are intended to include intraperitoneal injection or intravenous infusion as the route of administration and administration of the test compound either alone or in a combination therapy.

The inhibition of tumor growth values are shown in Table 8 at various test concentrations, as indicated. For compounds with multiple values at one test concentration, each value represents a separate assay result.

TABLE 8

(percent inhibition)

| Cpd | (mg/kg) | BT474 | A431 | N87 |
|---|---|---|---|---|
| 169 | 100 | ND | 55.4 | ND |
| 232 | 100 | ND | ND | 30.3 |
| 233 | 100 | ND | 2.2 | 38.3 |
| 245 | 100 | ND | ND | 48.7 |
| 250 | 100 | ND | 25.4, 51.8 | 68.9, 66.7 |
| 257 | 100 | ND | ND | 71.2 |
| 259 | 100 | ND | ND | 46.8 |
| 261 | 100 | 98 | 86.1, 80.1 | 75.4, 82.3 |
| 261 | 50 | ND | ND | 71 |
| 261 | 30 | ND | 54.1 | ND |
| 261 | 25 | ND | ND | 69.6 |
| 261 | 10 | ND | 44 | ND |
| 262 | 100 | ND | ND | 70.5 |
| 263 | 100 | ND | ND | 18.1 |

While the foregoing specification teaches the principles of the present invention, with examples provided for the purpose of illustration, it will be understood that the practice of the invention encompasses all of the usual variations, adaptations and modifications as come within the scope of the following claims and their equivalents.

Throughout this application, various publications are cited. The disclosure of these publications is hereby incorporated by reference into this application to describe more fully the state of the art to which this invention pertains.

What is claimed is:

1. A compound of Formula (I)

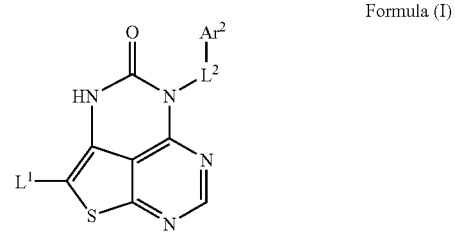

Formula (I)

or a stereoisomer or a pharmaceutically acceptable salt thereof, wherein

L$^1$ is selected from the group consisting of hydrogen, —N(R$_1$R$_2$), —C(O)N(R$_1$R$_2$), —C(O)O(R$_1$), —S(C$_{1-4}$ alkyl), NO$_2$, —(CH$_2$)$_p$—Ar$^1$, —C(O)—(CH$_2$)$_p$—Ar$^1$, —N(R$_1$)—(CH$_2$)$_p$—Ar$^1$, —N(R$_1$)C(O)—(CH$_2$)—Ar$^1$, -N(R$_1$)C(O)N(R$_2$)—(CH$_2$)$_p$—Ar$_1$ and -C(O)N(R$_1$)-(CH2)$_p$—Ar$^1$, R$_1$ is selected from the group consisting of hydrogen, C$_{1-8}$alkyl, C$_{1-8}$alkoxy-C$_{1-8}$alkyl, amino-C$_{1-8}$alkoxy-C$_{1-8}$alkyl and C$_{1-8}$alkyl-amino-C$_{1-8}$alkoxy-C$_{1-8}$alkyl;

R$_2$ is selected from the group consisting of hydrogen, C$_{1-8}$alkyl, C$_{1-8}$alkoxy-C$_{1-8}$alkyl, hydroxy-C$_{1-8}$alkyl, amino-C$_{1-8}$alkyl, C$_{1-8}$alkyl-amino-C$_{1-8}$alkyl and C$_{1-8}$alkoxy-carbonyl-amino-C$_{1-8}$alkyl;

p is 0, 1, 2, 3 or 4,

L$^2$ is selected from the group consisting of —(C$_{1-8}$alkyl)-, —N(R$_1$)— and a bond, Ar$^1$ is selected from the group consisting of aryl, heteroaryl, benzofused heteroaryl, heterocyclyl and benzofused heterocyclyl, each optionally substituted with one, two, three, four or five substituents independently selected from the group consisting of (1) $C_{1-8}$alkyl,
(2) $C_{2-8}$alkenyl,
(3) $C_{2-8}$alkynyl,
(4) $C_{1-8}$alkoxy,
wherein each (1), (2), (3) and (4) is optionally substituted with one, two or three substituents independently selected from the group consisting of
(i) $C_{3-8}$ cycloalkyl,
(ii) aryl,
(iii) heteroaryl,
(iv) heterocyclyl,
wherein each (i), (ii), (iii) and (iv) is optionally substituted with one, two, three, four or five substituents independently selected from the group consisting of
  (a) $C_{1-8}$alkyl,
  (b) $C_{1-8}$alkoxy,
  (c) $C_{1-8}$alkoxy-$C_{1-8}$alkyl,
  (d) halo-$C_{1-8}$alkyl,
  (e) hydroxy-$C_{1-8}$alkyl,
  (f) $C_{1-8}$alkoxy-carbonyl,
  (g) amino optionally mono or disubstituted with $C_{1-8}$alkyl or $C_{1-8}$alkoxy-carbonyl,
  (h) cyano,
  (i) halogen,
  (j) hydroxy,
  (k) amino-$C_{1-8}$alkyl optionally mono or disubstituted on amino with $C_{1-8}$alkyl,
  (l) $C_{3-8}$cycloalkyl,
  (m) $C_{3-8}$cycloalkyl-$C_{1-8}$alkyl,
  (n) heterocyclyl optionally substituted with one or two $C_{1-8}$alkyl substituents, and
  (o) heterocyclyl-$C_{1-8}$alkyl optionally substituted on heterocyclyl with one or two $C_{1-8}$alkyl substituents,
(v) amino optionally mono or disubstituted with a substituent independently selected from the group consisting of
  (a) $C_{1-8}$alkyl,
  (b) $C_{1-8}$alkoxy-$C_{1-8}$alkyl,
  (c) hydroxy-$C_{1-8}$alkyl,
  (d) $C_{3-8}$cycloalkyl,
  (e) heterocyclyl optionally substituted with one or two $C_{1-8}$alkyl substituents, and
  (f) heterocyclyl-$C_{1-8}$alkyl optionally substituted on heterocyclyl with one or two $C_{1-8}$alkyl substituents,
(vi) hydroxy,
(vii) halogen, and
(viii) $C_{1-8}$alkoxy-carbonyl,
(5) amino optionally mono or disubstituted with a substituent independently selected from the group consisting of
(i) $C_{1-8}$alkyl,
(ii) $C_{1-8}$alkoxy-$C_{1-8}$alkyl,
(iii) amino-$C_{1-8}$alkyl optionally mono or disubstituted on amino with $C_{1-8}$alkyl,
(iv) hydroxy-$C_{1-8}$alkyl,
(v) $C_{3-8}$cycloalkyl, (vi) heterocyclyl optionally substituted with one or two $C_{1-8}$alkyl substituents, and (vii) heterocyclyl-$C_{1-8}$alkyl optionally substituted on heterocyclyl with one or two $C_{1-8}$alkyl substituents,
(6) cyano,
(7) halogen,
(8) hydroxy,
(9) $C_{3-8}$cycloalkyl,
(10) aryl,
(11) heteroaryl,
(12) heterocyclyl,
(13) —O— substituted with a substituent selected from the group consisting of
(i) $CF_3$,
(ii) $C_{3-8}$cycloalkyl,
(iii) aryl,
(iv) heteroaryl, and
(v) heterocyclyl,
(14) heterocyclyl-$SO_2$ optionally substituted on heterocyclyl with one or two $C_{1-8}$alkyl substituents,
(15) C(O) substituted with a substituent selected from the group consisting of
(i) hydrogen,
(ii) hydroxy,
(iii) $C_{1-8}$alkyl,
(iv) $C_{1-8}$alkoxy, and
(v) amino optionally mono or disubstituted with a substituent independently selected from the group consisting of
  (a) $C_{1-8}$alkyl,
  (b) $C_{1-8}$alkoxy-$C_{1-8}$alkyl,
  (c) amino-$C_1$alkyl optionally mono or disubstituted on amino with $C_{1-8}$alkyl,
  (d) hydroxy-$C_{1-8}$alkyl,
  (e) heterocyclyl-$C_{1-8}$alkyl optionally substituted on heterocyclyl with one or two $C_1$alkyl substituents,
  (f) $C_{3-8}$cycloalkyl, and
  (g) aryl; and
(16) amino-$SO_2$ optionally mono or disubstituted on amino with a substituent independently selected from the group consisting of
(i) $C_{1-8}$alkyl,
(ii) $C_{1-8}$alkoxy-$C_{1-8}$alkyl,
(iii) amino-$C_{1-8}$alkyl optionally mono or disubstituted on amino with $C_{1-8}$alkyl,
(iv) hydroxy-$C_{1-8}$alkyl,
(v) heterocyclyl-$C_{1-8}$alkyl optionally substituted on heterocyclyl with one or two $C_{1-8}$alkyl substituents,
(vi) $C_{3-8}$cycloalkyl, and
(vii) aryl; and 2
$Ar^2$ is selected from the group consisting of aryl, heteroaryl, benzofused heteroaryl, heterocyclyl and benzofused heterocyclyl, each optionally substituted with one, two, three, four or five substituents independently selected from the group consisting of
(1) $C_{1-8}$alkyl,
(2) $C_{2-8}$alkenyl,
(3) $C_{2-8}$alkynyl,
(4) $C_{1-8}$alkoxy,
wherein each (1), (2), (3) and (4) is optionally substituted with one, two or three substituents independently selected from the group consisting of
(i) $C_{1-8}$alkoxy,
(ii) cyano,
(iii) halogen,
(iv) hydroxy,
(v) $C_{3-8}$cycloalkyl,
(vi) aryl,
(vii) heteroaryl,
(viii) heterocyclyl,
wherein each (v), (vi), (vii) and (viii) is optionally substituted with one, two, three, four or five substituents independently selected from the group consisting of
  (a) $C_{1-8}$alkyl,
  (b) $C_{1-8}$alkoxy,
  (c) $C_{1-8}$alkoxy-$C_{1-8}$alkyl,
  (d) amino optionally mono or disubstituted with $C_{1-8}$alkyl,
  (e) cyano,
  (f) halogen,
  (g) halo-$C_{1-8}$alkyl, (h) hydroxy,
(i) hydroxy-$C_{1-8}$alkyl,
(j) $C_{3-8}$cycloalkyl, and
(k) heterocyclyl optionally substituted with one or two $C_{1-8}$alkyl substituents,
(ix) amino optionally mono or disubstituted with a substituent independently selected from the group consisting of
  (a) $C_{1-8}$alkyl,
  (b) $C_{1-8}$alkoxy-$C_{1-8}$alkyl,
  (c) hydroxy-$C_{1-8}$alkyl,
  (d) $C_{3-8}$cycloalkyl,
  (e) heterocyclyl optionally substituted with one or two $C_1$alkyl substituents, and
  (f) heterocyclyl-$C_1$alkyl optionally substituted on heterocyclyl with one or two $C_{1-8}$alkyl substituents, and
(x) C(O)amino optionally mono or disubstituted with a substituent independently selected from the group consisting of
  (a) $C_{1-8}$alkyl,
  (b) $C_{1-8}$alkoxy-$C_{1-8}$alkyl,
  (c) hydroxy-$C_{1-8}$alkyl,
  (d) $C_{3-8}$cycloalkyl,
  (e) aryl optionally substituted with one to three halogen substituents,
  (f) heterocyclyl optionally substituted with one or two $C_{1-8}$alkyl substituents, and
  (g) heterocyclyl-$C_{1-8}$alkyl optionally substituted on heterocyclyl with one or two $C_{1-8}$alkyl substituents,
(5) NH, NHC(O), N, S, S(O), $SO_2$ or O substituted with one or two substituents independently selected from the group consisting of
  (i) hydrogen,
  (ii) $C_{1-8}$alkyl,
  (iii) $C_{1-8}$alkoxy-$C_{1-8}$alkyl,
  (iv) amino-$C_{1-8}$alkyl optionally mono or disubstituted on amino with $C_{1-8}$alkyl,
  (v) hydroxy-$C_{1-8}$alkyl,
  (vi) aryl,
  (vii) heteroaryl,
  (viii) benzofused heteroaryl,
  (ix) $C_{3-8}$cycloalkyl,
  (x) heterocyclyl,
  xi) benzofused heterocyclyl,
  (xii) aryl-$C_{1-8}$alkyl,
  (xiii) heteroaryl-$C_{1-8}$alkyl,
  (xiv) benzofused heteroaryl-$C_{1-8}$alkyl,
  (xv) $C_{3-8}$cycloalkyl-$C_{1-8}$alkyl,
  (xvi) heterocyclyl-$C_{1-8}$alkyl, and
  (xvii) benzofused heterocyclyl-$C_{1-8}$alkyl,
  wherein each aryl, $C_{3-8}$cycloalkyl, heteroaryl, benzofused heteroaryl, heterocyclyl and benzofused heterocyclyl in one or more of from (vi) to (xvii) is optionally substituted with one, two, three, four or five substituents independently selected from the group consisting of
    (a) $C_{1-8}$alkyl,
    (b) $C_{1-8}$alkoxy,
    (c) $C_{1-8}$alkoxy-$C_{1-8}$alkyl,
    (d) amino optionally mono or disubstituted with $C_{1-8}$alkyl, and
    (e) halogen,
(6) C(O) substituted with a substituent independently selected from the group consisting of
  (i) hydrogen,
  (ii) $C_{1-8}$alkyl optionally substituted with one, two or three substituents independently selected from the group consisting of
    (a) cyano,
    (b) halogen, and
    (c) hydroxy,
  (iii) $C_{1-8}$alkoxy,
  (iv) hydroxy, and
  (v) $C_{1-8}$alkoxy-$C_{1-8}$alkoxy,
(7) cyano,
(8) halogen,
(9) hydroxy,
(10) nitro,
(11) $C_{3-8}$cycloalkyl,
(12) aryl,
(13) heteroaryl,
(14) benzofused heteroaryl,
(15) heterocyclyl, and
(16) benzofused heterocyclyl;
wherein each (11), (12), (13), (14), (15) and (16) is optionally substituted with one, two, three, four or five substituents independently selected from the group consisting of
  (i) $C_{1-8}$alkyl,
  (ii) cyano,
  (iii) halogen,
  (iv) hydroxy,
  (v) nitro,
  (vi) $C_{3-8}$cycloalkyl,
  (vii) $C_{3-8}$cycloalkyl-$C_{1-8}$alkyl,
  (viii) aryl,
  (ix) aryl-$C_{1-8}$alkyl,
  (x) heteroaryl,
  (xi) heteroaryl-$C_{1-8}$alkyl,
  (xii) heterocyclyl, and
  (xiii) heterocyclyl-$C_{1-8}$alkyl.

2. The compound of claim 1, wherein $L^1$ is selected from the group consisting of hydrogen, —$N(R_1R_2)$, —$C(O)N(R_1R_2)$, —$C(O)O(R_1)NO_2$, —$(CH_2)_p$—$Ar^1$, —$C(O)$—$(CH_2)_p$—$Ar^1$, —$N(R_1)C(O)$—$(CH_2)_p$—$Ar^1$, —$C(O)N(R_1)$—$(CH_2)_p$—$Ar^1$ and —$N(R_1)C(O)N(R_2)$—$(CH_2)_p$—$Ar^1$.

3. The compound of claim 1, wherein $L_1$ is selected from the group consisting of hydrogen, —$N(R_1R_2)$, —$C(O)N(R_1R_2)$, —$C(O)O(R_1)$, $NO_2$, —$(CH_2)_p$—$Ar^1$, —$C(O)$—$(CH_2)_p$—$Ar^1$, —$N(R_1)C(O)$—$(CH_2)_p$—$Ar^1$ and —$C(O)N(R_1)$—$(CH_2)_p$—$Ar^1$.

4. The compound of claim 1, wherein $R_1$ is selected from the group consisting of hydrogen, $C_{1-8}$alkyl and $C_{1-8}$alkoxy-$C_{1-8}$alkyl.

5. The compound of claim 1, wherein $R_2$ is selected from the group consisting of hydrogen, $C_{1-8}$alkyl, hydroxy-$C_{1-8}$alkyl, amino-$C_{1-8}$alkyl, $C_{1-8}$alkyl-amino-$C_{1-8}$alkyl and $C_{1-8}$alkoxy-carbonyl-amino-$C_{1-8}$alkyl.

6. The compound of claim 1, wherein p is 0, 1, 2 or 3.

7. The compound of claim 1, wherein $L^2$ is selected from the group consisting of —($C_{1-8}$alkyl)- and a bond.

8. The compound of claim 1, wherein $L^2$ is a bond.

9. The compound of claim 1, wherein $Ar^1$ is selected from the group consisting of aryl, heteroaryl and heterocyclyl, each optionally substituted with one, two, three, four or five substituents independently selected from the group consisting of
  (1) $C_{1-8}$alkyl, $C_{2-8}$ alkenyl and $C_{1-8}$alkoxy, each optionally substituted with one, two or three substituents independently selected from the group consisting of
    (i) heterocyclyl optionally substituted with one, two or three $C_{1-8}$alkyl, $C_{1-8}$alkoxy, hydroxy-$C_{1-8}$alkyl, amino, $C_{1-8}$alkyl-amino, $C_{1-8}$alkoxy-carbonyl-amino, halogen or hydroxy substituents (ii) amino optionally mono or disubstituted with a substituent independently selected from the group consisting of
(a) $C_{1-8}$alkyl,
(b) heterocyclyl optionally substituted with one or two $C_{1-8}$alkyl substituents, and
(c) heterocyclyl-$C_{1-8}$alkyl optionally substituted on heterocyclyl with one or two $C_{1-8}$alkyl substituents, and
(iii) hydroxy,
(iv) halogen, and
(v) $C_{1-8}$alkoxy-carbonyl,
(2) amino optionally mono or disubstituted with a substituent independently selected from the group consisting of
(i) $C_{1-8}$alkyl,
(ii) heterocyclyl optionally substituted with one or two $C_{1-8}$alkyl substituents, and
(iii) heterocyclyl-$C_{1-8}$alkyl optionally substituted on heterocyclyl with one or two $C_{1-8}$alkyl substituents,
(3) cyano,
(4) halogen,
(5) hydroxy,
(6) heteroaryl,
(7) heterocyclyl, and
(8) $C_{1-8}$alkoxy-carbonyl.

10. The compound of claim 1, wherein $Ar^2$ is selected from the group consisting of aryl, heteroaryl, benzofused heteroaryl, heterocyclyl and benzofused heterocyclyl, each optionally substituted with one, two, three, four or five substituents independently selected from the group consisting of
(1) $C_{1-8}$alkyl,
(2) $C_{2-8}$alkynyl,
(3) $C_{1-8}$alkoxy,
wherein each (1) and (3) is optionally substituted with one, two or three substituents independently selected from the group consisting of aryl, heteroaryl and heterocyclyl, wherein aryl is optionally substituted with one, two, three, four or five substituents independently selected from the group consisting of
(i) $C_{1-8}$alkyl,
(ii) $C_{1-8}$alkoxy,
(iii) amino optionally mono or disubstituted with $C_{1-8}$alkyl,
(iv) cyano,
(v) halogen, and
(vi) hydroxy,
(4) NH, NHC(O), S, S(O), $SO_2$ or O substituted with a substituent selected from the group consisting of aryl, heteroaryl and aryl-$C_{1-8}$alkyl, each optionally substituted on aryl, and heteroaryl with one, two, three, four or five substituents independently selected from the group consisting of
(i) $C_{1-8}$alkyl,
(ii) $C_{1-8}$alkoxy,
(iii) amino optionally mono or disubstituted with $C_{1-8}$alkyl, and
(iv) halogen,
(5) C(O) substituted with a substituent independently selected from the group consisting of
(i) hydrogen,
(ii) $C_{1-8}$alkyl,
(iii) $C_{1-8}$alkoxy, and
(iv) hydroxy,
(6) cyano,
(7) halogen,
(8) hydroxy,
(9) nitro,
(10) $C_{3-8}$cycloalkyl,
(11) aryl optionally substituted with one, two, three, four or five substituents independently selected from the group consisting of
(i) $C_{1-8}$alkyl,
(ii) cyano,
(iii) halogen,
(iv) hydroxy, and
(v) nitro,
(12) heteroaryl,
(13) benzofused heteroaryl,
(14) heterocyclyl, and
(15) benzofused heterocyclyl.

11. The compound of claim 1, wherein $Ar^2$ is selected from the group consisting of aryl, heteroaryl, benzofused heteroaryl and benzofused heterocyclyl, each optionally substituted with one, two, three or four substituents independently selected from the group consisting of
(1) $C_{1-8}$alkyl,
(2) $C_{2-8}$alkynyl,
(3) $C_{1-8}$alkoxy,
wherein each (1) and (3) is optionally substituted with one substituent selected from the group consisting of aryl, heteroaryl and heterocyclyl, wherein aryl is optionally substituted with halogen,
(4) NHC(O), S, S(O) or O substituted with a substituent selected from the group consisting of aryl, heteroaryl and aryl-$C_{1-8}$alkyl, each optionally substituted on aryl and heteroaryl with $C_{1-8}$alkyl or halogen,
(5) halogen,
(6) aryl optionally substituted with $C_{1-8}$alkyl or halogen, and
(7) heterocyclyl.

12. The compound of claim 1, wherein
$L^1$ is selected from the group consisting of hydrogen, —N(R_1R_2), —C(O)N(R_1R_2), —C(O)O(R_1), NO_2, —(CH_2)_p—Ar^1, —C(O)—(CH_2)_p—Ar^1, —N(R_1)C(O)—(CH_2)_p—Ar^1 and —C(O)N(R_1)—(CH_2)_p—Ar^1;
$R_1$ is selected from the group consisting of hydrogen, $C_{1-8}$alkyl and $C_{1-8}$alkoxy-$C_{1-8}$alkyl;
$R_2$ is selected from the group consisting of hydrogen, $C_{1-8}$alkyl, hydroxy-$C_{1-8}$alkyl, amino-$C_{1-8}$alkyl, $C_{1-8}$alkyl-amino-$C_{1-8}$alkyl and $C_{1-8}$alkoxy-carbonyl-amino-$C_{1-8}$alkyl;
p is 0, 1, 2 or 3;
$L^2$ is selected from the group consisting of —($C_{1-8}$alkyl)- and a bond;
$Ar^1$ is selected from the group consisting of aryl, heteroaryl and heterocyclyl, each optionally substituted with one, two, three, four or five substituents independently selected from the group consisting of
(1) $C_{1-8}$alkyl, $C_{2-8}$alkenyl and $C_{1-8}$alkoxy, each optionally substituted with one, two or three substituents independently selected from the group consisting of
(i) heterocyclyl optionally substituted with one, two or three $C_{1-8}$alkyl, $C_{1-8}$alkoxy, hydroxy —$C_{1-8}$alkyl, amino, $C_{1-8}$alkyl-amino, $C_{1-8}$alkoxy-carbonyl-amino, halogen or hydroxy substituents
(ii) amino optionally mono or disubstituted with a substituent independently selected from the group consisting of
(a) $C_{1-8}$alkyl,
(b) heterocyclyl optionally substituted with one or two $C_{1-8}$alkyl substituents, and
(c) heterocyclyl —$C_{1-8}$alkyl optionally substituted on heterocyclyl with one or two $C_{1-8}$alkyl substituents, and
(iii) hydroxy,
(iv) halogen, and
(v) $C_{1-8}$alkoxy-carbonyl, (2) amino optionally mono or disubstituted with a substituent independently selected from the group consisting of
(i) $C_{1-8}$alkyl,
(ii) heterocyclyl optionally substituted with one or two $C_{1-8}$alkyl substituents, and
(iii) heterocyclyl—$C_{1-8}$alkyl optionally substituted on heterocyclyl with one or two $C_{1-8}$alkyl substituents,
(3) cyano,
(4) halogen,
(5) hydroxy,
(6) heteroaryl,
(7) heterocyclyl, and
(8) $C_{1-8}$alkoxy-carbonyl; and
$Ar^2$ is selected from the group consisting of aryl, heteroaryl, benzofused heteroaryl and benzofused heterocyclyl, each optionally substituted with one, two, three or four substituents independently selected from the group consisting of
(1) $C_1$alkyl,
(2) $C_2$alkynyl,
(3) $C_1$alkoxy,
wherein each (1) and (3) is optionally substituted with one substituent selected from the group consisting of aryl, heteroaryl and heterocyclyl, wherein aryl is optionally substituted with halogen,
(4) NHC(O), S, S(O) or O substituted with a substituent selected from the group consisting of aryl, heteroaryl and aryl-$C_{1-8}$alkyl, each optionally substituted on aryl and heteroaryl with $C_{1-8}$alkyl or halogen,
(5) halogen,
(6) aryl optionally substituted with $C_{1-8}$alkyl or halogen, and
(7) heterocyclyl.

13. A compound of Formula (Ia):

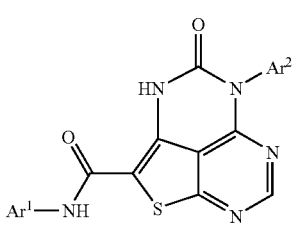

Formula (Ia)

and pharmaceutically acceptable salts thereof, wherein
$Ar^1$ is selected from 3,4-(OCH$_3$)$_2$-phenyl, 4-(CH$_2$-piperidin-1-yl)phenyl, thiazol-2-yl, pyridin-3-yl, 6-[NH(CH$_2$)$_3$-morpholin-4-yl]pyridin-3-yl, 4-(CH$_2$-pyrrolidin-1-yl)phenyl, 4-OCH$_3$-3-OH-phenyl, 4-CH$_2$N(CH$_3$)$_2$-phenyl, 4-(CH$_2$-morpholin-4-yl)phenyl, 4-[CH$_2$-(4-CH$_3$-piperazin-1-yl)]phenyl, 4-(CH$_2$NHCH$_2$-(2R)-tetrahydro-furan-2-yl)phenyl, 6-CN-pyridin-3-yl, 4-OH-3-OCH$_3$-phenyl, 3-OCH$_3$-4-[O(CH$_2$)$_2$-morpholin-4-yl]phenyl, 3-OCH$_3$-4-[O(CH$_2$)$_3$-piperidin-1-yl]phenyl, 3-OCH$_3$-4-[O(CH$_2$)$_2$-piperidin-1-yl]phenyl, 6-CH$_2$NH$_2$-pyridin-3-yl, 4-(CH$_2$NH-piperidin-4-yl)phenyl, 3-OCH$_3$-4-(OCH$_2$-tetrahydro-pyran-2-yl)phenyl, 4-[OCH$_2$-(1-CH$_3$-piperidin-3-yl)]phenyl, 4-[CH$_2$N(CH$_3$)CH$_2$-(2R)-tetrahydro-furan-2-yl]phenyl, 1-CO$_2$C(CH$_3$)$_3$-piperidin-4-yl, 1-CH$_3$-piperidin-4-yl, 4-(morpholin-4-yl)phenyl, 4-[((CH$_2$)$_2$-piperidin-1-yl]phenyl, 4-[CH(OH)CH$_2$-morpholin-4-yl]phenyl, 3-OCH$_3$-4-(CH$_2$-morpholin-4-yl)phenyl, 4-[CH$_2$-(1-CH$_3$-piperazin-4-yl)]phenyl, 3-F-4-(CH$_2$-morpholin-4-yl)phenyl, 4-(tetrazol-2-yl)phenyl, 4-[CH═CHC(O)OCH$_2$CH$_3$]phenyl, 3-OCH$_2$CH$_3$-4-(CH$_2$-morpholin-4-yl)phenyl1, 4-CH$_3$-piperazin-1-yl, 3-(CH$_2$-morpholin-4-yl)phenyl, 3-Cl-4-(CH$_2$-morpholin-4-yl)phenyl, 3-OCH$_3$-4-(CH$_2$-morpholin-4-yl)phenyl, 3-OCH$_3$-4-(CH$_2$-piperidin-1-yl)phenyl, 3-CF$_3$-4-(CH$_2$-morpholin-4-yl)phenyl, 3-CH$_3$-4-(CH$_2$-morpholin-4-yl)phenyl, 4-[CH$_2$-(4-OH-piperidin-1-yl)]phenyl, 4-[CH$_2$-(3-F-piperidin-1-yl)]phenyl, 3-OCF$_3$-4-(CH$_2$-morpholin-1-yl)phenyl, 4-{CH$_2$-[2,6-cis-(CH$_3$)2-morpholin-4-yl]}phenyl, 3-OCH$_3$-4-(CH$_2$-morpholin-1-yl)phenyl, 4-[CH$_2$-(4-F-piperidin-1-yl)]phenyl, 4-{CH$_2$-[3,5-(CH$_3$)$_2$-morpholin-4-yl]}phenyl, 4-[CH$_2$-(4-CH$_2$OH-piperidin-1-yl)]phenyl, 4-[CH$_2$-(4-CH$_3$-piperidin-1-yl)]phenyl, 4-[CH$_2$-(3-CH$_2$OH-piperidin-1-yl)]phenyl, 3-N(CH$_3$)$_2$-4-(CH$_2$-morpholin-4-yl)phenyl, 4-{CH$_2$-[4-NHC(O)OC(CHQ$_3$-piperidin-l-yl]}phenyl, 4-[CH$_2$-(4-NH$_2$-piperidin-1-yl)]phenyl, 4-{CH$_2$-[4-N(CH$_3$)$_2$-piperidin-l-yl]}phenyl, 4-[CH$_2$-(4-OCH$_3$-piperidin-1-yl)]phenyl, 3-OH-4-(CH$_2$-morpholin-4-yl)phenyl or 4-{CH$_2$-[4,4-(CH$_3$)$_2$-piperidin-l-yl]}phenyl; and
$Ar^2$ is selected from 3-Cl-4-F-phenyl, 3-(C═CH)-phenyl, 2-Cl-4-F-phenyl, 2,4-Cl$_2$-phenyl, 2-Cl-3,4,5-(OCH$_3$)$_3$-phenyl, 3,4,5-(OCH$_3$)$_3$-phenyl, 2,4-Cl$_2$-5-OCH3-phenyl, 3-Br-phenyl, 2-F-4-Br-phenyl, 3-Cl-4-(OCH$_2$-pyridin-2-yl)phenyl, 2-Cl-5-OCH$_3$-phenyl, 2,4-Cl$_2$-5-(3-F-benzyloxy)phenyl, 5-Cl-benzo[1,3]dioxol-4-yl, 2-F-4-OCH$_3$-phenyl, 2-OCH$_3$-5-Cl-phenyl, 2-(4-Cl-phenyl)-5-C(CH$_3$)$_3$-2H-pyrazol-3-yl, 1-(3-F-benzyl)indazol-5-yl, 3-OCH$_3$-4-Br-phenyl, 1-(3-F-benzyl)indol-5-yl, 4-phenoxy-phenyl, 2,6-Cl$_2$-phenyl, 3-Br-4-CH$_3$-phenyl, 2-CH$_3$-5-Br-phenyl, 4-(4-F-phenoxy)phenyl, 3-F-4-phenoxy-phenyl, 3-CH$_3$-4-(6-CH$_3$-pyridin-3-yloxy)phenyl, 3-Cl-4-OCH$_3$-phenyl, 4-morpholin-4-yl-phenyl, 3-Cl-4-(6-CH$_3$-pyridin-3-yloxy)phenyl, 4-(3-F-phenoxy)phenyl, 3-Cl-4-phenoxy-phenyl, 4-(4-Cl-phenyl)phenyl, 2-Cl-4-F-phenyl, 2-Cl-6-CH$_3$-phenyl, 2-Cl-phenyl, 3-Br-4-F-phenyl, 3-Cl-4-(3-F-phenoxy)phenyl, 4-(benzyl)phenyl, 4-(S-phenyl)phenyl, 3-Br-4-(OCH$_2$-pyridin-2-yl)phenyl, 3-Br-4-OCH$_3$-phenyl, 3-Br-4-phenoxy-phenyl, 2-(3-F-benzyl)-3H-benzoimidazol-5-yl, 4-Br-phenyl, 3-phenoxy-phenyl, 4-[S(O)-phenyl]phenyl, 3-Cl-4-(pyridin-3-yloxy)phenyl, 3-Cl-4-(OCH$_2$-thien-2-yl)phenyl, 4-(pyridin-3-yloxy)phenyl, 3-Cl-4-(OCH$_2$-furan-2-yl)phenyl, 4-[NHC(O)-phenyl]phenyl, benzofuran-7-yl or 3-Cl-4-(3-F-benzyloxy)phenyl.

14. A compound of Formula (Ib):

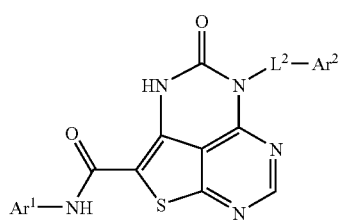

Formula (Ib)

and pharmaceutically acceptable salts thereof, wherein
$Ar^1$ is selected from 4-(CH$_2$-piperidin-1-yl)phenyl, 4-(CH$_2$-morpholin-4-yl)phenyl or 1-CH$_3$-piperidin-4-yl;
$L^2$ is CH(R—CH$_3$); and
$Ar^2$ is phenyl.

15. A compound of Formula (Ic):

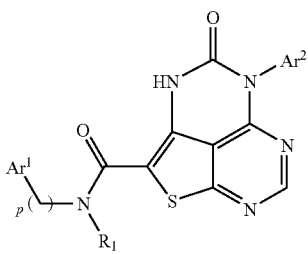

Formula (Ic)

and pharmaceutically acceptable salts thereof, wherein
R$_1$ is selected from hydrogen, CH$_3$ or (CH$_2$)$_2$OCH(CH$_3$)$_2$;
p is 0, 1, 2 or 3;
Ar$^1$ is selected from 4-NH$_2$-phenyl, morpholin-4-yl, furan-2-yl, 2-F-phenyl, 4-(CH$_2$-morpholin-4-yl)phenyl or pyridin-2-yl; and
Ar$^2$ is selected from 3-Cl-4-F-phenyl, 1-(3-F-benzyl)indol-5-yl, 4-phenoxy-phenyl or 4-(morpholin-4-yl)phenyl.

16. A compound of Formula (Id):

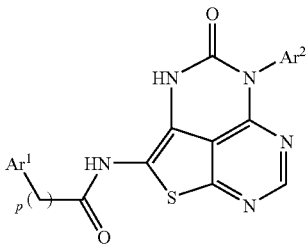

Formula (Id)

and pharmaceutically acceptable salts thereof, wherein
Ar$^1$ is 3,4-(OCH$_3$)$_2$-phenyl; p is 0 or 1; and Ar$^2$ is 3-Cl-4-F-phenyl.

17. A compound of Formula (Ie):

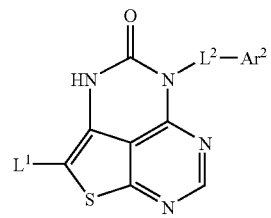

Formula (Ie)

and pharmaceutically acceptable salts thereof, wherein
L$^1$ is selected from hydrogen, CO$_2$H, phenyl, 3,4-(OCH$_3$)$_2$-phenyl, C(O)-pyrrolidin-1-yl, CO$_2$CH$_3$, CO$_2$CH$_2$CH$_3$, C(O)N(CH$_3$)$_2$, C(O)NH(CH$_2$)$_3$OH, C(O)NH(CH$_2$)$_3$NH—CO$_2$C(CH$_3$)$_2$, NO$_2$, NH$_2$, C(O)-[3,4-(OCH$_3$)$_2$-phenyl], C(O)NH(CH$_2$)$_3$N(CH$_3$)$_2$, C(O)-{4-[(CH$_2$)$_2$-morpholin-4-yl]-piperazin-1-yl}, C(O)-(4-CH$_3$-[1,4]diazepan-1-yl) or C(O)-(4-CH$_3$-piperazin-1-yl);
L$^2$ is selected from a bond, —CH$_2$— or —CH(R—CH$_3$)—; and
Ar$^2$ is selected from 3-Cl-4-F-phenyl, 3-Cl-4-(OCH$_2$-pyridin-2-yl)phenyl, 2-F-4-Br-phenyl, 2,4-Cl$_2$-5-OCH$_3$-phenyl, 3,4,5-(OCH$_3$)$_3$-phenyl, 2-Cl-5-OCH$_3$-phenyl, 5-Cl-benzo[1,3]dioxol-4-yl, 2,4-Cl$_2$-5-(3-F-benzyloxy)phenyl, 1-(3-F-benzyl)indol-5-yl, 1-(3-F-benzyl)indazol-5-yl, 3-OCH$_3$-4-Br-phenyl, 4-(4-F-phenoxy)phenyl, 3-Br-4-CH$_3$-phenyl, 2-CH$_3$-5-Br-phenyl, 4-phenoxy-phenyl, 4-(morpholin-4-yl)phenyl, 3-F-4-phenoxy-phenyl, 4-(3-F-phenoxy)phenyl, 3-Cl-4-phenoxy-phenyl, 3-Br-4-F-phenyl, phenyl, 4-Br-phenyl, 3-F-phenyl, 4-(S-phenyl)phenyl, 2-(3-F-benzyl)-3H-benzoimidazol-5-yl, 3-Cl-4-(OCH$_2$-furan-2-yl)phenyl, 3-Cl-4-(OCH$_2$-thien-2-yl)phenyl, 4-[NHC(O)-phenyl]phenyl or 2-Cl-4-F-phenyl.

18. A compound selected from the group consisting of:
5-(3-chloro-4-fluoro-phenyl)-4-oxo-4,5-dihydro-3H-1-thia-3,5,6,8-tetraaza-acenaphthylene-2-carboxylic acid (3,4-dimethoxy-phenyl)-amide,
5-(3-chloro-4-fluoro-phenyl)-4-oxo-4,5-dihydro-3H-1-thia-3,5,6,8-tetraaza-acenaphthylene-2-carboxylic acid (4-piperidin-1-ylmethyl-phenyl)-amide,
5-(3-chloro-4-fluoro-phenyl)-4-oxo-4,5-dihydro-3H-1-thia-3,5,6,8-tetraaza-acenaphthylene-2-carboxylic acid thiazol-2-ylamide,
5-(3-chloro-4-fluoro-phenyl)-4-oxo-4,5-dihydro-3H-1-thia-3,5,6,8-tetraaza-acenaphthylene-2-carboxylic acid pyridin-3-ylamide,
5-(3-chloro-4-fluoro-phenyl)-4-oxo-4,5-dihydro-3H-1-thia-3,5,6,8-tetraaza-acenaphthylene-2-carboxylic acid [6-(3-morpholin-4-yl-propylamino)-pyridin-3-yl[-amide,
5-(3-chloro-4-fluoro-phenyl)-4-oxo-4,5-dihydro-3H-1-thia-3,5,6,8-tetraaza-acenaphthylene-2-carboxylic acid (4-pyrrolidin-1-ylmethyl-phenyl)-amide,
5-(3-chloro-4-fluoro-phenyl)-4-oxo-4,5-dihydro-3H-1-thia-3,5,6,8-tetraaza-acenaphthylene-2-carboxylic acid (4-morpholin-1-ylmethyl-phenyl)-amide,
5-(3-chloro-4-fluoro-phenyl)-4-oxo-4,5-dihydro-3H-1-thia-3,5,6,8-tetraaza-acenaphthylene-2-carboxylic acid [4-(4-methyl-piperazin-1-ylmethyl)-phenyl]-amide,
5-(3-ethynyl-phenyl)-4-oxo-4,5-dihydro-3H-1-thia-3,5,6,8-tetraaza-acenaphthylene-2-carboxylic acid (4-pyrrolidin-1-ylmethyl-phenyl)-amide,
5-(2-chloro-4-fluoro-phenyl)-4-oxo-4,5-dihydro-3H-1-thia-3,5,6,8-tetraaza-acenaphthylene-2-carboxylic acid (4-morpholin-4-ylmethyl-phenyl)-amide,
5-(3-chloro-4-fluoro-phenyl)-4-oxo-4,5-dihydro-3H-1-thia-3,5,6,8-tetraaza-acenaphthylene-2-carboxylic acid [4-({[(2R)-tetrahydro-ftiran-2-ylmethyl]-amino}-methyl)-phenyl]-amide,
5-(3-chloro-4-fluoro-phenyl)-4-oxo-4,5-dihydro-3H-1-thia-3,5,6,8-tetraaza-acenaphthylene-2-carboxylic acid (4-hydroxy-3-methoxy-phenyl)-amide,
5-(3-chloro-4-fluoro-phenyl)-4-oxo-4,5-dihydro-3H-1-thia-3,5,6,8-tetraaza-acenaphthylene-2-carboxylic acid [3-methoxy-4-(2-morpholin-4-yl-ethoxy)-phenyl]-amide,
5-(3-chloro-4-fluoro-phenyl)-4-oxo-4,5-dihydro-3H-1-thia-3,5,6,8-tetraaza-acenaphthylene-2-carboxylic acid [3-methoxy-4-(3-piperidin-1-yl-propoxy)-phenyl]-amide,
5-(3-chloro-4-fluoro-phenyl)-4-oxo-4,5-dihydro-3H-1-thia-3,5,6,8-tetraaza-acenaphthylene-2-carboxylic acid [3-methoxy-4-(2-piperidin-4-yl-ethoxy)-phenyl]-amide,
5-(3-chloro-4-fluoro-phenyl)-4-oxo-4,5-dihydro-3H-1-thia-3,5,6,8-tetraaza-acenaphthylene-2-carboxylic acid (6-aminomethyl-pyridin-3-yl)-amide, 5-(2,4-dichloro-phenyl)-4-oxo-4,5-dihydro-3H-1-thia-3,5,6,8-tetraaza-acenaphthylene-2-carboxylic acid (4-piperidin-1-ylmethyl-phenyl)-amide, 5-(2,4-dichloro-phenyl)-4-oxo-4,5-dihydro-3H-1-thia-3,5,6,8-tetraaza-acenaphthylene-2-carboxylic acid (4-morpholin-4-ylmethyl-phenyl)-amide, 5-(3-bromo-phenyl)-4-oxo-4,5-dihydro-3H-1-thia-3,5,6,8-tetraaza-acenaphthylene-2-carboxylic acid (4-morpholin-4-ylmethyl-phenyl)-amide, 5-(2,4-dichloro-5-methoxy-phenyl)-4-oxo-4,5-dihydro-3H-1-thia-3,5,6,8-tetraaza-acenaphthylene-2-carboxylic acid (4-pyrrolidin-1-ylmethyl-phenyl)-amide, 5- [3-chloro-4-(pyridin-2-ylmethoxy)-phenyl]-4-oxo-4,5-dihydro-3H-1-thia-3,5,6,8-tetraaza-acenaphthylene-2-carboxylic acid (3,4-dimethoxy-phenyl)-amide, 5-(2-chloro-5-methoxy-phenyl)-4-oxo-4,5-dihydro-3H-1-thia-3,5,6,8-tetraaza-acenaphthylene-2-carboxylic acid [3-methoxy-4-(2-morpholin-4-yl-ethoxy)-phenyl]-amide, 5-(2-chloro-5-methoxy-phenyl)-4-oxo-4,5-dihydro-3H-1-thia-3,5,6,8-tetraaza-acenaphthylene-2-carboxylic acid (4-morpholin-4-ylmethyl-phenyl)-amide, 5-[3-chloro-4-(pyridin-2-ylmethoxy)-phenyl]-4-oxo-4,5-dihydro-3H-1-thia-3,5,6,8-tetraaza-acenaphthylene-2-carboxylic acid (4-morpholin-4-ylmethyl-phenyl)-amide, 5-(5-chloro-benzo[1,3]dioxol-4-yl)-4-oxo-4,5-dihydro-3H-1-thia-3,5,6,8-tetraaza-acenaphthylene-2-carboxylic acid (4-morpholin-4-ylmethyl-phenyl)-amide, 5-(3-bromo-phenyl)-4-oxo-4,5-dihydro-3H-1-thia-3,5,6,8-tetraaza-acenaphthylene-2-carboxylic acid [3-methoxy-4-(2-piperidin-1-yl-ethoxy)-phenyl]-amide, 5-(3-bromo-phenyl)-4-oxo-4,5-dihydro-3H-1-thia-3,5,6,8-tetraaza-acenaphthylene-2-carboxylic acid [6-(3-morpholin-4-yl-propylamino)-pyridin-3-yl]-amide, 5-(2-fluoro-4-methoxy-phenyl)-4-oxo-4,5-dihydro-3H-1-thia-3,5,6,8-tetraaza-acenaphthylene-2-carboxylic acid (4-morpholin-4-ylmethyl-phenyl)-amide, 5-(2-fluoro-4-methoxy-phenyl)-4-oxo-4,5-dihydro-3H-1-thia-3,5,6,8-tetraaza-acenaphthylene-2-carboxylic acid [3-methoxy-4-(2-morpholin-4-yl-ethoxy)-phenyl]-amide, 5-(5-chloro-2-methoxy-phenyl)-4-oxo-4,5-dihydro-3H-1-thia-3,5,6,8-tetraaza-acenaphthylene-2-carboxylic acid (4-piperidin-1-ylmethyl-phenyl)-amide, 5-(5-chloro-2-methoxy-phenyl)-4-oxo-4,5-dihydro-3H-1-thia-3,5,6,8-tetraaza-acenaphthylene-2-carboxylic acid (3,4-dimethoxy-phenyl)-amide, 5-(5-chloro-2-methoxy-phenyl)-4-oxo-4,5-dihydro-3H-1-thia-3,5,6,8-tetraaza-acenaphthylene-2-carboxylic acid [3-methoxy-4-(2-piperidin-1-yl-ethoxy)-phenyl]-amide, 5-[1-(3-fluoro-benzyl)-1H-indazol-5-yl]-4-oxo-4,5-dihydro-3H-1-thia-3,5,6,8-tetraaza-acenaphthylene-2-carboxylic acid (4-piperidin-1-ylmethyl-phenyl)-amide, 5-(4-bromo-3-methoxy-phenyl)-4-oxo-4,5-dihydro-3H-1-thia-3,5,6,8-tetraaza-acenaphthylene-2-carboxylic acid (4-piperidin-1-ylmethyl-phenyl)-amide, 5-(4-bromo-3-methoxy-phenyl)-4-oxo-4,5-dihydro-3H-1-thia-3,5,6,8-tetraaza-acenaphthylene-2-carboxylic acid (4-morpholin-4-ylmethyl-phenyl)-amide, 5-[3-chloro-4-(pyridin-2-ylmethoxy)-phenyl]-4-oxo-4,5-dihydro-3H-1-thia-3,5,6,8-tetraaza-acenaphthylene-2-carboxylic acid [3-methoxy-4-(2-morpholin-4-yl-ethoxy)-phenyl]-amide, 5-[1-(3-fluoro-benzyl)-1H-indol-5-yl]-4-oxo-4,5-dihydro-3H-1-thia-3,5,6,8-tetraaza-acenaphthylene-2-carboxylic acid (4-piperidin-1-ylmethyl-phenyl)-amide, 5- [3-chloro-4-(pyridin-2-ylmethoxy)-phenyl]-4-oxo-4,5-dihydro-3H-1 -thia-3,5,6,8-tetraaza-acenaphthylene-2-carboxylic acid (4-piperidin-1-ylmethyl-phenyl)-amide, 5-[3-chloro-4-(pyridin-2-ylmethoxy)-phenyl]-4-oxo-4,5-dihydro-3H-1-thia-3,5,6,8-tetraaza-acenaphthylene-2-carboxylic acid [4-(4-methyl-piperazin-1-ylmethyl)-phenyl]-amide, 4-({5-[1-(3-fluoro-benzyl)-1H-indol-5-yl]-4-oxo-4,5-dihydro-3H-1-thia-3,5,6,8-tetraaza-acenaphthylene-2-carbonyl}-amino)-piperidine-1-carboxylic acid tert-butyl ester, 5-[1-(3-fluoro-benzyl)-1H-indol-5-yl]-4-oxo-4,5-dihydro-3H-1-thia-3,5,6,8-tetraaza-acenaphthylene-2-carboxylic acid (1-methyl-piperidin-4-yl)-amide, 5-[1-(3-fluoro-benzyl)-1H-indol-5-yl]-4-oxo-4,5-dihydro-3H-1-thia-3,5,6,8-tetraaza-acenaphthylene-2-carboxylic acid (2-morpholin-4-yl-ethyl)-amide, 5-[1-(3-fluoro-benzyl)-1H-indol-5-yl]-4-oxo-4,5-dihydro-3H-1-thia-3,5,6,8-tetraaza-acenaphthylene-2-carboxylic acid (3-morpholin-4-yl-propyl)-amide, 4-oxo-5-(4-phenoxy-phenyl)-4,5-dihydro-3H-1-thia-3,5,6,8-tetraaza-acenaphthylene-2-carboxylic acid (4-piperidin-1-ylmethyl-phenyl)-amide, 4-oxo-5-(4-phenoxy-phenyl)-4,5-dihydro-3H-1-thia-3,5,6,8-tetraaza-acenaphthylene-2-carboxylic acid (4-morpholin-4-ylmethyl-phenyl)-amide, 4-oxo-5-(4-phenoxy-phenyl)-4,5-dihydro-3H-1-thia-3,5,6,8-tetraaza-acenaphthylene-2-carboxylic acid [4-(4-methyl-piperazin-1-ylmethyl)-phenyl]-amide, 4-oxo-5-(4-phenoxy-phenyl)-4,5-dihydro-3H-1-thia-3,5,6,8-tetraaza-acenaphthylene-2-carboxylic acid (3,4-dimethoxy-phenyl)-amide, 4-oxo-5-(4-phenoxy-phenyl)-4,5-dihydro-3H-1-thia-3,5,6,8-tetraaza-acenaphthylene-2-carboxylic acid [3-methoxy-4-(2-piperidin-1-yl-ethoxy)-phenyl]-amide, 5-(2,6-dichloro-phenyl)-4-oxo-4,5-dihydro-3H-1-thia-3,5,6,8-tetraaza-acenaphthylene-2-carboxylic acid (4-morpholin-4-ylmethyl-phenyl)-amide, 4-oxo-5-(4-phenoxy-phenyl)-4,5-dihydro-3H-1-thia-3,5,6,8-tetraaza-acenaphthylene-2-carboxylic acid (3-hydroxy-propyl)-amide, 5-(3-bromo-4-methyl-phenyl)-4-oxo-4,5-dihydro-3H-1-thia-3,5,6,8-tetraaza-acenaphthylene-2-carboxylic acid (4-morpholin-4-ylmethyl-phenyl)-amide, 5-(5-bromo-2-methyl-phenyl)-4-oxo-4,5-dihydro-3H-1-thia-3,5,6,8-tetraaza-acenaphthylene-2-carboxylic acid (4-morpholin-4-ylmethyl-phenyl)-amide, 5-[4-(4-fluoro-phenoxy)-phenyl]-4-oxo-4,5-dihydro-3H-1-thia-3,5,6,8-tetraaza-acenaphthylene-2-carboxylic acid (4-morpholin-4-ylmethyl-phenyl)-amide, 5-(3-bromo-4-methyl-phenyl)-4-oxo-4,5-dihydro-3H-1-thia-3,5,6,8-tetraaza-acenaphthylene-2-carboxylic acid (4-piperidin-1-ylmethyl-phenyl)-amide, 5-(3-fluoro-4-phenoxy-phenyl)-4-oxo-4,5-dihydro-3H-1-thia-3,5,6,8-tetraaza-acenaphthylene-2-carboxylic acid (4-morpholin-4-ylmethyl-phenyl)-amide, 5-(3-fluoro-4-phenoxy-phenyl)-4-oxo-4,5-dihydro-3H-1-thia-3,5,6,8-tetraaza-acenaphthylene-2-carboxylic acid [4-(2-piperidin-1-yl-ethyl)-phenyl]-amide, 5-(3-fluoro-4-phenoxy-phenyl)-4-oxo-4,5-dihydro-3H-1-thia-3,5,6,8-tetraaza-acenaphthylene-2-carboxylic acid [4-(4-methyl-piperazin-1-ylmethyl)-phenyl]-amide, 5-(4-morpholin-4-yl-phenyl)-4-oxo-4,5-dihydro-3H-1-thia-3,5,6,8-tetraaza-acenaphthylene-2-carboxylic acid (4-morpholin-4-ylmethyl-phenyl)-amide, 5-[3-chloro-4-(6-methyl-pyridin-3-yloxy)-phenyl]-4-oxo-4,5-dihydro-3H-1-thia-3,5,6,8-tetraaza-acenaphthylene-2-carboxylic acid (4-morpholin-4-ylmethyl-phenyl)-amide, 5-[4-(3-fluoro-phenoxy)-phenyl]-4-oxo-4,5-dihydro-3H-1-thia-3,5,6,8-tetraaza-acenaphthylene-2-carboxylic acid (4-piperidin-1-ylmethyl-phenyl)-amide, 5-[4-(3-fluoro-phenoxy)-phenyl]-4-oxo-4,5-dihydro-3H-1-thia-3,5,6,8-tetraaza-acenaphthylene-2-carboxylic acid [4-(2-piperidin-1-yl-ethyl)-phenyl]-amide, 5-[4-(3-fluoro-phenoxy)-phenyl]-4-oxo-4,5-dihydro-3H-1-thia-3,5,6,8-tetraaza-acenaphthylene-2-carboxylic acid (3-hydroxy-propyl)-amide, 5-[4-(3-fluoro-phenoxy)-phenyl]-4-oxo-4,5-dihydro-3H-1-thia-3,5,6,8-tetraaza-acenaphthylene-2-carboxylic acid (4-morpholin-4-ylmethyl-phenyl)-amide, 5-(3-chloro-4-phenoxy-phenyl)-4-oxo-4,5-dihydro-3H-1-thia-3,5,6,8-tetraaza-acenaphthylene-2-carboxylic acid (4-piperidin-1-ylmethyl-phenyl)-amide, 5-(3-chloro-4-phenoxy-phenyl)-4-oxo-4,5-dihydro-3H-1-thia-3,5,6,8-tetraaza-acenaphthylene-2-carboxylic acid [4-(2-piperidin-1-yl-ethyl)-phenyl]-amide, 5-(3-chloro-4-phenoxy-phenyl)-4-oxo-4,5-dihydro-3H-1-thia-3,5,6,8-tetraaza-acenaphthylene-2-carboxylic acid (3-hydroxy-propyl)-amide, 5-(3-chloro-4-phenoxy-phenyl)-4-oxo-4,5-dihydro-3H-1-thia-3,5,6,8-tetraaza-acenaphthylene-2-carboxylic acid (4-morpholin-4-ylmethyl-phenyl)-amide, 5-[1-(3-fluoro-benzyl)-1H-indol-5-yl]-4-oxo-4,5-dihydro-3H-1-thia-3,5,6,8-tetraaza-acenaphthylene-2-carboxylic acid (3-amino-propyl)-amide, 5-(2-chloro-4-fluoro-phenyl)-4-oxo-4,5-dihydro-3H-1-thia-3,5,6,8-tetraaza-acenaphthylene-2-carboxylic acid [3-methoxy-4-(2-piperidin-1-yl-ethoxy)-phenyl]-amide, 5-(2-chloro-4-fluoro-phenyl)-4-oxo-4,5-dihydro-3H-1-thia-3,5,6,8-tetraaza-acenaphthylene-2-carboxylic acid (4-piperidin-1-ylmethyl-phenyl)-amide, 5-(2-chloro-6-methyl-phenyl)-4-oxo-4,5-dihydro-3H-1-thia-3,5,6,8-tetraaza-acenaphthylene-2-carboxylic acid (4-morpholin-4-ylmethyl-phenyl)-amide, 5-(2-chloro-6-methyl-phenyl)-4-oxo-4,5-dihydro-3H-1-thia-3,5,6,8-tetraaza-acenaphthylene-2-carboxylic acid (4-piperidin-1-ylmethyl-phenyl)-amide, 5-(2-chloro-6-methyl-phenyl)-4-oxo-4,5-dihydro-3H-1-thia-3,5,6,8-tetraaza-acenaphthylene-2-carboxylic acid [4-(1-hydroxy-2-morpholin-4-yl-ethyl)-phenyl]-amide, 5-(2-chloro-phenyl)-4-oxo-4,5-dihydro-3H-1-thia-3,5,6,8-tetraaza-acenaphthylene-2-carboxylic acid (4-morpholin-4-ylmethyl-phenyl)-amide, 5-(2-chloro-phenyl)-4-oxo-4,5-dihydro-3H-1-thia-3,5,6,8-tetraaza-acenaphthylene-2-carboxylic acid (4-piperidin-1-ylmethyl-phenyl)-amide, 5-(2-chloro-phenyl)-4-oxo-4,5-dihydro-3H-1-thia-3,5,6,8-tetraaza-acenaphthylene-2-carboxylic acid [4-(4-methyl-piperazin-1-ylmethyl)-phenyl]-amide, 5-(3-bromo-4-fluoro-phenyl)-4-oxo-4,5-dihydro-3H-1-thia-3,5,6,8-tetraaza-acenaphthylene-2-carboxylic acid (4-morpholin-4-ylmethyl-phenyl)-amide, 5-(3-bromo-4-fluoro-phenyl)-4-oxo-4,5-dihydro-3H-1-thia-3,5,6,8-tetraaza-acenaphthylene-2-carboxylic acid (4-piperidin-1-ylmethyl-phenyl)-amide, 5-[3-chloro-4-(3-fluoro-phenoxy)-phenyl]-4-oxo-4,5-dihydro-3H-1-thia-3,5,6,8-tetraaza-acenaphthylene-2-carboxylic acid (4-piperidin-1-ylmethyl-phenyl)-amide, 5-[3-chloro-4-(3-fluoro-phenoxy)-phenyl]-4-oxo-4,5-dihydro-3H-1-thia-3,5,6,8-tetraaza-acenaphthylene-2-carboxylic acid [3-methoxy-4-(2-piperidin-1-yl-ethoxy)-phenyl]-amide, 5-[3-chloro-4-(3-fluoro-phenoxy)-phenyl]-4-oxo-4,5-dihydro-3H-1-thia-3,5,6,8-tetraaza-acenaphthylene-2-carboxylic acid (4-morpholin-4-ylmethyl-phenyl)-amide, 5-(4-benzyl-phenyl)-4-oxo-4,5-dihydro-3H-1-thia-3,5,6,8-tetraaza-acenaphthylene-2-carboxylic acid [3-methoxy-4-(2-piperidin-1-yl-ethoxy)-phenyl]-amide, 5-(4-benzyl-phenyl)-4-oxo-4,5-dihydro-3H-1-thia-3,5,6,8-tetraaza-acenaphthylene-2-carboxylic acid (4-piperidin-1-ylmethyl-phenyl)-amide, 5-(4-benzyl-phenyl)-4-oxo-4,5-dihydro-3H-1-thia-3,5,6,8-tetraaza-acenaphthylene-2-carboxylic acid (4-morpholin-4-ylmethyl-phenyl)-amide, 4-oxo-5-(4-phenoxy-phenyl)-4,5-dihydro-3H-1-thia-3,5,6,8-tetraaza-acenaphthylene-2-carboxylic acid [4-(2-piperidin-1-yl-ethyl)-phenyl]-amide, 4-oxo-5-(4-phenoxy-phenyl)-4,5-dihydro-3H-1-thia-3,5,6,8-tetraaza-acenaphthylene-2-carboxylic acid [3-methoxy-4-(2-morpholin-4-yl-ethoxy)-phenyl]-amide, 4-oxo-5-(4-phenylsulfanyl-phenyl)-4,5-dihydro-3H-1-thia-3,5,6,8-tetraaza-acenaphthylene-2-carboxylic acid (4-piperidin-1-ylmethyl-phenyl)-amide, 4-oxo-5-(4-phenoxy-phenyl)-4,5-dihydro-3H-1-thia-3,5,6,8-tetraaza-acenaphthylene-2-carboxylic acid [4-(1-hydroxy-2-morpholin-4-yl-ethyl)-phenyl]-amide, 5-[1-(3-fluoro-benzyl)-1H-indazol-5-yl]-4-oxo-4,5-dihydro-3H-1-thia-3,5,6,8-tetraaza-acenaphthylene-2-carboxylic acid (4-morpholin-4-ylmethyl-phenyl)-amide, 4-oxo-5-(4-phenoxy-phenyl)-4,5-dihydro-3H-1-thia-3,5,6,8-tetraaza-acenaphthylene-2-carboxylic acid (3-methoxy-4-morpholin-4-ylmethyl-phenyl)-amide, 5-[1-(3-fluoro-benzyl)-1H-indazol-5-yl]-4-oxo-4,5-dihydro-3H-1-thia-3,5,6,8-tetraaza-acenaphthylene-2-carboxylic acid (1-methyl-piperidin-4-yl)-amide, 4-oxo-5-(4-phenylsulfanyl-phenyl)-4,5-dihydro-3H-1-thia-3,5,6,8-tetraaza-acenaphthylene-2-carboxylic acid (4-morpholin-4-ylmethyl-phenyl)-amide, 5-[3-bromo-4-(pyridin-2-ylmethoxy)-phenyl]-4-oxo-4,5-dihydro-3H-1-thia-3,5,6,8-tetraaza-acenaphthylene-2-carboxylic acid (4-morpholin-4-ylmethyl-phenyl)-amide, 5-(3-bromo-phenyl)-4-oxo-4,5-dihydro-3H-1-thia-3,5,6,8-tetraaza-acenaphthylene-2-carboxylic acid (3-methoxy-4-morpholin-4-ylmethyl-phenyl)-amide, 5-(3-bromo-4-phenoxy-phenyl)-4-oxo-4,5-dihydro-3H-1-thia-3,5,6,8-tetraaza-acenaphthylene-2-carboxylic acid (4-morpholin-4-ylmethyl-phenyl)-amide, 5-(3-bromo-4-phenoxy-phenyl)-4-oxo-4,5-dihydro-3H-1-thia-3,5,6,8-tetraaza-acenaphthylene-2-carboxylic acid (4-piperidin-1-ylmethyl-phenyl)-amide, 5-(3-bromo-4-phenoxy-phenyl)-4-oxo-4,5-dihydro-3H-1-thia-3,5,6,8-tetraaza-acenaphthylene-2-carboxylic acid (3-methoxy-4-morpholin-4-ylmethyl-phenyl)-amide, 4-oxo-5-(4-phenylsulfanyl-phenyl)-4,5-dihydro-3H-1-thia-3,5,6,8-tetraaza-acenaphthylene-2-carboxylic acid (1-methyl-piperidin-4-yl)-amide, 5-(4-bromo-phenyl)-4-oxo-4,5-dihydro-3H-1-thia-3,5,6, 8-tetraaza-acenaphthylene-2-carboxylic acid (4-piperidin-1-ylmethyl-phenyl)-amide, 5-(4-bromo-phenyl)-4-oxo-4,5-dihydro-3H-1-thia-3,5,6, 8-tetraaza-acenaphthylene-2-carboxylic acid (4-morpholin-4-ylmethyl-phenyl)-amide, 4-oxo-5-(3-phenoxy-phenyl)-4,5-dihydro-3H-1-thia-3,5, 6,8-tetraaza-acenaphthylene-2-carboxylic acid (4-piperidin-1-ylmethyl-phenyl)-amide, 4-oxo-5-(3-phenoxy-phenyl)-4,5-dihydro-3H-1-thia-3,5, 6,8-tetraaza-acenaphthylene-2-carboxylic acid [4-(4-methyl-piperazin-1-ylmethyl)-phenyl ]-amide, 4-oxo-5-(3-phenoxy-phenyl)-4,5-dihydro-3H-1-thia-3,5, 6,8-tetraaza-acenaphthylene-2-carboxylic acid (3-methoxy-4-morpholin-4-ylmethyl-phenyl)-amide, 5-(4-bromo-phenyl)-4-oxo-4,5-dihydro-3H-1-thia-3,5,6, 8-tetraaza-acenaphthylene-2-carboxylic acid (3-methoxy-4-morpholin-4-ylmethyl-phenyl)-amide, 4-oxo-5-(4-phenoxy-phenyl)-4,5-dihydro-3H-1-thia-3,5, 6,8-tetraaza-acenaphthylene-2-carboxylic acid (3-fluoro-4-morpholin-4-ylmethyl-phenyl)-amide, 4-oxo-5-(4-phenoxy-phenyl)-4,5-dihydro-3H-1-thia-3,5, 6,8-tetraaza-acenaphthylene-2-carboxylic acid (3-ethoxy-4-morpholin-4-ylmethyl-phenyl)-amide, 5-[3-chloro-4-(pyridin-3-yloxy)-phenyl]-4-oxo-4,5-dihydro-3H-1-thia-3,5,6,8-tetraaza-acenaphthylene-2-carboxylic acid (4-morpholin-4-ylmethyl-phenyl)-amide, 5-[3-chloro-4-(pyridin-3-yloxy)-phenyl]-4-oxo-4,5-dihydro-3H-1-thia-3,5,6,8-tetraaza-acenaphthylene-2-carboxylic acid (4-piperidin-1-ylmethyl-phenyl)-amide, 4-oxo-5-(4-phenoxy-phenyl)-4,5-dihydro-3H-1-thia-3,5, 6,8-tetraaza-acenaphthylene-2-carboxylic acid (1-methyl-piperidin-4-yl)-amide, 4-oxo-5-(4-phenylsulfanyl-phenyl)-4,5-dihydro-3H-1-thia-3,5,6,8-tetraaza-acenaphthylene-2-carboxylic acid (3-dimethylamino-propyl)-amide, 4-oxo-5-(4-phenylsulfanyl-phenyl)-4,5-dihydro-3H-1-thia-3,5,6,8-tetraaza-acenaphthylene-2-carboxylic acid [4-(4-methyl-piperazin-1-ylmethyl)-phenyl]-amide, 4-oxo-5-(4-phenylsulfanyl-phenyl)-4,5-dihydro-3H-1-thia-3,5,6,8-tetraaza-acenaphthylene-2-carboxylic acid (3-methoxy-4-morpholin-4-ylmethyl-phenyl)-amide, 4-oxo-5-(4-phenoxy-phenyl)-4,5-dihydro-3H-1-thia-3,5, 6,8-tetraaza-acenaphthylene-2-carboxylic acid (3-morpholin-4-ylmethyl-phenyl)-amide, 4-oxo-5-(4-phenoxy-phenyl)-4,5-dihydro-3H-1-thia-3,5, 6,8-tetraaza-acenaphthylene-2-carboxylic acid (3-chloro-4-morpholin-4-ylmethyl-phenyl)-amide, 4-oxo-5-(4-phenylsulfanyl-phenyl)-4,5-dihydro-3H-1-thia-3,5,6,8-tetraaza-acenaphthylene-2-carboxylic acid (3-methoxy-4-piperidin-1-ylmethyl-phenyl)-amide, 5-[3-chloro-4-(thiophen-2-ylmethoxy)-phenyl]-4-oxo-4, 5-dihydro-3H-1-thia-3,5,6,8-tetraaza-acenaphthylene-2-carboxylic acid (4-morpholin-4-ylmethyl-phenyl)-amide, 5-[3-chloro-4-(thiophen-2-ylmethoxy)-phenyl]-4-oxo-4, 5-dihydro-3H-1-thia-3,5,6,8-tetraaza-acenaphthylene-2-carboxylic acid (4-piperidin-1-ylmethyl-phenyl)-amide, 5-[3-chloro-4-(thiophen-2-ylmethoxy)-phenyl]-4-oxo-4, 5-dihydro-3H-1-thia-3,5,6,8-tetraaza-acenaphthylene-2-carboxylic acid (3-methoxy-4-piperidin-1-ylmethyl-phenyl)-amide, 5-[3-chloro-4-(thiophen-2-ylmethoxy)-phenyl]-4-oxo-4, 5-dihydro-3H-1-thia-3,5,6,8-tetraaza-acenaphthylene-2-carboxylic acid (3-methoxy-4-morpholin-4-ylmethyl-phenyl)-amide, 5-[3-chloro-4-(thiophen-2-ylmethoxy)-phenyl]-4-oxo-4, 5-dihydro-3H-1-thia-3,5,6,8-tetraaza-acenaphthylene-2-carboxylic acid (1-methyl-piperidin-4-yl)-amide, 4-oxo-5-(4-phenoxy-phenyl)-4,5-dihydro-3H-1-thia-3,5, 6,8-tetraaza-acenaphthylene-2-carboxylic acid (3-methyl-4-morpholin-4-ylmethyl-phenyl)-amide, 4-oxo-5-(4-phenoxy-phenyl)-4,5-dihydro-3H-1-thia-3,5, 6,8-tetraaza-acenaphthylene-2-carboxylic acid [4-(4-hydroxy-piperidin-1-ylmethyl)-phenyl]-amide, 4-oxo-5-(4-phenoxy-phenyl)-4,5-dihydro-3H-1-thia-3,5, 6,8-tetraaza-acenaphthylene-2-carboxylic acid [4-(3-fluoro-piperidin-1-ylmethyl)-phenyl]-amide, 4-oxo-5-[4-(pyridin-3-yloxy)-phenyl]-4,5-dihydro-3H-1-thia-3,5,6,8-tetraaza-acenaphthylene-2-carboxylic acid (3-methoxy-4-morpholin-4-ylmethyl-phenyl)-amide, 4-oxo-5-[4-(pyridin-3-yloxy)-phenyl]-4,5-dihydro-3H-1-thia-3,5,6,8-tetraaza-acenaphthylene-2-carboxylic acid (4-morpholin-4-ylmethyl-phenyl)-amide, 4-oxo-5-(4-phenoxy-phenyl)-4,5-dihydro-3H-1-thia-3,5, 6,8-tetraaza-acenaphthylene-2-carboxylic acid (4-morpholin-4-ylmethyl-3 -trifluoromethoxy-phenyl)-amide, 4-oxo-5-(4-phenoxy-phenyl)-4,5-dihydro-3H-1-thia-3,5, 6,8-tetraaza-acenaphthylene-2-carboxylic acid (4-morpholin-4-ylmethyl-3-trifluoromethoxy-phenyl)-amide, 4-oxo-5-(4-phenoxy-phenyl)-4,5-dihydro-3H-1-thia-3,5, 6,8-tetraaza-acenaphthylene-2-carboxylic acid (3-methoxy-4-piperidin-1-ylmethyl-phenyl)-amide, 5-[3-chloro-4-(furan-2-ylmethoxy)-phenyl]-4-oxo-4,5-dihydro-3H-1-thia-3,5,6,8-tetraaza-acenaphthylene-2-carboxylic acid (3-methoxy-4-piperidin-1-ylmethyl-phenyl)-amide, 5-[3-chloro-4-(furan-2-ylmethoxy)-phenyl]-4-oxo-4,5-dihydro-3H-1-thia-3,5,6,8-tetraaza-acenaphthylene-2-carboxylic acid (4-piperidin-1-ylmethyl-phenyl)-amide, 5-[3-chloro-4-(furan-2-ylmethoxy)-phenyl]-4-oxo-4,5-dihydro-3H-1-thia-3,5,6,8-tetraaza-acenaphthylene-2-carboxylic acid (4-morpholin-4-ylmethyl-phenyl)-amide, 5-[3-chloro-4-(furan-2-ylmethoxy)-phenyl]-4-oxo-4,5-dihydro-3H-1-thia-3,5,6,8-tetraaza-acenaphthylene-2-carboxylic acid (3-methoxy-4-morpholin-4-ylmethyl-phenyl)-amide, 4-oxo-5-(4-phenoxy-phenyl)-4,5-dihydro-3H-1-thia-3,5, 6,8-tetraaza-acenaphthylene-2-carboxylic acid [4-(4-fluoro-piperidin-1-ylmethyl)-phenyl]-amide, 5-benzofuran-7-yl-4-oxo-4,5-dihydro-3H-1-thia-3,5,6,8-tetraaza-acenaphthylene-2-carboxylic acid [4-(2-piperidin-1-yl-ethyl)-phenyl]-amide, 5-[3-chloro-4-(3-fluoro-benzyloxy)-phenyl]-4-oxo-4,5-dihydro-3H-1-thia-3,5,6,8-tetraaza-acenaphthylene-2-carboxylic acid [4-(4-methyl-piperazin-1-ylmethyl)-phenyl]-amide, 4-oxo-5-(4-phenoxy-phenyl)-4,5-dihydro-3H-1-thia-3,5, 6,8-tetraaza-acenaphthylene-2-carboxylic acid [4-(3,5-dimethyl-morpholin-4-ylmethyl)-phenyl]-amide, 4-oxo-5-(4-phenoxy-phenyl)-4,5-dihydro-3H-1-thia-3,5, 6,8-tetraaza-acenaphthylene-2-carboxylic acid [4-(4-hydroxymethyl-piperidin-1-ylmethyl)-phenyl]-amide, 4-oxo-5-(4-phenoxy-phenyl)-4,5-dihydro-3H-1-thia-3,5, 6,8-tetraaza-acenaphthylene-2-carboxylic acid [4-(4-methyl-piperidin-1-ylmethyl)-phenyl]-amide, 4-oxo-5-(4-phenoxy-phenyl)-4,5-dihydro-3H-1-thia-3,5, 6,8-tetraaza-acenaphthylene-2-carboxylic acid [4-(3-hydroxymethyl-piperidin-1-ylmethyl)-phenyl]-amide, 4-oxo-5-(4-phenoxy-phenyl)-4,5-dihydro-3H-1-thia-3,5,6,8-tetraaza-acenaphthylene-2-carboxylic acid (3-dimethylamino-4-morpholin-4-ylmethyl-phenyl)-amide,

[1-(4-{[4-oxo-5-(4-phenoxy-phenyl)-4,5-dihydro-3H-1-thia-3,5,6,8-tetraaza-acenaphthylene-2-carbonyl]-amino}-benzyl)-piperidin-4-yl]-carbamic acid tert-butyl ester, 4-oxo-5-(4-phenoxy-phenyl)-4,5-dihydro-3H-1-thia-3,5,6,8-tetraaza-acenaphthylene-2-carboxylic acid [4-(4-amino-piperidin-1-ylmethyl)-phenyl]-amide, 4-oxo-5-(4-phenoxy-phenyl)-4,5-dihydro-3H-1-thia-3,5,6,8-tetraaza-acenaphthylene-2-carboxylic acid [4-(4-dimethylamino-piperidin-1-ylmethyl)-phenyl]-amide, 4-oxo-5-(4-phenoxy-phenyl)-4,5-dihydro-3H-1-thia-3,5,6,8-tetraaza-acenaphthylene-2-carboxylic acid [4-(4-methoxy-piperidin-1-ylmethyl)-phenyl]-amide, 4-oxo-5-(4-phenoxy-phenyl)-4,5-dihydro-3H-1-thia-3,5,6,8-tetraaza-acenaphthylene-2-carboxylic acid (3-hydroxy-4-morpholin-4-ylmethyl-phenyl)-amide, and 4-oxo-5-(4-phenoxy-phenyl)-4,5-dihydro-3H-1-thia-3,5,6,8-tetraaza-acenaphthylene-2-carboxylic acid [4-(4,4-difluoro-piperidin-1-ylmethyl)-phenyl]-amide.

19. The compound of any of claim 1 to 18, wherein the compound is a protein kinase inhibitor, wherein the protein kinase is selected from EGFR, HER-2, HER-4, c-Src, Lyn or c-Abl.

20. The compound of any of claim 1 to 18, wherein the compound is a prodrug thereof.

21. The compound of any of claim 1 to 18, wherein the compound is an isolated form thereof.

22. The compound of any of claim 1 to 18, wherein the compound is a metabolite form thereof.

23. The compound of any of claim 1 to 18, wherein the compound is labeled with a ligand for use as a marker, and wherein the ligand is a radioligand selected from deuterium or tritium.

24. A pharmaceutical composition comprising an effective amount of a compound of any of claim 1 to 18.

25. The pharmaceutical composition of claim 24, wherein the effective amount of the compound is in a range of from about 0.001 mg/kg to about 300 mg/kg of body weight per day.

26. A medicament comprising an effective amount of the compound of any of claim 1 to 18.

27. The medicament of claim 26, wherein the effective amount of the compound is in a range of from about 0.001 mg/kg to about 300 mg/kg of body weight per day.

* * * * *